United States Patent
Bier et al.

(10) Patent No.: US 11,091,780 B2
(45) Date of Patent: Aug. 17, 2021

(54) METHODS FOR AUTOCATALYTIC GENOME EDITING AND NEUTRALIZING AUTOCATALYTIC GENOME EDITING AND COMPOSITIONS THEREOF

(71) Applicant: The Regents of the University of California, Oakland, CA (US)

(72) Inventors: Ethan Bier, San Diego, CA (US); Valentino Gantz, San Diego, CA (US); Stephen Hedrick, Solana Beach, CA (US)

(73) Assignee: The Regents of the University of California, Oakland, CA (US)

(*) Notice: Subject to any disclaimer, the term of this patent is extended or adjusted under 35 U.S.C. 154(b) by 446 days.

(21) Appl. No.: 15/761,156

(22) PCT Filed: Sep. 19, 2016

(86) PCT No.: PCT/US2016/052424
§ 371 (c)(1),
(2) Date: Mar. 19, 2018

(87) PCT Pub. No.: WO2017/049266
PCT Pub. Date: Mar. 23, 2017

(65) Prior Publication Data
US 2020/0080111 A1    Mar. 12, 2020

Related U.S. Application Data

(60) Provisional application No. 62/220,630, filed on Sep. 18, 2015, provisional application No. 62/221,298, filed on Sep. 21, 2015, provisional application No. 62/221,309, filed on Sep. 21, 2015, provisional application No. 62/256,479, filed on Nov. 17, 2015, provisional application No. 62/266,022, filed on Dec. 11, 2015.

(51) Int. Cl.
| | |
|---|---|
| *C12N 15/63* | (2006.01) |
| *C12N 15/79* | (2006.01) |
| *C07H 21/02* | (2006.01) |
| *C07H 21/04* | (2006.01) |
| *C12N 15/90* | (2006.01) |
| *A01K 67/033* | (2006.01) |

(52) U.S. Cl.
CPC ........ *C12N 15/907* (2013.01); *A01K 67/0339* (2013.01); *A01K 2207/10* (2013.01); *A01K 2217/075* (2013.01); *A01K 2217/15* (2013.01); *A01K 2217/203* (2013.01); *A01K 2227/706* (2013.01); *A01K 2267/03* (2013.01); *C07H 21/04* (2013.01); *C12N 15/63* (2013.01); *C12N 15/79* (2013.01); *C12N 2310/20* (2017.05); *C12N 2510/00* (2013.01); *C12N 2800/90* (2013.01); *C12N 2830/006* (2013.01)

(58) Field of Classification Search
CPC .... C12N 15/63; C12N 15/79; C12N 2510/00; C12N 2310/20; C07H 21/02; C07H 21/04
USPC ........... 424/93.21; 435/320.1, 455; 536/23.1, 536/23.5
See application file for complete search history.

(56) References Cited

FOREIGN PATENT DOCUMENTS

| | | |
|---|---|---|
| WO | 2014/191128 A1 | 12/2014 |
| WO | 2015/088643 A1 | 6/2015 |
| WO | 2015/136001 A1 | 9/2015 |

OTHER PUBLICATIONS

Porteus et al., 2018, US 20180119140 A1, effective filing date, Apr. 6, 2015.*
Meissner et al., 2016, US 20160348073 A1, effective filing date, Mar. 27, 2015.*
Zhu et al., 2015 (Published on line Feb. 27, 2015), Retrovirology, vol. 12, p. 1-7.*
Striepen et al., 2016, US 2016016224 A1, effective filing date, Aug. 2, 2013.*
PCT International Search Report for PCT Application No. PCT/US2016/052424 dated Mar. 27, 2017 (19 pages).
Gantz et al., "The Mutagenic Chain Reaction: A Method for Converting Heterozygous to Homozygous Mutations," Science, 2015, 11 pages.
Woo et al., "Auto-Excision of Selectable Marker Genes from Transgenic Tobacco via a Stress Inducible FLP/FRT Site-Specific Recombination System," Transgenic Res., 2009, 11 pages.
Supplementary Partial European Search Report for EP Application No. 16 84 7523 dated Mar. 14, 2019 (18 pages).
Hai et al., "One-Step Generation of Knockout Pigs by Zygote Injection of CRISP/Cas System," Cell Research, 2014, 24:372-375.

(Continued)

*Primary Examiner* — Shin Lin Chen
(74) *Attorney, Agent, or Firm* — Eversheds Sutherland (US) LLP

(57) ABSTRACT

Described herein are methods and compositions for autocatalytic genome editing and neutralizing autocatalytic genome editing. The autocatalytic genome editing may be based on genomic integration of a construct containing multiple elements or on a trans-complementation approach, in which genetic elements can be propagated separately. The disclosure provides a method for autocatalytic genome editing based on the CRISPR/CAS9 system, and methods of use thereof, in animals, humans, and plants for eliminating pathogens, targeting suppression of crop pests, strategies to combat virus (e.g., HIV) and other diseases (e.g., cancer) caused by retrovirus, as well as to generate homozygous mutations that are transmitted to nearly all offspring.

19 Claims, 79 Drawing Sheets
Specification includes a Sequence Listing.

(56) References Cited

OTHER PUBLICATIONS

Jao et al., "Efficient Multiplex Biallelic Zebrafish Genome Editing Using a CRISP Nuclease System," Proceedings of the National Academy of Sciences, 2013, 110:34 with Supporting Information (16 pages).
Platt et al., "CRISPR-Cas9 Knockin Mice for Genome Editing and Cancer Modeling," Cell, 2014, 159:440-455.

* cited by examiner

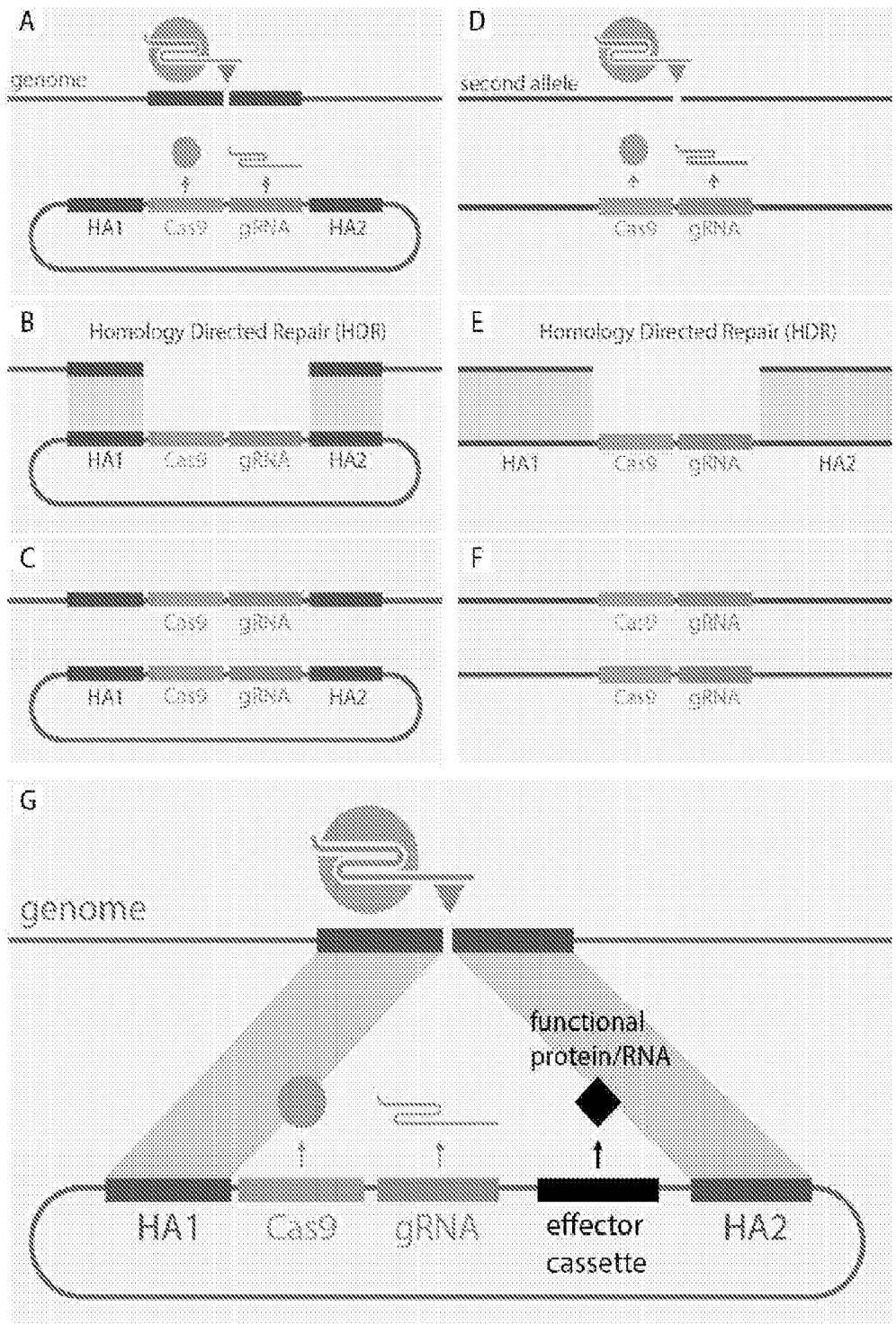
FIGURE 1A-G

Mendelian Inheritance

Yellow

MCR Inheritance

Yellow

Yellow MCR Construct

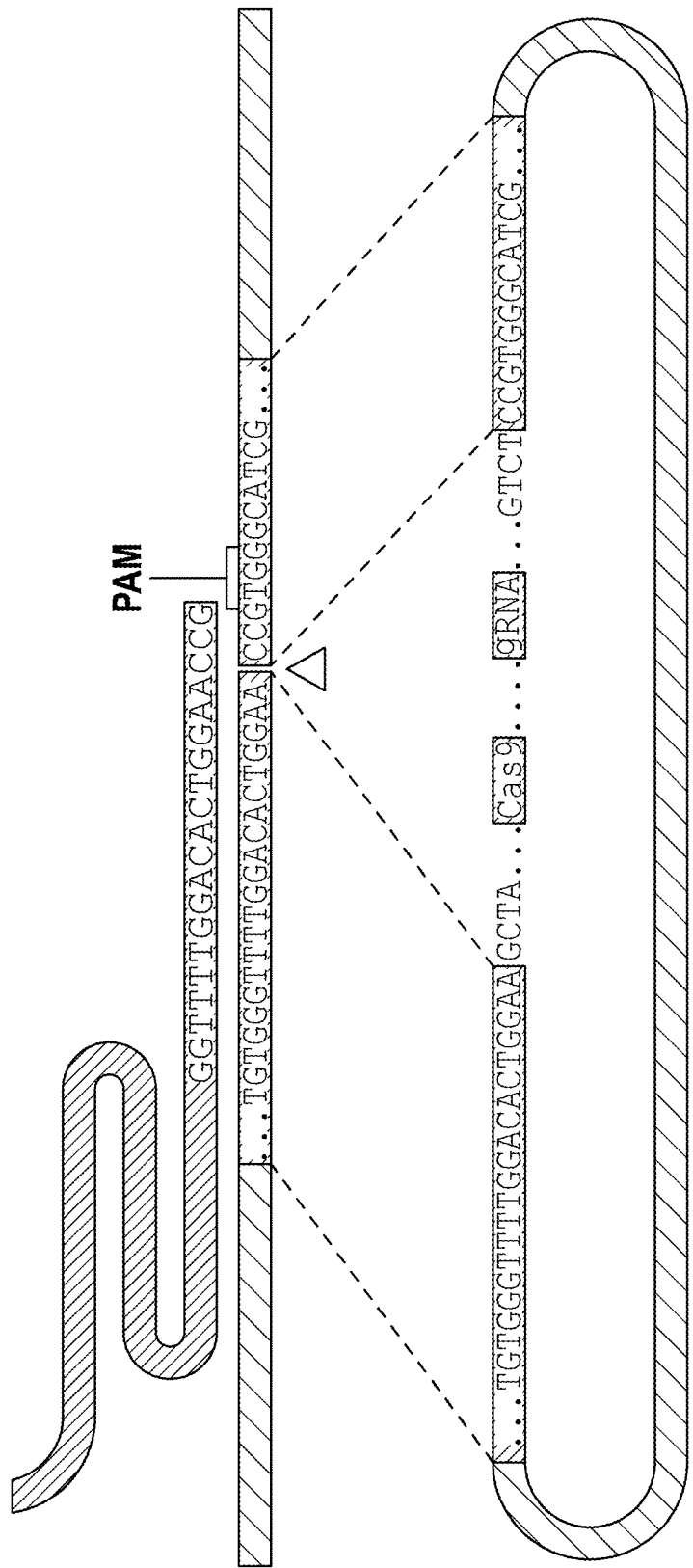
FIG. 2I Yellow MCR Construct

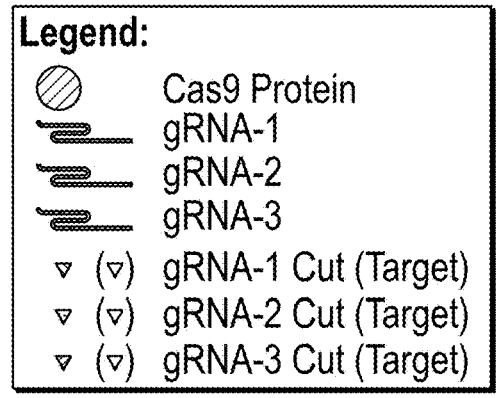
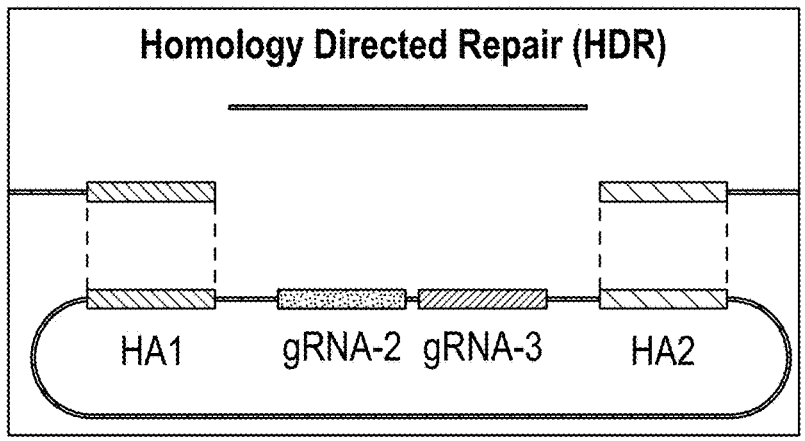
FIG. 4B
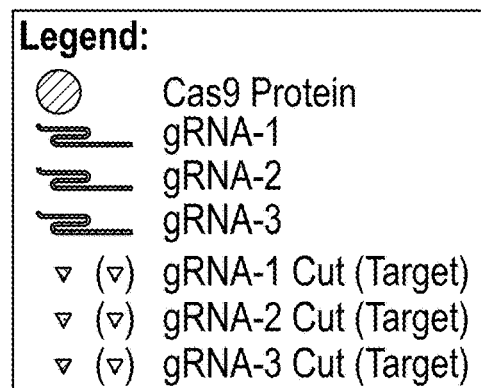
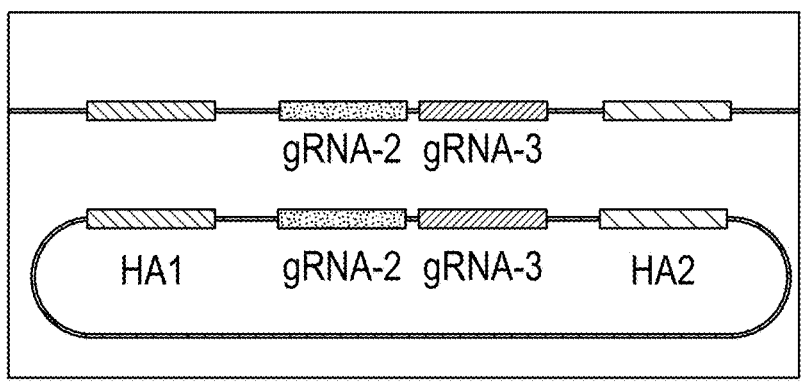
FIG. 4C

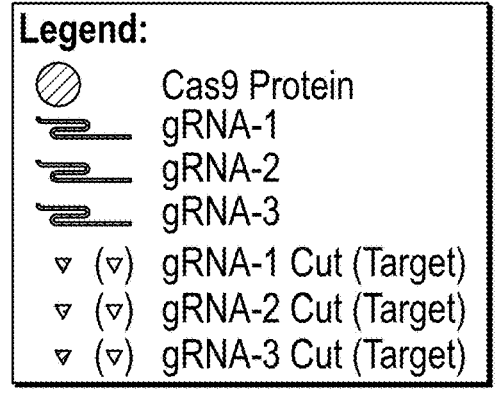
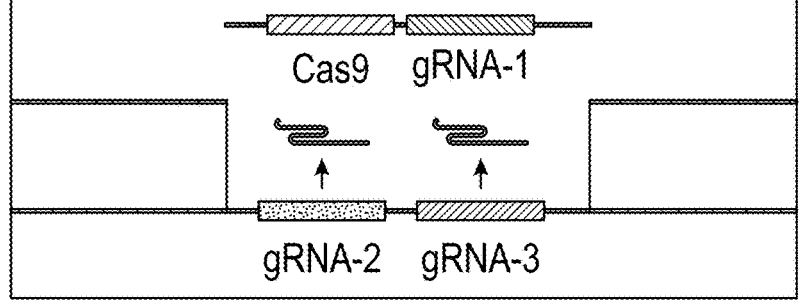
FIG. 4E
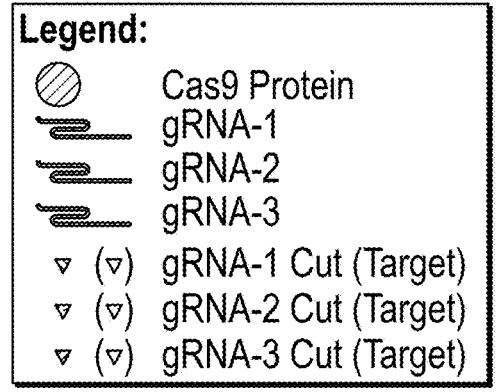
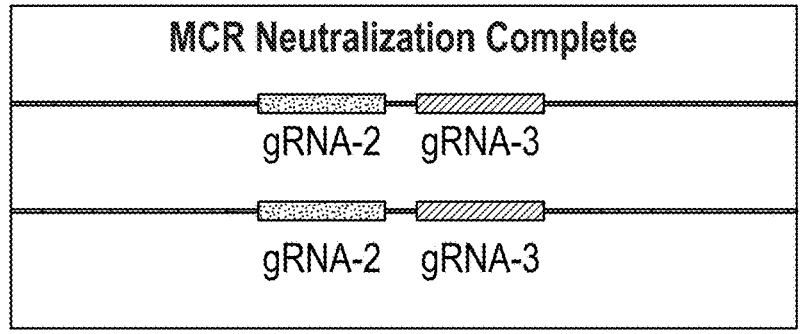
FIG. 4F

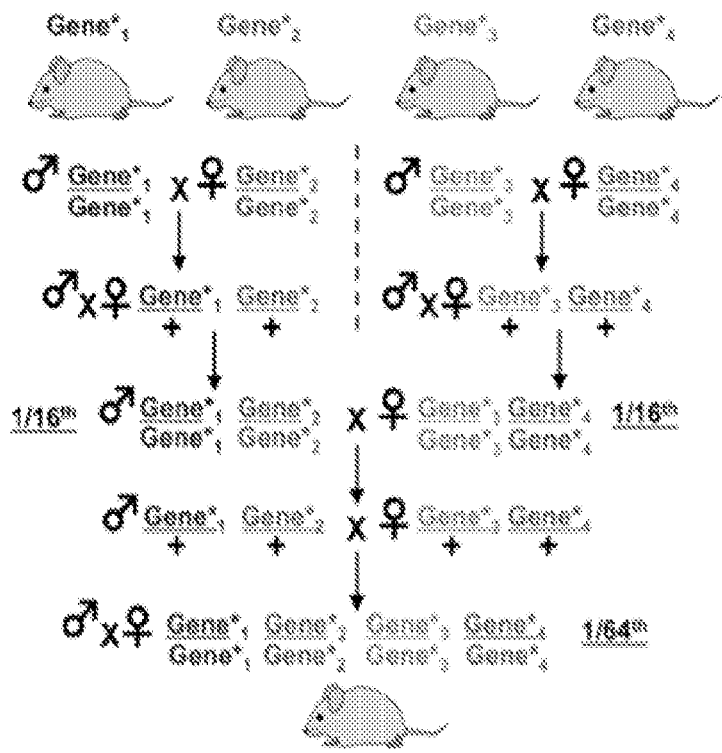
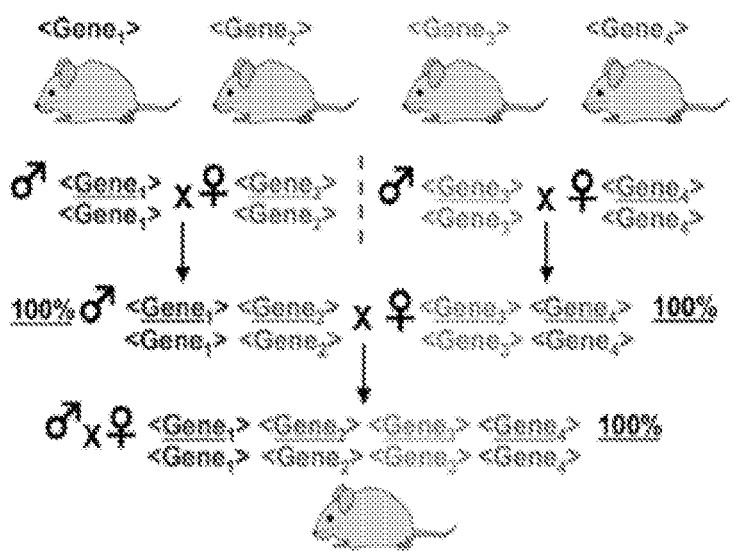
FIGURE 5

Copy Cat (cc) Vectors: gRNAs Flanked by Homology Arms, Denoted <gRNA>

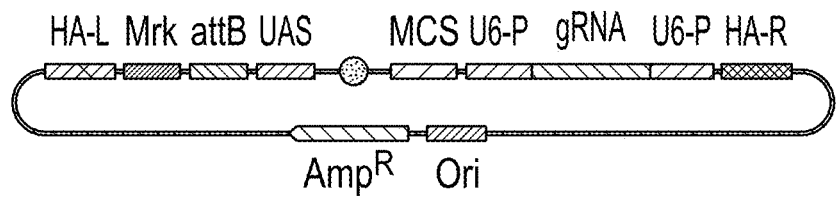

1) cc Cloning Vectors Lack a Source of Cas9 but Carry a gRNA and Homology arms for Targeted Insertion to Specific Sites Along a Chromosome 2) When cc Elements are Combined with a Source of Cas9 They Get Copied (cced) Via "Active Genetics" to the other Chromosome 3) One can Cross Out Cas9 Source to Return to Standard "Passive" Mendelian Genetics.

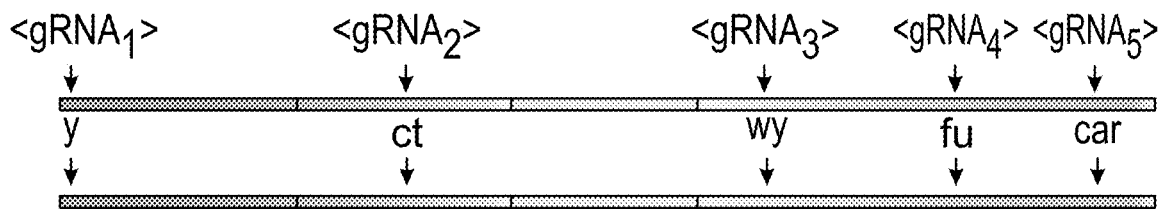

FIG. 13

Combining a complex array of transgenes and classic lethal alleles:

<gR₁:UAS-X> m₁<gR₂:UAS-Y>/Cyo; <gR₃:GAL4-Y> <gR₄:RFP> m₂/TM3

Second chromosome: <gR₁:UAS-X>, mutation m₁, <gR₂:UAS-Y>
Third chromosome: <gR₃:GAL4-Y>, <gR₄:RFP>, mutation m₂

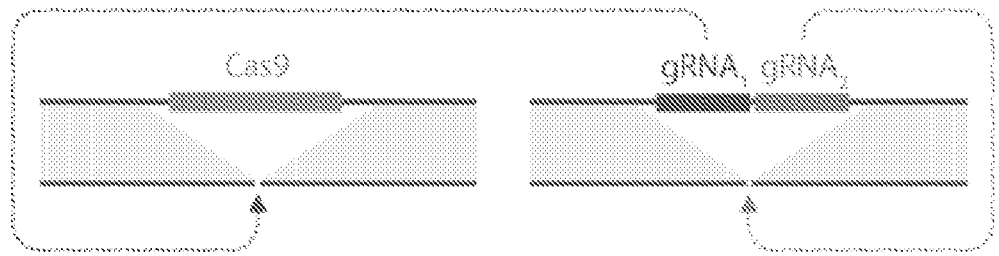

FIGURE 20

Growth Equations (solutions at 1% vs 10% seeding frequencies):

1) Separately encoded traditional cas9 and gRNA transgenes:
   $f(n) = 1 - (1 - c_0 g_0)^n \cong c_0 g_0 n$. Graphed (green line) for $c_0 = g_0 = 0.01$ (left) or 0.1 (right).

2) Separately encoded cas9 and homology flanked gRNA, <gRNA>, transgenes.
   $f(n) = 1 - (1 - c_0)^n \cong c_0 n$. Graphed (red) for $c_0 = g_0 = 0.01$ (left) or 0.1 (right).

3) MCR: combined <cas9, gRNA>
   $f(n) = 1 - (1 - c_0)^{(2^n)} \cong c_0 2^n$. Graphed (blue) for $c_0 = 0.01$ (left) or 0.1 (right).

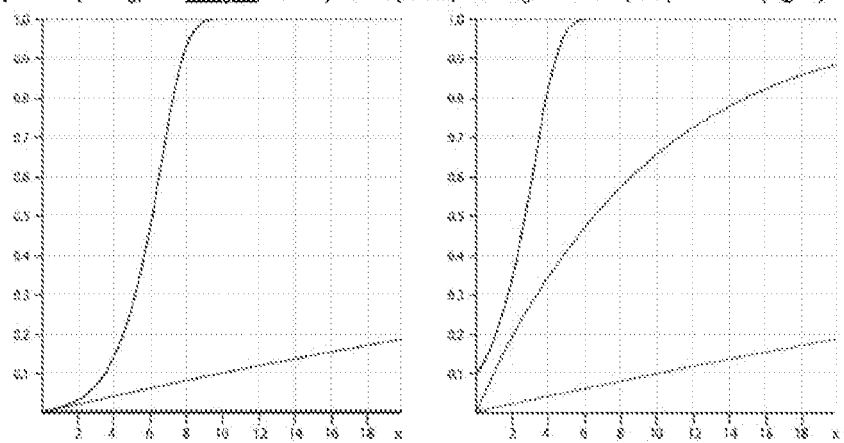

FIGURE 21

Potential Application: Malaria
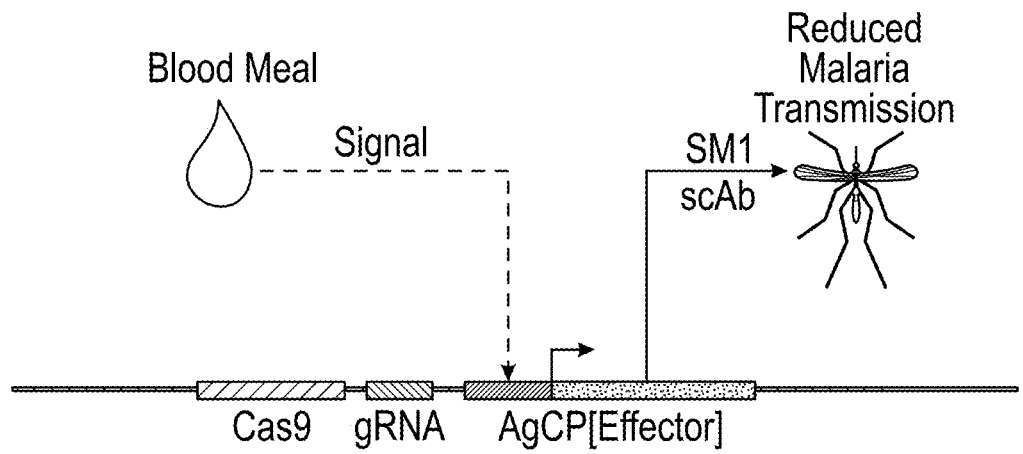
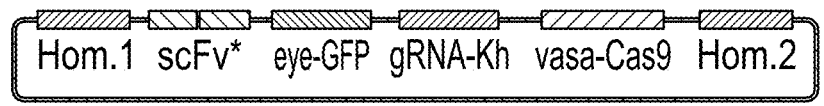
Kynurenine Hydroxylase Locus (kh) = Cinnabar in D. mel. -> White Eyes
Kh-MCR
scFv* = Transgene Cassestte Carrying Two Anti-Malarial Single Chain Antibodies
Fitness-Neutral 44C Locus
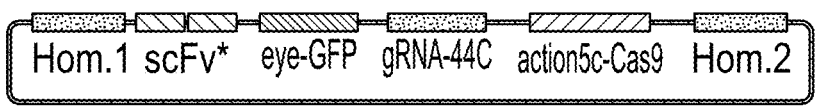
44C-MCR
FIG. 22

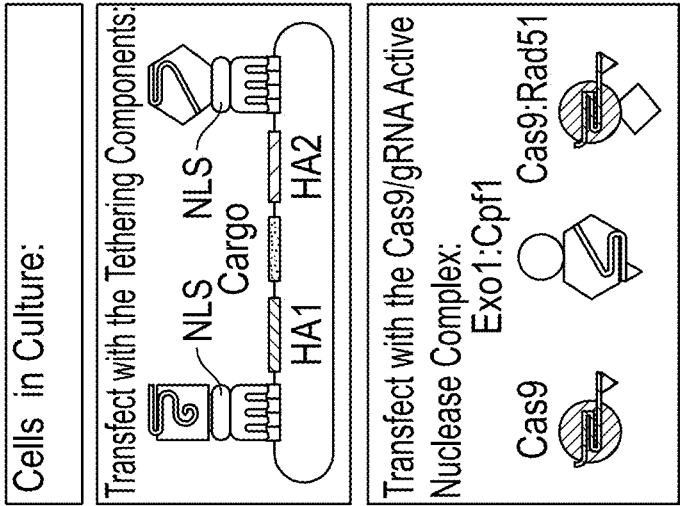
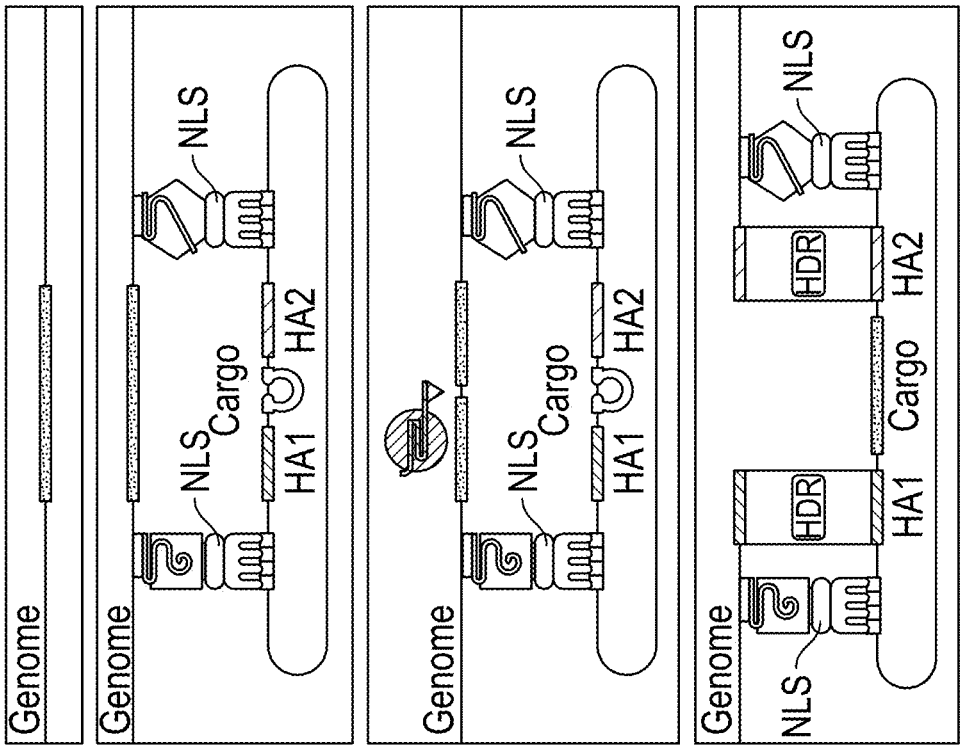
FIG. 26

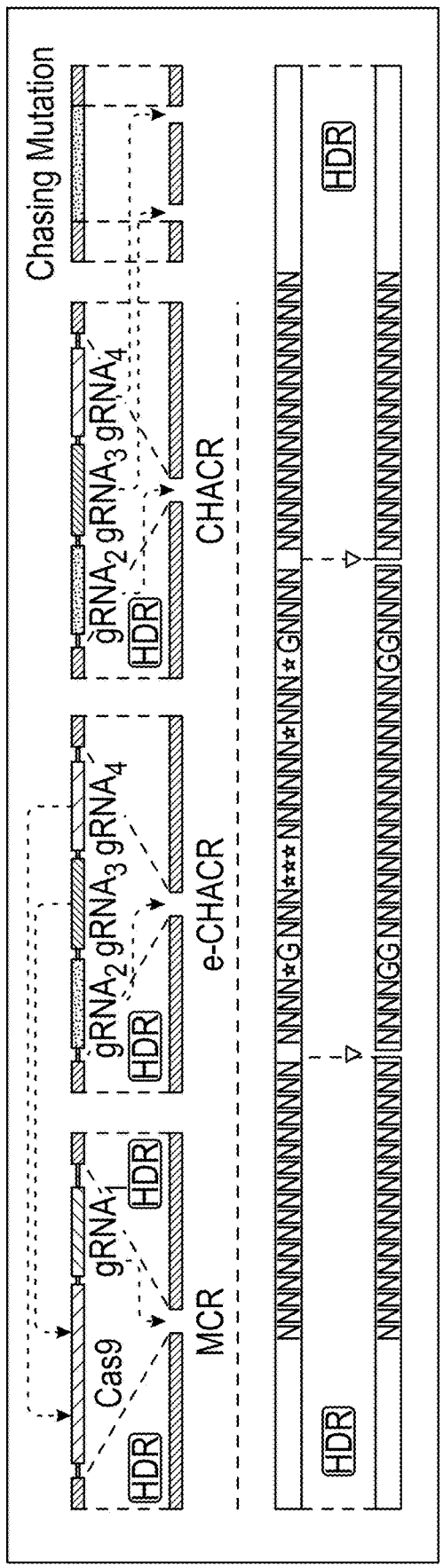
FIG. 28C
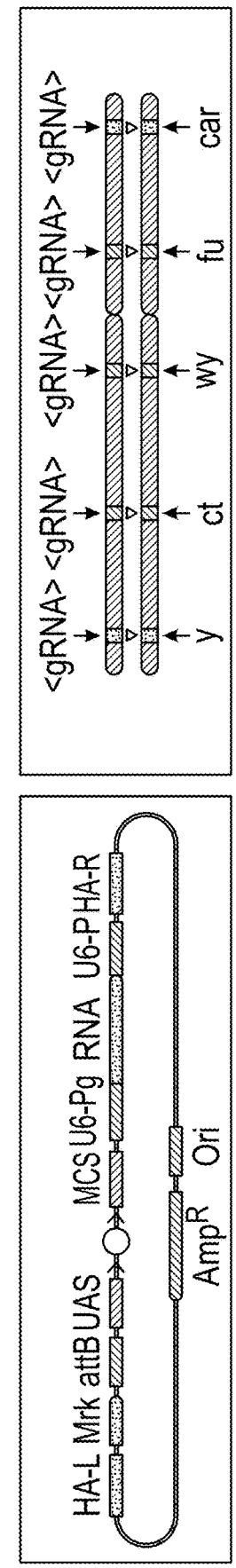
FIG. 28E
FIG. 28D

CopyCat (CC) Elements:
gRNAs Flanked by Homology arms, Denoted <gRNA>

CC Elements Copied or "cc-ed"
in the Presence of a Transacting Source of Cas9

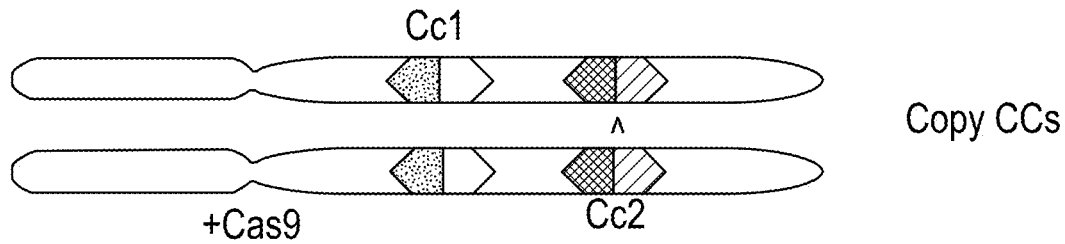

FIG. 32

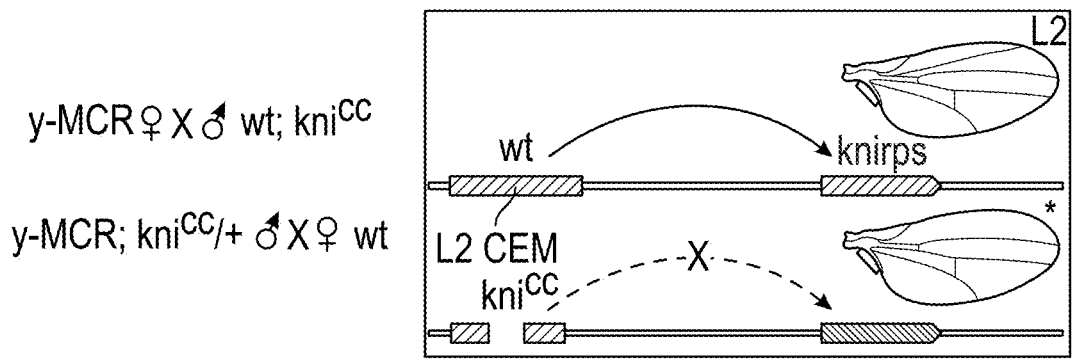

9 Individual Crosses -> 270 ♀ Progeny:

268 ♀ Progeny y-Pigmentation: 99.3% y-MCR

4 Crosses (128 ♀ Progeny): 100% kni$^{CC}$ | 70% of DsRed Marked kni$^{CC}$ Display
3 Crosses (82 ♀ Progeny): 89% kni$^{CC}$ | Mutant Vein Phenototype.
2 Crosses (60 ♀ Progeny): 50% kni$^{CC}$

Conclusion: Germline and Somatic kni$^{CC}$ Activities are separable events.

FIG. 33

Omel Kxx locus 36kb pVG165_pCPD4-DGPP-AB-Pump

Sequence: TETHR Open Reading Frame.dna (Linear / 4035 bp)
Features: 10 Visible, 12 Total

```
5' ATGGACTATAAGGACCACGACGGAGACTACAAGGATCATGATATTGATTACAAAGACGATGACGA
3' TACCTGATATTCCTGGTGCTGCCTCTGATGTTCCTAGTACTATAACTAATGTTTCTGCTACTGCT
    D  Y  K  D  H  D  G  D  Y  K  D  H  D  I  D  Y  K  D  D  D
                        5              10              15             20
                                    3xFLAG
```

```
TAAGgaGCCCCCAAAGAAGAAGCGGAAGGTCGGGGGTCAGGCGGAACAGAGAATTACAC
ATTCcctCGGGGGTTTCTTCTTCGCCTTCCAGCCCCCAGTCCGCTTGTCTCTTAATGTG
  K  G  A  P  K  K  K  R  K  V  G  G  G  S  G  E  Q  R  I  T
                      130                                  S
              3xFLAG    SV40 NLS      (In Frame with SV40 NLS) CRO First Repeat
```

```
TCAAGGACTATGCCATGAGaTTCGGGCAAACTAAAAACAGCAAAAGACTtgGGTGTTTACCAAtcc
AgTTCCTGATACGGTACTCtAAGCCCGTTTGATTTTGTCGTTTTCTGaaCCCACAAATGGTTagg
  L  K  D  Y  A  M  R  F  G  Q  T  K  T  A  K  D  L  G  V  Y  Q  S
                    10              15              20           25
                              CRO First Repeat
```

```
AGGTGGAAGAGGACAACCGGCAACGAGAGCTGTGTCCACCAAAGAGCAGATCAGCCGGAACAGCAAGGCC
    ----+----|----+----|----+----|----+----|----+----|----+----|----+----|
                                                                      1170
TCCACCTTCTCCTGTTGGCCGTTGCTCGTCGACAGGTGGTTTCTCGTCTAGTCGGCCTTGTCGTTCCGG
   E  V  E  E  D  T  G  N  E  L  S  T  K  E  Q  I  S  R  N  S  K  A
       125           130           135           140
   ////////////////////////////////////////////////////////////////>
                               SaCas9

CTGGAAGAGAAATACGTGGCCGAACTGCAGCTGAGCGTTGACGTTGAGCTTGAAGAAAAGACGGCTGAAGTGCGGGGG
    ----+----|----+----|----+----|----+----|----+----|----+----|----+----|
                                                                      1235
GACCTTCTCTTTATGCACCGGCTTGACGTCGACTCGCAACTGCAAGCTTCTTTTCTGCCGACTTCACGCCCC
   L  E  K  Y  V  A  E  L  Q  L  E  R  L  K  K  D  G  E  V  R  G
     145           150           155           160           165
   ////////////////////////////////////////////////////////////////>
                               SaCas9

CAGCATCAACAGATTCAAGACCAGCGACTACGTGAAGGAAGCCAAACAGCTGCTGAAGGTGCAGA
    ----+----|----+----|----+----|----+----|----+----|----+----|----+----|
                                                                      1300
GTCGTAGTTGTCTAAGTTCTGGTCGCTGATGCACTTCCTTCGGTTTGTCGACGACTTCCACGTCT
   S  I  N  R  F  K  T  S  D  Y  V  K  E  A  K  Q  L  L  K  V  Q
         170           175           180           185
   ////////////////////////////////////////////////////////////////>
                               SaCas9
```

```
CCGACCCTGTACAACGCCCTGAACGACCTGAACAATCTCGTGATCACCAGGGACGAGAACGAGAAG      1560
GGCTGGGACATGTTGCGGGACTTGCTGGACTTGTTAGAGCACTAGTGGTCCCTGCTCTTGCTCTTC
       A  D  L  Y  N  A  L  N  D  L  N  N  L  V  I  T  R  D  E  N  E  K
              255            260            265            270
```

SaCas9

```
CTGGAATATTACGAGAAGTTCCAGATCATCGAGAACGTGTTCAAGCAGAAGAAGCCCACCCT          1625
GACCTTATAATGCTCTTCAAGGTCTAGTAGCTCTTGCACAAGTTCGTCTTCTTCGGGTGGGA
    L  E  Y  Y  E  K  F  Q  I  I  E  N  V  F  K  Q  K  K  K  P  T  L
       275            280            285            290        295
```

SaCas9

```
GAAGGTGGACCTGTCTCAGCAGAGAAGAGATCCCCACCACCCTGGTGTGGACGACTTCATCCTGAGCC    2080
CTTCCACCTGGACAGAGTCGTCTCTTCTTCTAGGGGTGGTGGGACCACCTGCTGAAGTAGGACTCGG
          K  V  D  L  S  Q  Q  K  E  I  P  T  T  L  V  D  D  F  I  L  S
              430              435              440              445
                                    SaCas9

CCGTCGTGAAGAGAAGCTTCATCCAGAGCATCAAAGTGATCAACGCCATCATCAAGAAGTACGGC    2145
GGCAGCACTTCTCTTCGAAGTAGGTCTCGTAGTTTCACTAGTTGCGGTAGTAGTTCTTCATGCCG
        P  V  V  K  R  S  F  I  Q  S  I  K  V  I  N  A  I  I  K  K  Y  G
            450              455              460              465
                                    SaCas9
```

```
AGCTACGAAACCTTCAAGAAGCACATCCTGAATCTGGCCAAGGGCAGAATCAGCAAGAC
                                                         2600
TTCTTcgGTCGTTCTTCGTGTAGGACTTAGACCGGTTCCCGTCGTAGTCGTTCTGTTCTAG
              605                 610               615       620
 S  Y  E  T  F  K  K  H  I  L  N  L  A  K  G  R  I  S  K  T
```

SaCas9

```
CAAGAAAAGATATCTGCTGGAAGAACGGGAACATCAACAGGTTCTCCGTGCAGAAAGACTTCATCA
                                                                2665
GTTCTTTTCTATAGACGACCTTCTTGCCCTTGTAGTTGTCCAAGAGGCACGTCTTTCTGAAGTAGT
              625                 630               635        640
 K  K  E  Y  L  L  E  E  R  D  I  N  R  F  S  V  Q  K  D  F  K
```

SaCas9

FIG. 38E
(Continued)

```
ACCGGAACCTGGTGGATACCAGATACGCCACCAGAGGCCTGATGAAGCTGCTGCGGAGCTACTTC
         |         |         |         |         |         |
TGGCCTTGGACCACCTATGGTCTATGCGGTGGTCTCCGGACTACTTCGACGACGCCTCGATGAAG  2730
                                                          |
        645         650         655         660
         N  R  N  L  V  D  T  R  Y  A  T  R  G  L  N  K  L  L  R  S  Y  F  >
                              SaCas9

AGAGTGAACAACCTGAAGCTGAAAGTCCATCAATGGGCGCTTCACCAGCTTTTCTGCGGGCG
         |         |         |         |         |         |
TCTCACTTGTTGGACTTCGACTTTCAGGTAGTTACCCGCGAAGTGGTCGAAAGACGCCCGC   2795
                                                             |
        665         670         675         680         685
         R  V  N  K  L  D  V  K  V  K  S  I  N  G  G  F  T  S  F  L  R  >
                              SaCas9

GAAGTGGAAGTTTAAGAAAAGAGCGGAACAAGGGTACAAGCACCACGCGCCGAGGACGCCCTGATCA
         |         |         |         |         |         |
GTTCACCTTCAAATTCTTTTCTCGCCTTGTTCCCCATGTTCGTGGTGCGCGGCTCCTGCGGGACTAGT  2860
                                                                |
        690         695         700         705
         K  W  K  F  K  K  E  R  N  K  G  Y  K  N  N  A  E  D  A  L  I  >
                              SaCas9

```
ACCGGGTGTGGACAAGAAGCCTAATAGAGAGCTGATTAACGACACCCTGTACTCCACCCGGAAGGAC   3120
     ---+---------+---------+---------+---------+---------+---------+
TGGCCCACCTGTTCTTCGGATTATCTCTCGACTAATTGCTGTGGGACATGAGGTGGGCCTTCCTG
                775          780          785          790
     N  R  V  D  K  K  P  N  R  E  L  I  N  D  T  L  Y  S  T  K  K  D
                                                                       >
                              SaCas9

GACAAGGGCAACACCCTGATCGTGAACAATCTGAACGGCCTGTACGACAAGGACAATGACAAGCT   3185
     ---+---------+---------+---------+---------+---------+---------+
CTGTTCCCGTTGTGGGACTAGCACTTCTTAGACTTGCCGGACATGCTGTTCCTGTTACTGTTCGA
          795          800          805          810          815
     D  K  G  N  T  L  I  V  N  N  L  I  G  L  Y  D  K  D  N  D  K  L
                                                                       >
                              SaCas9
```

```
GTATTACGGCAACAAACTGAACGCCCATCTGGACATCACCGACGACTACCCCAACAGCAGAAAACA
          |         |         |         |         |         |
CATAATGCCGTTGTTTGACTTGCGGGTAGACCTGTAGTGGCTGCTGATGGGGTTGTCGTCTTTGT
                                                        3445
 Y  G  N  K  L  N  A  H  L  D  I  T  D  D  Y  P  N  S  R  N
          885                 890                 895                 900
```

SaCas9

```
AGGTCGTGAAGCTGTCCCTGAAGCCCTACAGATTCGACGTGTACCTGGACAATGGGGTGTACAAG
          |         |         |         |         |         |
TCCAGCACTTCGACAGGGACTTCGGGATGTCTAAGCTGCACATGGACCTGTTACCGCACATGTTC
                                                        3510
 K  V  V  K  L  S  L  K  P  Y  R  F  D  V  Y  L  D  N  G  V  Y  K
          905                 910                 915                 920
```

SaCas9

```
TTCGTTGACCGTGAAGAATCTGGATGTGATCAAAAAGAAAAACTACTACGAAGTGAATAGCAAGTG
          |         |         |         |         |         |
AAGCACTGGCACTTCTTAGACCTACACTAGTTTTTTCTTTTTGATGCTTCACTTATCGTTCAC
                                                        3575
 F  V  T  V  K  N  L  D  V  I  K  K  E  N  Y  Y  E  V  N  S  K  C
 925                 930                 935                 940                 945
```

SaCas9

METHODS FOR AUTOCATALYTIC GENOME EDITING AND NEUTRALIZING AUTOCATALYTIC GENOME EDITING AND COMPOSITIONS THEREOF

CROSS REFERENCE TO RELATED APPLICATIONS

This application claims the priority benefit of PCT/US2016/052424 filed on Sep. 19, 2016, which claims the benefit of U.S. Provisional Application No. 62/220,630, filed Sep. 18, 2015; U.S. Provisional Application No. 62/221,298, filed Sep. 21, 2015; U.S. Provisional Application No. 62/221,309, filed Sep. 21, 2015; U.S. Provisional Application No. 62/256,479, filed Nov. 17, 2015; and U.S. Provisional Application No. 62/266,022, filed Dec. 11, 2015; which applications are incorporated herein by reference.

STATEMENT AS TO FEDERALLY SPONSORED RESEARCH

This invention was made with government support under NS029870, AI070654, GM117321, and AI131081 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 16, 2020, is named 24978-0384_SL.txt and is 54,811 bytes in size.

BACKGROUND

CRISPRs (clustered regularly interspaced short palindromic repeats) are DNA loci containing short repetitions of base sequences. Each repetition is followed by short segments of "spacer DNA" from previous exposures to a virus. CRISPRs are found in approximately 40% of sequenced bacteria genomes and 90% of sequenced archaea. CRISPRs are often associated with Cas genes that code for proteins related to CRISPRs. The CRISPR/Cas system is a prokaryotic immune system that confers resistance to foreign genetic elements such as plasmids and phages and provides a form of acquired immunity. CRISPR spacers recognize exogenous genetic elements and the Cas protein cuts them in a manner analogous to RNAi in eukaryotic organisms. Improved methods and compositions for use in eukaryotic cells and organisms are needed for improved genomic engineering technologies.

A problem currently faced by many CRISPR/Cas systems is the residual presence of Cas proteins in the target cells. Here, the disclosure provides, among other things, methods and compositions for erasing exogenous Cas from genetically modified immune cells such that use of these cells in clinical applications is more readily apparent.

Such a CRISPR/Cas system is useful for genetic engineering applications, such as genetically engineering immune cells to express a CAR and/or a TCR to recognize and bind to the target antigen expressed by and/or bound to a target cell. Because genetically engineered immune cells must be activated, proliferative and able to survive in order to eliminate a subject's disease through activation of pathways triggered by CAR and/or TCR, additional polynucleotides are often useful in combination with CAR and/or TCR-based therapies, such a negative regulatory molecule, a cytokine, and/or a cytokine receptor or the like. In addition, should the subject's disease relapse following treatment, the genetically engineered immune cells must be enabled to elicit a memory response in order to treat the relapsed disease. An important concern arising from CAR and/or TCR-based immune cell therapies is that the genetically engineered cells often cause unwanted side effects in a patient, for example, triggering an autoimmune response.

There is a clear need to generate immune cells having such therapeutic applications without extensive manipulation prior to administration to a subject in need. Reducing the number of different transductions and/or transfections, the number of ex vivo rounds of cell division, different types of selective pressure and the like increases the likelihood genetically engineered cells behave as intended in the subject. In addition, a means for silencing or eliminating CAR and/or TCR expressing immune cells following completion of therapeutic goals is needed so as to prevent off-target effects of genetically engineered immune cells, such as autoimmune effects.

The present disclosure addresses such problems by combining the novel gene transfer mechanism of CRISPR/Cas system described further herein to deliver large amounts of DNA in a biallelic manner, such that immune cells are genetically modified for antigen recognition by a CAR or TCR, with the option that immune cell behavior is regulated, for example by expression of cytokines, cytokine receptors, or the like and/or signaling by negative regulatory pathways is reduced, for example, by disruption of endogenous gene loci involved in negative regulatory pathways and/or expression of modified negative regulatory molecules. In addition, the present disclosure provides for safety mechanisms to control the behavior of genetically modified immune cells, for example, regulated expression systems, expression of suicide genes, disruption of genes involved in cell survival and the like.

Genome engineering tools available in *Drosophila* are among the most advanced in organisms. Yet, even with these powerful tools in hand it remains a challenge to replace large contiguous segments of the genome, for example, 100-200 kb with corresponding sequences from other organisms using existing technology.

Existing transgenesis vectors either insert randomly into the genome, for example, piggyback transposons, or into a small set of defined recombination docking sites (e.g., the Φ31C (phi31C) system). Transgenic individuals are then recovered as heterozygotes and experimenters must go through an additional two generations to obtain homozygotes. As a result, these manipulations require multiple steps and are laborious in the fruit fly, and are currently prohibitive in other non-model organisms. Further, it would be close to impossible to do this on a much larger scale, for example, with hundreds of loci that would be required for creating genetically chimeric organisms.

Active genetic systems, which can convert sister chromosomes in a single step, are therefore likely to play a prominent role in accelerating such large-scale genome restructuring. The current disclosure provides methods and compositions to address challenges associated with large-scale genome engineering.

Gene-drives are genetic elements that can be passed on to more than 50% of the progeny of individuals that carry such elements.

SUMMARY

The present disclosure discloses methods and compositions for selectively introducing or neutralizing the exponential spread of Mutagenic Chain Reaction (MCR) elements from organisms carrying them that do not affect organisms lacking such elements.

MCR for autocatalytic genome editing is based on genomic integration of an MCR construct containing multiple elements. The MCR disclosure either: a) injects the MCR construct as a DNA plasmid into the germline of an organism and obtains transgenic organisms carrying this insertion on one copy of a chromosome from which it often spreads to the other chromosome (creating potential homozygous mutations) as well as propagating the same mutation via the germline to most of its offspring, or b) introduces the MCR construct into somatic cells in an organism (e.g., using a plasmid or viral expression vector) such that the construct spreads to other cells within that organism. Therefore, the MCR provides an autocatalytic method to generate homozygous mutations that propagate with high fidelity via the germline to most of the progeny which become homozygous for the mutation. At an early stage, MCR elements can constitute a form of gene-drive.

In another embodiment, the present disclosure also provides for selective deletion and neutralization of MCR elements, in a system referred to as the Neutralizing Chain Reaction (NCR). NCR elements are often comprised of a number of elements whereby to inject the construct as a DNA plasmid together with a plasmid source of Cas9 protein into the germline of an organism and obtain transgenic organisms carrying this insertion. Organisms carrying this construct would then be crossed to MCR individuals (or released into an environment containing MCR individuals) whereupon NCR would act on the MCR chromosome to delete the MCR element and could also restore function of the host locus via a recoded transgene. Alternatively, in another embodiment, an active genetic element (e.g., MCR=a form of a gene-drive element, or CopyCat=CHACR element) inserted at another chromosomal location could produce guide RNAs (gRNAs) that target cleavage of the Cas9 gene at nucleotides encoding amino acid residues critical for Cas9 catalytic activity. Such elements, referred to as e-CHACRs could also be used in combination with NCR elements to increase the neutralization of MCR elements.

The present disclosure is based on a well-known bacterial immunity function known as the CRISPR/Cas9 system that is based on two elements. The first element, Cas9, is an endonuclease that has a binding site for the second element, which is the guide polynucleotide (e.g., guide RNA). The guide polynucleotide (e.g., guide RNA) directs the Cas9 protein to double stranded DNA templates (e.g., a bacteriophage integrated into the bacterial chromosome) based on sequence homology. The Cas9 protein then cleaves that template leading to secondary mutations during DNA repair. The CRISPR/Cas system has been used for gene editing (e.g., adding, disrupting or changing the sequence of specific genes) and gene regulation in many species. By delivering the Cas9 protein and appropriate guide polynucleotides (e.g., guide RNAs) into a cell, the organism's genome is often cut at a desired location. This system has recently been found to be adaptable to many organisms including mammalian cells, fruit flies, and plants. The broad adaptability of this system has led to significant strides in refining this system and the generation of many applications. The present disclosure is often applied to animal cells, mammalian cells, non-human primate cells and human cells, for example.

In other embodiments, the present disclosure describes a cellular composition for administration to a subject in need thereof, the cellular composition comprising, a plurality of genetically modified immune cells, the plurality of genetically modified immune cells genetically modified to express an engineered polypeptide, wherein the genetic modification comprises, transducing a plurality of immune cells with a first vector, the first vector encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a first target genomic sequence in the plurality of immune cells; and, transducing the plurality of immune cells with a second vector, the second vector encoding a TAT-tagged Cas9 protein, wherein the first guide ribonucleic acid directs the TAT-tagged Cas9 protein to cleave the first target genomic sequence in the plurality of immune cells.

In some embodiments, the present disclosure describes a cellular composition for administration to a subject in need thereof, the cellular composition comprising, a plurality of genetically modified immune cells, the plurality of genetically modified immune cells genetically modified to express an engineered polypeptide, wherein the genetic modification comprises, transfecting a plurality of immune cells with a first plasmid, the first plasmid encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and delivering a TAT-tagged Cas9 protein, wherein the first guide ribonucleic acid directs the TAT-tagged Cas9 protein to cleave the target genomic sequence in the plurality of immune cells, to the plurality of immune cells.

In other embodiments, the present disclosure describes a cellular composition for administration to a subject in need thereof, the cellular composition comprising, a plurality of genetically modified immune cells, the plurality of genetically modified immune cells genetically modified to express an engineered polypeptide, wherein the genetic modification comprises, transducing a plurality of immune cells with a first vector, the first vector encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a first target genomic sequence in the plurality of immune cells; and, delivering a TAT-tagged Cas9 protein, wherein the first guide ribonucleic acid directs the TAT-tagged Cas9 protein to cleave the target genomic sequence in the plurality of immune cells, to the plurality of immune cells.

In some embodiments, the present disclosure describes a method of preparing a cellular composition of genetically modified immune cells genetically modified to express an engineered polypeptide for administration to a subject in need thereof, the method of preparing the cellular composition of genetically modified immune cells comprising, transfecting a plurality of immune cells with a first plasmid, the first plasmid encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and transfecting the plurality of immune cells with a second plasmid, the second plasmid encoding a TAT-tagged Cas9 protein, wherein the first guide ribonucleic acid directs the TAT-tagged Cas9 protein to cleave the target genomic sequence in the plurality of immune cells.

In other embodiments, the present disclosure describes a method of preparing a cellular composition of genetically modified immune cells genetically modified to express an engineered polypeptide for administration to a subject in need thereof, the method of preparing the cellular composition of genetically modified immune cells comprising, transducing a plurality of immune cells with a first vector, the first vector encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and transducing the plurality of immune cells with a second vector, the second vector encoding a TAT-tagged Cas9 protein, wherein the first guide ribonucleic acid directs the TAT-tagged Cas9 protein to cleave the target genomic sequence in the plurality of immune cells.

In some embodiments, the present disclosure describes a method of preparing a cellular composition of genetically modified immune cells genetically modified to express an engineered polypeptide for administration to a subject in need thereof, the method of preparing the cellular composition of genetically modified immune cells comprising, transfecting a plurality of immune cells with a first plasmid, the first plasmid encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and delivering a TAT-tagged Cas9 protein, wherein the first guide ribonucleic acid directs the TAT-tagged Cas9 protein to cleave the target genomic sequence in the plurality of immune cells, to the plurality of immune cells.

In other embodiments, the present disclosure describes a method of preparing a cellular composition of genetically modified immune cells genetically modified to express an engineered polypeptide for administration to a subject in need thereof, the method of preparing the cellular composition of genetically modified immune cells comprising, transducing a plurality of immune cells with a first vector, the first vector encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and, delivering a TAT-tagged Cas9 protein, wherein the first guide ribonucleic acid directs the TAT-tagged Cas9 protein to cleave the target genomic sequence in the plurality of immune cells, to the plurality of immune cells.

In some embodiments, the present disclosure describes a method of neutralizing a mutagenic chain reaction (MCR) element in a cell, the method comprising genomically integrating a neutralizing chain reaction (NCR) element from an NCR construct into the cell, wherein the MCR element comprises, at least one sequence encoding at least one guide polynucleotide, wherein the at least one sequence encoding at least one guide polynucleotide is genomically integrated in the cell; and a gene encoding an endonuclease; the NCR element comprises, at least one sequence encoding at least one guide polynucleotide directing cleavage within or on both sides of the MCR element; and at least one sequence encoding at least two guide polynucleotides directing cleavage within or outside of the MCR element or no gene encoding an endonuclease; and the NCR construct comprises, the NCR element; and homology arms flanking the at least one guide polynucleotide that directly abut the endonuclease cut site(s) determined by the at least one guide polynucleotide. In some embodiments, the guide polynucleotides are guide RNAs, and wherein the cell comprises an endonuclease or a gene encoding an endonuclease; and wherein an expression cassette encoding a chimeric antigen receptor (CAR) is genomically integrated in a cell.

In other embodiments, the NCR construct does not comprise a gene encoding an endonuclease. In some embodiments, the NCR element does not comprise a gene encoding an endonuclease. In some embodiments, the at least one sequence encoding at least one guide polynucleotide in the NCR element comprises a different sequence than the at least one sequence encoding at least one guide polynucleotide in the MCR element. In some embodiments, the at least one sequence encoding at least one guide polynucleotide in the NCR element directs cleavage within the MCR element. In some embodiments, the at least one sequence encoding at least one guide polynucleotide in the NCR element directs cleavage within the gene encoding the endonuclease. In some embodiments, the at least one sequence encoding at least one guide polynucleotide in the NCR element directs cleavage within the at least one sequence encoding at least one guide polynucleotide in the MCR element. In some embodiments, the at least one sequence encoding at least one guide polynucleotide in the NCR element directs cleavage on both sides of the MCR element. In some embodiments, the at least one sequence encoding at least one guide polynucleotide in the NCR element directs cleavage on both sides of the gene encoding the endonuclease. In some embodiments, the at least one sequence encoding at least one guide polynucleotide in the NCR element directs cleavage on both sides of the at least one sequence encoding at least one guide polynucleotide in the MCR element, and wherein the cell comprises an endonuclease or a gene encoding an endonuclease; and wherein an expression cassette encoding a chimeric antigen receptor (CAR) is genomically integrated in a cell.

In some embodiments, the present disclosure describes a construct for neutralizing autocatalytic genome editing, the construct comprising, at least one sequence encoding at least one guide polynucleotide directing cleavage within or on both sides of the MCR element, homology arms flanking the at least one guide polynucleotide that directly abut the endonuclease cut site(s) determined by the at least one guide polynucleotide; and at least one sequence encoding at least two guide polynucleotides directing cleavage within or outside of the MCR element or no gene encoding an endonuclease, wherein the MCR element comprises, at least one sequence encoding at least one guide polynucleotide, wherein the at least one sequence encoding at least one guide polynucleotide is genomically integrated in a cell; and a gene encoding an endonuclease, and wherein the cell comprises an endonuclease or a gene encoding an endonuclease; and wherein an expression cassette encoding a chimeric antigen receptor (CAR) is genomically integrated in a cell.

In some embodiments, the present disclosure describes a method of genomically integrating a neutralizing chain reaction (NCR) element into a cell, the method comprising, introducing into the cell an NCR construct comprising, at least one sequence encoding at least one guide polynucleotide directing cleavage within or on both sides of an MCR element, homology arms flanking the at least one guide polynucleotide that directly abut the endonuclease cut site(s) determined by the at least one guide polynucleotide; and at least one sequence encoding at least two guide polynucleotides directing cleavage within or outside of the MCR element or no gene encoding an endonuclease; and genomically integrating an NCR element comprising, at least one sequence encoding at least one guide polynucleotide directing cleavage within or on both sides of the MCR element; and at least one sequence encoding at least two guide polynucleotides directing cleavage within or outside of the MCR element or no gene encoding an endonuclease, wherein the MCR element comprises, at least one sequence encoding at least one guide polynucleotide; and a gene encoding an endonuclease; and wherein the cell comprises an endonuclease or a gene encoding an endonuclease. In some embodiments, the guide polynucleotides are guide RNAs, and wherein the cell comprises an endonuclease or a gene encoding an endonuclease; and wherein an expression cassette encoding a chimeric antigen receptor (CAR) is genomically integrated in a cell.

In some embodiments, the present disclosure describes a construct for autocatalytic genome editing, the construct comprising a gene encoding an endonuclease, at least one sequence encoding at least one guide polynucleotide, an effector cassette, and homology arms flanking the gene, the at least one sequence, and the cassette, wherein the homology arms directly abut the endonuclease cut site(s) determined by the at least one guide polynucleotide. In some embodiments, the guide polynucleotides are guide RNAs, and wherein the cell comprises an endonuclease or a gene encoding an endonuclease; and wherein an expression cassette encoding a chimeric antigen receptor (CAR) is genomically integrated in a cell.

In some embodiments, the present disclosure describes a construct for neutralizing autocatalytic genome editing, the construct comprising, at least one guide polynucleotide directing cleavage within or outside of the MCR element and no gene encoding an endonuclease; or at least two guide polynucleotides directing cleavage within or outside of the MCR element; homology arms flanking the at least two guide polynucleotides that directly abut the endonuclease cut sites determined by the guide polynucleotides; and an expression cassette encoding a chimeric antigen receptor (CAR), a T cell receptor (TCR) or a negative regulatory molecule.

In other embodiments, the present disclosure describes a method for autocatalytic genome editing, the method comprising genomically integrating a construct comprising, a gene encoding an endonuclease, a sequence encoding one or more guide polynucleotides, an effector cassette encoding a chimeric antigen receptor (CAR), a T cell receptor (TCR) or a negative regulatory molecule, and homology arms flanking the gene, the sequence, and the cassette that target insertion of the gene, the sequence, and the cassette into the genome at the site determined by the sequence flanking the one or more guide polynucleotides.

In some embodiments, the present disclosure describes a construct for autocatalytic genome editing, the construct comprising a gene encoding an endonuclease, a sequence encoding one or more guide polynucleotides, an effector cassette encoding a chimeric antigen receptor (CAR), a T cell receptor (TCR) or a negative regulatory molecule, and homology arms flanking the gene, the sequence, and the cassette that target insertion of the gene, the sequence, and the cassette into the genome at the site determined by the sequence flanking the one or more guide polynucleotides.

The present disclosure discloses methods and compositions for inserting a nucleic acid cargo sequence into a nucleic acid target sequence using a bivalent nucleic acid binding protein.

One aspect of the disclosure provides a method for inserting a nucleic acid cargo sequence into a nucleic acid target sequence, the method comprising:
  forming a nucleoprotein complex comprising the nucleic acid cargo sequence, the nucleic acid target sequence, and a bivalent nucleic acid binding protein, wherein the bivalent nucleic acid binding protein comprises a first and a second nucleic acid binding domain;
  cleaving the target nucleic acid sequence; and
  inserting the nucleic acid cargo sequence into the nucleic acid target sequence.

One aspect of the disclosure provides a method for forming a nucleoprotein complex, the method comprising:
  binding a bivalent nucleic acid binding protein to a donor cargo vector comprising a nucleic acid cargo sequence; and
  binding the bivalent nucleic acid binding protein to a nucleic acid target sequence, wherein the bivalent nucleic acid binding protein comprises a first and a second nucleic acid binding domain.

One aspect of the disclosure provides a bivalent nucleic acid binding protein, comprising:
  a first nucleic acid binding domain;
  a second nucleic acid binding domain; and
  a nuclear localization signal.

One aspect of the disclosure provides a nucleoprotein complex, comprising:
  a bivalent nucleic acid binding protein;
  a donor cargo vector comprising a nucleic acid cargo sequence; and
  a nucleic acid target sequence;
  wherein the bivalent nucleic acid binding protein binds to the donor cargo vector and the nucleic acid target sequence.

One aspect of the disclosure provides an oligonucleotide with complementarity to both the genomic region to be targeted for HDR and to sequences carried on a donor cargo vector such that it should serve as a bridging element. Some portion of the nucleotides in this "Oligo-Clamp" could be locked nucleotides that have a higher melting temperature in double stranded nucleic acid hybrids than standard nucleotides (see FIGS. 39-41). In some cases, the melting temperature is higher by about or at least about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, or 20° C.

One aspect of the disclosure provides a method for inserting a nucleic acid cargo sequence into a nucleic acid target sequence, the method comprising: forming a nucleic acid complex comprising the nucleic acid cargo sequence, the nucleic acid target sequence, a first nucleic acid probe, and a second nucleic acid probe; cleaving the target nucleic acid sequence; and inserting the nucleic acid cargo sequence into the nucleic acid target sequence. In some cases, the nucleic acid complex is formed intracellularly. In some cases, the nucleic acid complex is formed in vitro. In some cases, the method further comprises forming a pre-complex comprising the nucleic acid cargo sequence, the first nucleic acid probe, and the second nucleic acid probe. In some cases, the first and second nucleic acid probes bind to the donor cargo vector. In some cases, the first and second nucleic acid probes bind to the donor cargo vector and the nucleic acid target sequence. In some cases, the first and second nucleic acid probes are RNA or LNA. In some cases, the first and second nucleic acid probes are single stranded. In some cases, the first and second nucleic acid probes bind to the nucleic acid target sequence and/or to the donor cargo vector. In some cases, the first and second nucleic acid probes are specific for different sequences. In some cases, the first and second nucleic acid probes bind to the donor cargo vector with a first binding domain and bind to the nucleic acid target sequence with a second binding domain. In some cases, the first and second binding domains of the first and second nucleic acid probes are different. In some cases, the first and second binding domains of the first and second nucleic acid probes are about or at least about 10, 15, 20, 25, 30, 35, 40, 45, 50, 100, 500, or 1000 nucleotides in length. In some cases, the method further comprises transfecting the nucleic acid cargo sequence, donor cargo vector, first nucleic acid probe, and/or second nucleic acid probe into a cell.

In some embodiments of any method or nucleoprotein complex described herein, the nucleoprotein complex is formed intracellularly. In some embodiments of any method or nucleoprotein complex described herein, the nucleoprotein complex is formed in vitro. In some embodiments of any method described herein, the method further comprises forming a pre-complex comprising the nucleic acid cargo sequence and the bivalent nucleic acid binding protein. In some embodiments of any method described herein, the method further comprises providing a nuclease. In some embodiments of any method described herein, the method further comprises expressing a nuclease. In some embodiments of any method described herein, the nuclease is expressed off a plasmid or a chromosome. In some embodiments of any method described herein, the cleaving the target nucleic acid is accomplished using a nuclease. In some embodiments of any method described herein, the endonuclease is an RNA-guided endonuclease. In some embodiments of any method described herein, the method further comprises providing a guide polynucleotide (e.g., guide RNA). In some embodiments of any method described herein, the endonuclease is a Cas protein. In some embodiments of any method described herein, the endonuclease is Cas9 or Cpf1. In some embodiments of any method described herein, the inserting the nucleic acid cargo sequence into the nucleic acid target sequence occurs by homology directed repair. In some embodiments of any method described herein, the inserting the nucleic acid cargo sequence into the nucleic acid target sequence occurs with an efficiency of at least 25%, at least 50%, at least 75%, at least 80%, at least 85%, at least 90%, at least 95%, at least 96%, at least 97%, at least 98%, at least 99%, at least 99.5%, or at least 99.9%. In some embodiments of any method described herein, the method further comprises transfecting the nucleic acid cargo sequence, donor cargo vector, and/or bivalent nucleic acid binding protein into a cell. In some embodiments of any method described herein, the cell is derived from an animal, human, microorganism, insect, plant, or any combination thereof. In some embodiments of any method described herein, the cell is derived from a model organism. In some embodiments of any method described herein, the cell is from a prokaryote, eukaryote, protist, fungus, invertebrate animal, vertebrate animal, microorganism, pathogen, agriculture pest, or any combination thereof.

In some embodiments of any method, bivalent nucleic acid binding protein, or nucleoprotein complex described herein, the nucleic acid cargo sequence is DNA. In some embodiments of any method, bivalent nucleic acid binding protein, or nucleoprotein complex described herein, the nucleic acid cargo sequence is at least 5, 10, 17, or 50 kb in length. In some embodiments of any method, bivalent nucleic acid binding protein, or nucleoprotein complex described herein, the nucleic acid cargo sequence is located on a donor cargo vector.

In some embodiments of any method, bivalent nucleic acid binding protein, or nucleoprotein complex described herein, the bivalent nucleic acid binding protein binds to the donor cargo vector. In some embodiments of any method, bivalent nucleic acid binding protein, or nucleoprotein complex described herein, the bivalent nucleic acid binding protein binds to the donor cargo vector and the nucleic acid target sequence. In some embodiments of any method, bivalent nucleic acid binding protein, or nucleoprotein complex described herein, the donor cargo vector is a plasmid. In some embodiments of any method, bivalent nucleic acid binding protein, or nucleoprotein complex described herein, the donor cargo vector comprises homology arms that flank the nucleic acid cargo sequence and that are homologous to sequences in the nucleic acid target sequence. In some embodiments of any method, bivalent nucleic acid binding protein, or nucleoprotein complex described herein, the homology arms directly abut a cleavage site in the nucleic acid target sequence. In some embodiments of any method, bivalent nucleic acid binding protein, or nucleoprotein complex described herein, the homology arms are at least 50, 100, 500, 1000, 1100, 1200, 1300, 1400, or 1500 nucleotides in length.

In some embodiments of any method, bivalent nucleic acid binding protein, or nucleoprotein complex described herein, the nucleic acid target sequence is DNA (e.g., genomic DNA, chromosomal DNA, or mitochondrial DNA).

In some embodiments of any method, bivalent nucleic acid binding protein, or nucleoprotein complex described herein, the bivalent nucleic acid binding protein binds to the nucleic acid target sequence. In some embodiments of any method, bivalent nucleic acid binding protein, or nucleoprotein complex described herein, the bivalent nucleic acid binding protein is a single polypeptide. In some embodiments of any method, bivalent nucleic acid binding protein, or nucleoprotein complex described herein, the bivalent nucleic acid binding protein further comprises a nuclear localization signal.

In some embodiments of any method, bivalent nucleic acid binding protein, or nucleoprotein complex described herein, the nucleic acid binding domain is a DNA binding domain. In some embodiments of any method, bivalent nucleic acid binding protein, or nucleoprotein complex described herein, the DNA binding domain binds to double-stranded DNA. In some embodiments of any method, bivalent nucleic acid binding protein, or nucleoprotein complex described herein, the DNA binding domain is sequence specific. In some embodiments of any method, bivalent nucleic acid binding protein, or nucleoprotein complex described herein, the first and second nucleic acid binding domains are specific for different sequences. In some embodiments of any method, bivalent nucleic acid binding protein, or nucleoprotein complex described herein, the first nucleic acid binding domain binds to the nucleic acid target sequence. In some embodiments of any method, bivalent nucleic acid binding protein, or nucleoprotein complex described herein, the first nucleic acid binding domain is a DNA binding domain. In some embodiments of any method, bivalent nucleic acid binding protein, or nucleoprotein complex described herein, the first nucleic acid binding domain comprises a nuclease-deficient endonuclease such as a nuclease-deficient RNA-guided endonuclease. In some embodiments of any method, bivalent nucleic acid binding protein, or nucleoprotein complex described herein, the endonuclease is an RNA-guided endonuclease.

In some embodiments of any method described herein, the method further comprises providing a guide polynucleotide. In some embodiments of any bivalent nucleic acid binding protein described herein, the bivalent nucleic acid binding protein further comprises a guide polynucleotide. In some embodiments of any nucleoprotein complex described herein, the nucleoprotein complex further comprises a guide polynucleotide. In some embodiments of any method, bivalent nucleic acid binding protein, or nucleoprotein complex described herein, the guide polynucleotide is a guide RNA.

In some embodiments of any method, bivalent nucleic acid binding protein, or nucleoprotein complex described herein, the endonuclease is a Cas protein. In some embodiments of any method, bivalent nucleic acid binding protein, or nucleoprotein complex described herein, the endonuclease is Cas9 or Cpf1.

In some embodiments of any method, bivalent nucleic acid binding protein, or nucleoprotein complex described herein, the second nucleic acid binding domain is a DNA binding domain. In some embodiments of any method, bivalent nucleic acid binding protein, or nucleoprotein complex described herein, the second nucleic acid binding domain is selected from the group consisting of zinc finger, TALEN, lambda Cro protein, and any combination thereof. In some embodiments of any method, bivalent nucleic acid binding protein, or nucleoprotein complex described herein, the second nucleic acid binding domain binds to the donor cargo vector.

In some embodiments of any method, bivalent nucleic acid binding protein, or nucleoprotein complex described herein, the nucleoprotein complex further comprises a second bivalent nucleic acid protein comprising a third and a fourth nucleic acid binding domain. In some embodiments of any method, bivalent nucleic acid binding protein, or nucleoprotein complex described herein, the first, second, third, and fourth nucleic acid binding domains are specific for different sequences. In some embodiments of any method, bivalent nucleic acid binding protein, or nucleoprotein complex described herein, the third nucleic acid binding domain binds to the nucleic acid target sequence. In some embodiments of any method, bivalent nucleic acid binding protein, or nucleoprotein complex described herein, the third nucleic acid binding domain comprises a nuclease-deficient endonuclease. In some embodiments of any method, bivalent nucleic acid binding protein, or nucleoprotein complex described herein, the fourth nucleic acid binding domain is selected from the group consisting of a zinc finger, TALEN, lambda Cro protein, and any combination thereof. In some embodiments of any method, bivalent nucleic acid binding protein, or nucleoprotein complex described herein, the fourth nucleic acid binding domain binds to the donor cargo vector. In some embodiments of any method, bivalent nucleic acid binding protein, or nucleoprotein complex described herein, the second bivalent nucleic acid binding protein further comprises a nuclear localization signal.

In some embodiments, the bivalent nucleic acid binding protein could be substituted with an Oligo-Clamp consisting of nucleotides complementary to both the targeted genome sequence and to sequences present on the donor cargo vector such that one end of the Oligo-Clamp sequence forms a hybrid with the genome target DNA and the other portion of the Oligo-Clamp forms a stable hybrid with the donor cargo vector effecting a briding of the donor cargo to the site of intended HDR-mediated recombination of the vector sequences into the genome.

The present invention discloses methods and compositions for selectively neutralizing the spread of Mutagenic Chain Reaction (MCR) elements or genes encoding endonucleases from cells or organisms carrying them that do not affect cells or organisms lacking such elements.

One aspect of the invention provides a method of neutralizing a gene encoding an endonuclease in a cell or organism, the method comprising:

introducing at least one nucleotide insertion, deletion, and/or substitution in the gene encoding an endonuclease; wherein:
the cell or organism comprises a genomically integrated erasing-Construct Hitchhiking on the Autocatalytic Chain Reaction (e-CHACR) element comprising:
(a) a sequence encoding a first guide polynucleotide directing cleavage within or on both sides of the gene encoding an endonuclease; and
(b) a sequence encoding a second guide polynucleotide directing cleavage outside the gene encoding an endonuclease.

One aspect of the invention provides a method of neutralizing a mutagenic chain reaction (MCR) element in a cell or organism, the method comprising:

introducing at least one nucleotide insertion, deletion, and/or substitution in the MCR element; wherein:
the cell or organism comprises a genomically integrated erasing-Construct Hitchhiking on the Autocatalytic Chain Reaction (e-CHACR) element;
the MCR element comprises:
(a) a sequence encoding a guide polynucleotide that is genomically integrated in the cell or organism; and
(b) a gene encoding an endonuclease; and
the e-CHACR element comprises:
(a) a sequence encoding a first guide polynucleotide directing cleavage within or on both sides of the MCR element; and
(b) a sequence encoding a second guide polynucleotide directing cleavage outside the MCR element.

In some embodiments, the first guide polynucleotide in the e-CHACR element directs cleavage within the sequence encoding the guide polynucleotide in the MCR element. In some embodiments, the first guide polynucleotide in the e-CHACR element directs cleavage within the gene encoding the endonuclease in the MCR element.

In some embodiments of any method described herein, the method further comprises genomically integrating the e-CHACR element from an e-CHACR construct into the cell or organism, wherein the e-CHACR construct comprises:
(a) the e-CHACR element; and
(b) homology arms flanking the sequence that directly abut the endonuclease cut site determined by the second guide polynucleotide.

In some embodiments of any method described herein, the e-CHACR element is genomically integrated at a site directed by the second guide polynucleotide.

In some embodiments of any method described herein, the at least one nucleotide insertion, deletion, and/or substitution is introduced at a position directed by a guide polynucleotide in the e-CHACR element.

In some embodiments of any method described herein, the at least one nucleotide insertion, deletion, and/or substitution inhibits an activity of the endonuclease. In some embodiments, the activity is selected from the group consisting of nucleic acid cleavage, nucleic acid binding, nucleic acid methylation, and any combination thereof.

In some embodiments of any method described herein, the sequence in the e-CHACR element encodes a third, fourth, and/or fifth guide polynucleotide directing cleavage within the gene encoding an endonuclease.

In some embodiments, at least one or two guide polynucleotides can direct cleavage on both sides of the gene encoding an endonuclease or the MCR element. In some embodiments, a recoded wild-type allele of the locus into which the gene encoding an endonuclease or the MCR element has integrated can be provided wherein the guide polynucleotide cleavage sites are mutated to be resistant to endonuclease cleavage at those sites. For example, if a stock carrying both an e-CHACR and a recoded e-CHACR-resistant allele is crossed with a stock carrying the MCR, the result can be deletion of the gene encoding an endonuclease or the MCR element and correction of the deleted segment (e.g., via HDR) using the wild-type allele (e.g., to restore nearly wild-type function to the allele previously mutated by insertion of the gene encoding an endonuclease or the MCR element).

In some embodiments, the e-CHACR could be used in combination with an NCR or ERACR element to augment neutralization of an MCR or gene-drive element.

In some embodiments of any method described herein, the guide polynucleotides have different sequences. In some embodiments of any method described herein, the guide polynucleotides direct cleavage at different sites. In some embodiments of any method described herein, the guide polynucleotides each direct one cleavage site. In some embodiments of any method described herein, the guide polynucleotides are guide RNAs.

In some embodiments of any method described herein, the endonuclease is an RNA-guided endonuclease. In some embodiments of any method described herein, the endonuclease is a Cas protein. In some embodiments of any method described herein, the endonuclease is Cas9. In some embodiments of any method described herein, the endonuclease is Cpf1.

In some embodiments of any method described herein, the cell or organism is a cell. In some embodiments of any method described herein, the cell or organism is an organism.

In some embodiments of any method described herein, the genomically integrating comprises genomically integrating into a chromosome of the cell or organism.

In some embodiments of any method described herein, the gene encoding an endonuclease is genomically integrated in the cell or organism. In some embodiments of any method described herein, the gene encoding an endonuclease is not genomically integrated in the cell or organism. In some embodiments of any method described herein, the gene encoding an endonuclease is located on a plasmid or artificial chromosome.

In some embodiments of any method described herein, the method comprises introducing at least two, at least three, at least four, at least five, or at least ten nucleotide insertions, deletions, and/or substitutions in the gene encoding the endonuclease. In some embodiments of any method described herein, the method further comprises introducing the nucleotide insertions, deletions, and/or substitutions in the gene encoding the endonuclease via non-homologous end joining (NHEJ).

In some embodiments of any method described herein, the method further comprises introducing at least one, at least two, at least three, at least four, at least five, or at least ten amino acid insertion, deletion, and/or substitution in the endonuclease. In some embodiments of any method described herein, the method further comprises introducing the amino acid insertions, deletions, and/or substitutions in the endonuclease via non-homologous end joining (NHEJ).

In some embodiments of any method described herein, the e-CHACR construct does not comprise a gene encoding an endonuclease. In some embodiments of any method described herein, the e-CHACR element does not comprise a gene encoding an endonuclease.

In some embodiments of any method described herein, the e-CHACR element is genomically integrated using homology directed repair. In some embodiments of any method described herein, the e-CHACR element is not genomically integrated using non-homologous end joining. In some embodiments of any method described herein, the e-CHACR element is genomically integrated with an efficiency of at least 25%, at least 50%, at least 75%, at least 80%, at least 85%, at least 90%, or at least 95%.

In some embodiments of any method described herein, the e-CHACR construct is located on a plasmid. In some embodiments of any method described herein, the e-CHACR construct is located on a chromosome.

In some embodiments of any method described herein, the homology arms in the e-CHACR construct are located on a plasmid. In some embodiments of any method described herein, the homology arms in the e-CHACR construct are located on a chromosome. In some embodiments of any method described herein, the homology arms in the e-CHACR construct are at least 25, at least 50, at least 100, at least 150, at least 200, at least 250, at least 500, at least 600, at least 700, at least 800, at least 900, at least 1000, or at least 1500 nucleotides in length.

In some embodiments of any method described herein, the e-CHACR construct is injected as a DNA plasmid into a germline of an organism to obtain a transgenic organism.

In some embodiments of any method described herein, the method further comprises generating homozygous mutations in the cell or organism.

In some embodiments of any method described herein, the method further comprises genomically integrating the e-CHACR element into both copies of a chromosome of the cell or organism.

In some embodiments of any method described herein, the method further comprises propagating the e-CHACR element via the germline to offspring of the organism.

In some embodiments of any method described herein, the method further comprises genomically integrating the e-CHACR element into a first cell or organism and crossing or mating the first cell or organism with a second cell or organism comprising a gene encoding an endonuclease (e.g., to generate the cell or organism).

In some embodiments of any method described herein, the method further comprises genomically integrating the e-CHACR element into a first cell or organism and crossing or mating the first cell or organism with a second cell or organism comprising an MCR element (e.g., to generate the cell or organism).

In some embodiments of any method described herein, the e-CHACR construct is introduced into somatic cells in the organism.

In some embodiments of any method described herein, the method further comprises spreading the e-CHACR element to other cells within the organism.

In some embodiments of any method described herein, the e-CHACR construct is injected as a DNA plasmid into a germline or introduced via DNA plasmid or viral expression vector into somatic cells of the organism to obtain transgenic organisms resulting in homozygous or nearly fully converted germline mutations.

In some embodiments of any method described herein, the e-CHACR construct is introduced using a plasmid or viral expression vector.

In some embodiments of any method described herein, the organism is an animal, human, microorganism, insect, plant, or any combination thereof. In some embodiments of any method described herein, the organism is a model organism. In some embodiments of any method described herein, the organism is a virus, prokaryote, eukaryote, protist, fungus, invertebrate animal, vertebrate animal, microorganism, pathogen, agriculture pest, or any combination thereof.

In some embodiments of any method described herein, the cell is from a prokaryote, eukaryote, protist, fungus, invertebrate animal, vertebrate animal, microorganism, pathogen, agriculture pest, or any combination thereof.

One aspect of the invention provides an expression vector comprising an erasing-Construct Hitchhiking on the Autocatalytic Chain Reaction (e-CHACR) construct; wherein:
  the e-CHACR construct comprises:
    (a) the e-CHACR element; and
    (b) homology arms flanking the sequence that directly abut the endonuclease cut site determined by the second guide polynucleotide; and
  the e-CHACR element comprises:
    (a) a sequence encoding a first guide polynucleotide directing cleavage within a gene encoding an endonuclease; and
    (b) a sequence encoding a second guide polynucleotide directing cleavage outside the gene encoding an endonuclease.

In some embodiments of any expression vector described herein, the sequence in the e-CHACR element encodes a third, fourth, and/or fifth guide polynucleotide directing cleavage within the gene encoding an endonuclease.

In some embodiments of any expression vector described herein, the sequence in the e-CHACR element encodes a third, fourth, and/or fifth guide polynucleotide directing cleavage on either side of the MCR.

In some embodiments of any expression vector described herein, the guide polynucleotides have different sequences. In some embodiments of any expression vector described herein, the guide polynucleotides direct cleavage at different sites. In some embodiments of any expression vector described herein, the guide polynucleotides each direct one cleavage site. In some embodiments of any expression vector described herein, the guide polynucleotides are guide RNAs.

In some embodiments of any expression vector described herein, the endonuclease is an RNA-guided endonuclease. In some embodiments of any expression vector described herein, the endonuclease is a Cas protein. In some embodiments of any expression vector described herein, the endonuclease is Cas9. In some embodiments of any expression vector described herein, the endonuclease is Cpf1.

In some embodiments of any expression vector described herein, the endonuclease cut site is located on a genome of a cell or organism. In some embodiments of any expression vector described herein, the endonuclease cut site is located on a chromosome of a cell or organism. In some embodiments of any expression vector described herein, the endonuclease cut site is located on a plasmid or artificial chromosome.

In some embodiments of any expression vector described herein, the e-CHACR construct does not comprise a gene encoding an endonuclease. In some embodiments of any expression vector described herein, the e-CHACR element does not comprise a gene encoding an endonuclease. In some embodiments of any expression vector described herein, the e-CHACR construct is located on a plasmid. In some embodiments of any expression vector described herein, the e-CHACR construct is located on a chromosome.

In some embodiments of any expression vector described herein, the homology arms in the e-CHACR construct are located on a plasmid. In some embodiments of any expression vector described herein, the homology arms in the e-CHACR construct are located on a chromosome. In some embodiments of any expression vector described herein, the homology arms in the e-CHACR construct are at least 50, at least 100, at least 150, at least 200, at least 250, at least 500, at least 600, at least 700, at least 800, at least 900, at least 1000, or at least 1500 nucleotides in length.

In some embodiments of any expression vector described herein, the sequence in the e-CHACR element encodes two guide polynucleotides directing cleavage on either side of the gene encoding an endonuclease or the MCR element. In some embodiments, the cleavage sites directed by the guide polynucleotides are spaced apart from the gene encoding an endonuclease or the MCR element by about or at least about 500 bp, 600 bp, 700 bp, 800 bp, 900 bp, or 1 kb.

One aspect of the invention provides a cell or organism comprising an expression vector described herein.

One aspect of the invention provides a cell or organism comprising a genomically integrated erasing-Construct Hitchhiking on the Autocatalytic Chain Reaction (e-CHACR) element, wherein:
  the e-CHACR element comprises:
    (a) a sequence encoding a first guide polynucleotide directing cleavage within a gene encoding an endonuclease; and
    (b) a sequence encoding a second guide polynucleotide directing cleavage outside the gene encoding an endonuclease, wherein the e-CHACR element is genomically integrated at a site the second guide polynucleotide directs cleavage.

One aspect of the invention provides a cell or organism comprising a genomically integrated erasing-Construct Hitchhiking on the Autocatalytic Chain Reaction (e-CHACR) element, wherein:

the e-CHACR element comprises:
(a) a sequence encoding a first guide polynucleotide directing cleavage within an MCR element; and
(b) a sequence encoding a second guide polynucleotide directing cleavage outside the MCR element, wherein the e-CHACR element is genomically integrated at a site the second guide polynucleotide directs cleavage; and the MCR element comprises:
(a) a genomically integrated sequence encoding a guide polynucleotide; and
(b) a gene encoding an endonuclease.

In some embodiments of any cell or organism described herein, the first guide polynucleotide in the e-CHACR element directs cleavage within the sequence encoding the guide polynucleotide in the MCR element. In some embodiments of any cell or organism described herein, the first guide polynucleotide in the e-CHACR element directs cleavage within the gene encoding the endonuclease in the MCR element.

In some embodiments of any cell or organism described herein, the sequence in the e-CHACR element encodes a third, fourth, and/or fifth guide polynucleotide directing cleavage within the gene encoding an endonuclease.

In some embodiments of any cell or organism described herein, the guide polynucleotides have different sequences. In some embodiments of any cell or organism described herein, the guide polynucleotides direct cleavage at different sites. In some embodiments of any cell or organism described herein, the guide polynucleotides each direct one cleavage site. In some embodiments of any cell or organism described herein, the guide polynucleotides are guide RNAs.

In some embodiments of any cell or organism described herein, the guide polynucleotides direct cleavage at sites flanking the gene encoding an endonuclease or the MCR element. In some embodiments, the cleavage sites directed by the guide polynucleotides are spaced apart from the gene encoding an endonuclease or the MCR element by about or at least about 500 bp, 600 bp, 700 bp, 800 bp, 900 bp, or 1 kb.

In some embodiments of any cell or organism described herein, the endonuclease is an RNA-guided endonuclease. In some embodiments of any cell or organism described herein, the endonuclease is a Cas protein. In some embodiments of any cell or organism described herein, the endonuclease is Cas9. In some embodiments of any cell or organism described herein, the endonuclease is Cpf1.

In some embodiments of any cell or organism described herein, the cell or organism is a cell. In some embodiments of any cell or organism described herein, the cell or organism is an organism.

In some embodiments of any cell or organism described herein, the e-CHACR element is genomically integrated into a chromosome of the cell or organism. In some embodiments of any cell or organism described herein, the e-CHACR element is genomically integrated into both copies of a chromosome of the cell or organism.

In some embodiments of any cell or organism described herein, the gene encoding an endonuclease is genomically integrated in the cell or organism. In some embodiments of any cell or organism described herein, the gene encoding an endonuclease is not genomically integrated in the cell or organism. In some embodiments of any cell or organism described herein, the gene encoding an endonuclease is located on a plasmid or artificial chromosome in the cell or organism.

In some embodiments of any cell or organism described herein, the e-CHACR element does not comprise a gene encoding an endonuclease.

In some embodiments of any cell or organism described herein, the e-CHACR element is in a germline cell. In some embodiments of any cell or organism described herein, the e-CHACR element is in a somatic cell.

In some embodiments of any cell or organism described herein, the organism is an animal, human, microorganism, insect, plant, or any combination thereof. In some embodiments of any cell or organism described herein, the organism is a model organism. In some embodiments of any cell or organism described herein, the organism is a virus, prokaryote, eukaryote, protist, fungus, invertebrate animal, vertebrate animal, microorganism, pathogen, agriculture pest, or any combination thereof. In some embodiments of any cell or organism described herein, the cell is from a prokaryote, eukaryote, protist, fungus, invertebrate animal, vertebrate animal, microorganism, pathogen, agriculture pest, or any combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

The publication "Gantz and Bier, The mutagenic chain reaction: a method for converting heterozygous to homozygous mutations (2015) *Science* 348, 442-4" is herein incorporated by reference in its entirety.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 1A-1G are a scheme outlining the Mutagenic Chain Reaction (MCR).

FIGS. 2A-2I are an experimental demonstration of MCR in *Drosophila*.

FIGS. 4A-4G are a scheme outlining the Neutralizing Chain Reaction (NCR).

FIG. 5 shows a comparison of inheritance via traditional Mendelian versus active genetics.

FIG. 12A discloses SEQ ID NOS 33-35, respectively, in order of appearance.

FIG. 13 is a scheme outlining active genetics using CopyCat cloning vector.

FIG. 20 shows an illustrative scheme for a trans-complementing mutagenic chain reaction (MCR). Two separate trans-complementing elements <cas9> and a <gRNA> shown inserted on two different chromosomes together create a drive system that results in each element being copied to the sister chromosome. Such a dual element arrangement is functionally equivalent to that of a single-unit coupled <cas9; gRNA> MCR element. In this scheme, gRNA2 cleaves at the Cas9 insertion site while gRNA1 cleaves at the <gRNA1,2> insertion site.

FIG. 21 illustrates growth equations at different seeding frequencies.

FIG. 22 illustrates a potential application of the methods of the disclosure to treat malaria.

FIG. 25A discloses SEQ ID NOS 37 and 34-35, respectively, in order of appearance.

FIGS. 28A-28F depict an exemplary scheme outlining ERACRs, CHACRs, and copy-cat <gRNA> constructs. FIG. 28C discloses SEQ ID NO: 38.

FIG. 32 is a scheme outlining active genetics enabled by CopyCat elements.

FIG. 33 is a scheme outlining an exemplary CHACR element.

FIGS. 38A-H are a scheme outlining an exemplary TETHR open reading frame. FIGS. 38A-H disclose the nucleotide sequence as SEQ ID NO: 39 and the amino acid sequence as SEQ ID NO: 40.

DETAILED DESCRIPTION

Autocatalytic genome editing and neutralizing autocatalytic genome editing in immune cells The disclosure provides methods, termed the Mutagenic Chain Reaction (MCR), and compositions for autocatalytic genome editing based on genomic integration of a portion of an MCR construct containing multiple elements. In certain embodiments, the MCR construct comprises: 1) a gene encoding an endonuclease (e.g., a Cas protein such as the Cas9 protein); 2) one or more sequences encoding one or more guide polynucleotides (e.g., guide RNAs such as sgRNA, gRNA or chiRNA); 3) an effector cassette (e.g., a DNA sequence that carries out a function including, but not limited to, protein coding gene, non-coding RNA, cis-regulatory region, DNA binding site, or any other structural or functional element); and 4) homology arms flanking the gene, one or more sequences, and effector cassette. In some instances, expression of the endonuclease is be regulated. In some instances, the sequence encoding one or more guide polynucleotides is under the control of a separate promoter such as an RNA-polymerase-I or -III promoter (e.g., the U6 RNA pol-III promoter). The guide polynucleotide (e.g., guide RNA) once expressed bind to the endonuclease (e.g., Cas9 protein) and direct site directed cleavage of the genome at one or more specific sites. In some instances, the homology arms directly abut the endonuclease cleavage sites. In some instances, the homology arms target insertion of the gene, one or more sequences, and effector cassette into the genome (e.g., via Homology Directed Repair (HDR)) at the precise endonuclease cleavage site(s) determined by the one or more guide polynucleotides (e.g., guide RNA(s)). In some instances, an MCR construct is a DNA plasmid.

The disclosure further provides the method of inserting a portion of an MCR construct into the germline of an organism and obtaining a transgenic organism carrying the insertion on one copy of a chromosome from which it spreads to the other chromosome. In some embodiments, the method further comprises generating a homozygous mutation. In some embodiments, the transgenic organism propagates a mutation via the germline to a plurality of its offspring, as shown in FIGS. 2A-2I. The disclosure further provides the method of introducing an MCR construct into somatic cells of an organism (e.g., using a plasmid or viral expression vector) such that the construct spreads to other cells within that organism, as shown in FIGS. 3A-3D.

Figure 2A:
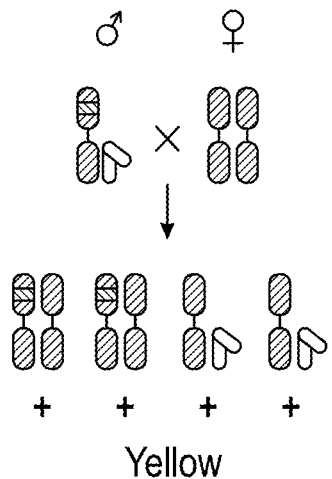
Figure 2B:
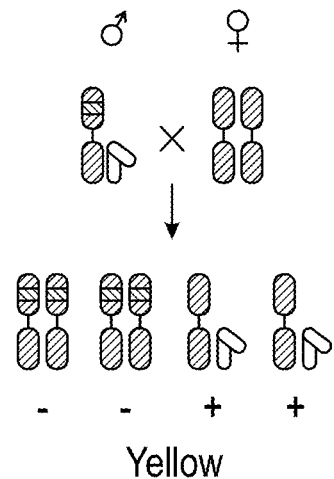
Figure 2C:
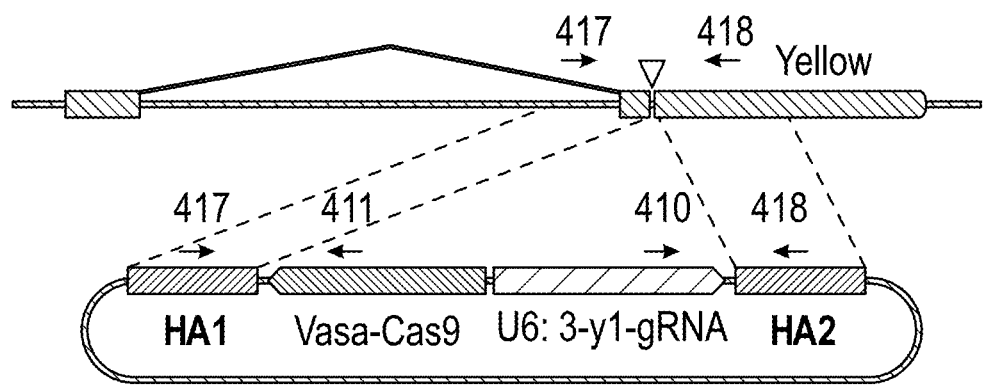

An MCR construct comprises a single guide polynucleotide (e.g., guide RNA). In these embodiments, the homology arms directly abut the single cut site, leading to insertion of the MCR element at the cut site (e.g., as shown in FIG. 2I). An MCR construct comprises two guide polynucleotides (e.g., guide RNAs) that direct cleavage at a certain distance apart. In such embodiments, the MCR construct comprises flanking homology arms ending precisely at the two cut sites, and the MCR element leads to deletion of host genome sequences between the cut sites and insertion of the MCR element within that deletion. The disclosure function to a) inject the MCR construct as a DNA plasmid into the germline of an organism and obtain transgenic organisms carrying this insertion on one copy of a chromosome from which it spreads to the other chromosome (creating potential homozygous mutations) as well as propagating the mutation via the germline a plurality of the offspring, often the plurality is most of the offspring (see FIG. 1A-F, FIGS. 2A and 2B) or b) introduce the MCR construct into somatic cells in an organism (e.g., using a plasmid or viral expression vector) such that the construct would spread to other cells within that organism (see FIGS. 3A-3D).

An MCR construct is integrated into a defined site on a single copy of a chromosome. For instance, specific targeting via the guide polynucleotide (e.g., guide RNA) directs the endonuclease (e.g., Cas9) to cleave the genome at a specific site, and the MCR construct is inserted into the site by homologous repair using the homology arms as a template. An MCR insertion event takes place in a germline cell or a somatic cell. By carrying the elements necessary for insertion into the same site on a second copy of the chromosome, the MCR element cleaves the other allele in a cell at the same place and insert itself into the second copy of the chromosome thereby resulting in the insertion becoming homozygous. The MCR insertion becomes homozygous in the germline, resulting in progeny of an individual carrying an MCR allele inheriting it. The mutation spreads from a single chromosome to both chromosomes in the next generation to once again become homozygous. As shown in FIGS. 2A-2I in a proof-of-principle example of MCR-directed mutagenesis of the *Drosophila* yellow locus, >95% of tested somatic and germline cells are homozygous. MCR mutations are often homozygous and spread via the germline to a plurality of the offspring, often the plurality is most of the offspring.

FIGS. 1A-1G are a scheme outlining an example of a Mutagenic Chain Reaction (MCR). A plasmid or virally-encoded cassette carrying genes encoding Cas9 protein and a guide RNA (gRNA) targeting a genomic sequence of interest, flanked by homology arms corresponding to the genomic sequences straddling the target site results in cleavage (FIG. 1A) and homology driven insertion (FIGS. 1B and 1C) of the sequences encoding the Cas9 and gRNA elements into the targeted locus. The inserted cassette expresses Cas9 protein and gRNA leading to cleavage (FIG. 1D) and homology directed insertion of the cassette into the second allele to render the mutation homozygous (FIGS. 1E and 1F). The MCR construct further comprises an effector cassette (e.g., a protein or RNA coding sequence) (FIG. 1G).

Provided in certain embodiments is also a method for selectively neutralizing or removing the spread of the MCR elements from organisms carrying them. In some embodiments, the method does not affect organisms lacking MCR elements. This method for selective deletion or neutralization of MCR elements is termed a Neutralizing Chain Reaction (NCR). NCR and Elements for Reversing the Autocatalytic Chain Reaction (ERACR) are used interchangeably throughout the present disclosure and are not intended to comprise different interpretations as an NCR is an ERACR. An NCR construct comprises 1) two guide polynucleotides (e.g., guide RNAs) directing cleavage at the same locus as the MCR element but outside of the MCR element (e.g., to target deletion of MCR sequences from the genome), and 2) homology arms flanking the NCR cassette that directly abut the endonuclease (e.g., Cas9) cut sites determined by the guide polynucleotides (e.g., guide RNAs). An NCR construct optionally comprises a recoded gene or cis-regulatory element that restores a genetic function mutated by the MCR of the locus mutated by the MCR element that cannot be cut by the guide polynucleotide(s) (e.g., guide RNA(s)) carried by the MCR element. For example, in the embodiment of an MCR disrupting the coding region of a gene, sequences encoding this gene would directly abut the left homology arm (based on an orientation in which transcription of the gene locus is from left to right) so that it is in frame with the undisturbed portion of the gene and carries 3' UTR sequences necessary for producing a functional and stable coding mRNA product. An NCR construct optionally comprises an effector cassette. An NCR construct does not often comprise a gene encoding an endonuclease, such as Cas9.

An NCR construct be transfected as a DNA plasmid together with a plasmid source of Cas9 protein into the germline of an organism to obtain transgenic organisms carrying this insertion. Organisms carrying this construct are crossed with MCR individuals (e.g., released into an environment containing MCR individuals) whereupon the NCR would act on the MCR chromosome to delete the MCR element and restore function of the host locus via the recoded transgene.

An NCR deletes or neutralizes a consequence of having performed MCR (FIGS. 4A-4F). In some embodiments, the NCR construct is specific for deletion of MCR sequences since it carries guide polynucleotides (e.g., guide RNAs) that lead to cleavage of host sequences flanking the MCR (thereby cutting out completely) but does not carry the gene encoding Cas9. Since the NCR element lacks Cas9 function, it acts via its guide polynucleotides (e.g., guide RNAs) in organisms carrying a source of Cas9 (e.g., MCR organisms). In addition, the NCR element carries a correcting cassette (e.g., coding region of gene or cis-regulatory element) that has been recorded at the original guide-RNA cleavage site(s) to be immune to MCR cleavage. These two properties selectively correct and neutralize the effects of an MCR element.

FIGS. 4A-4F is a scheme outlining the Neutralizing Chain Reaction (NCR). A plasmid (or virally-encoded) cassette carrying two genes encoding two separate gRNA targeting sites flanking the genomic sequence with the previous MCR insertion, flanked by homology arms corresponding to the genomic sequences adjacent to the target sites and identically matching the generated chromosome ends (A) and homology driven insertion (B,C) of the core NCR cassette into the targeted wild type locus driven by externally supplied endonuclease (e.g., Cas9) (either by genomic or plasmid source). An NCR inserted cassette (C) would be activated starting a Neutralizing Chain Reaction (NCR) when such animals are crossed with ones carrying its MCR correspondent mutation (D) in which embodiment the reaction would analogously progress to convert the MCR into an NCR allele (E,F) resulting in removal of the endonuclease (e.g., Cas9) gene (F), and thus complete MCR inactivation. In contrast to the MCR, when the NCR is combined with a wild type allele, genome editing does not occur since no source of endonuclease (e.g., Cas9 protein) is available to induce the necessary cleavage (G).

In other embodiments, the present disclosure describes a method of neutralizing a mutagenic chain reaction (MCR) element from a cell, the method comprising genomically integrating a neutralizing chain reaction (NCR) construct into the cell, wherein the MCR element comprises, at least one sequence encoding at least one guide polynucleotide; and a gene encoding an endonuclease; an expression cassette encoding a chimeric antigen receptor (CAR), a T cell receptor (TCR) or a negative regulatory molecule; and the NCR construct comprises at least one guide polynucleotide directing cleavage within or outside of the MCR element and no gene encoding an endonuclease; or at least two guide polynucleotides directing cleavage within or outside of the MCR element; and homology arms flanking the at least two guide polynucleotides that directly abut the endonuclease cut sites determined by the guide polynucleotides, and wherein an expression cassette encoding a chimeric antigen receptor (CAR) is genomically integrated in a cell. In some embodiments, the guide polynucleotides are guide RNAs.

In some embodiments, the present disclosure describes a method of neutralizing a mutagenic chain reaction (MCR) element in a cell, the method comprising genomically integrating a neutralizing chain reaction (NCR) element from an NCR construct into the cell, wherein the MCR element comprises, at least one sequence encoding at least one guide polynucleotide, wherein the at least one sequence encoding at least one guide polynucleotide is genomically integrated in the cell; and a gene encoding an endonuclease; the NCR element comprises, at least one sequence encoding at least one guide polynucleotide directing cleavage within or on both sides of the MCR element; and at least one sequence encoding at least two guide polynucleotides directing cleavage within or outside of the MCR element or no gene encoding an endonuclease; and the NCR construct comprises, the NCR element; and homology arms flanking the at least one guide polynucleotide that directly abut the endonuclease cut site(s) determined by the at least one guide polynucleotide, and wherein an expression cassette encoding a chimeric antigen receptor (CAR) is genomically integrated in a cell. In some embodiments, the guide polynucleotides are guide RNAs.

In some embodiments, the endonuclease is a Cas protein. In some embodiments, the Cas protein is Cas9.

In some embodiments, the cell is an immune cell. In some embodiments, the immune cell is a T cell.

In other embodiments, the genomically integrating comprising genomically integrating into a chromosome of the cell. In some embodiments, the gene encoding an endonuclease is genomically integrated in the cell. In some embodiments, the gene encoding an endonuclease is not genomically integrated in the cell. In some embodiments, the gene encoding an endonuclease is located on a plasmid or artificial chromosome.

In some embodiments, the at least one sequence encoding at least one guide polynucleotide in the MCR element is genomically integrated in the cell. In some embodiments, the MCR element is genomically integrated in the cell. In some embodiments, the method further comprises deletion of the gene encoding the endonuclease from the genome. In some embodiments, the method further comprises deletion of the at least one sequence encoding at least one guide polynucleotide in the MCR element from the genome. In some embodiments, the method further comprises deletion of the MCR element from the genome.

In other embodiments, the method further comprises disruption of the gene encoding the endonuclease. In some embodiments, the disruption of the gene encoding the endonuclease in the genome comprises a deletion, insertion, or mutation of at least one amino acid of the endonuclease.

In some embodiments, directing cleavage within or on both sides of the MCR element comprises directing cleavage on the same allele as the MCR element.

In other embodiments, the NCR construct does not comprise a gene encoding an endonuclease. In some embodiments, the NCR element does not comprise a gene encoding an endonuclease. In some embodiments, the at least one sequence encoding at least one guide polynucleotide in the NCR element comprises a different sequence than the at least one sequence encoding at least one guide polynucleotide in the MCR element. In some embodiments, the at least one sequence encoding at least one guide polynucleotide in the NCR element directs cleavage within the MCR element. In some embodiments, the at least one sequence encoding at least one guide polynucleotide in the NCR element directs cleavage within the gene encoding the endonuclease. In some embodiments, the at least one sequence encoding at least one guide polynucleotide in the NCR element directs cleavage within the at least one sequence encoding at least one guide polynucleotide in the MCR element. In some embodiments, the at least one sequence encoding at least one guide polynucleotide in the NCR element directs cleavage on both sides of the MCR element. In some embodiments, the at least one sequence encoding at least one guide polynucleotide in the NCR element directs cleavage on both sides of the gene encoding the endonuclease. In some embodiments, the at least one sequence encoding at least one guide polynucleotide in the NCR element directs cleavage on both sides of the at least one sequence encoding at least one guide polynucleotide in the MCR element, In some embodiments, the NCR construct comprises one guide polynucleotide. In some embodiments, the one guide polynucleotide directs one cleavage site. In some embodiments, the one guide polynucleotide directs cleavage within the MCR element. In some embodiments, the one guide polynucleotide directs cleavage within the gene encoding the endonuclease. In some embodiments, the one guide polynucleotide directs cleavage within the at least one sequence encoding at least one guide polynucleotide in the MCR element.

In some embodiments, the one guide polynucleotide directs two cleavage sites. In some embodiments, the one guide polynucleotide directs cleavage on both sides of the endonuclease. In some embodiments, the one guide polynucleotide directs cleavage on both sides of the at least one sequence encoding at least one guide polynucleotide in the MCR element. In some embodiments, the one guide polynucleotide directs cleavage on both sides of the MCR element.

In other embodiments, the NCR construct comprises two guide polynucleotides. In some embodiments, the two guide polynucleotides direct two cleavage sites.

In some embodiments, the two guide polynucleotides direct cleavage within the MCR element. In some embodiments, the two guide polynucleotides direct cleavage within the gene encoding the endonuclease. In some embodiments, the two guide polynucleotides direct cleavage within the at least one sequence encoding at least one guide polynucleotide in the MCR element.

In some embodiments, the two guide polynucleotides direct cleavage on both sides of the gene encoding the endonuclease. In some embodiments, the two guide polynucleotides direct cleavage on both sides of the at least one sequence encoding at least one guide polynucleotide in the MCR element. In some embodiments, the two guide polynucleotides direct cleavage on both sides of the MCR element.

In some embodiments, the at least one sequence encoding at least two guide polynucleotides in the NCR element comprises at least two sequences encoding at least two guide polynucleotides. In some embodiments, the NCR element is genomically integrated using homology directed repair. In some embodiments, the NCR element is not genomically integrated using non-homologous end joining. In some embodiments, the NCR element is genomically integrated with an efficiency of at least 25%. In some embodiments, the NCR element is genomically integrated with an efficiency of at least 50%. In some embodiments, the NCR element is genomically integrated with an efficiency of at least 75%.

In some embodiments, the NCR construct is located on a plasmid. In some embodiments, the NCR construct is located on a chromosome. In some embodiments, the homology arms in the NCR construct are located on a plasmid. In some embodiments, the homology arms in the NCR construct are located on a chromosome. In some embodiments, the homology arms in the NCR construct are at least 50 nucleotides in length. In some embodiments, the homology arms in the NCR construct are at least 100 nucleotides in length. In some embodiments, the MCR element is located on a first copy of a chromosome and the NCR element is located on a second copy of a chromosome.

In some embodiments, the NCR element further comprises a corrected recoded gene or cis-regulatory element that is not cut by the at least one guide polynucleotide in the MCR element. In some embodiments, the NCR element further comprises a corrected effector cassette.

In some embodiments, the method further comprises restoring a genetic function of a locus mutated by the MCR element.

In some embodiments, the method further comprises generating homozygous mutations in the cell.

In some embodiments, the method further comprises genomically integrating the NCR element into both copies of a chromosome of the cell.

In some embodiments, the NCR construct is introduced using a plasmid or viral expression vector. In some embodiments, the organism is an animal, a mammal, a non-human primate, or a human. In some embodiments, the cell is from an animal, a mammal, a non-human primate, or a human.

In some embodiments, the present disclosure describes a construct for neutralizing autocatalytic genome editing, the construct comprising, at least one sequence encoding at least one guide polynucleotide directing cleavage within or on both sides of the MCR element, homology arms flanking the at least one guide polynucleotide that directly abut the endonuclease cut site(s) determined by the at least one guide polynucleotide; and at least one sequence encoding at least two guide polynucleotides directing cleavage within or outside of the MCR element or no gene encoding an endonuclease, wherein the MCR element comprises, at least one sequence encoding at least one guide polynucleotide, wherein the at least one sequence encoding at least one guide polynucleotide is genomically integrated in a cell; and a gene encoding an endonuclease, and wherein the cell comprises an endonuclease or a gene encoding an endonuclease; and wherein an expression cassette encoding a chimeric antigen receptor (CAR) is genomically integrated in a cell.

In some embodiments, the present disclosure describes a method of genomically integrating a neutralizing chain reaction (NCR) element into a cell, the method comprising, introducing into the cell an NCR construct comprising, at least one sequence encoding at least one guide polynucleotide directing cleavage within or on both sides of an MCR element, homology arms flanking the at least one guide polynucleotide that directly abut the endonuclease cut site(s) determined by the at least one guide polynucleotide; and at least one sequence encoding at least two guide polynucleotides directing cleavage within or outside of the MCR element or no gene encoding an endonuclease; and genomically integrating an NCR element comprising, at least one sequence encoding at least one guide polynucleotide directing cleavage within or on both sides of the MCR element; and at least one sequence encoding at least two guide polynucleotides directing cleavage within or outside of the MCR element or no gene encoding an endonuclease, wherein the MCR element comprises, at least one sequence encoding at least one guide polynucleotide; and a gene encoding an endonuclease; and wherein the cell comprises an endonuclease or a gene encoding an endonuclease. In some embodiments, the guide polynucleotides are guide RNAs, and wherein the cell comprises an endonuclease or a gene encoding an endonuclease; and wherein an expression cassette encoding a chimeric antigen receptor (CAR) is genomically integrated in a cell.

In some embodiments, NCR constructs are designed to avoid or minimize having any nucleic acid identity to sequences carried on the MCR construct it is designed to delete. Such designs may exhibit increased efficiency in deleting and replacing MCR elements.

In some embodiments, the endonuclease is a Cas protein. In some embodiments, the Cas protein is Cas9.

In some embodiments, the cell is an immune cell. In some embodiments, the immune cell is a T cell.

In some embodiments, the cell does not comprise the MCR element. In some embodiments, the cell does comprise the MCR element.

In some embodiments, the NCR construct is introduced using a plasmid or viral expression vector. In some embodiments, the NCR construct does not comprise a gene encoding an endonuclease. In some embodiments, the NCR element does not comprise a gene encoding an endonuclease.

In some embodiments, the organism is a model organism. In some embodiments, the organism is an animal, a mammal, a non-human primate, or a human. In some embodiments, the cell is from an animal, a mammal, a non-human primate, or a human.

In some embodiments, the present disclosure describes a method for autocatalytic genome editing, the method comprising genomically integrating a mutagenic chain reaction (MCR) element from an MCR construct into a cell, wherein, the MCR element comprises a gene encoding an endonuclease, at least one sequence encoding at least one guide polynucleotide, and an effector cassette; and the MCR construct comprises, the MCR element; and homology arms flanking the MCR element, wherein the homology arms directly abut the endonuclease cut site(s) determined by the at least one guide polynucleotide.

In some embodiments, the endonuclease is a Cas protein. In some embodiments, the Cas protein is Cas9.

In some embodiments, the cell is an immune cell. In some embodiments, the immune cell is a T cell.

In some embodiments, the guide polynucleotide once expressed binds to the endonuclease and directs site directed cleavage of the genome at a specific site.

In some embodiments, the sequence encoding one or more guide polynucleotides is under a control of a separate promoter. In some embodiments, the separate promoter is an RNA-polymerase-I or III promoter.

In some embodiments, the construct is injected as a DNA plasmid into a germline of the organism to obtain a transgenic organism. In some embodiments, homozygous mutations are created wherein said transgenic organism carrying the inserted construct on one copy of a chromosome from which it spreads to another chromosome. In some embodiments, mutations are created wherein said transgenic organism carrying the inserted construct is propagated via the germline to offspring.

In some embodiments, the MCR construct is introduced into somatic cells in an organism so that said construct can be spread to other cells within that organism. In some embodiments, the MCR construct is introduced using a plasmid or viral expression vector.

In some embodiments, the organism is from an animal, a mammal, a non-human primate, or a human. In some embodiments, the cell is from an animal, a mammal, a non-human primate, or a human.

In some embodiments, the autocatalytic genome editing targets a disease independent of the type and stage of disease progression. In some embodiments, the disease is cancer.

In some embodiments, the autocatalytic genome editing generates scoreable recessive mutant phenotypes in a single generation.

In some embodiments, the present disclosure describes a construct for autocatalytic genome editing, the construct comprising a gene encoding an endonuclease, at least one sequence encoding at least one guide polynucleotide, an effector cassette, and homology arms flanking the gene, the at least one sequence, and the cassette, wherein the homology arms directly abut the endonuclease cut site(s) determined by the at least one guide polynucleotide. In some embodiments, the guide polynucleotides are guide RNAs, and wherein the cell comprises an endonuclease or a gene encoding an endonuclease; and wherein an expression cassette encoding a chimeric antigen receptor (CAR) is genomically integrated in a cell.

In some embodiments, the endonuclease is a Cas protein. In some embodiments, the Cas protein is Cas9.

In some embodiments, the one or more guide polynucleotides once expressed bind to the Cas9 protein and direct site directed cleavage of the genome at a specific site. In some embodiments, the sequence encoding one or more guide polynucleotides is under a control of a separate promoter. In some embodiments, the separate promoter is an RNA-polymerase-I or III promoter.

In some embodiments, the construct is injected as a DNA plasmid into a germline or introduced via DNA plasmid or viral expression vector into somatic cells of the organism to obtain a transgenic organism resulting in homozygous mutations or mutations passed on to progeny.

A CopyCat element is similar to an NCR in that the CopyCat element often carries one or two gRNAs and not Cas9. The CopyCat element often differs from an NCR in that the gRNA(s) are directed (via homology arms flanking the gRNA cut sites) to a locus in the genome other than an MCR. CopyCats carrying a single gRNA would insert into the cleaved site while those carrying two gRNAs targeting nearby sequences in a region of the genome would delete the region between those cut sites and insert themselves into the gap.

Described herein are methods for generating genetically engineered immune cells having biallelic insertion of polynucleotides encoding a polypeptide or not encoding a polypeptide.

In some embodiments, the present disclosure describes a cellular composition for administration to a subject in need thereof, the cellular composition comprising a plurality of genetically modified immune cells, the plurality of genetically modified immune cells genetically modified to express an engineered polypeptide, wherein the genetic modification comprises transfecting a plurality of immune cells with a first plasmid, the first plasmid encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells, and transfecting the plurality of immune cells with a second plasmid, the second plasmid encoding a TAT-tagged Cas9 protein, wherein the first guide ribonucleic acid directs the TAT-tagged Cas9 protein to cleave the target genomic sequence in the plurality of immune cells.

In other embodiments, the present disclosure describes a cellular composition for administration to a subject in need thereof, the cellular composition comprising, a plurality of genetically modified immune cells, the plurality of genetically modified immune cells genetically modified to express an engineered polypeptide, wherein the genetic modification comprises, transducing a plurality of immune cells with a first vector, the first vector encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a first target genomic sequence in the plurality of immune cells; and, transducing the plurality of immune cells with a second vector, the second vector encoding a TAT-tagged Cas9 protein, wherein the first guide ribonucleic acid directs the TAT-tagged Cas9 protein to cleave the first target genomic sequence in the plurality of immune cells.

In some embodiments, the present disclosure describes a cellular composition for administration to a subject in need thereof, the cellular composition comprising, a plurality of genetically modified immune cells, the plurality of genetically modified immune cells genetically modified to express an engineered polypeptide, wherein the genetic modification comprises, transfecting a plurality of immune cells with a first plasmid, the first plasmid encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and delivering a TAT-tagged Cas9 protein, wherein the first guide ribonucleic acid directs the TAT-tagged Cas9 protein to cleave the target genomic sequence in the plurality of immune cells, to the plurality of immune cells.

In other embodiments, the present disclosure describes a cellular composition for administration to a subject in need thereof, the cellular composition comprising, a plurality of genetically modified immune cells, the plurality of genetically modified immune cells genetically modified to express an engineered polypeptide, wherein the genetic modification comprises, transducing a plurality of immune cells with a first vector, the first vector encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a first target genomic sequence in the plurality of immune cells; and, delivering a TAT-tagged Cas9 protein, wherein the first guide ribonucleic acid directs the TAT-tagged Cas9 protein to cleave the target genomic sequence in the plurality of immune cells, to the plurality of immune cells.

In some embodiments, the first and the second plasmids are co-transfected into the plurality of immune cells. In other embodiments, the first and the second vectors are co-transduced into the plurality of immune cells.

In some embodiments, the first plasmid is co-administered with the TAT-tagged Cas9 protein into the plurality of immune cells. In other embodiments, the first plasmid is co-administered with the TAT-tagged Cas9 protein into the plurality of immune cells.

In some embodiments, the genetic modification further comprises, forming an endonuclease complex in the plurality of immune cells, wherein the endonuclease complex comprises the TAT-tagged Cas9 and the first guide ribonucleic acid, cleaving a first allele of the first target genomic sequence in the plurality of immune cells by the endonuclease complex, inserting the first guide ribonucleic acid, the second guide ribonucleic acid, and the effector cassette encoding the engineered polypeptide into the cleaved portion of the first allege of the first target genomic sequence, cleaving a second allele of the first target genomic sequence in the plurality of immune cells by the endonuclease complex; and inserting the first guide ribonucleic acid, the second guide ribonucleic acid, and the effector cassette encoding the engineered polypeptide into the cleaved portion of the second allege of the first target genomic sequence In some embodiments, inserting further comprises homology directed repair. In some embodiments, steps of the method cause a biallelic insertional mutation into the first target genomic sequence.

In some embodiments, the genetic modification further comprises cleaving the second target genomic sequence in the plurality of immune cells, wherein the second guide ribonuclease directs the TAT-tagged Cas9 to cleave the second target genomic sequence at a catalytic residue. In some embodiments, cleaving further comprises non-homologous end-joining. In some embodiments, cleaving results in a biallelic mutation of the second target genomic sequence.

In some embodiments, the plurality of immune cells is selected from a group consisting of T cells, natural killer cells, B cells, macrophages, monocytes, neutrophils and antigen presenting cells. In some embodiments, the engineered polypeptide is selected from a group consisting of a chimeric antigen receptor, a T cell receptor and a negative regulatory receptor.

In some embodiments, the first target genomic sequence or the second target genomic sequence is naturally occurring in the plurality of immune cells. In some embodiments, the first target genomic sequence encodes a polypeptide of a first regulatory pathway in the plurality of immune cells. In some embodiments, the first regulatory pathway comprises argininosuccinate synthase 1.

In some embodiments, the second target genomic sequence encodes a polypeptide of a second regulatory pathway in the plurality of immune cells. In some embodiments, the second regulatory pathway comprises CTLA-4, BTLA, PD-1, TIM-3, LAIR-1, Siglecs, TIGIT or Lag-3.

In some embodiments, the first target genomic sequence or the second target genomic sequence is a non-naturally occurring sequence inserted into the genomic DNA of the plurality of immune cells. In some embodiments, the non-naturally occurring sequence is of bacterial, viral, mammalian or synthetic origin. In some embodiments, the non-naturally occurring sequence is a binding site for a polypeptide.

In some embodiments, the polypeptide binds to a molecule, wherein the molecule is a drug, an amino acid or a hairpin RNA. In some embodiments, the drug is tamoxifen or tetracycline. In some embodiments, the first target genomic sequence or the second target genomic sequence encodes a suicide gene. In some embodiments, the suicide gene is Bax or Bcl-2.

In some embodiments, the chimeric antigen receptor comprises an scFV recognizing an antigen selected from the group consisting of CD19, CD20, CD30, CD33, CD44v7/8, CD122, α-folate receptor, CAIX, CEA, FBP, L1CAM, EGP-2, EGP-40, ERB-B2, heregulin, fetal acetylcholine receptor, GD2, GD3, Her2/neu, IL-13R-a2, KDR, LeY, k-light chain, MAGE-A1, mesothelin, MUC-1, NKG2D ligands, NKG2D receptors, oncofetal antigen, PSCA, PSMA, VEGF-R2, TAG-72 and TAA targeted by mAb IgE. In some embodiments, the negative regulatory receptor comprises an antigen recognition domain, wherein the antigen binding domain recognizes an antigen selected from the group consisting of CTLA-4, BTLA, PD-1, TIM-3, LAIR-1, Siglecs, TIGIT and Lag-3. In some embodiments, the scFV further comprises two different scFV regions so as to recognize more than one antigen. In some embodiments, the scFV region further comprises a linker between the two different scFV regions. In some embodiments, the linker is flexible.

In some embodiments, the antigen recognition domain further comprises two different antigen recognition domains so as to recognize more than one antigens. In some embodiments, the antigen recognition domain further comprises a linker between the two different antigen recognition domains. In some embodiments, the linker is flexible.

In some embodiments, the present disclosure describes a method of preparing a cellular composition of genetically modified immune cells genetically modified to express an engineered polypeptide for administration to a subject in need thereof, the method of preparing the cellular composition of genetically modified immune cells comprising, transfecting a plurality of immune cells with a first plasmid, the first plasmid encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and transfecting the plurality of immune cells with a second plasmid, the second plasmid encoding a TAT-tagged Cas9 protein, wherein the first guide ribonucleic acid directs the TAT-tagged Cas9 protein to cleave the target genomic sequence in the plurality of immune cells.

In other embodiments, the present disclosure describes a method of preparing a cellular composition of genetically modified immune cells genetically modified to express an engineered polypeptide for administration to a subject in need thereof, the method of preparing the cellular composition of genetically modified immune cells comprising, transducing a plurality of immune cells with a first vector, the first vector encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and transducing the plurality of immune cells with a second vector, the second vector encoding a TAT-tagged Cas9 protein, wherein the first guide ribonucleic acid directs the TAT-tagged Cas9 protein to cleave the target genomic sequence in the plurality of immune cells.

In some embodiments, the present disclosure describes a method of preparing a cellular composition of genetically modified immune cells genetically modified to express an engineered polypeptide for administration to a subject in need thereof, the method of preparing the cellular composition of genetically modified immune cells comprising, transfecting a plurality of immune cells with a first plasmid, the first plasmid encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and delivering a TAT-tagged Cas9 protein, wherein the first guide ribonucleic acid directs the TAT-tagged Cas9 protein to cleave the target genomic sequence in the plurality of immune cells, to the plurality of immune cells.

In other embodiments, the present disclosure describes a method of preparing a cellular composition of genetically modified immune cells genetically modified to express an engineered polypeptide for administration to a subject in need thereof, the method of preparing the cellular composition of genetically modified immune cells comprising, transducing a plurality of immune cells with a first vector, the first vector encoding, a first guide ribonucleic acid targeting a first target genomic sequence in the plurality of immune cells, a second guide ribonucleic acid targeting a second target genomic sequence in the plurality of immune cells, an effector cassette encoding the engineered polypeptide, a first flanking genomic sequence, and, a second flanking genomic sequence, wherein the first flanking genomic sequence and the second flanking genomic sequence flank a target genomic sequence in the plurality of immune cells; and, delivering a TAT-tagged Cas9 protein, wherein the first guide ribonucleic acid directs the TAT-tagged Cas9 protein to cleave the target genomic sequence in the plurality of immune cells, to the plurality of immune cells.

In some embodiments, the first and the second plasmids are co-transfected into the plurality of immune cells. In some embodiments, the first and the second vectors are co-transduced into the plurality of immune cells. In some embodiments, the first plasmid is co-administered with the TAT-tagged Cas9 protein into the plurality of immune cells. In some embodiments, the first plasmid is co-administered with the TAT-tagged Cas9 protein into the plurality of immune cells.

In some embodiments, the genetic modification further comprises, forming an endonuclease complex in the plurality of immune cells, wherein the endonuclease complex comprises the TAT-tagged Cas9 and the first guide ribonucleic acid, cleaving a first allele of the first target genomic sequence in the plurality of immune cells by the endonuclease complex, inserting the first guide ribonucleic acid, the second guide ribonucleic acid, and the effector cassette encoding the engineered polypeptide into the cleaved portion of the first allege of the first target genomic sequence, cleaving a second allele of the first target genomic sequence in the plurality of immune cells by the endonuclease complex; and inserting the first guide ribonucleic acid, the second guide ribonucleic acid, and the effector cassette encoding the engineered polypeptide into the cleaved portion of the second allege of the first target genomic sequence In some embodiments, inserting further comprises homology directed repair. In some embodiments, the genetic modification further comprises biallelic insertional mutation into the first target genomic sequence.

In some embodiments, the genetic modification further comprises, cleaving the second target genomic sequence in the plurality of immune cells, wherein the second guide ribonuclease directs the TAT-tagged Cas9 to cleave the second target genomic sequence at a catalytic residue. In some embodiments, the cleaving further comprises non-homologous end-joining. In some embodiments, the cleaving results in a biallelic mutation of the second target genomic sequence.

In some embodiments, the plurality of immune cells is selected from a group consisting of T cells, natural killer cells, B cells, macrophages, monocytes, neutrophils and antigen presenting cells. In some embodiments, the engineered polypeptide is selected from a group consisting of a chimeric antigen receptor, a T cell receptor and a negative regulatory receptor. In some embodiments, the first target genomic sequence or the second target genomic sequence is naturally occurring in the plurality of immune cells.

In some embodiments, the first target genomic sequence encodes a polypeptide of a first regulatory pathway in the plurality of immune cells. In some embodiments, the first regulatory pathway comprises argininosuccinate synthase 1.

In some embodiments, the second target genomic sequence encodes a polypeptide of a second regulatory pathway in the plurality of immune cells. In some embodiments, the second regulatory pathway comprises CTLA-4, BTLA, PD-1, TIM-3, LAIR-1, Siglecs, TIGIT or Lag-3.

In some embodiments, the first target genomic sequence or the second target genomic sequence is a non-naturally occurring sequence inserted into the genomic DNA of the plurality of immune cells. In some embodiments, the non-naturally occurring sequence is of bacterial, viral, mammalian or synthetic origin. In some embodiments, the non-naturally occurring sequence is a binding site for a polypeptide.

In some embodiments, the polypeptide binds to a molecule, wherein the molecule is a drug, an amino acid or a hairpin RNA. In some embodiments, the drug is tamoxifen or tetracycline. In some embodiments, the first target genomic sequence or the second target genomic sequence encodes a suicide gene. In some embodiments, the suicide gene is Bax or Bcl-2.

In some embodiments, the chimeric antigen receptor comprises an scFV recognizing an antigen selected from the group consisting of CD19, CD20, CD30, CD33, CD44v7/8, CD122, α-folate receptor, CAIX, CEA, FBP, L1CAM, EGP-2, EGP-40, ERB-B2, heregulin, fetal acetylcholine receptor, GD2, GD3, Her2/neu, IL-13R-a2, KDR, LeY, k-light chain, MAGE-A1, mesothelin, MUC-1, NKG2D ligands, NKG2D receptors, oncofetal antigen, PSCA, PSMA, VEGF-R2, TAG-72 and TAA targeted by mAb IgE. In some embodiments, the scFV further comprises two different scFV regions so as to recognize more than one antigen. In some embodiments, the scFV region further comprises a linker between the two different scFV regions. In some embodiments, the linker is flexible.

In some embodiments, the antigen recognition domain further comprises two different antigen recognition domains so as to recognize more than one antigens. In some embodiments, the antigen recognition domain further comprises a linker between the two different antigen recognition domains. In some embodiments, the linker is flexible.

In some embodiments, the negative regulatory receptor comprises an antigen recognition domain, wherein the antigen binding domain recognizes an antigen selected from the group consisting of CTLA-4, BTLA, PD-1, TIM-3, LAIR-1, Siglecs, TIGIT and Lag-3.

In some embodiments, a vector comprising polynucleotides are often introduced into an immune cell, often a T cell, along with purified Cas9 protein to achieve biallelic insertion of a portion of the polynucleotides of the vector. In some embodiments, the polynucleotides further comprise gRNA, a single gRNA (e.g., gRNA1), two gRNA (e.g., gRNA1 and gRNA2) or more gRNAs. In some embodiments, the Cas9 protein is tagged with TAT tag, often the TAT tag is useful for purifying Cas9 protein. The Cas9 protein interacts with gRNA resulting in biallelic chromosomal insertion of some of the polypeptides of the vector.

Figure 6A:
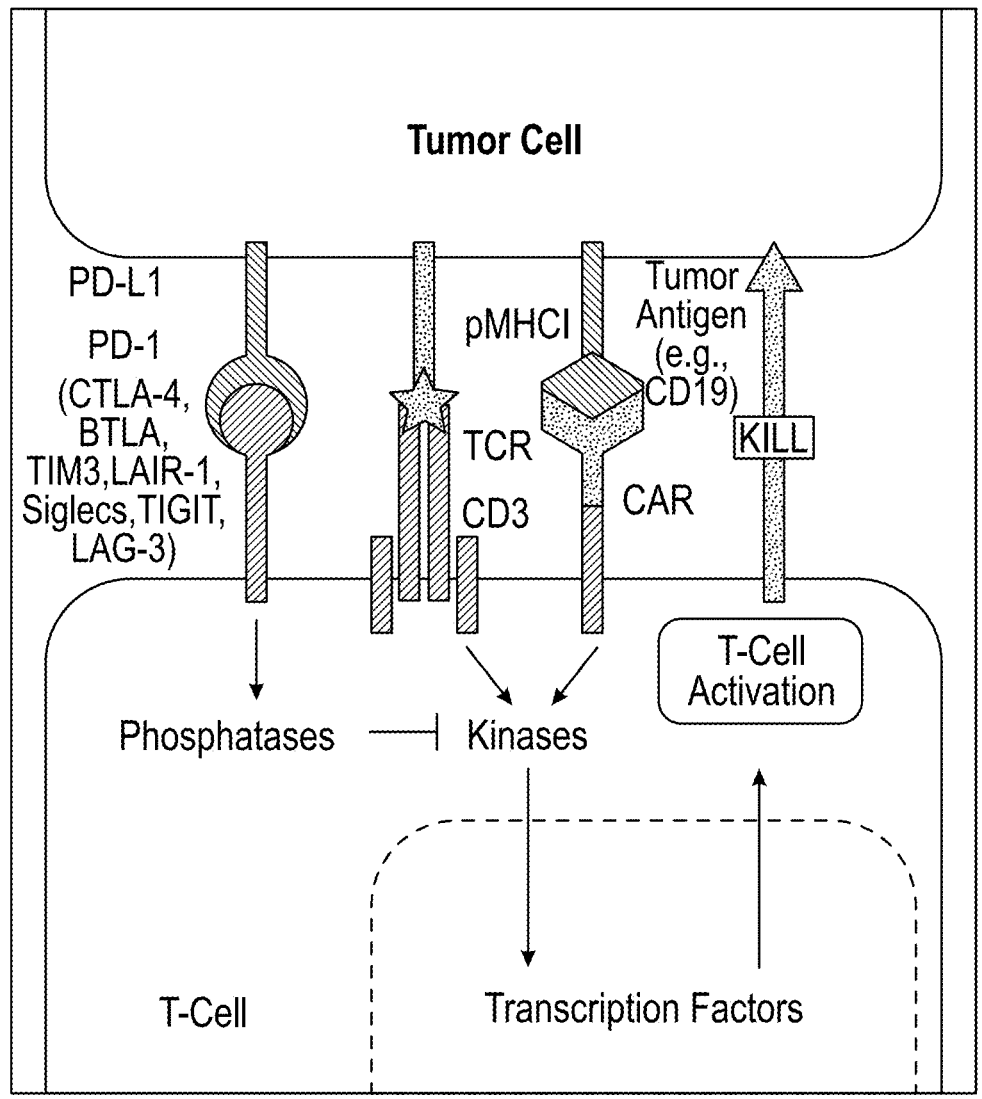
FIG. 6A is a schematic illustration of an immune cell genetically modified for biallelic expression of an engineered polypeptide as described herein interacting with an antigen presenting cell.
Figure 6B:
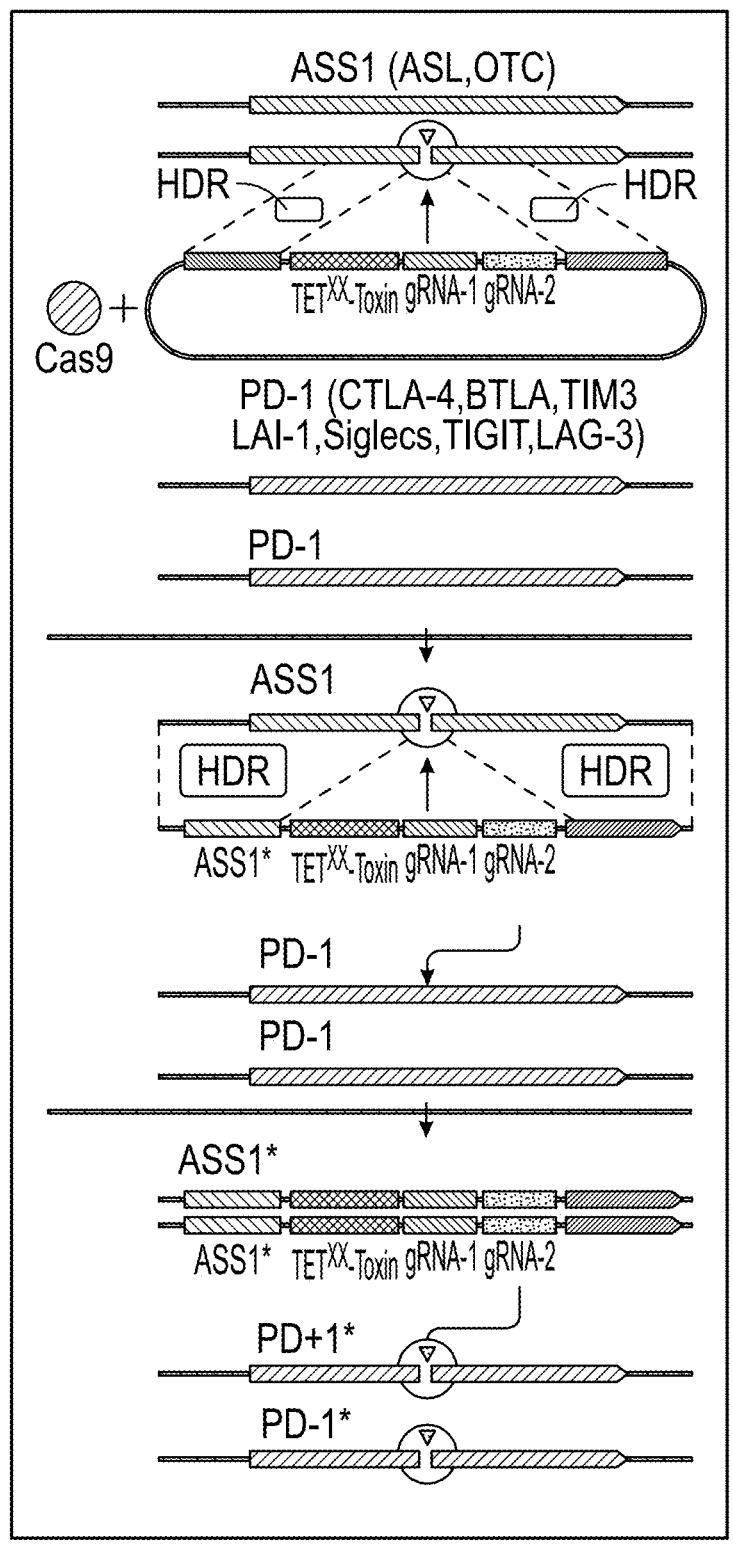
FIG. 6B is a schematic illustration demonstrating the use of the CRISPR/Cas9 system of the present disclosure to genetically modify an immune cell for biallelic disruption of the PD1 gene and for arginine auxotrophy using a tetracycline responsive promoter by insertion into the ASS1 locus.
Figure 6C:
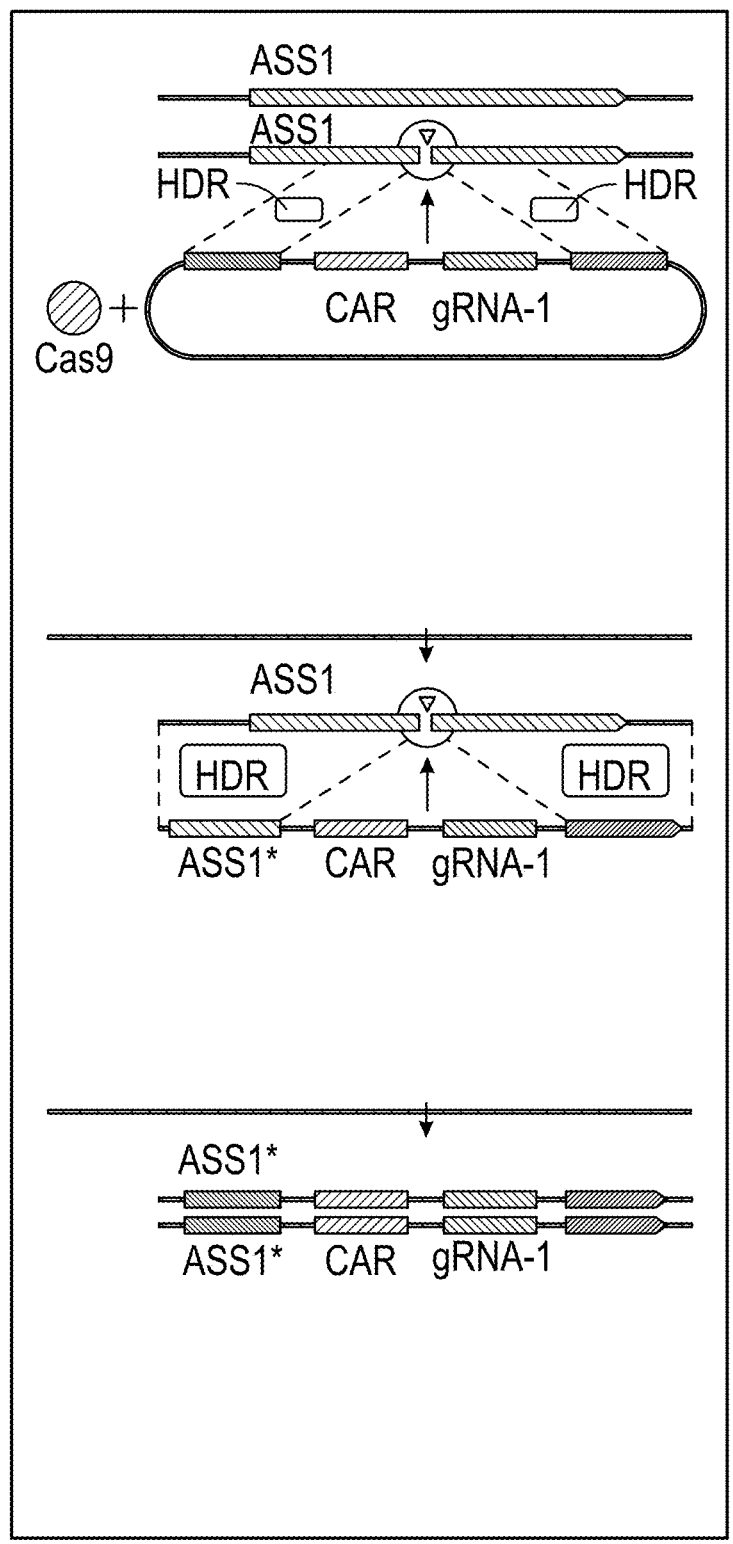
FIG. 6C is a schematic illustration demonstrating the use of the CRISPR/Cas9 system of the present disclosure to genetically modify an immune cell for biallelic expression of a chimeric antigen receptor under arginine auxotrophy by insertion of the CAR cassette into the ASS1 locus using gRNA cassettes.
Figure 6D:
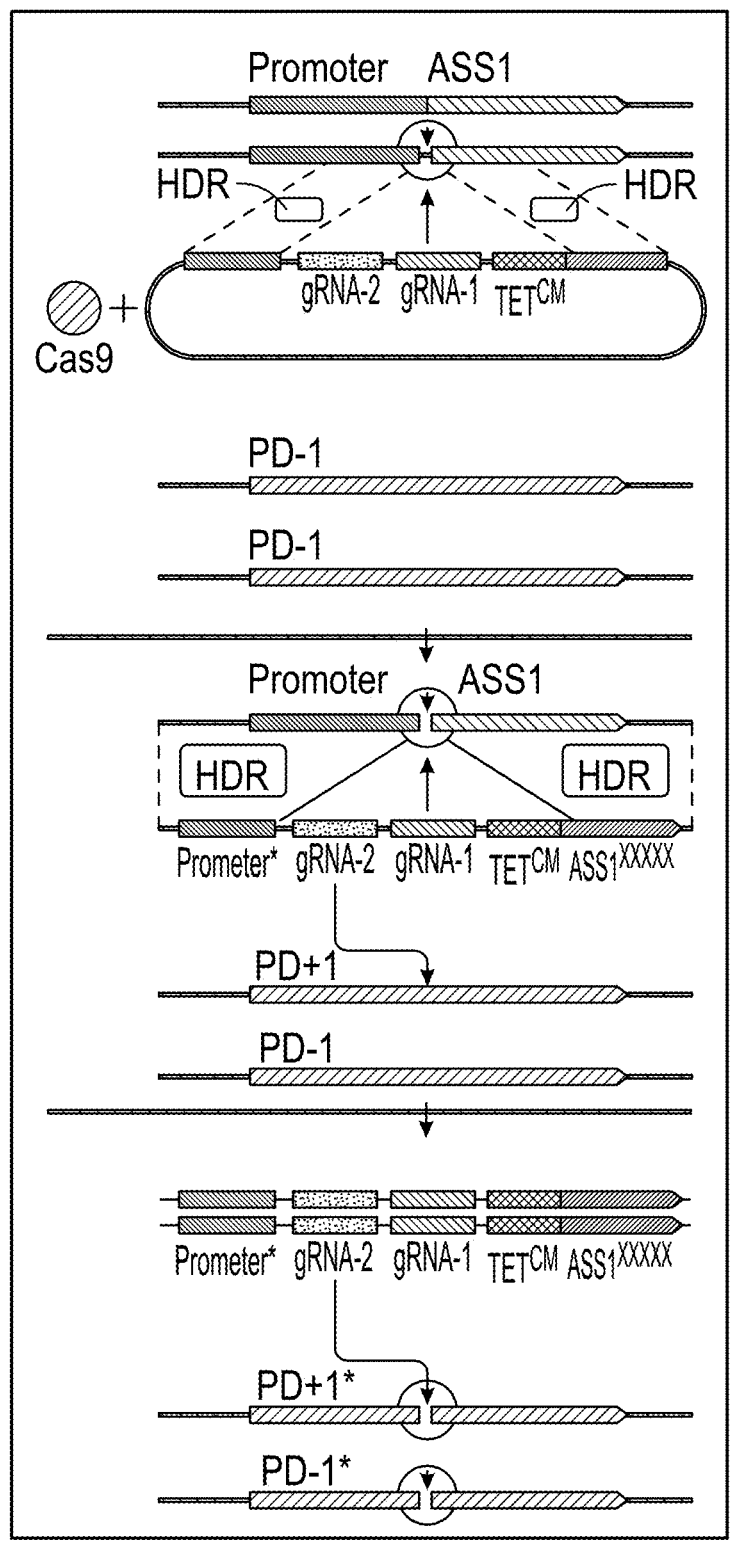
FIG. 6D is a schematic illustration demonstrating biallelic insertion of the present disclosure at a locus to regulate the ASS1 gene with the drug responsive TET-on promoter and to disrupt the PD-1 gene.

In some embodiments, the vector comprises cassettes of polynucleotides including, but not limited to, a gRNA1 targeting Cas9-mediated insertion of the gRNA1 into a locus of the immune cell genomic DNA. For example, the locus is targeted by a sequence of polynucleotides comprising the gRNA1 cassette, such as, the locus required for arginine biosynthesis (e.g., ASS1) thereby rendering the immune cells auxotrophic for arginine either by abolishing ASS1 function (FIG. 6B and FIG. 6D). By way of another example, the locus is targeted by a sequence of polynucleotides comprising the gRNA1 cassette, such as by placing expression of the gene or locus required for arginine biosynthesis (e.g., ASS1) under control of a drug-responsive gene expression system. In some embodiments, the vector comprises cassettes of polynucleotides including, but not limited to, an effector cassette, for example, an effector cassette encoding a CAR, encoding a toxin gene and/or encoding a regulatory system for expression such as a drug regulatory system. (FIG. 6C). In some embodiments, the vector comprises cassettes of polynucleotides including, but not limited to, a gRNA2 that targets a gene encoding an inhibitory receptor (e.g., PD-1, CTLA-4, BTLA, TIM3, LAIR-1, Siglecs, TIGIT, LAG-3) and targeting Cas9-mediated insertion of the gRNA2 into the immune cell genomic DNA at the desired locus.

A Chimeric Antigen Receptor (CAR) often includes at least, but is not limited to, an antigen recognition portion, a transmembrane portion and an intracellular portion. The antigen recognition portion is often similar to an antigen recognition portion of an antibody or is any polypeptide generally capable of i) recognizing to an antigen on a target cell or ii) binding to an antigen on a target cell. The antigen recognition portion, otherwise referred to herein as the scFV includes, but is not limited to, the antigen recognition portion to recognize, but is not limited to, the following antigens, or families of proteins including each of the following antigens; CD19, CD20, CD30, CD33, CD44v7/8, CD122, α-folate receptor, CAIX, CEA, FBP, L1CAM, EGP-2, EGP-40, ERB-B2, heregulin, fetal acetylcholine receptor, GD2, GD3, Her2/neu, IL-13R-a2, KDR, LeY, k-light chain, MAGE-A1, mesothelin, MUC-1, NKG2D ligands, NKG2D receptors, oncofetal antigen, PSCA, PSMA, VEGF-R2, TAG-72 and TAA targeted by mAb IgE. In some embodiments, the scFV further comprises two different scFV regions so as to recognize more than one of the antigens selected from the group wherein the scFV region further comprises a linker between the two different scFV regions. By "recognition", "recognizing" and the like, said antigen recognition portion responds to the presence of a given antigen with the response affected as a conformational change, a change in behavior by the immune cell expressing the CAR, or the like. The antigen recognition portion of the CAR is specific to a given polypeptide sequence of an antigen, a given shape of an antigen or a combination of the polypeptide sequence and the same of the antigen. The antigen recognition portion recognizes a single antigen, a set of antigens having homology to a single antigen or the like. Often the homology is less than 1%, less than 2%, less than 3%, less than 5%, less than 10%, less than 15%, less than 20%, less than 25% or less than 30% different from the single antigen. (FIG. 6C)

By "recognition", "recognizing" and the like, the antigen recognition portion responds to the presence of a given antigen with the response affected as a conformational change, a change in behavior by the immune cell expressing the CAR, TCR, Negative Regulatory Polypeptide, Inhibitory Polypeptide, Negative Regulatory Receptor, Inhibitory Receptor, or the like. The antigen recognition portion of the CAR, TCR, Negative Regulatory Polypeptide, Inhibitory Polypeptide, Negative Regulatory Receptor, Inhibitory Receptor, or the like is specific to a given polypeptide sequence of an antigen, a given shape of an antigen or a combination of the polypeptide sequence and the same of the antigen. The antigen recognition portion recognizes a single antigen, a set of antigens having homology to a single antigen or the like. Often the homology is less than 1%, less than 2%, less than 3%, less than 5%, less than 10%, less than 15%, less than 20%, less than 25% or less than 30% different from the single antigen.

The methods and compositions described herein are efficient at generating biallelic insertions of effector molecules (e.g., CARs, TCRs, negative inhibitory receptors, cytokines, cytokine receptors, costimulatory receptors and the like). In some embodiments, the effector molecules comprise a naturally occurring polynucleotide sequence or a naturally occurring polynucleotide sequence modified so as to mutate one or more amino acid residues of the effector molecule. Additionally, the methods and compositions described herein are useful for genetically engineering cells to comprise larger inserts of polynucleotides into the genome, often with high efficiency and fidelity. The use of large inserts is beneficial to deliver a plurality of desired cassettes, often by targeted insertion and the expression of which is regulated by cis-regulatory mechanisms. For example, a plurality of CARs, TCRs and negative regulatory molecules as well as cytokines, cytokine receptors, costimulatory molecules and the like are considered in addition to gRNAs targeting other loci such as receptors for inhibitory pathways, or conditional cis-regulatory sequences that could be targeted for insertion adjacent to endogenous genes placed under regulatory control by agents such as drugs, small molecules or the like. Any combination of CARs, TCRs and negative regulatory molecules as well as cytokines, cytokine receptors, costimulatory molecules and the like, as well as receptors for inhibitory pathways, or conditional cis-regulatory sequences is understood as useful with the methods and compositions described herein.

Accordingly, an integrated set of cassettes are delivered into immune cells, such as T cells, in a single round of treatment so as to reduce both the number of ex vivo cell divisions and minimize the time from isolation of immune cells from a subject to administration of genetically engineered immune cells to a patient in need thereof, often targeting the disease or condition, such as cancer. For example, such advantages could mean the difference between life and death in a subject with late-stage metastatic cancer.

The methods and compositions described herein are often for administration to a subject in need thereof. Often, administration of an immunogenic composition includes routes of administration including, but not limited to, intravenous, intraarterial, subcutaneous, subdural, intramuscular, intrancranial, intrasternal, intratumoral, or additional techniques known to those of ordinary skill in the art.

Immune cells are genetically engineered as described herein to comprise one of the following, a gRNA1, an expression cassette or a plurality of expression cassettes or a gRNA 2. Immune cells are genetically engineered as described herein to comprise more than one of the following, a gRNA1, an expression cassette or a plurality of expression cassettes or a gRNA 2. In an exemplary embodiment, immune cells are genetically engineered as described herein to comprise a gRNA1, an expression cassette or a plurality of expression cassettes or a gRNA 2 which should result in the generation of long acting transgenic immune cells that target specific cells having a or of a disease or a condition of the subject. In an exemplary embodiment, the immune cells are T cells that target cancer via endogenous pMHCI-mediated and/or CAR-mediated antigen recognition that are auxotrophic for arginine due to disruption of the ASS1 gene. T cells should eliminate the targeted cancer cell and is regulated by treatment with agents that affect the pathway targeted by an effector cassette of the vector, such as a toxin, a pro-apoptotic factor (e.g., Bax), a molecule tagging the cell for immune recognition, for example, an agent could deplete levels of free arginine (e.g., arginine deiminase "ADI", or "arginase I") or induce expression of an effector gene so as to avoid complications with the treatment, such as autoimmune affects, toxicity to non-target cells or other complications known to one of ordinary skill in the art.

Other exemplary means of controlling T cells include, but are not limited to, targeted insertion of the cassette into other genes required for synthesis of arginine (e.g., ASL, OTC), of other amino acids (e.g., asparagine synthetase "ASY", or serine biosynthetic enzymes) or of enzymes required for production of cell non-autonomous metabolites (e.g., an activated form of Pyruvate Kinase 2 "PKM2"). In addition, insertion of a drug responsive cis-regulatory sequences targeted next to a gene of interest could either silence or activate expression of that gene by providing or withdrawing the drug of the responsive cis-regulatory sequences. Drug responsive cis-regulatory sequences include those known to one of ordinary skill in the art, such as for example, but not limited to, the tetracycline on/off system and the tamoxifen system.

As described further herein, a constitutive promoter is a nucleotide sequence which causes the nucleic acid sequence, often in an expression cassette, encoding a polypeptide to be produced in the immune cell. On the contrary, an "inducible" promoter is a nucleotide sequence which causes the nucleic acid sequence, often in an expression cassette, encoding a polypeptide to be produced in the immune cell when an inducer (e.g., small molecule inducible transcription factor, such as those which respond to the presence of small molecules such as tamoxifen, arginine, etc.) is present in the cell. A tissue-specific promoter is a nucleotide sequence which causes the nucleic acid sequence, often in an expression cassette, encoding a polypeptide to be produced in the immune cell if the immune cell is an immune cell of the tissue type corresponding to the type of tissue associated with the promoter.

Described herein are compositions of genetically engineered immune cells as well as methods for preparation of compositions of genetically engineered immune cells and methods for treatment of a disease such as cancer, using genetically engineered immune cells proteins expressing CARs, TCRs and/or modified negative or inhibitory molecules. The immune cells described herein are genetically engineered using the CRISPR and Cas9 as described herein. Using the CRISPR/Cas9 system as described herein, CARs, TCRs and/or modified negative or inhibitory molecules are transferred into immune cells using a method having at least the following benefits, (1) biallelic insertion of a polynucleotide into the DNA of the immune cells, (2) targeted insertion using a gRNA, and, (3) transfer of large amounts of polynucleotides into the DNA at the gRNA directed insertion site of the immune cells. Three examples of the methods and compositions described herein are depicted in FIGS. 1A-1D.

CRISPR/Cas System

DNA cuts generated by an endonuclease such as Cas9 may be corrected using different cellular repair mechanisms, including error-prone Non-homologous End Joining (NHEJ)

and Homology Directed Repair (HDR). Both MCR or NCR elements are often integrated into a genome using homology directed repair.

In general, traditional CRISPR application use NHEJ (~5-20% efficiency). The mutagenic chain reaction or neutralizing chain reaction may use HDR (~90-100% efficiency). The broader term active genetics applies to the use of any construct in which a Cas9 source drives the insertion of a DNA cassette into a particular locus using a gRNA encoded within that cassette. MCR elements, NCR elements, and CopyCat elements are examples of active genetic elements. Active genetic-based applications may be more efficient than traditional CRISPR in generating precise genome edits. In some embodiments, the efficiency of an MCR or NCR element integrating into a genome is about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some embodiments, the efficiency of an MCR or NCR element integrating into a genome is at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, or 99.9%. In some embodiments, the efficiency of an MCR or NCR element integrating into a genome is up to about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100%. In some embodiments, the efficiency of allelic conversion of an MCR or NCR element into a genome is about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some embodiments, the efficiency of allelic conversion of an MCR or NCR element into a genome is at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, or 99.9%. In some embodiments, the efficiency of allelic conversion of an MCR or NCR element into a genome is up to about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100%.

Active genetic elements, such as for example, the MCR, NCR, and/or CopyCat elements, are often used to copy DNA fragments >10 kb. DNA of such size allows for flexibility when engineering applications from plants to human therapies. In some embodiments, the MCR or NCR element integrated into a genome is about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, or more than 50 kilobases (kb) in length. In some embodiments, active genetic elements, such as for example, the MCR, NCR, and/or CopyCat element integrated into a genome is at least about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, or more than 50 kilobases (kb) in length. In some embodiments, the MCR or NCR element integrated into a genome is up to about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, or more than 50 kilobases (kb) in length.

MCR elements nearly double their frequency in a population at each generation, as they convert chromosomes derived from non-MCR parents to the MCR condition. This results in a potent gene drive systems for spreading beneficial genes or exogenous DNA fragments throughout populations of animal, mammalian, non-human primate and primate cells. The same autocatalytic property could be engineered to spread effector transgenes among specific cell populations within an individual (e.g.: cancerous cells). This property enables new gene therapy approaches. In some embodiments, the frequency of an MCR or NCR element increases in a population in a generation by a factor of about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, or more than 3. In some embodiments, the frequency of an MCR or NCR element increases in a population in a generation by a factor of at least about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, or more than 3. In some embodiments, the frequency of an MCR or NCR element increases in a population in a generation by a factor of up to about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, or more than 3.

Endonucleases are enzymes that cleave the phosphodiester bond within a polynucleotide chain. Endonucleases include, but are not limited to, Cas proteins, restriction endonucleases, meganucleases, homing endonucleases, TAL effector nucleases, and Zinc finger nucleases. Restriction endonucleases include, but are not limited to, Type I, Type II, Type III, Type IV, and Type V endonucleases, any one of which further include subtypes. Cas proteins include, but are not limited to, Cas1, Cas1B, Cas2, Cas3, Cas3' (Cas3-prime), Cas3" (Cas3-double prime), Cas4, Cas5, Cas6, Cas6e (formerly referred to as Embodiment, Cse3), Cas6f (i.e., Csy4), Cas7, Cas8, Cas8a1, Cas8a2, Cas8b, Cas8c, Cas9 (also known as Csn1 and Csx12), Cas10, Cas10d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, and modified versions thereof. An endonuclease is Cas9, and is often a Cas9 from *S. pyogenes, S. pneumoniae, S. aureus*, or *S. thermophilus*.

A Cas9 protein may recognize a protospacer adjacent motif (PAM) sequence comprising NGG. A Cas9 protein may recognize a protospacer adjacent motif (PAM) sequence that does not comprise NGG. A Cas9 protein may recognize a protospacer adjacent motif (PAM) sequence comprising NNGRRT, such as TTGAAT or TTGGGT.

An endonuclease may have DNA cleavage activity, such as Cas9. In some embodiments, an endonuclease directs cleavage of one or both strands at the location of a target sequence, such as within the target sequence and/or within the complement of the target sequence. In some embodiments, an endonuclease directs cleavage of one or both strands within about or at least about 1, 2, 3, 4, 5, 6, 7, 8, 9, 10, 15, 20, 25, 50, 100, 200, 500, or more base pairs from the first or last nucleotide of a target sequence.

In some embodiments, an endonuclease is mutated with respect to a corresponding wild-type enzyme such that the mutated endonuclease lacks the ability to cleave one or both strands of a target polynucleotide containing a target sequence. For example, an aspartate-to-alanine substitution (e.g., D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In some embodiments, the Cas protein (e.g., Cas9 protein) may be a nickase. In aspects of the disclosure, nickases may be used for genome editing via homologous recombination. In some embodiments, a Cas9 nickase may be used in combination with guide polynucleotide(s), e.g., two guide polynucleotides, which target respectively sense and antisense strands of the DNA target. Two or more catalytic domains of Cas9 (RuvC I, RuvC II, and RuvC III) may be mutated to produce a mutated Cas9 substantially lacking DNA cleavage activity. In some embodiments, a D10A mutation is combined with one or more of H840A, N854A, or N863A mutations to produce a Cas9 enzyme substantially lacking DNA cleavage activity. In some embodiments, an endonuclease is considered to substantially lacking DNA cleavage activity when the DNA cleavage activity of the mutated endonuclease is about or less than about 25%, 20%, 15%, 10%, 5%, 4%, 3%, 2%, 1%, 0.5%, 0.1%, 0.05%, 0.01%, or lower than 0.01% with respect to its non-mutated form.

In some embodiments, a gene encoding an endonuclease (e.g., a Cas protein such as Cas9) is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cell of interest by replacing at least one codon (e.g., about or at least about 1, 2, 3, 4, 5, 10, 15, 20, 25, 50, or more than 50 codons) of the native sequence with codons that are more frequently or most frequently used in the genes of that host cell while maintaining the native amino acid sequence. Various species may exhibit particular bias for certain codons of a particular amino acid. Codon bias (differences in codon usage between organisms) may correlate with the efficiency of translation of messenger RNA (mRNA), which may depend on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. In some embodiments, one or more codons (e.g., 1, 2, 3, 4, 5, 10, 15, 20, 25, 50, more than 50, or all codons) in a sequence encoding an endonuclease correspond to the most frequently used codon for a particular amino acid. In certain embodiments, a gene encoding an endonuclease may not be codon optimized.

In some embodiments, an endonuclease is part of a fusion protein comprising one or more heterologous peptide or protein domains (e.g., about or at least about 1, 2, 3, 4, 5, 6, 7, 8, 9, 10, or more than 10 domains in addition to an endonuclease). An endonuclease fusion protein may comprise any additional peptide or protein sequence, and optionally a linker sequence between any two domains. Examples of peptide or protein domains that may be fused to an endonuclease include, without limitation, epitope tags, reporter gene sequences, localization signals, and protein domains having one or more of the following activities: methylase activity, demethylase activity, transcription activation activity, transcription repression activity, transcription release factor activity, histone modification activity, RNA cleavage activity, and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), other fluorescent proteins, and autofluorescent proteins including blue fluorescent protein (BFP). An endonuclease may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Examples of localization signals include, but are not limited to, nuclear localization signals (e.g., SV40 large T-antigen, acidic M9 domain of hnRNP A1), cytoplasmic localization signals, mitochondrial localization signals, nuclear export signals, chloroplast localization signals, and endoplasmic reticulum retention signals. In some embodiments, a tagged endonuclease is used to identify the location of a target sequence.

As used herein, the term "guide polynucleotide", refers to a polynucleotide sequence that can form a complex with an endonuclease (e.g., Cas protein such as Cas9) and enables the endonuclease to recognize and optionally cleave a target site on a polynucleotide such as DNA. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond, or linkage modification such as, but not limited to, locked nucleic acid (LNA), peptide nucleic acid (PNA), bridged nucleic acid (BNA), 5-methyl dC, 2,6-Diaminopurine, 2'-Fluoro A, 2'-Fluoro U, 2'-O-Methyl RNA, Phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. In some embodiments, the guide polynucleotide does not solely comprise ribonucleic acids (RNAs). In other embodiments, the guide polynucleotide does solely comprise ribonucleic acids (RNAs). A guide polynucleotide that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease. The CER domain of the double molecule guide polynucleotide comprises two separate molecules that are hybridized along a region of complementarity. The two separate molecules can be RNA, DNA, and/or RNA-DNA combination sequences. In some embodiments, the duplex guide polynucleotide does not solely comprise ribonucleic acids (RNAs). In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). In some embodiments, the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides).

The guide polynucleotide can also be a single molecule comprising a first nucleotide sequence domain (referred to as Variable Targeting domain or VT domain) that is complementary to a nucleotide sequence in a target DNA and a second nucleotide domain (referred to as endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments, the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides).

The term "variable targeting domain" or "VT domain" is used interchangeably herein and refers to a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

In some embodiments, an MCR or NCR construct or element comprises about 1, 2, 3, 4, 5, 6, 7, 8, 9, 10, 15, 20, 25, 30, 35, 40, 45, 50, or more than 50 guide polynucleotides. In some embodiments, an MCR or NCR construct or element comprises at least about 1, 2, 3, 4, 5, 6, 7, 8, 9, 10, 15, 20, 25, 30, 35, 40, 45, 50, or more than 50 guide polynucleotides. In some embodiments, an MCR or NCR construct or element comprises up to about 1, 2, 3, 4, 5, 6, 7, 8, 9, 10, 15, 20, 25, 30, 35, 40, 45, 50, or more than 50 guide polynucleotides.

In some embodiments, an MCR, ERACR, CHACR, or e-CHACR construct or element comprises about or at least about 1, 2, 3, 4, 5, 6, 7, 8, 9, 10, 15, 20, 25, 30, 35, 40, 45, 50, or more than 50 guide polynucleotides. In some embodiments, an MCR, ERACR, CHACR, or e-CHACR construct or element comprises up to about 1, 2, 3, 4, 5, 6, 7, 8, 9, 10, 15, 20, 25, 30, 35, 40, 45, 50, or more than 50 guide polynucleotides.

In general, a guide polynucleotide is any polynucleotide sequence having sufficient complementarity with a target polynucleotide sequence to hybridize with the target sequence and direct sequence-specific binding of a CRISPR complex to the target sequence. In some embodiments, the degree of complementarity between a guide polynucleotide and its corresponding target sequence, when optimally aligned using a suitable alignment algorithm, is about or at least about 50%, 55%, 60%, 65%, 70%, 75%, 80%, 85%, 90%, 95%, 96%, 97%, 98%, 99%, 99.5%, 99.9%, or 100%.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide polynucleotide is about or at least about 5, 10, 11, 12, 13, 14, 15, 16, 17, 18, 19, 20, 21, 22, 23, 24, 25, 26, 27, 28, 29, 30, 35, 40, 45, 50, 75, or more than 75 nucleotides in length. In some embodiments, a guide polynucleotide is up to about 75, 50, 45, 40, 35, 30, 25, 20, 15, 12, or fewer than 12 nucleotides in length. The ability of a guide polynucleotide to direct sequence-specific binding of a CRISPR complex to a target sequence may be assessed by any suitable assay.

A guide polynucleotide may be selected to target any target sequence. In some embodiments, the target sequence is a sequence within a genome of a cell. Exemplary target sequences include those that are unique in the target genome.

A homology arm is about 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, or more than 500 nucleotides in length. In some embodiments, homology arms on an MCR, NCR, or CopyCat construct are the same length, similar lengths, or different lengths. In some embodiments, the degree of complementarity between a homology arm and its corresponding target sequence, when optimally aligned using a suitable alignment algorithm, is about or more than about 50%, 55%, 60%, 65%, 70%, 75%, 80%, 85%, 90%, 95%, 96%, 97%, 98%, 99%, 99.5%, 99.9%, or 100%. In some instances, the homology arms directly abut the endonuclease cleavage sites.

Genetic Modification of Target Polynucleotides by CRISPR/Cas System

A cell has been genetically modified by exogenous DNA, e.g., a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication.

Methods of introducing a nucleic acid into a host cell are known in the art, and any known method is often used to introduce a nucleic acid (e.g., an expression construct) into a cell. Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

Figure 2D:
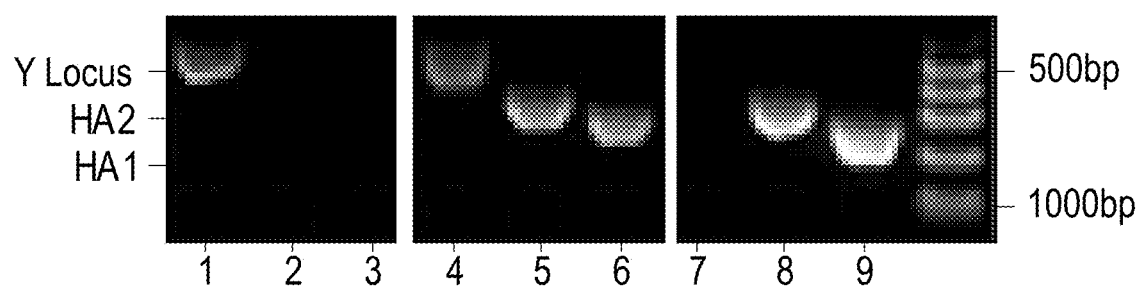
Figure 2E:
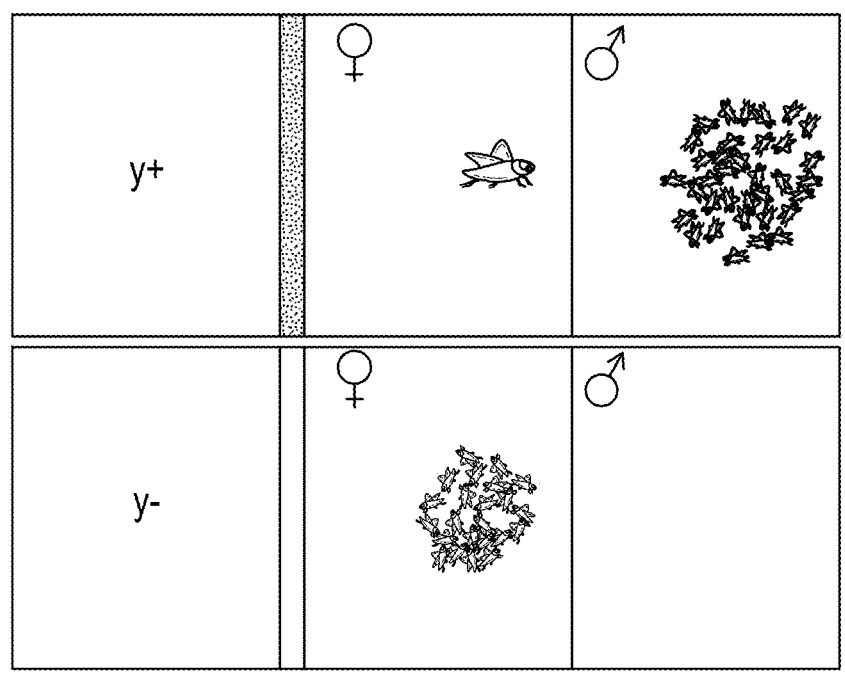
Figures 2F, 2G, 2H:
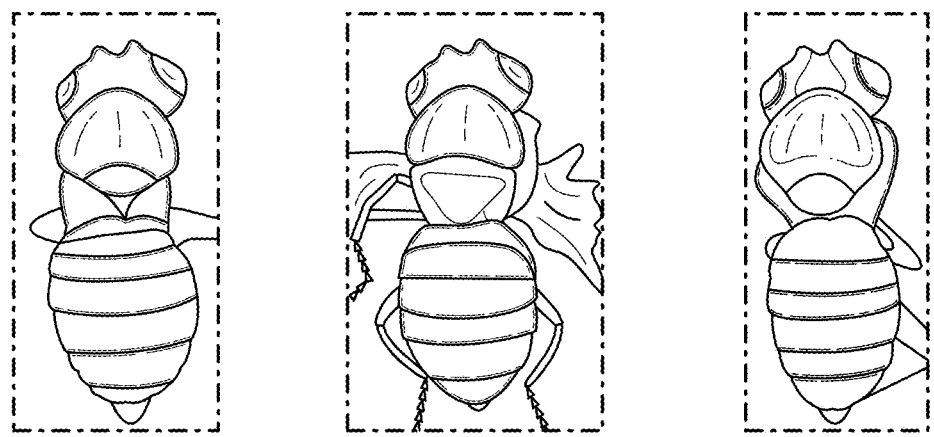
Figure 3A:
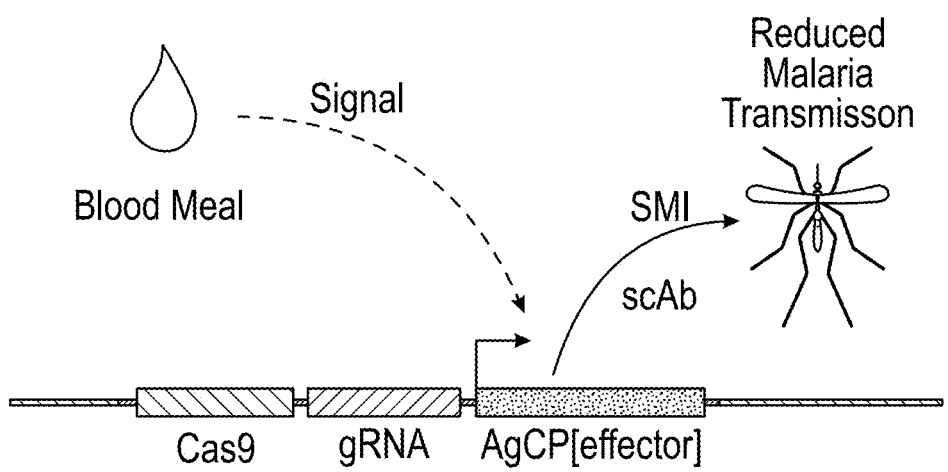
FIGS. 3A-3D describes some potential applications of MCR.
Figure 3B:
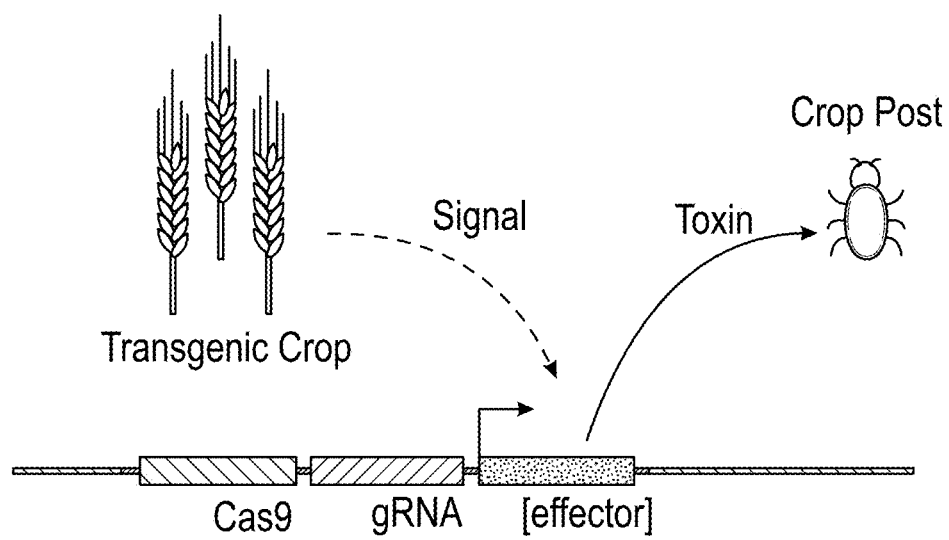
Figure 3C:
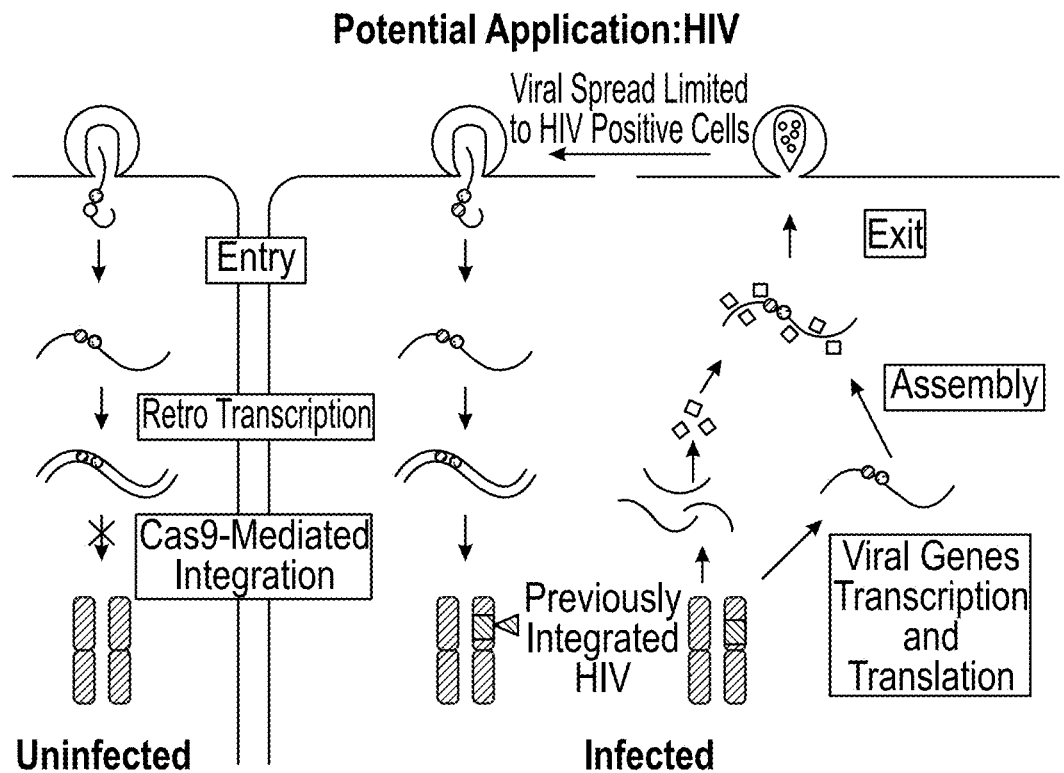
Figure 3D:
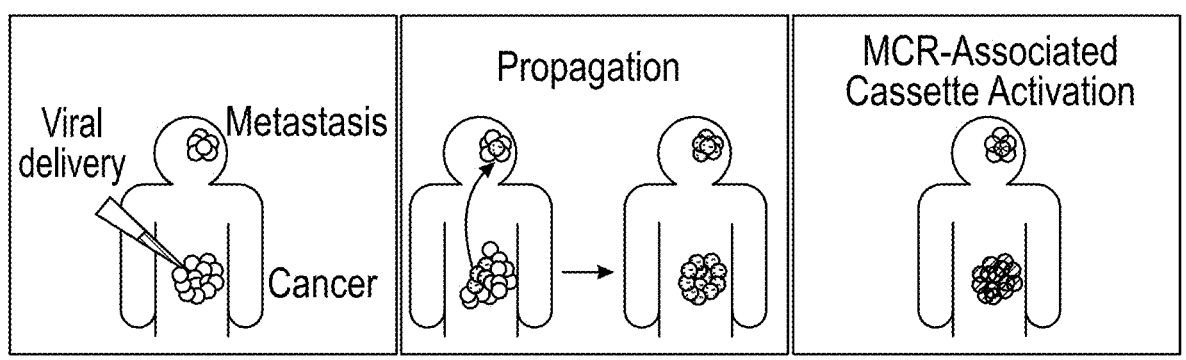
Figure 4A:
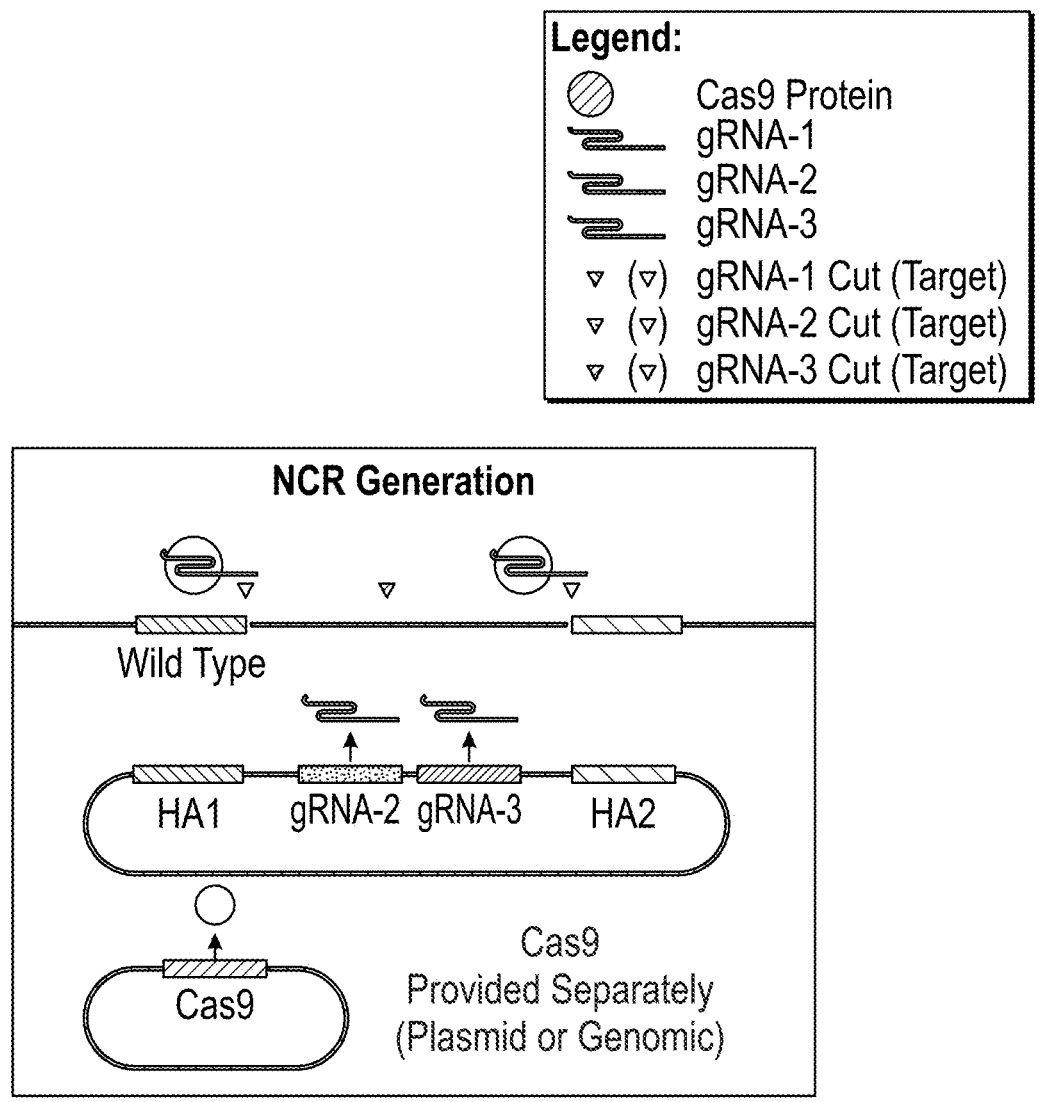
Figure 4D:
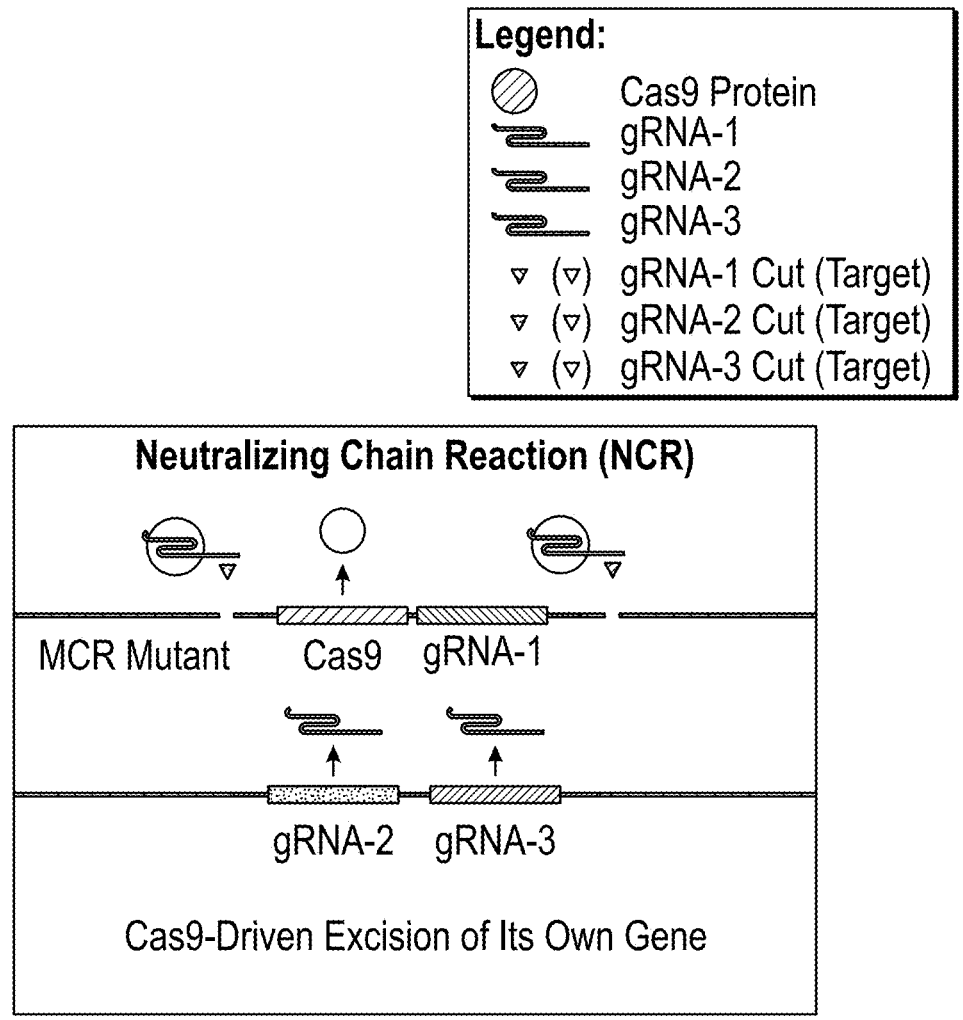
Figure 4G:
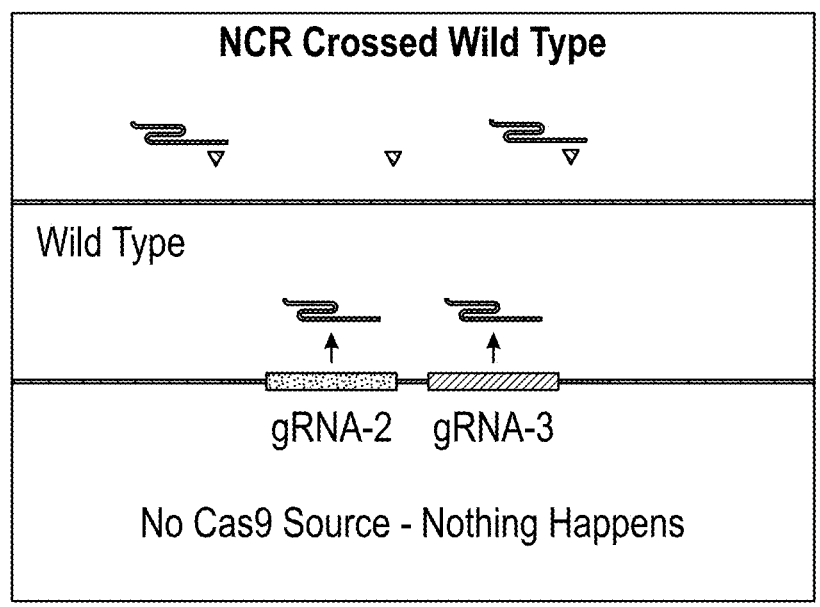

FIGS. 2A-2I are an experimental demonstration of MCR in *Drosophila*. A) Standard Mendelian inheritance of a homozygous trait in which all offspring are heterozygous for that trait. B) MCR based inheritance results in the initially heterozygous allele converting the second allele and the individual becoming homozygous (or nearly so) for that mutation. C) Diagram of y-MCR construct. The two y homology arms flanking the vasa-Cas9 and y- gRNA transgenes are indicated as well as the locations of the PCR primers used for analysis of the genomic insertion site which are listed in the methods section. D) PCR analysis of y-MCR F1 ♀ and a sibling ♂ showing functional bands corresponding to insertion of the y-MCR construct into the chromosomal y locus as well a band amplified from the y locus without an MCR insertion. As expected, y-MCR F1 ♂ with a single X- chromosome display MCR derived PCR products, while both MCR and non-insertional alleles were amplified from all 6 tested y-MCR F1 ♀. E) A low magnification view of flies emerging from the cross of y-w- MCR F1 ♀ to y+w- ♂ showing that almost all progeny have the y- phenotype. F) A high magnification view of a full body y-w-MCR F1 ♀. G) A rare mosaic female with 50% of the body y- and 50% y+ with the dividing line running the length of the body. H) A y+w- control fly. I) Example of DNA sequences at junction of homology arms with an MCR element (y-MCR) illustrating how the homology arms precisely abut the gRNA cut site to the nucleotide. MCR elements may be used for gene therapy purposes to either fix mutant genes or eliminate gene functions contributing to a disease state. An MCR construct supplied to somatic cells within an individual via a replicating vector (e.g., a virus) could insert into diseased cells carrying specific sequences (e.g., retroviral insertions or cancer cell specific mutations) and then spread to other cells within that organism (FIGS. 3C and 3D). Such constructs by virtue of carrying effector cassettes could then be engineered to combat the disease by killing the diseased cells (e.g., by inducing production of a toxin or a cell surface molecule to alert the host immune system) or by altering them in some other way (e.g., by repairing a gene or restoring a necessary cellular function).

Applications of the CRISPR/Cas System

FIGS. 3A-3D describes some potential applications of MCR. A) Application of MCR to attenuate mosquito borne malaria in which an effector cassette encoding the SM1 peptide, which is conditionally activated by a blood meal (AgCP promoter) or a single chain antibody (scFvs) directed against the malarial agent *P. falciparum* (7), is inserted along with core MCR elements (Cas9 and gRNA) into a non-coding region of the mosquito genome. The SM1 peptide limits passage of *P. falciparum* through the gut, a required step in its exploitation of that vector host (6). Spread of such an MCR construct through the mosquito population should follow an exponential trajectory that could lead to complete spread throughout a host population in 35 generations if transmission is as efficient as shown for the y-MCR element in *Drosophila*, and making the assumption of no reduced fitness being associated with the MCR, a single individual carrying an MCR construct could spread the MCR element to an entire population. It is notable that in such models, the percentage of the MCR element in the population could increase from 1% to 100% in 9 generations. B) A scheme similar to that in panel A wherein transgenic crops produce a signal (e.g., hormone) that activates expression of toxin to control a specific pest engineered to spread an MCR cassette carrying the toxin. C) MCR based spread of an Integrase-deficient Cas9/gRNA-dependent retroviral (e.g., HIV) construct directing its insertion into a chromosomal inserted provirus thereby rendering that proviral element inactive. Induction and maturation of such targeted proviruses should lead to the production of assembled viruses which could then infect all other CD4+ helper T-cells but integrates into the genomes of cells carrying proviral insertions. This within-organism spread of the MCR construct could eventually incapacitate all proviruses leading to the eventual clearance of the HIV infection. D) An analogous retrovirally propagated MCR element directs its insertion into a cancer-specific genomic sequence. Infection and spread of this element throughout the body should lead to its selective insertion in cancer cells (in primary and metastatic tumors). When testing of patient cells indicates that the MCR has spread effectively to all cancer cells, an effector cassette carried by the MCR could be activated (e.g., by a hormone) to induce apoptosis or flag cells for destruction by the immune system.

For example, if a gene was introduced, which when expressed an MCR could spread that gene within cells of a single individual afflicted with a disease such as HIV or cancer. The disclosure targets insertion of the construct into DNA sequences that are specific to diseased cells and then carry some type of cassette that could kill, fix, or reprogram the diseased cells.

Selectively targeting cancer cells: MCRs designed to spread between cells in the body may be developed that target nucleotide differences between the cancer cell and normal cells, for rapid detection by deep sequencing. Types of cancer in which cancer-cell specific sequences are identified (e.g., chromosomal rearrangements) and are often targeted by a construct comprising a cancer-specific gRNA carried by an MCR packaged in an Integrase-deficient retrovirus or adenovirus. Such an MCR-viral construct should infect both normal and cancer cells in the patient, but could insert into the genome of cancer cells (FIG. 3D). For an element engineered to replicate and spread from cell-to-cell, an initial infection of a small subset of cancer cells may result in spread of the MCR-virus until the great majority of cancer cells contained the construct even if the primary tumor had metastasized. Infection of cancer cells could be readily monitored by physicians and once MCR-viral delivery became widespread, the cancer would be progressively attacked by activating drug-inducible effectors carried by the MCR. Such effectors could include toxins, agents triggering apoptosis, or cellular antigens that flag cells for immune recognition. Similar generalized strategies to combat cancer that are independent of the type of cancer or stage of cancer progression may be targeted using MCRs.

Cancers include, but are not limited to, Acute lymphoblastic leukemia (ALL); Acute myeloid leukemia; Adrenocortical carcinoma; AIDS-related cancers; AIDS-related lymphoma; Anal cancer; Appendix cancer; Astrocytoma, childhood cerebellar or cerebral; Basal-cell carcinoma; Bile duct cancer, extrahepatic; Bladder cancer; Bone tumor, osteosarcoma/malignant fibrous histiocytoma; Brain cancer; Brain tumor, cerebellar astrocytoma; Brain tumor, cerebral astrocytoma/malignant glioma; Brain tumor, ependymoma; Brain tumor, medulloblastoma; Brain tumor, supratentorial primitive neuroectodermal tumors; Brain tumor, visual pathway and hypothalamic glioma; Brainstem glioma; Breast cancer; Bronchial adenomas/carcinoids; Burkitt's lymphoma; Carcinoid tumor, childhood; Carcinoid tumor, gastrointestinal; Carcinoma of unknown primary; Central nervous system lymphoma, primary; Cerebellar astrocytoma, childhood; Cerebral astrocytoma/malignant glioma, childhood; Cervical cancer; Childhood cancers; Cholangiocarcinoma; Chondrosarcoma; Chronic lymphocytic leukemia; Chronic myelogenous leukemia; Chronic myeloproliferative disorders; Colon cancer; Cutaneous T-cell lymphoma; Desmoplastic small round cell tumor; Endometrial cancer;

Ependymoma; Esophageal cancer; Ewing's sarcoma in the Ewing family of tumors; Extracranial germ cell tumor, childhood; Extragonadal germ cell tumor; Extrahepatic bile duct cancer; Eye cancer, intraocular melanoma; Eye cancer, retinoblastoma; Gallbladder cancer; Gastric (stomach) cancer; Gastric carcinoid; Gastrointestinal carcinoid tumor; Gastrointestinal stromal tumor (GIST); Germ cell tumor: extracranial, extragonadal, or ovarian; Gestational trophoblastic tumor; Glioma of the brain stem; Glioma, childhood cerebral astrocytoma; Glioma, childhood visual pathway and hypothalamic; Hairy cell leukemia; Head and neck cancer; Heart cancer; Hepatocellular (liver) cancer; Hodgkin lymphoma; Hypopharyngeal cancer; Hypothalamic and visual pathway glioma, childhood; Intraocular melanoma; Islet cell carcinoma (endocrine pancreas); Kaposi sarcoma; Kidney cancer (renal cell cancer); Laryngeal cancer; Leukaemia, acute lymphoblastic (also called acute lymphocytic leukaemia); Leukaemia, acute myeloid (also called acute myelogenous leukemia); Leukaemia, chronic lymphocytic (also called chronic lymphocytic leukemia); Leukaemias; Leukemia, chronic myelogenous (also called chronic myeloid leukemia); Leukemia, hairy cell; Lip and oral cavity cancer; Liposarcoma; Liver cancer (primary); Lung cancer, non-small cell; Lung cancer, small cell; Lymphoma, AIDS-related; Lymphoma, Burkitt; Lymphoma, cutaneous T-Cell; Lymphoma, Hodgkin; Lymphoma, primary central nervous system; Lymphomas; Lymphomas, Non-Hodgkin (an old classification of all lymphomas except Hodgkin's); Macroglobulinemia, Waldenström; Male breast cancer; Malignant fibrous histiocytoma of bone/osteosarcoma; Medulloblastoma, childhood; Melanoma; Melanoma, intraocular (eye); Merkel cell cancer; Mesothelioma, adult malignant; Mesothelioma, childhood; Metastatic squamous neck cancer with occult primary; Mouth cancer; Multiple endocrine neoplasia syndrome, childhood; Multiple myeloma/plasma cell neoplasm; Mycosis fungoides; Myelodysplastic syndromes; Myelodysplastic/myeloproliferative diseases; Myelogenous leukemia, chronic; Myeloid leukemia, adult acute; Myeloid leukemia, childhood acute; Myeloma, multiple (cancer of the bone-marrow); Myeloproliferative disorders, chronic; Nasal cavity and paranasal sinus cancer; Nasopharyngeal carcinoma; Neuroblastoma; Non-Hodgkin lymphoma; Non-small cell lung cancer; Oligodendroglioma; Oral cancer; Oropharyngeal cancer; Osteosarcoma/malignant fibrous histiocytoma of bone; Ovarian cancer; Ovarian epithelial cancer (surface epithelial-stromal tumor); Ovarian germ cell tumor; Ovarian low malignant potential tumor; Pancreatic cancer; Pancreatic cancer, islet cell; Paranasal sinus and nasal cavity cancer; Parathyroid cancer; Penile cancer; Pharyngeal cancer; Pheochromocytoma; Pineal astrocytoma; Pineal germinoma; Pineoblastoma and supratentorial primitive neuroectodermal tumors, childhood; Pituitary adenoma; Plasma cell neoplasia/Multiple myeloma; Pleuropulmonary blastoma; Primary central nervous system lymphoma; Prostate cancer; Rectal cancer; Renal cell carcinoma (kidney cancer); Renal pelvis and ureter, transitional cell cancer; Retinoblastoma; Rhabdomyosarcoma, childhood; Salivary gland cancer; Sarcoma, Ewing family of tumors; Sarcoma, Kaposi; Sarcoma, soft tissue; Sarcoma, uterine; Sezary syndrome; Skin cancer (melanoma); Skin cancer (non-melanoma); Skin carcinoma, Merkel cell; Small cell lung cancer; Small intestine cancer; Soft tissue sarcoma; Squamous cell carcinoma; Squamous neck cancer with occult primary, metastatic; Stomach cancer; Supratentorial primitive neuroectodermal tumor, childhood; T-Cell lymphoma, cutaneous; Testicular cancer; Throat cancer; Thymoma and thymic carcinoma; Thymoma, childhood; Thyroid cancer; Thyroid cancer, childhood; Transitional cell cancer of the renal pelvis and ureter; Trophoblastic tumor, gestational; Unknown primary site, cancer of, childhood; Unknown primary site, carcinoma of, adult; Ureter and renal pelvis, transitional cell cancer; Urethral cancer; Uterine cancer, endometrial; Uterine sarcoma; Vaginal cancer; Visual pathway and hypothalamic glioma, childhood; Vulvar cancer; Waldenström macroglobulinemia; Wilms tumor (kidney cancer), childhood; and any combination thereof.

Treating Diseases or Conditions:

MCR elements are often designed that treat diseases or conditions by selectively adding, deleting, or mutating genes. For example, genes that encode immunogenic proteins may be targeted to reduce or eliminate immunogenicity. Allergens in food may be reduced by targeting the genes encoding the allergen in the organism (e.g., peanut, tree nut, cow (or other source of milk), chicken (or other source of egg), wheat, soy, fish, shellfish) from which the food was derived. Specific cells may be targeted, such as beta cells (role in diabetes) or cells and/or genes involved in autoimmune disorders.

Accelerating Genetic Manipulations and Genome Engineering.

An active MCR drive may provide faster propagation of a genetic trait than a passive Mendelian inheritance. A set of copycat cloning vectors may be generated to be used for active genetics into which a transgene may be cloned, targeted for genomic insertion at a desired site, and then homozygosed in the presence of an unlinked source of Cas9. For example, FIG. 5 shows the assembly of mutations A-D in four paralogs of a mouse gene to study a specific trait (e.g., CNS function). Using standard genetics, mutant A is crossed with mutant B to recover double heterozygotes, which are then back crossed to each other to recover double homozygotes at a rate of 1/16. This procedure is repeated for mutant C and mutant D. To assemble all four mutations, the AB mutants are crossed with the CD mutants to recover 1/64 quadruple mutant progeny in the fourth generation. Using MCRs or related "copy-cat" elements, mutant A may be crossed with mutant B to produce 100% AB progeny. Mutant C may be crossed with mutant D to produce 100% CD double mutants. The AB double mutant may be crossed with the CD double mutant to recover 100% quadruple mutants in two generations instead of four using standard genetics. This improvement may cut breeding time in half and increase the percentage of double and quadruple mutants to test (e.g., 100% versus 1/64 (1.6%) for the final cross).

Similar methods may be used to generate libraries of model organisms; generate specific strains, breeds, or mutants of a model organism; for one-step mutagenesis schemes to generate scoreable recessive mutant phenotypes in a single generation; facilitate basic genetic manipulations in diverse experimental and agricultural organisms (e.g., accelerating the generation of combinatorial mutants and facilitating mutagenesis in polyploid organisms); accelerate genetic manipulations in animals (e.g., primates) or plants (e.g., trees) with a long generation time; and for gene therapy.

Model organisms include, but are not limited to, viruses, prokaryotes, eukaryotes, protists, fungi, plants, invertebrate animals, vertebrate animals, and any combination thereof. A model organism may include, but is not limited to, a mammal, human, non-human mammal, a domesticated animal (e.g., laboratory animals, household pets, or livestock), non-domesticated animal (e.g., wildlife), dog, cat, rodent, mouse, hamster, cow, bird, chicken, fish, pig, horse, goat, sheep, rabbit, and any combination thereof.

Invertebrate animal model organisms include, but are not limited to, *Amphimedon queenslandica; Arbacia punctulata; Aplysia; Branchiostoma floridae; Caenorhabditis elegans; Caledia captiva* (Orthoptera); *Callosobruchus maculatus; Chorthippus parallelus; Ciona intestinalis; Daphnia* spp.; *Coelopidae; Diopsidae; Drosophila* (e.g., *Drosophila melanogaster*); *Euprymna scolopes; Galleria mellonella; Gryllus bimaculatus; Hydra; Loligo pealei; Macrostomum lignano; Mnemiopsis leidyi; Nematostella vectensis; Oikopleura dioica; Oscarella carmela; Parhyale hawaiensis; Platynereis dumerilii; Podisma* spp.; *Pristionchus pacificus; Scathophaga stercoraria; Schmidtea mediterranea; Stomatogastric ganglion; Strongylocentrotus purpuratus; Symsagittifera roscoffensis; Tribolium castaneum; Trichoplax adhaerens; Tubifex tubifex*; and any combination thereof.

Vertebrate animal model organisms include, but are not limited to, Laboratory mice; *Bombina bombina, Bombina variegata*; Cat (*Felis sylvestris catus*); Chicken (*Gallus gallus domesticus*); Cotton rat (*Sigmodon hispidus*); Dog (*Canis lupus familiaris*); Golden hamster (*Mesocricetus auratus*); Guinea pig (*Cavia porcellus*); Little brown bat (*Myotis lucifugus*); Medaka (*Oryzias latipes*, or Japanese ricefish); Mouse (*Mus musculus*); *Poecilia reticulata*; Rat (*Rattus norvegicus*); Rhesus macaque (or Rhesus monkey) (*Macaca mulatta*); Sea lamprey (*Petromyzon marinus*); Takifugu (*Takifugu rubripes*); *Xenopus tropicalis; Xenopus laevis*; Zebra finch (*Taeniopygia guttata*); Zebrafish (*Danio rerio*); African Killifish (*Nothobranchius furzeri*) and any combination thereof.

Chimeric Antigen Receptors (CAR)s

The present disclosure includes compositions, methods for generating compositions and methods for administering compositions of immune cells genetically engineered using the CRISPR/Cas9 system described herein to express a chimeric antigen receptor (CAR). CARs are an artificial means for achieving activation of immune cells, often T cells, against a diseased cell, such as a tumor cell. Structurally, CARs comprise a single-chain antibody and a CD3 polypeptide which, upon activation in response to binding to an antigen detected by the single-chain antibody, often a tumor antigen such as CD19 expressed by B-cell acute lymphoblastic leukemia. FIG. 6A and FIG. 6C. The present disclosure further includes compositions, methods for generating compositions and methods for administering compositions of immune cells genetically engineered using the CRISPR/Cas9 system described herein to express a plurality of CARs wherein each of the plurality of CARs is encoded by a different polynucleotide in a single immune cell, for example, 2 CARs, 3 CARs, 4 CARs, 5 CARs, 6 CARs, 7 CARs, 8 CARs, 9 CARs, 10 CARs or greater than 10 CARs. In this way, expression of a plurality of different CARs by a single immune cell expands the antigens recognized by the single immune cell so as to target multiple tumor antigens.

As used herein, "antibody fragment" and "antibody binding domain" refer to a portion of an antibody comprising the antigen recognition portion, i.e., an antigenic determining variable region of an antibody sufficient to confer recognition and binding of the antigen recognition portion to a target, such as an antigen, i.e., the epitope. Examples of antibody fragments include, but are not limited to, Fab and variable "Fv" fragment and single-chain Fv ("scFv") antibody fragments and other fragment, combinations of fragments or types of antibodies known or knowable to one of ordinary skill in the art.

As described herein, CARs often comprise a plurality of domains, including but not limited to, an scFV domain, an extracellular domain, a transmembrane domain, an intracellular domain and a co-stimulatory domain.

The term "scFv" refers to a fusion protein comprising at least one antibody fragment including, but not limited to, a variable region of a light chain and a variable region of a heavy chain. Often, the light and heavy chain variable regions are linked, either directly or via a short flexible polypeptide linker, for example, continuously linked, and are capable of being expressed as a single polypeptide chain.

Unless specified, as used herein an scFv comprising both a variable light chain ("VL") and a variable heavy chain ("VH") variable regions are positioned in the scFv either with the VL near the N-terminal end or the VL near the C-terminal end of the protein, polypeptide or peptide. The scFv often further comprises a linker such that the ordering of the VL, linker and VH relative to the N-terminal end or the C-terminal end of the protein is either VL-linker-VH or VH-linker-VL.

In some embodiments, the scFV comprises an antigen binding domain or a plurality of antigen binding domains and depends upon the type and number of antigens expressed by a target cell, for example a B-cell acute lymphoblastic leukemia cell. Often, the antigen binding domain may be selected in order to recognize an antigen, for example a cell surface marker on target cells associated with a disease or condition. For example, cell surface markers recognized by the antigen binding domain of the CAR includes macromolecules associated with viral and bacterial diseases or infections, autoimmune diseases and cancerous diseases. The antigen binding domain of the scFV may be selected from any domain that binds the antigen including, but not limited to, a monoclonal antibody, a polyclonal antibody, a recombinant antibody, or a functional fragment thereof, for example, a heavy chain variable domain (VH) and a light chain variable domain (VL).

In some embodiments, the scFV targets CD19, often but not limited to, human CD19, humanized CD19 or non-human CD19. Often, the anti-CD19 binding domain is a fragment, for example, an scFV comprising a Fv, a Fab, a (Fab')2, or a bi-functional hybrid antibody.

For example, the anti-CD19 binding domain of the scFV often comprises one or more of the following, a light chain complementary determining region 1 (LC CDR1), a light chain complementary determining region 2 (LC CDR2), or a light chain complementary determining region 3 (LC CDR3) For another example, the anti-CD19 binding domain often comprises one or more of the following, a heavy chain complementary determining region 1 (HC CDR1), a heavy chain complementary determining region 2 (HC CDR2), or a heavy chain complementary determining region 3 (HC CDR3). The anti-CD19 scFV often comprises one or more LC CDRs and one or more HC CDRs, one or more LC CDRs or one or more HC CDRs.

In one embodiment, the scFv comprises a light chain variable region of an amino acid sequence having at least one, two, three, four, five, six, seven, eight, nine or ten modifications but not more than 40, 35, 30, 25, 20, 15 or 10 modifications of the amino acid sequence relative to the natural or original amino acid sequence. In another embodiment, the scFv comprises an amino acid sequence with 95-99% relative to the natural or original amino acid sequence.

In another embodiment, the scFv comprises a heavy chain variable region of an amino acid sequence having at least one, two, three, four, five, six, seven, eight, nine or ten modifications but not more than 40, 35, 30, 25, 20, 15 or 10 modifications of the amino acid sequence relative to the natural or original amino acid sequence. In another embodiment, the scFv comprises an amino acid sequence with 95-99% relative to the natural or original amino acid sequence.

In an embodiment, the anti-CD19 binding domain comprises a light chain variable region attached to a heavy chain variable region, where the attachment comprises a linker. The linker sequence may comprise any naturally occurring amino acid. For example, the linker is a G/S linker with sequence (GnSn)n and where any of the three n values corresponds to a value of 1 or a value of greater than 1, for example, any of the three n values is 1, 2, 3, 4, 5, 6, 7, 8, 9, 10, 11, 12, 13, 14, 15, or greater than 15. Often, the linker is a $(G_4S)_n$ linker and n is either 1, 2, 3, 4, 5, 6, 7, 8, 9 or 10, preferably 3, 4 or 5 (SEQ ID NO: 9). However, the linker is optionally a $(G_3S)_n$ linker and n is either 1, 2, 3, 4, 5, 6, 7, 8, 9 or 10, preferably 3, 4 or 5 (SEQ ID NO: 10). Variation in the linker length may affect activity of the CAR, for example, linker length often retains, enhances or impairs activity, the desired outcome differs between types of diseases or conditions.

Importantly, the light chain variable region and heavy chain variable region is often in any orientation, for example, light chain variable region-linker-heavy chain variable region or heavy chain variable region-linker-light chain variable region or optionally includes more than one light chain variable region, more than one heavy chain variable region and in any orientation having a linker between each light or heavy chain variable region.

T-Cell Receptors (TCR)s

The present disclosure includes compositions, methods for generating compositions and methods for administering compositions of immune cells genetically engineered using the CRISPR/Cas9 system described herein to express T cell receptors (TCR)s. TCRs are an endogenous and naturally occurring means for achieving activation of T cells, against a diseased cell, such as a tumor cell, and are expressed on T cells, including CD4$^+$ and CD8$^+$ T cells. Where "T cell" is used herein, it is understood that, unless specified, T cell includes all types of T cells, including but not limited to CD4+ and CD8$^+$ T cells, at any number of stages of differentiation and/or maturity, for example, activated, naive or the like. In some embodiments, a TCR comprises two chains, an alpha chain and a beta chain, further, in some additional embodiments, the TCR often comprises a gamma chain, a delta chain or both a gamma chain and a delta chain. TCRs are expressed as a complex along with a CD3 polypeptide, the complex having an extracellular, a transmembrane and an intracellular portion. In most embodiments, the extracellular portion comprises a variable and a constant portion, the variable portion distal from the T cell and further comprising an antigen binding domain which recognizes a peptide or a fragment thereof presented by the major histocompatibility complex (MHC) class I or class II of an antigen presenting cell. For example, CD4$^+$ ("helper") T cells recognize MHCII peptides and CD8$^+$ ("cytotoxic") T cells recognize MHCI peptides.

As described herein, a vector comprising polynucleotides encoding a TCR, or a plurality of TCRs, or a TCR with a plurality of subunits, is inserted into a T cell such that the TCR is expressed by the T cell. In some embodiments, the polynucleotides encoding the TCR render the TCR specific to detect a single polypeptide. In other embodiments, the polynucleotides encoding the TCR render the TCR specific to detect a family of polypeptides. Often the polypeptide and/or the family of polypeptides, is associated with a diseased cell, such as for example, a tumor cell, a cancer cell or an autoimmune cell. Such polypeptides considered useful and contemplated as detected by TCRs of the present disclosure are known to those of ordinary skill in the art and include, but are not limited to, CD19, CD20, CD30, CD33, CD44v7/8, CD122, α-folate receptor, CAIX, CEA, FBP, L1CAM, EGP-2, EGP-40, ERB-B2, heregulin, fetal acetylcholine receptor, GD2, GD3, Her2/neu, IL-13R-a2, KDR, LeY, k-light chain, MAGE-A1, mesothelin, MUC-1, NKG2D ligands, NKG2D receptors, oncofetal antigen, PSCA, PSMA, VEGF-R2, TAG-72 and TAA targeted by mAb IgE.

As used herein, a "T Cell Receptor (TCR)" or "TCR" includes at least, but is not limited to, an antigen recognition portion, a transmembrane portion and an intracellular portion. The antigen recognition portion is often similar to an antigen recognition portion of an antibody or is any polypeptide generally capable of i) recognizing to an antigen on a target cell or ii) binding to an antigen on a target cell. The antigen recognition portion includes, but is not limited to, the antigen recognition portion to recognize, but is not limited to, the following antigens, or families of proteins including each of the following antigens; CD19, CD20, CD30, CD33, CD44v7/8, CD122, α-folate receptor, CAIX, CEA, FBP, L1CAM, EGP-2, EGP-40, ERB-B2, heregulin, fetal acetylcholine receptor, GD2, GD3, Her2/neu, IL-13R-a2, KDR, LeY, k-light chain, MAGE-A1, mesothelin, MUC-1, NKG2D ligands, NKG2D receptors, oncofetal antigen, PSCA, PSMA, VEGF-R2, TAG-72 and TAA targeted by mAb IgE. By "recognition", "recognizing" and the like, said antigen recognition portion responds to the presence of a given antigen with the response affected as a conformational change, a change in behavior by the T cell expressing the TCR, or the like. The antigen recognition portion of the TCR is specific to a given polypeptide sequence of an antigen, a given shape of an antigen or a combination of the polypeptide sequence and the same of the antigen. The antigen recognition portion recognizes a single antigen, a set of antigens having homology to a single antigen or the like. Often the homology is less than 1%, less than 2%, less than 3%, less than 5%, less than 10%, less than 15%, less than 20%, less than 25% or less than 30% different from the single antigen.

TCRs are engaged by binding to a complex comprising a MHCI and a polypeptide bound by the MHCI. Often the polypeptide is a fragment of a peptide presented by an antigen presenting cell on the MHCI. In some embodiments, the MHCI-polypeptide complex engages a specific TCR. Upon engagement, the TCR generates a signal which regulates gene expression by the T cells. For example, following detection of the MHCI-polypeptide complex, the TCR signals via CD3 and at least one downstream kinase to phosphorylate transcription factors controlling gene expression. In many embodiments, phosphorylation activates transcription factors positively regulating genes required for T-cell mediated killing of tumor cells. FIG. 6A.

Extracellular Domains

As described herein, the extracellular domain useful with CARs is derived of a natural source, from a recombinant source, from a synthetic source or directly manufactured. In some embodiments, the extracellular domain may be derived from any protein, peptide or polypeptide, and often is derived from a protein having a membrane-bound or transmembrane portion such that the extracellular domain is immediately distal to a transmembrane portion. Any suitable extracellular domain known to one of ordinary skill in the art may be useful with the CARs disclosed or contemplated herein, for example, the extracellular domain may include a linker and an extracellular domain, or a plurality of extracellular domains derived from the VH, VL, VH CDR1/2/3, VL CDR 1/2/3 or the like regions, chains or portions of an antibody or of a fragment thereof.

Transmembrane Domain

As described herein, the methods and compositions comprise immune cells genetically engineered to express a polypeptide, for example, a CAR, a TCR, a negative inhibitory peptide or the like. A transmembrane domain includes a transmembrane region (e.g., a portion spanning the cellular membrane including amino acids contacting the phospholipid bilayer and the transmembrane space between the bilayer) and an adjacent region (e.g., one or more additional amino acids flanking the transmembrane region distal to the lipid bilayer and not within the lipid bilayer, for example, including but not limited to one, two, three, four, five, six, seven, eight, nine, ten and up to 20 amino acids of the amino acids flanking the lipid bilayer.

The transmembrane domain is either homologous or heterologous to the extracellular domain, for example, the transmembrane and extracellular domains of a CAR is either derived from the same protein, or the transmembrane and extracellular domains of a CAR is derived from two different proteins. In some embodiments, the transmembrane domain may be derived from a natural (e.g., a transmembrane protein known to one of ordinary skill in the art and useful in combination with the present disclosure where the transmembrane domain signals to the intracellular domain upon recognition of a target), a synthetic or a recombinant source. A transmembrane domain may include, but is not limited to, transmembrane region(s) of TCR alpha, TCR beta, TCR zeta, CD28, CD3 epsilon, CD45, CD4, CD8, CD80, CD86, CD134, CD137 and may include a portion of one or portions of a plurality of the above or the transmembrane region of a family including one or more than one of the above.

In some embodiments, the transmembrane domain is either directly attached to the extracellular region (e.g., of the CAR) or attached to the extracellular region by a hinge derived from a polypeptide. The hinge may be derived from the same protein as the transmembrane domain or the same protein as the extracellular region or derived from a different protein as the transmembrane domain or a different protein as the extracellular region or a different protein from both the transmembrane and the extracellular region. In some embodiments, the hinge is derived from a human protein or a non-human protein, for example, the hinge is derived from a hinge region of an immunoglobin, including, but not limited to, the hinge region of a class G immunoglobin, such as the IgG4 hinge region. In other embodiments, the hinge is derived from a hinge region of a naturally occurring protein having a hinge region and retains 80% or greater homology to the naturally occurring hinge region from which it was derived. For example, the hinge region of a CAR retains 80% or greater, 85% or greater, 90% or greater, 95% or greater, 97% or greater, 99% or greater, 99.5% or greater homology to the naturally occurring hinge region from which it was derived.

Linkers

A linker refers to a series of amino acid residues, often a peptide, and for example, comprises mostly glycine residues, serine residues, or a combination of glycine and serine residues, and links variable heavy and variable light chain regions, often of an scFV, together in any order or combination required to confer a desired antigen recognition. Often, the linker is flexible such that conformational changes in the antigen, the scFV or the environment is adapted for. In some embodiments, the linker is a G/S linker with sequence (GnSn)n and where any of the three n values corresponds to a value of 1 or a value of greater than 1, for example, any of the three n values is 1, 2, 3, 4, 5, 6, 7, 8, 9, 10, 11, 12, 13, 14, 15, or greater than 15.

In some embodiments, the linker is often a short polypeptide sequence, comprising between 2 and 10 amino acids in length and connects two domains of a peptide useful with the disclosure provided herein. For example, a linker connects the transmembrane domain and the cytoplasmic region of a peptide, such as a CAR. The linker is often a single glycine amino acid residue and a single serine amino acid residue or may comprise a longer amino acid sequence of glycine and serine amino acids. For example, the linker is any one of or multiples of the following, GS, GGSGGS (SEQ ID NO: 11), GGGSGGGS (SEQ ID NO: 12), GGGGSGGGGS (SEQ ID NO: 13), GSGS (SEQ ID NO: 14), GGSGGSGGSGS (SEQ ID NO: 15), GGGSGGGSGGGSGGGS (SEQ ID NO: 16), GGGGSGGGGSGGGGSGGGGS (SEQ ID NO: 17) and the like.

Cytoplasmic Domain

The cytoplasmic domain of the polypeptides of the present disclosure, including CARs, TCRs and negative inhibitory molecules include an intracellular signaling domain. In some embodiments, the intracellular signaling domain is either a portion of CD3, for example, CD3 delta, CD3 epsilon and/or CD3 gamma. For example, the intracellular signaling domain is either derived from a portion of CD3 delta or from a portion of CD3 delta and CD3 epsilon, co-receptors for a TCR full-length molecules or a functional fragment thereof and intracellular signaling domains contemplated by the present disclosure, or known to one of ordinary skill in the art is either used with a CAR, a TCR and/or a negative inhibitory molecule. Activation of an intracellular signaling domain may occur in response to recognition of an antigen by a CAR, a TCR and/or a negative regulatory molecule. In many embodiments, activation of an intracellular signaling domain activates, increases or decreases cytolytic or helper function of a T cell expressing the CAR or TCR. For example, activation of an intracellular signaling domain induces gene transcription and protein translation such as of cytokines. In some embodiments, activation of an intracellular signaling domain induces secretion of cytokines.

Immune cells are activated by a plurality of cytoplasmic signaling domains, including antigen-dependent primary activation, for example by the TCR, and antigen-independent manner, for example, with a costimulatory signal. In some embodiments, the primary signaling domain regulates activity of the TCR complex, for example, through stimulation and activation of immunoreceptor tyrosine-based activation motifs (ITAMs) or inhibition. For example, ITAMs useful with the present disclosure is either derived from one or more than one of the following molecules, CD3 zeta, FcR beta or FcR gamma, CD3 delta, CD3 epsilon or CD3 gamma. In some embodiments, the costimulatory costimulatory signaling domain is derived from the intracellular domain of a costimulatory molecule and any costimulatory molecule known by one of ordinary skill in the art that, upon activation, results in an altered response of the immune cell to an antigen, is used with the present disclosure. For example, costimulatory domains are derived from costimulatory molecules including the following as well as the families each molecule belongs to, but are not limited to, CD28, 4-1BB, PD1, LFA-1, NKG2D, B7-H3, CD27 and the like.

In some embodiments, a single intracellular signaling and/or costimulatory domain is a portion of a CAR, a TCR or a negative regulatory molecule. In other embodiments, more than one intracellular signaling and/or costimulatory domain is either a portion of a CAR, a TCR or a negative regulatory molecule. Where more than one intracellular signaling and/or costimulatory domain is used, the more than one intracellular signaling and/or costimulatory domain is either derived from the same intracellular signaling molecule and/or costimulatory molecule or different intracellular signaling molecules and/or costimulatory molecules and is either arranged in the CAR, the TCR or the negative regulatory molecule in any useful ordering. In some embodiments, a polypeptide linker sequence is either used to link the more than one intracellular signaling and/or costimulatory domain to one another. Suitable linkers include those of the present disclosure, a single amino acid such as a glycine or a serine or a double of glycine and serine.

The intracellular signaling domain refers to an intracellular portion of a molecule which effects the intracellular environment of the cell comprising the intracellular signaling domain. The intracellular signaling domain generates a signal that often causes a positive effect of the immune cell such as an immune effector function, which includes, but is not limited to, cytokine production, cytokine secretion, hyperplasia, proliferation, degranulation, cytolytic activity, T cell helper activity, Natural Killer (NK) activity, cellular maturation, apoptosis, reduced expression of certain inhibitory polypeptides known to those of ordinary skill in the art and/or increased expression of certain promoting polypeptides known to those of ordinary skill in the art.

In some embodiments, the intracellular signaling domain comprises a primary stimulation domain, an antigen dependent simulation domain, antigen independent stimulation or a co-stimulatory intracellular domain. Often, the primary stimulation domain is immunoreceptor tyrosine-based activation motif (ITAM), for example, ITAMs encoded by proteins expressed by immune cells such as, but not limited to, CD3 (delta, epsilon, gamma and zeta) and FcR (gamma and beta), and DAP10.

In some embodiments, the costimulatory intracellular domain is derived from a costimulatory molecule which, upon binding to a costimulatory ligand, elicits a costimulatory response in the immune cell. Often costimulation of an immune cell causes proliferation, increased gene expression, increased protein translation, or modification of genetic material or protein material, such as for example, phosphorylation or acetylation, respectively. Costimulatory molecules are known to those of ordinary skill in the art and often include the following examples or families of proteins including each of the following, but are not limited to, MHC class 1 molecules, BTLA, Toll-like receptors, Toll ligand receptors, cytokine receptors, integrins, signaling lymphocytic activation molecules, NK cellular receptors, GITR, ICOS, NKG2C, B7-H3, B7-H1, OX40, CD28, ICAM-1, LFA-1, TNFRs, and 4-1BB. As described above, the costimulatory intracellular domain is derived from a costimulatory molecule and often is the intracellular portion of a costimulatory molecule, or a plurality of intracellular portions of the same costimulatory molecules or a plurality of costimulatory molecules. Often, the intracellular signaling domain comprises a functional fragment of the costimulatory molecule's intracellular portion, or the entire costimulatory molecule's intracellular portion.

A stimulatory molecule or a stimulatory domain refers to a molecule or portion thereof expressed by an immune cell, often a T cell, that provides the primary cytoplasmic signaling sequence(s) that regulate primary activation of an immune complex, often the TCR complex, in a stimulatory way for at least some embodiment of the immune cell signaling pathway activated downstream of activation of the immune complex, often a T cell signaling pathway. In some embodiments, the primary signal is initiated by, for example in T cells, binding of a TCR/CD3 complex with an MHC molecule comprising peptide. In this example, a T cell response is elicited by recognition of the MHC presented peptide by the TCR/CD3 complex, where the T cell response includes, but is not limited to, increased proliferation, activation of a plurality of pathways, differentiation of the T cell, cytokine production and/or secretion, changes in gene expression and/or protein translation, activation of other cell types and the like. As described above, ITAMs are often activated and cause changes in T cell behavior, such as stimulation. Examples of ITAMs described elsewhere herein are considered useful as portions of or entire stimulatory molecules and/or stimulatory domains.

Negative Regulatory Molecules

As described herein, the methods and compositions are useful for expression of negative regulatory molecules including a Negative Regulatory Polypeptide, an Inhibitory Polypeptide, a Negative Regulatory Receptor and an Inhibitory Receptor are used interchangeably throughout the disclosure, and refer to a polypeptide expressed on the surface of the genetically engineered immune cell which, when recognized by a different cell, cause the genetically engineered immune cell to no longer respond to signals arising from a CAR or a TCR expressed by the immune cell. A Negative Regulatory Polypeptide, an Inhibitory Polypeptide, a Negative Regulatory Receptor and an Inhibitory Receptor includes at least, but are not limited to, an antigen recognition portion, a transmembrane portion and an intracellular portion where the intracellular portion often is disabled to prevent intracellular signaling and the natural effect of receptor activation. The antigen recognition portion is often similar to an antigen recognition portion of an antibody or is any polypeptide generally capable of i) recognizing to an antigen on a target cell or ii) binding to an antigen on a target cell. The antigen recognition portion includes, but is not limited to, the antigen recognition portion to recognize, but is not limited to, the following antigens or families of proteins including each of the following antigens; CTLA-4, BTLA, PD-1, TIM-3, LAIR-1, Siglecs, TIGIT and Lag-3. In some embodiments, the antigen recognition portion further comprises two different antigen recognition portions so as to recognize more than one of the antigens selected from the group wherein the antigen recognition portion further comprises a linker between the two different antigen recognition portions. (FIGS. 1A-1D). In some embodiments, the methods and compositions described herein include expression, for example but not limited to conditional expression, of a modified negative regulatory peptide and in other embodiments, the methods and compositions described herein include targeted disruption, for example by HDR, or gRNA-directed mutagenesis for example by NHEJ, of expression of a native and naturally occurring negative regulatory peptide.

In some embodiments, a negative regulatory molecule targets a cell for recognition by an immune cell of the subject's system so as to eliminate the cell expressing the negative regulatory molecule. As described herein, the negative regulatory molecule targeting the cell for recognition by the subject's immune system and elimination is operably linked to a constitutive promoter, a tissue-specific promoter or a drug-regulated promoter.

In some embodiments, the methods and CopyCat compositions described herein is either used to target insertion of a polynucleotide into a gene locus of a negative regulatory molecule such as but is not limited to, the following gene loci encoding expression of the below antigens or families of proteins including each of the following gene loci encoding expression of the below antigens; CTLA-4, BTLA, PD-1, TIM-3, LAIR-1, Siglecs, TIGIT and Lag-3. FIG. 6A. As described further herein, targeted insertion of a CopyCat element includes a gRNA or more than one gRNA. In some embodiments, polypeptides encoding a Cas9 protein are not be inserted into the immune cell genome and Cas9 is translated from polynucleotides encoding the same by a different mechanism, for example, a plasmid, a virus, and/or an episome comprising polynucleotides encoding Cas9 or a TAT-tagged Cas9. In some embodiments, the plasmid, the virus and/or the episome comprising polynucleotides encoding Cas9 or a TAT-tagged Cas9 protein is co-transfected or co-transformed with the vector comprising the CopyCat element polynucleotides. In other embodiments, a Cas9 protein and/or a TAT-tagged Cas9 protein are delivered to the immune cells by passing across, through, or the like, the immune cell membrane. The CopyCat vector often comprises expression cassettes of polynucleotides which insert biallelically into genomic DNA of an immune cell, in many embodiments, by HDR. In an embodiment, gRNA directs Cas9-mediated cleavage of the inhibitory locus, PD-1, at a catalytic residue. Upon cleavage, the genomic DNA is often repaired by non-homologous end joining leading to a biallelic mutation in the PD-1 locus which prevents PD-1 mediated inhibition of T-cell signaling pathways. FIG. 6B.

Expression Systems

The methods and compositions described herein is often useful with different mechanisms regulating gene expression such as constitutive expression, tissue-specific expression, inducible expression and nutrient dependent expression. In some embodiments, the CopyCat vector comprises polynucleotides (e.g., effector cassettes) for insertion into the host immune cell genome whereby the polynucleotides are under control of a constitutive promoter. For example, the CopyCat vector may comprise a polynucleotide encoding a CAR operably linked to a constitutive promoter so as to maximize expression of the CAR in the immune cell at all possible timepoints. By way of another example, the vector may comprise a polynucleotide encoding a CAR not operably linked to a constitutive promoter but rather comprising gRNA sequences targeting insertion of the CAR into a locus so as to become operably linked to a native promoter in the immune cell genomic DNA so as to maximize expression of the CAR in the immune cell at all possible timepoints. As described herein, any combination of or any number of CARs, TCRs and negative regulatory molecules as well as cytokines, cytokine receptors, costimulatory molecules and the like, as well as receptors for inhibitory pathways, or conditional cis-regulatory sequences is understood as useful with the methods and compositions described herein are considered useful with the expression systems described herein as well as those known to one of ordinary skill in the art. Further, any combination of or any number of CARs, TCRs and negative regulatory molecules as well as cytokines, cytokine receptors, costimulatory molecules and the like, as well as receptors for inhibitory pathways, or conditional cis-regulatory sequences are optionally operably linked to a constitutive promoter, a tissue-specific promoter or a regulatable promoter.

In other embodiments, the vector comprises polynucleotides for insertion into the host immune cell genome whereby the polynucleotides are under control of a tissue specific promoter. For example, the CopyCat vector may comprise a polynucleotide encoding a CAR operably linked to a tissue specific promoter of a T cell so as to limit expression to those T cells which are transduced with the vector. Should the vector comprising a CAR and the tissue specific promoter for a T cell become transduced into a B cell, the CAR would not be expressed. By way of another example, the vector may comprise a polynucleotide encoding a CAR not operably linked to a constitutive promoter but rather comprising gRNA sequences targeting insertion of the CAR into a locus so as to become operably linked to a native promoter or a tissue-specific promoter in the immune cell genomic DNA so as to maximize expression of the CAR in the immune cell at a timepoint, often more than one time point, and in many embodiments, the timepoint is a specific timepoint selected to achieve a particular outcome.

In additional embodiments, the CopyCat vector comprises polynucleotides for insertion into the host immune cell genome whereby the polynucleotides are under control of an inducible promoter. Types of inducible promoters include chemically regulated promoters and physically regulated promoters. For example, the CopyCat vector may comprise a polynucleotide encoding a CAR operably linked to an inducible promoter so as to limit expression to those T cells which are treated with an agent, and also express the agent-specific molecule, for example a non-naturally occurring transcription factor which is activated by the agent-specific molecule, and have been administered the agent. Such gene expression systems comprising inducible promoters are known to one of ordinary skill in the art and understood to apply to the methods and compositions described herein. For example, inducible gene expression systems useful with the present disclosure include, but are not limited to, chemically regulated promoters such as alcohol regulated promoters (e.g., the alcohol dehydrogenase I gene promoter and the transactivator protein AlcR), tetracycline regulated promoters, such as the tetracycline repressor protein, the tetracycline operator sequence and the tetracycline transactivator fusion protein, steroid-regulated systems including, but not limited to, those based on the glucocorticoid receptor, the human estrogen receptor, the ecdysone receptors and those based on the steroid, retinoid and/or thyroid receptor superfamilies, and also the metal-regulated promoters (e.g., those derived from metallothionein) and also pathogenesis-related proteins (e.g., salicylic acid, ethylene and benzothadiazole). In some embodiments, physically regulated promoters include light-sensitive and temperature-sensitive promoters. For example, light sensitive promoters includes, but are not limited to, light inducible and light repressible promoters that are known to one of ordinary skill in the art. By way of another example, temperature sensitive promoters includes, but are not limited to, heat shock promoters that are known to one of ordinary skill in the art.

In still further embodiments, promoters useful with the present disclosure includes nutrient dependent promoters (see FIG. 6B and FIG. 6D). For example, using the methods and compositions described herein, an immune cell transduced with the vectors described herein become auxotrophic for arginine. In some embodiments, a vector (e.g., a plasmid) encodes a guide RNA, or more than one guide RNAs as well as an effector cassette. As described herein, effector cassettes often comprise a polynucleotide sequence encoding a CAR, a TCR or a negative regulatory molecule, as well as genomic sequences precisely flanking the site at which a gRNA directs Cas9, a protein encoded, or more often not encoded, on the plasmid. In some embodiments, the Cas9 protein is a TAT-tagged Cas9 protein encoded by a plasmid, a virus, or an episome different from the CopyCat vector. The Cas9 protein is a TAT-tagged Cas9 protein encoded by a plasmid, a virus, or an episome different from the CopyCat vector is often co-transduced with the vector into the immune cell, to cleave a target gene, such as for example but not limited to, the argininosuccinate synthase 1 (ASS1) gene. In this example, the Cas9/gRNA1 endonuclease complex cleaves a first allele of the ASS1 gene leading to insertion of the CopyCat element carrying the CAR/gRNA1/gRNA2 cassette via homology directed repair (HDR) in the ASS1 gene at the cleaved locus. Following integration, the same Cas9/gRNA1 endonuclease complex cleaves a second allele, leading to insertion of the same CopyCat element carrying the CAR/gRNA1/gRNA2 cassette via HDR and thereby generates a biallelic insertional mutation into the ASS1 locus which renders the immune cell auxotrophic for arginine. Disruption of the ASS1 locus and auxotrophy for arginine renders the immune cells dependent on the arginine pathway for survival. One of ordinary skill in the art understands that following administration to a patient and clearance of tumor cells by the genetically engineered immune cells, activity of the genetically engineered immune cells in the patient is often regulated so as to avoid off-target (e.g., off tumor cell target) effects. For example, the patent could be treated with an ASS1 inhibitor (e.g., arginine deiminase—ADI, or arginase I) to selectively kill the genetically engineered immune cells as those cells, due to the ASS1 disruption, are unable to synthesize arginine and would be eliminated.

Additional examples useful with the methods and compositions described herein include genetically engineering immune cells, such as T cells, to express a gene encoding a toxin, a molecule which marks genetically engineered immune cells for recognition by the subject's immune system to be eliminated, for example as foreign entities, and/or a pro-apoptotic molecule is used to eliminate immune cells after the desired therapeutic benefits have been achieved.

Sources of and Preparation of Immune Cells

As described herein, methods and compositions are useful with immune cells, including but not limited to, T cells and natural killer cells. In some embodiments, immune cells are isolated from a subject, including, but not limited to, humans, non-human primates, dogs, pigs, cats, mice, rats, zebrafish, *drosophila* and transgenic species thereof. Immune cells may be isolated from a subject's peripheral blood, bone marrow, a lymph node, blood derived from an umbilical cord, a thymus, tissue isolated from a site of infection in the subject and/or a tumor or a cancer using techniques known to one of ordinary skill in the art, for example, such as apheresis. In some embodiments, immune cells may be isolated from blood collected from a subject. The blood collected from a subject includes, but is not limited to a unit of blood, residual blood in isolation kits, cord blood and the like as well as additional techniques known to one of ordinary skill in the art. For example, immune cells may be isolated from a subject's blood using a method including Ficoll separation, affinity techniques, such as for example antibody-based methods including magnetic and flow cytometry systems. In some embodiments, the blood may be further processed for collection and isolation of immune cells. Further processing of the blood includes, but is not limited, to, washing to remove plasma using a suitable buffer known to one of ordinary skill in the art, such as for example, phosphate buffered saline, and re-suspension of the plasma-free fraction in a suitable buffer or media.

In some embodiments, an immune cell type of interest may be isolated from other immune cells, and other types of cells in the blood, may be isolated by lysing red blood cells and depleting the cell types not of interest using centrifugation, for example, Ficoll, Percoll or counterflow elutriation. Should a specific subpopulation of immune cells be desired, for example but not limited to, T cell subtypes including, but not limited to, $CD3^+$, $CD4^+$, $CD8^+$, $CD28^+$, $CD45RA^+$, and $CD45RO^+$ expressing T cells, may be isolated from the larger population of T cells using positive or negative selection methods known to those of ordinary skill in the art. For example, subtypes of T cells may be isolated from a larger group of T cells by positive selection with antibody-mediated detection of the desired molecule expressed by the T cells (e.g., CD3 and CD28, using for example, anti-CD3/anti-CD28-conjugated beads, such as Dynabeads). The number of subtypes of cells isolated from the larger group of cells, amount of selective reagent required, duration of incubation of the selection agent with the population of cells, and the like, are readily determined by one of ordinary skill in the art where such parameters would be chosen to optimize isolation of the most amount of subtype cells from the larger type with the least amount of agent.

In some embodiments, negative selection may be desired relative to positive selection, for example, when engagement of a molecule expressed by the target cell could elicit an undesired response in the target cells. Isolation of a population of immune cells from a larger population of cells by negative selection may include a combination of antibodies directed to surface markers unique to the undesired cells. In this way, the cells not bound to antibodies are the target cells. Methods of negative selection include, but are not limited to, magnetic techniques (e.g., antibody conjugated to a ferrous residue and coupled with a magnetic column), flow cytometry, bead-based affinity techniques, and the like.

The timing of when blood is removed and the amount of blood removed from a subject so as to then isolate immune cells varies and each parameter may be selected by one of ordinary skill in the art. Often, blood may be collected at any time necessary, for any number of times necessary and at any amounts necessary so as to achieve sufficient numbers of the target cells for use with the methods and compositions as described herein. In some embodiments, the target cells is either expanded at any time point necessary or stored at any time point necessary, for later use. For example, storage may include ex vivo cell culture or freezing.

Therapeutic Applications

The methods and compositions described herein are considered useful for treating or preventing a disease or a condition in a subject. In some embodiments, methods and compositions described herein are provided for a disease or a condition including a cancer, for example, a cancer associated with expression of a molecule on the cancer cells. Often, the molecule expressed by the cancer cells comprises an extracellular portion capable of recognition by a molecule expressed by the genetically engineered immune cell, for example, a chimeric antigen receptor expressed by a T cell. As described herein, the CAR may be configured to recognize a molecule expressed by a cancer cell, such as for example, but not limited to, CD19, L1CAM, NY-ESO, or the like. In other embodiments, the molecule expressed by the cancer cells comprises an extracellular portion capable of recognition by a molecule expressed by the genetically engineered immune cell, for example, a T cell receptor expressed by a T cell. As described herein, the TCR may be configured to recognize a molecule expressed by a cancer cell, such as for example, but not limited to, CD19, L1CAM, NY-ESO, or the like. In some embodiments, the molecule expressed by the cancer cells comprises an extracellular portion capable of recognition by a molecule expressed by the genetically engineered immune cell, for example, a negative regulatory molecule expressed by a T cell. As described herein, the negative regulatory molecule may be configured to recognize a molecule expressed by a different cell, such as for example an antigen presenting cell, but not limited to, PD-1.

In some embodiments, the disclosure provided herein relates to methods and compositions of treating or preventing cancer in a subject. The methods described herein comprise administering a composition of genetically engineered immune cells, as described herein, to the subject from which the immune cells were isolated from. The genetically modified immune cells further comprise biallelic insertion of at least an expression cassette often mediated by Cas9. In some embodiments, biallelic insertion is targeted to a desired region of the immune cell genomic DNA. As an exemplary embodiment, the genetically engineered immune cells may comprise T cells which express a CAR recognizing CD19 such that a CD19-positive cancer is treated in the subject. A disease or condition associated with expression of CD19 includes, but is not limited to, malignancies and/or precancerous conditions associated with expression of CD19. Often, cancers associated with expression of CD19 by cancer cells are hematological cancers, such as, but not limited to, leukemias or lymphomas, such as, for example, acute leukemias (e.g., B-cell acute lymphoid leukemia, T-cell acute lymphoid leukemia, acute lymphoid leukemia), chronic leukemias (e.g., chronic myelogenous leukemia and chronic lymphoid leukemia). Additional diseases or conditions associated with expression of CD19 include, but are not limited to, Burkitt's lymphoma, diffuse large B cell lymphoma, follicular lymphoma, small cell follicular lymphoma, large cell follicular lymphoma, hairy cell leukemia, mantle cell lymphoma, multiple myeloma, non-Hodgkin's lymphoma, or the like.

The methods and compositions as described herein are considered useful for administration to a subject in need thereof where immune cells are genetically modified to express, for example, a CAR, a TCR and/or a negative regulatory molecule whereby the genetically modified immune cells are administered to a subject in need thereof so as to recognize and eliminate diseased cells, such as for example tumor cells, in the subject. In some embodiments, the genetically engineered immune cells, often T cells, may be administered to a subject in need and often, the genetically engineered immune cells, and/or progeny of the genetically engineered immune cells, may persist in the subject for one day, three days, one week, three weeks, one month, three months, six months, nine months, twelve months, fifteen months, eighteen months, two years, five years or ten years after administration to the subject in need thereof. For example, genetically engineered immune cells may persist due to activation of the CAR, TCR or negative regulatory molecule expressed by the genetically engineered immune cell. By way of another example, genetically engineered immune cells may persist due the responsiveness of a regulatory system, as described herein, to an agent which regulates transcription and translation of the CAR, TCR or negative regulatory molecule expressed by the genetically engineered immune cells. By way of yet another example, genetically engineered immune cells may persist due the responsiveness of a regulatory system, as described herein, to an agent which regulates survival of the genetically engineered immune cells, such as for example, by administration of agents which regulate a nutrient-dependent pathway in the genetically engineered immune cells, such as for example, arginine.

Procedures for modifying immune cells to express a protein encoded by an exogenous vector, plasmid or to respond to treatment with a purified protein, are well known to those of ordinary skill in the art. In some embodiments, immune cells are isolated from a subject, as described herein, and may be genetically engineered by transfection or transduction of the immune cells with a vector or a plasmid expressing the elements of the compositions as described herein. Such elements may include, but are not limited to, gRNA, an expression cassette, targeting sequences, systems for regulating expression of the expression cassette, and the like. Genetically engineered immune cells may be optionally expanded ex vivo. The genetically engineered immune cells may be administered to a subject in need thereof as a treatment for a condition or disease.

The methods and compositions as described herein are considered useful for, optional ex vivo expansion, and may be administered to a subject in need of prevention of a disease or a condition or in need of treatment of a disease or a condition. For example, the genetically engineered immune cells as described herein is either used in the treatment of diseases, disorders and conditions associated with expression of an antigen associated with a disease, disorder and/or a condition, such as but not limited to CD19. In some embodiments, genetically engineered immune cells as described herein may be administered to subject as a treatment for a proliferative disease, disorder or condition, such as a cancer or malignancy. As an exemplary embodiment, the genetically engineered immune cells may comprise T cells which express a CAR recognizing CD19 such that a CD19-positive cancer is treated in the subject. A disease or condition associated with expression of CD19 includes, but is not limited to, malignancies and/or precancerous conditions associated with expression of CD19. Often, cancers associated with expression of CD19 by cancer cells are hematological cancers, such as, but not limited to, leukemias or lymphomas, such as, for example, acute leukemias (e.g., B-cell acute lymphoid leukemia, T-cell acute lymphoid leukemia, acute lymphoid leukemia), chronic leukemias (e.g., chronic myelogenous leukemia and chronic lymphoid leukemia). Additional diseases or conditions associated with expression of CD19 include, but are not limited to, Burkitt's lymphoma, diffuse large B cell lymphoma, follicular lymphoma, small cell follicular lymphoma, large cell follicular lymphoma, hairy cell leukemia, mantle cell lymphoma, multiple myeloma, non-Hodgkin's lymphoma, or the like.

Further, a "disease antigen", a "cancer antigen" or a "tumor antigen" refers to antigens that are known to those of ordinary skill in the art, or newly found to be associated with such a condition, to be commonly associated with, and/or, specific to, such conditions. Often, disease antigens, cancer antigens and/or tumor antigens are derived from the following specific conditions and/or families of conditions, including but not limited to, cancers such as brain cancers, skin cancers, lymphomas, sarcomas, lung cancer, liver cancer, leukemias, uterine cancer, breast cancer, ovarian cancer, cervical cancer, bladder cancer, kidney cancer, hemangiosarcomas, bone cancers, blood cancers, testicular cancer, prostate cancer, stomach cancer, intestinal cancers, pancreatic cancer, and other types of cancers as well as pre-cancerous conditions such as hyperplasia or the like.

The methods and compositions described herein are efficient at generating biallelic insertions of effector genes (e.g., CARs, TCRs, negative inhibitory receptors, and the like). Additionally, the methods and compositions described herein are useful for genetically engineering cells to comprise larger inserts of polynucleotides into the genome, often with high efficiency and fidelity. The use of large inserts is beneficial to deliver a plurality of desired cassettes, often by targeted insertion and the expression of which is regulated by cis-regulatory mechanisms. For example, a plurality of CARs, TCRs and negative regulatory molecules are considered in addition to gRNAs targeting other loci such as receptors for inhibitory pathways, or conditional cis-regulatory sequences that could be targeted for insertion adjacent to endogenous genes placed under regulatory control by agents such as drugs, small molecules or the like. Accordingly, an integrated set of cassettes is delivered into immune cells, such as T cells, in a single round of treatment so as to reduce both the number of ex vivo cell divisions and minimize the time from isolation of immune cells from a subject to administration of genetically engineered immune cells to a patient in need thereof, often targeting the disease or condition, such as cancer. For example, such advantages could mean the difference between life and death in a subject with late-stage metastatic cancer.

"Subject" or "subjects" includes, but is not limited to, humans and non-human mammals such as mice, rats, pigs, dogs, cows, sheep, non-human primates, and the like. "Patients" refers to subjects suffering from, or at risk of developing, a disease, disorder or condition or otherwise, and in need of the compositions and methods provided herein.

As used herein, a "therapeutically effective amount" is the amount of a composition or an active element thereof sufficient to provide a beneficial effect or to otherwise reduce a detrimental effect to the individual administered the composition. By "therapeutically effective dose" as used herein, "therapeutically effective dose" refers to a dose which produces one or more desired or desirable effects, such as beneficial effects, for which one or more of the compositions as described herein, is administered. Often times, administration occurs one or more times over a period of time sufficient to achieve the desired, often beneficial, effect. The amount of a therapeutically effective dose and frequency of administration depends on the disease or condition targeted by the treatment, or aimed to be prevented by the treatment, and is understood by one skilled in the art using known techniques. The terms "effective amount" and "therapeutically effective amount" are used interchangeably herein.

In some embodiments, the genetically engineered immune cells of the present disclosure may be administered as a pharmaceutical composition, often comprising genetically engineered immune cells or comprising genetically engineered immune cells and cytokines, agents (e.g., tamoxifen, tetracycline, arginine, arginine degrading enzymes, and the like), or additional factors useful for achieving the therapeutic purpose of administering the genetically engineered immune cells to the subject in need thereof.

Pharmaceutical Compositions

The compositions and methods described herein are considered useful as pharmaceutical compositions for administration of genetically engineered immune cells to a subject in need thereof. Pharmaceutical compositions comprise at least genetically engineered immune cells and one or more pharmaceutically acceptable carriers, diluents or excipients. In some embodiments, the genetically engineered immune cells comprise TAT-tagged Cas9 protein. In some embodiments, pharmaceutical compositions may additionally comprise a cytokine, an agent (e.g., tamoxifen, tetracycline, arginine, arginine degrading enzymes, and the like). The compositions often further comprise buffers, antibiotics, steroids, carbohydrates, drugs (e.g., chemotherapy drugs), radiation, polypeptides, chelators, adjuvants and/or preservatives. Compositions of the present disclosure are in one embodiment formulated for intravenous administration.

Pharmaceutical compositions considered useful with the compositions and methods described herein may be administered to a subject in need thereof using a technique known to one of ordinary skill in the art which is suitable as a therapy for the disease or condition affecting the subject. One of ordinary skill in the art would understand that the amount, duration and frequency of administration of a pharmaceutical composition described herein to a subject in need thereof depends on several factors including, for example but not limited to, the health of the subject, the specific disease or condition of the patient, the grade or level of a specific disease or condition of the patient, the additional therapeutics the subject is being or has been administered, and the like.

The methods and compositions described herein are often for administration to a subject in need thereof. Often, administration of an immunogenic composition includes routes of administration including, but not limited to, intravenous, intraarterial, subcutaneous, subdural, intramuscular, intracranial, intrasternal, intratumoral, or additional techniques known to those of ordinary skill in the art.

As used herein, a "therapeutic" refers to a treatment for a disease or condition. A therapeutic effect in a subject having a disease or condition, or pre-disposed to have or is beginning to have the disease or condition, is obtained by a reduction, a suppression, a prevention, a remission, or an eradication of the condition or disease, or pre-condition or pre-disease state.

In some embodiments, genetically engineered immune cells of the present disclosure are administered to a subject in need thereof in a first administration, and in one or more additional administrations, such as for example, a second administration, a third administration, a fourth administration, a fifth administration, a tenth administration, and the like. The one or more additional administrations may be administered to the subject in need thereof minutes, hours, days, weeks or months following the first administration. In an exemplary embodiment, any one of the additional administrations are administered to the subject in need thereof less than 21 days, or less than 14 days, less than 10 days, less than 7 days, less than 4 days or less than 1 day after the first administration. The one or more administrations may occur more than once per day, more than once per week or more than once per month. In some embodiments, the administrations occur at a specified dose for a specified duration of time, often, the administrations may cease for a specified time, (e.g., a break) before subsequent administrations occur.

Large-Scale Genome Engineering

The term "active genetics" can refer to genetic manipulations in which a genetic element is copied from one chromosome to the identical insertion site on the sister chromosome using Cas9 and gRNA elements (e.g., MCRs or split cas9; <gRNA> drives).

The term "mutagenic Chain Reaction" (MCR) can refer to a method by which a cassette encoding Cas9 and a gRNA is inserted precisely into the gRNA cut site.

The term "split cas9; <gRNA>" can refer to a configuration in which a cas9 transgene inherited in a standard Mendelian fashion is combined with a gRNA flanked by homology arms (denoted as <gRNA>). In this situation, only the <gRNA> element can be actively copied to the other chromosome.

The term "allelic pump" can refer to a configuration formed by the combination of a traditional Mendelian source of cas9 and a <gRNA>, resulting in the production of a constant new number of <gRNA> alleles at each generation.

The term "copy-cat (cc) cloning vectors" can refer to a plasmid cloning vectors that in addition to having standard features (e.g., origin of replication, antibiotic resistance genes, multiple cloning sites) also carries a gRNA flanked by homology arms that direct insertion of the element into defined locations. Transgenes inserted into cc vectors can be readily rendered homozygous by providing a source of cas9 in trans.

The term "genetic drive" can refer to the inheritance of an allele of a diploid gene more than 50% of the time (i.e., more than by random chance alone).

The term "effector gene cassette" can refer to a transgene encoding a protein that when expressed exerts a desired effect (e.g., anti-malarial peptides expressed following a blood meal in mosquitoes or a drug inducible cell lethal gene in a cancer cell).

Figure 12A:
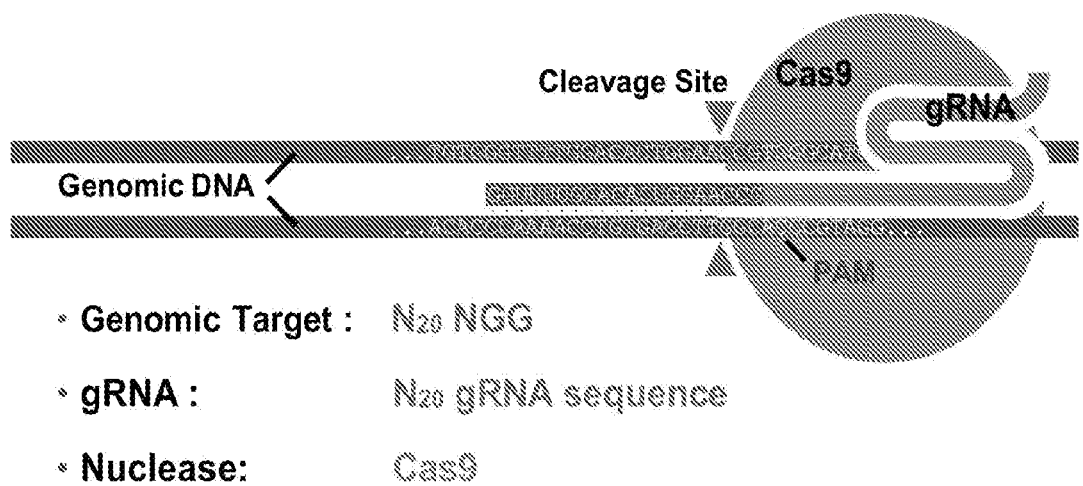
FIGS. 12A and 12B show an overview of CRISPR/Cas based genome editing.
Figure 12B:
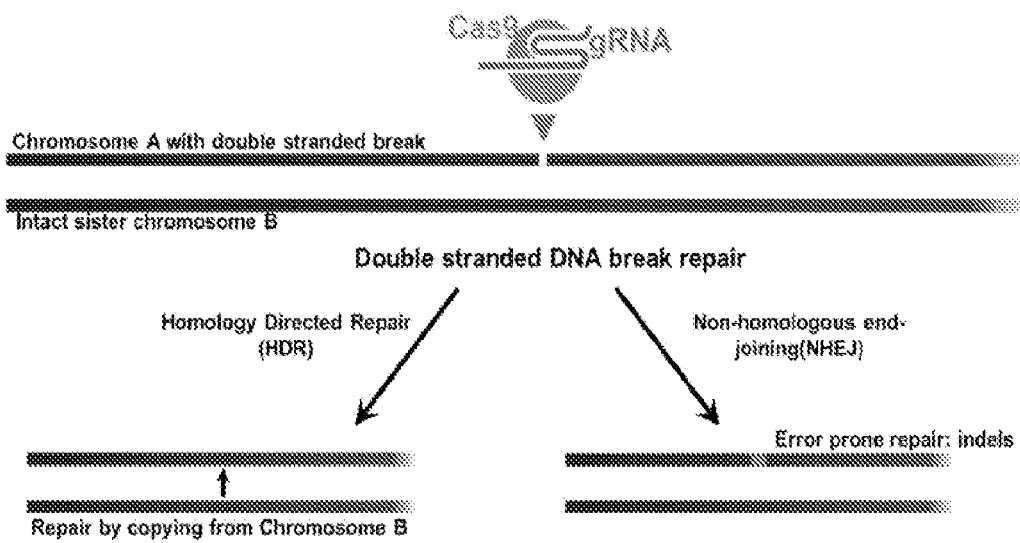

CRISPR/Cas system is a genome editing tool that can be used in a wide variety of organisms including diverse animals, plants and yeast (FIGS. 12A, 12B). Briefly, this system consists of two entities, the Cas protein (e.g., Cas9 endonuclease), which cleaves DNA templates on both strands, and a guide-RNA (gRNA), the first 20 nucleotides of which direct the Cas9 cleavage of a complementary target DNA at a site three nucleotides upstream the 3'-end of the gRNA target sequence (FIG. 12A). Following cleavage of a targeted genomic sequence by a Cas9/gRNA complex, one of two alternative DNA repair mechanisms can restore chromosomal integrity: 1) non-homologous end joining (NHEJ) which generates insertions and/or deletions of a few base-pairs (bp) of DNA at the gRNA cut site, or 2) homology-directed repair (HDR) which can correct the lesion via an additional "bridging" DNA template that spans the gRNA cut site. In *D. melanogaster*, individuals carrying sources of genomically-encoded germline Cas9 and gRNAs (or that have been injected with plasmid encoded sources of gRNAs) efficiently mutate the target sequence via NHEJ in the great majority of somatic cells, but also can undergo HDR repair in the germline when a DNA template containing homologous sequences is coinjected into the polar plasm.

The autocatalytic mutagenesis method described herein can combine features of the CRISPR/Cas9 system in a novel configuration, exploiting the cell's endogenous repair mechanism to generate self-homozygosing alleles.

Based on the CRISPR/Cas9 system, an autocatalytic genetic behavior with a self-propagating genetic element can be achieved in which insertional mutants are generated by a construct having three components: 1) a central segment encoding Cas9 (expressed in both somatic cells and the germline), 2) a gRNA targeted to a genomic sequence of interest, and 3) homology arms (HA) flanking the Cas9/gRNA cassette that match the two genomic sequences immediately adjacent to either side of the target cut site (FIG. 1). Such a tripartite construct can result in Cas9 cutting the genomic target at the site determined by the gRNA followed by insertion of the Cas9/gRNA-bearing cassette into that locus via HDR directed by the flanking sequences. Expression of Cas9 and the gRNA from the insertion allele can then lead to cleavage of the opposing allele (FIGS. 1A-1G) followed by HDR-driven insertion of the Cas9/gRNA cassette into the companion chromosome. In analogy to the polymerase chain reaction (PCR), which doubles the number of DNA templates each cycle, this trans-acting mutagenesis scheme can be referred to as the Mutagenic Chain Reaction (MCR), since it accomplishes the same end by in vivo DNA amplification. MCR can be efficient in both somatic and germline precursor cells if HDR acted more frequently than NHEJ to repair double-stranded DNA breaks created by gRNA cleavage.

In some embodiments, the disclosure provides for a split Cas protein and gRNA configuration, in which only the gRNA can be inserted at the cut site. A CopyCat (herein used interchangeably as CopyCat, CC, or cc) element can refer to this self-propagating gRNA. The Cas9 source can be supplied in-trans from another chromosome allowing the CopyCat element to be segregated away from the Cas9 source as desired, at which point it will obey the laws of standard Mendelian inheritance. In the presence of Cas9, however, the CopyCat element can be actively copied (or CC'ed) to its sister chromosome, resulting in it becoming homozygous.

The other existing elements to which CopyCat elements can be compared are MCRs in which the source of Cas9 and gRNA are inserted into the same locus (i.e., at the gRNA cut site). An advantage of the CopyCat element is that one can segregate the source of Cas9 away from the CopyCat element and then manipulate such element via standard Mendelian genetics whereas the MCR by its inherent design remains associated with the Cas9 source.

CopyCat elements can carry either a single gRNA, in which case they can simply insert themselves into the gRNA cut site, or two gRNAs cutting at some distance from each other, in which case the CopyCat element will generate a deletion between the two sites and then insert itself into that gap (e.g., 10 kb gap). A CopyCat element can carry, for example, 1, 2, 3, 4, 5, 6, 7, 8, 9, 10, or more than 10 gRNA.

In some embodiments, a CopyCat vector harbors a gRNA and flanking homology sequences to guide its insertion into a desired chromosomal location. In some embodiments, a CopyCat vector also contains multiple cloning sites (MCS). In some embodiments, a CopyCat vector also contains a dominant marker gene (Mrk) for identifying transgenic individuals.

In some embodiments, a CopyCat cloning vector or plasmid contains the following components: 1) one or two gRNAs targeting insertion of the associated sequence into a specific site in the genome. If there are two gRNAs, they can cut nearby targets on the same chromosome; 2) homology arms that directly abut the gRNA cut site(s); and 3) standard core features of cloning vectors including a bacterial origin of replication, a gene conferring antibiotic resistance, a multiple cloning site, a dominant selectable marker (e.g., GFP expressed in a surface visible cell type) and other optional features including a Φ31C docking site, a yeast upstream activating sequence (UAS), translation or transcription stop sequences, or FRT recombination sites (FIG. 8).

CopyCat elements can be integrated into the genome at their intended insertion site (i.e., determined by the gRNA(s)) by injecting the CopyCat plasmid DNA into the germline along with a plasmid encoding source of Cas9, or with purified Cas9 protein, or into a transgenic line expressing Cas9 genetically in the germline. For notational convenience CopyCat elements can be represented as <gRNA1; gRNA2; effectors> wherein the "< >" symbols indicate the chromosomal homology sequences that directly abut the gRNA cleavage site(s).

Figure 8:
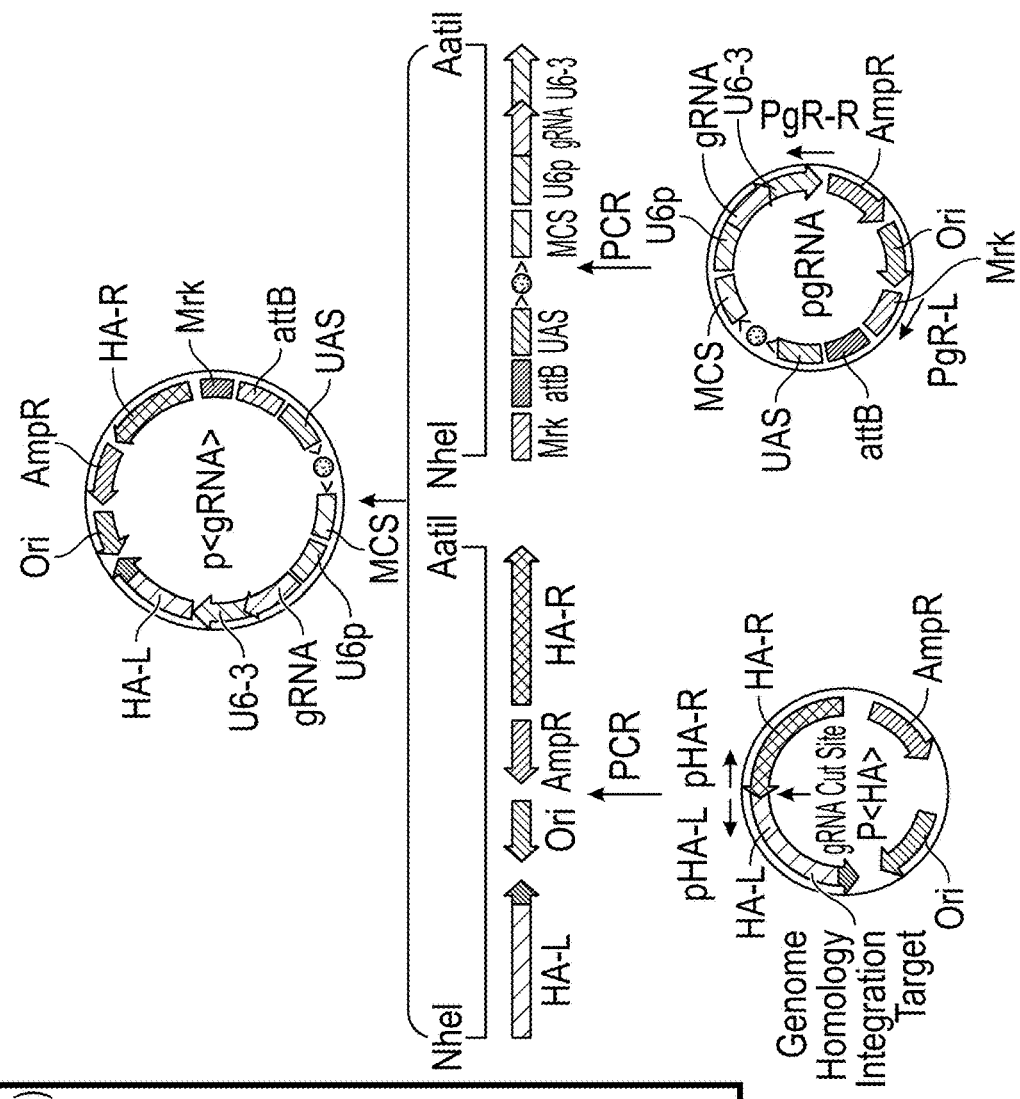
FIG. 8 depicts an illustrative scheme for constructing CopyCat transgenesis vectors.

CopyCat vectors, as illustrated in FIG. 8, can allow the cloning of transgenes into multiple cloning sites (MCS) as well as matched sets of gRNA(s) flanked by both 5' (U6p) and 3' (U6-3') U6-RNA regulatory elements, and homology arms (HA-L=left, HA-R=right), standard features of cloning vectors such as a bacterial origin of replication (Ori), a gene providing Ampicillin resistance (AmpR), as well as optional use cassettes such as a UAS promoter, an attB φ31C recombinase donor site, and an FRT-flanked transcriptional stop cassette (<Stop<).

A modular kit of cc vectors can be generated for any given organism to target sequences spaced along the various chromosomes to permit the flexible assembly of complex combinations of transgenes. cc elements can be designed to insert into coding regions of non-essential visible marker genes (e.g., pigment or bristle markers in *Drosophila*), into regulatory regions of essential genes that direct expression in a non-vital cell type (e.g., a wing specific cis-regulatory sequence of an essential *Drosophila* gene), or into fitness neutral sites (e.g., rosa26 in mice).

Figure 9:
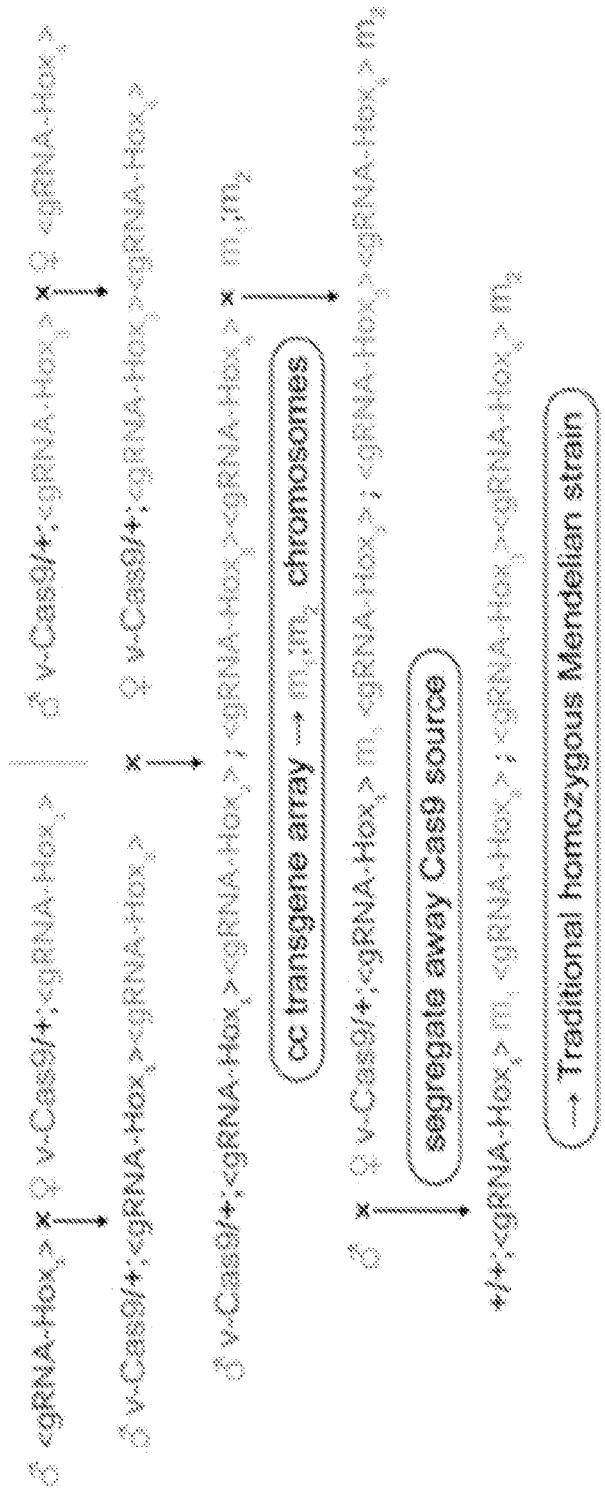
FIG. 9 illustrates an outline for genome sculpting using CopyCat elements. CopyCat elements are represented by the notation <gRNA> in which the symbols < > represent the fact that the gRNAs are flanked by genomic sequences abutting the gRNA cut site.

CopyCat elements can circumvent classic constraints imposed by Mendelian inheritance, including independent association of genes located on different chromosomes (or far apart on the same chromosome) and low recombination rates that can result from transgenes being inserted at nearby sites on the same chromosome. As illustrated in FIG. 9, the use of CopyCat elements can accelerate genetic manipulations by a factor of 2. In other embodiments CopyCat elements can permit the isolation of complex genetic recombinants that would be difficult if not impossible to recover using standard Mendelian methods due to the low frequency of organisms inheriting the desired genetic elements by chance (i.e., independent assortment of chromosomes or distantly linked genes (FIG. 9).

cc elements can insert at various loci along a chromosome (*D. melanogaster* X-chromosome shown as example) which are determined by their particular matched sets of gRNAs and homology arms. In the presence of a cas9 source, these elements can be copied to the sister chromosome thereby efficiently homozygosing the element with the inserted transgene.

Figures 14A, 14B:
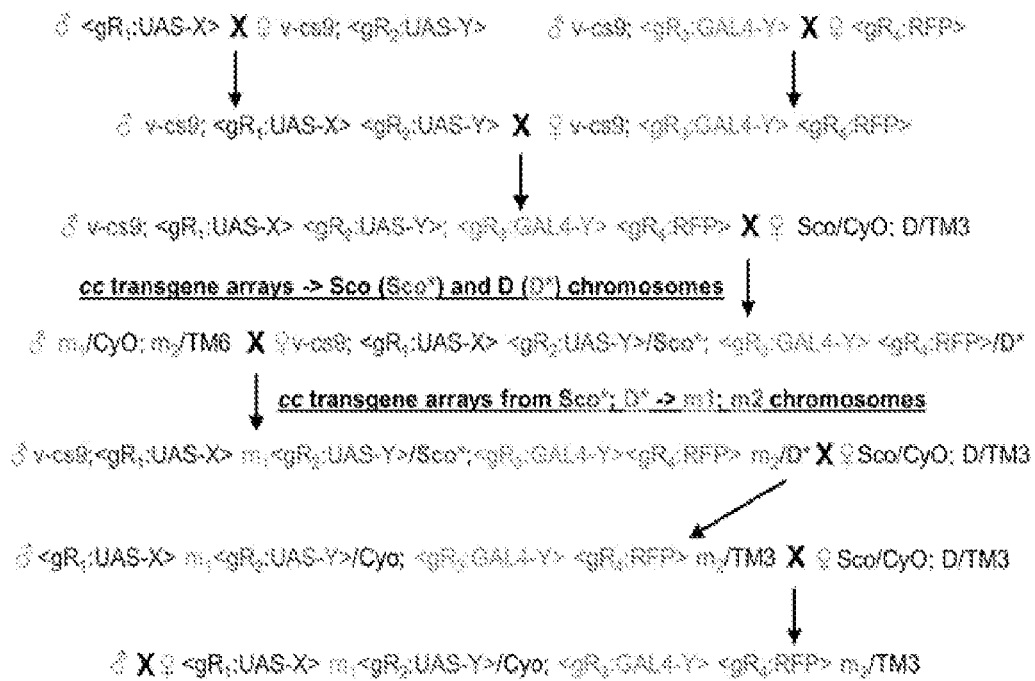
FIGS. 14A and 14B illustrate application of the CopyCat vector.
Figure 15:
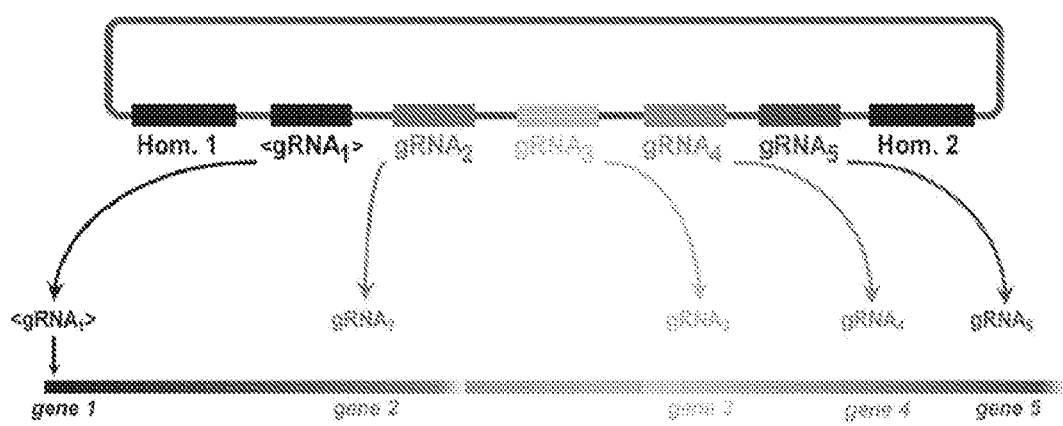
FIG. 15 illustrates applications of the CopyCat system.
Figure 16A:
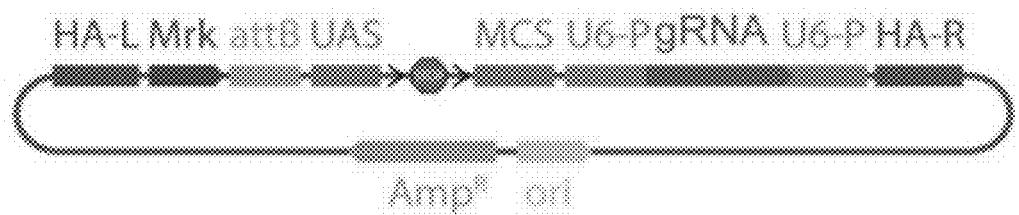
FIGS. 16A-16B show illustrative CopyCat vector and elements.
Figure 16B:
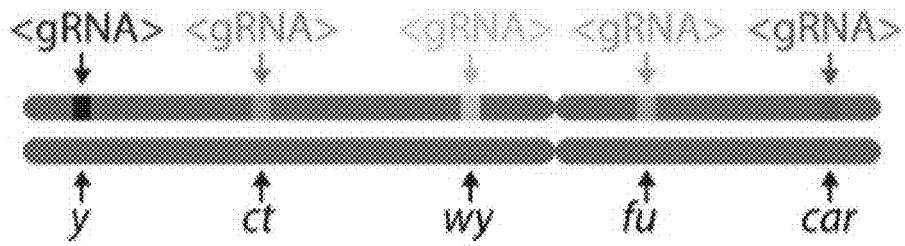
Figure 17:
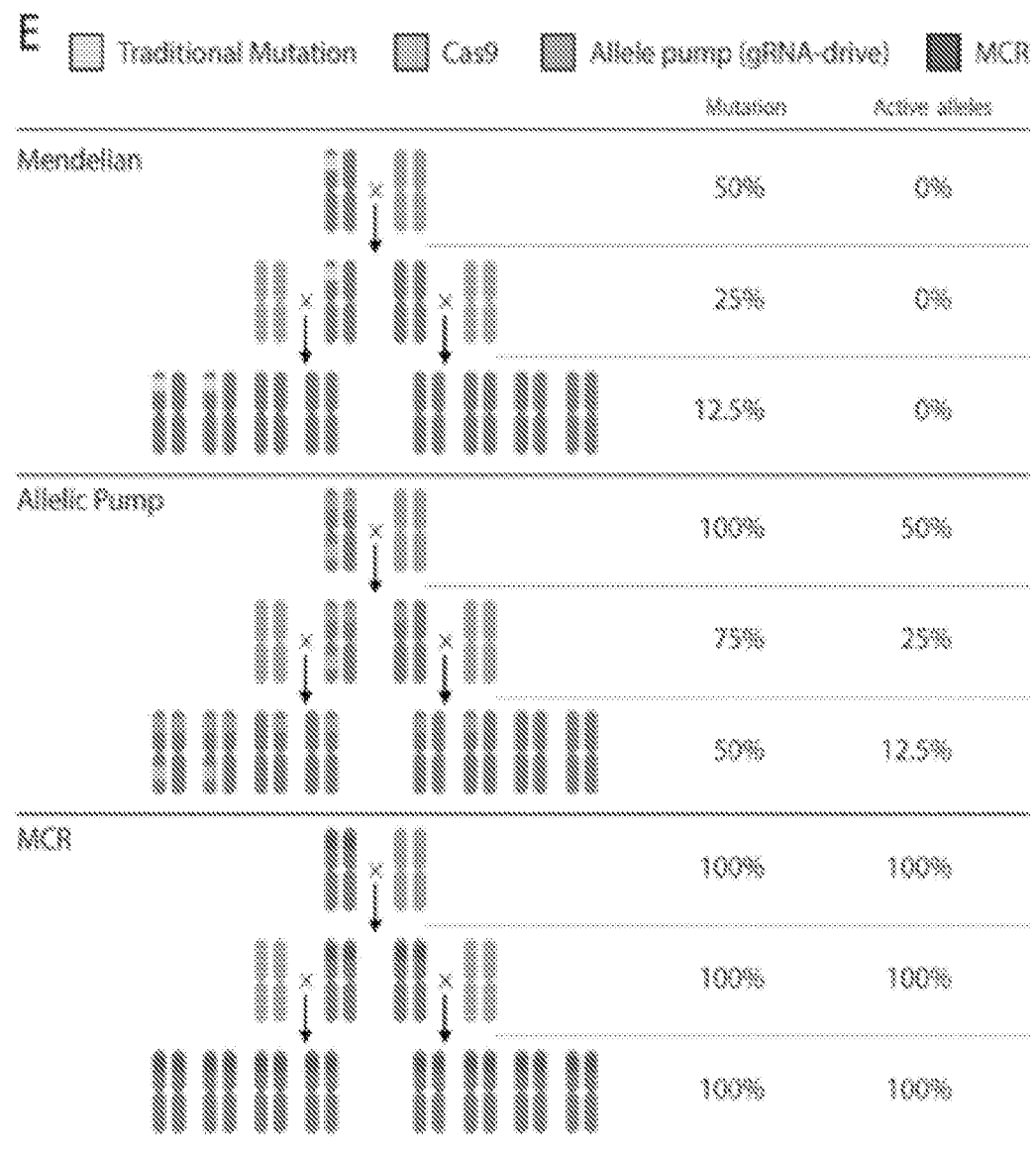
FIG. 17 illustrates a scheme depicting two generations of inheritance for a classic Mendelian allele (top), an allelic pump consisting of a separated source of cas9 and a <gRNA> (middle), and an MCR (bottom).

CopyCat elements mobilized by cas9 can be used to insert a variety of different transgenes at defined loci spaced throughout the genome. In the presence of an unlinked source of cas9, these elements can become homozygous and can be combined by crossing strains carrying insertions at different sites in the presence of cas9. The progeny can inherit both transgenes, which can then become homozygous and be transmitted together to their progeny. cc-elements can also be tailored to insert into loci of interest and generate mutant phenotypes, combining transgenesis with mutagenesis. Once assembled, an array of cc-transgenic elements can be launched onto another set of chromosomes (e.g., that carried traditional sets of Mendelian alleles) in the maintained presence of a cas9 source, by a process that can be referred to as cc-ing (e.g., example of targeting four Hox genes in FIGS. 14A-14B). One can then segregate away the source of cas9 and return back into the traditional stable Mendelian realm for example, for experimental analysis of the resulting mutant phenotypes. This facilitates assembly of complex arrays of transgenic constructs in combination with traditional alleles. Such vectors can be used to accelerate genetic manipulations involving combinatorial studies in polyploid crop plants, for example, by enabling the pairwise or higher order analysis of genetic variants conferring traits such as drought or pest resistance.

FIG. 9 illustrates combining four CopyCat mutants with two traditional alleles. It illustrates an example of how copy-cat elements can be used in a model vertebrate organism such as a mouse or fish to create a cas9-dependent quadruple knock-out of a set of target genes (e.g., Hox gene paralogs). Various transgene constructs can also be carried by each of the cc-elements (e.g., CRE/LOX components and fluorescent markers appropriate for expressing and analyzing the ability of a single Hox gene to substitute for the normal sets of genes in a given tissue). These cc elements/ mutant alleles can be assembled in two generations. Next, in the maintained presence of cas9, they can be combined with two traditional Mendelian alleles by cc-ing the Hox mutant alleles into the mutant background. The source of cas9 then can be removed by segregation, resulting in the complex assembly of mutant alleles and transgenes which can now behave according to standard Mendelian rules. Such a complex genetic assembly can be prohibitive using Mendelian inheritance.

CopyCat elements can be directed to insert anywhere in the genome. Primary transgenic individuals are typically homozygous for the element in both somatic and germline cells.

In some embodiments, CopyCat elements are used to enable large-scale replacement of chromosomal segments for purposes of genome engineering.

Single and double-cut CopyCat elements (generating gaps on the order of 10 kb) can copy themselves to the sister chromosome with nearly the same high efficiency as an MCR (e.g., ≈95%).

The present disclosure provides methods and compositions for large scale genome engineering using multiplex active genetics.

Figure 10:
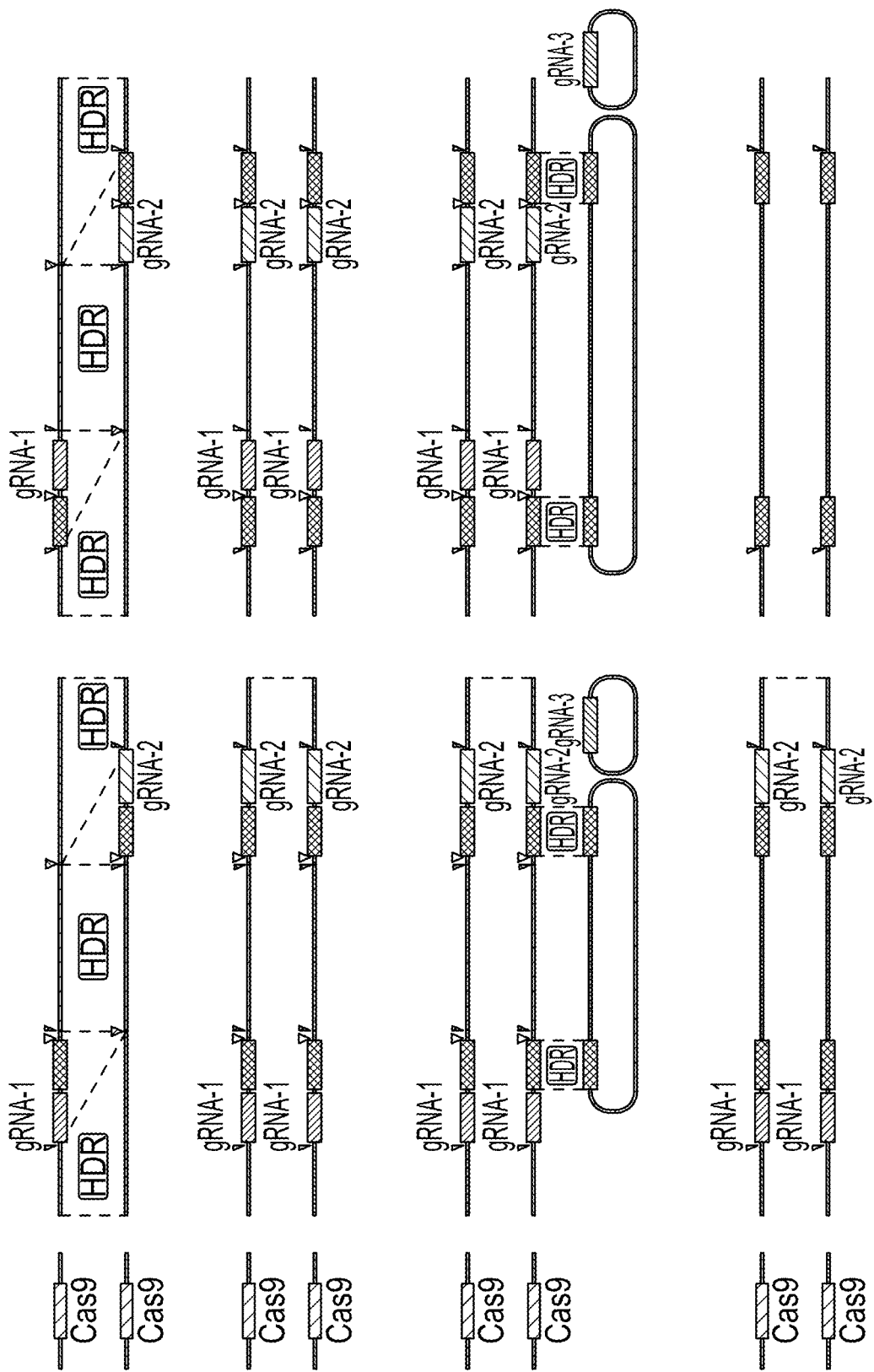
FIG. 10 illustrates assembly of a complex genotype using CopyCat elements.

In some embodiments, large deletions are generated and the active elements propagated with high efficiency by crossing two single-cut CopyCat elements that target distant sequences from each other (FIG. 10). Such elements can propagate efficiently on their own, while also generating a deletion of intervening sequences at some reasonable frequency. In some embodiments, the CopyCat elements also carry sequences homologous to the two ends of a BAC (Bacterial Artificial Chromosome) clone carrying a replacement insert of interest. In this case, deletions can be expected to be repaired via copying of BAC sequences injected into the germline, leading in one step to replacement of an arbitrary genome segment with a replacement sequence of choice.

CopyCat-mediated BAC replacements can be engineered in one of two ways: 1) maintain the capacity to actively convert wild type alleles (see FIG. 10, left) or 2) be inherited in a standard Mendelian fashion (see FIG. 10, right). Many such single-cut CopyCat elements can be generated in parallel and used to generate a series of replaced genome segments, which can then be rapidly stitched together to create either larger replaced contiguous segments of a single chromosome or combinations of different replaced-locus segments. Such multiplex active genetics approach can be useful in redesigning large segments of the genome within a reasonable time frame. In contrast, using existing traditional Mendelian-based methods such engineered genomes are likely to be very difficult or impossible to assemble.

In some embodiments, pairs of single-cut <gRNA> Copy-Cat elements are used to create precise replacements of large genomic segments as illustrated in a stepwise fashion in FIG. 10. The scheme can be used for developing active genetic tools for large-scale genome design. In the presence of Cas9, two stocks carrying single CopyCat elements inserting at opposite ends of region to be deleted (shown in dark gray) and replaced can be crossed each other to place them on the same chromosome (e.g., via Cas9-mediated copying). A stock carrying the two distantly separated Copy-Cat elements (<gRNA1> and <gRNA2>) can then be crossed to a wild-type (WT) stock and the resulting embryos can be injected with a BAC clone containing the desired replacement sequence (red) and a gRNA (gRNA3) that cuts a sequence carried on the ends of both CopyCat elements. The CopyCat elements can also include sequences homologous to the two ends of the BAC insert (red segments). Progeny from such embryos can be recovered in which the deleted sequence can be replaced with the BAC insert. Depending on whether the homology arms carried on the CopyCat elements face toward the deletion (left) or away from the deletion (right) the resulting replaced chromosomal segment can either be flanked by active CopyCat elements (left) or not (right).

In some embodiments, methods of the disclosure are used to facilitate basic genetic manipulations in diverse experimental and agricultural organisms (e.g., accelerating the generation of combinatorial mutants and facilitating mutagenesis in polyploid organisms). In some embodiments, methods of the disclosure are used to accelerate genetic manipulations in animals (e.g., primates) or plants (e.g., trees) with a long generation time.

In some embodiments, methods of the disclosure are used for large-scale genomic engineering such as genetic transplantation of entire organs or metabolic pathways.

Figure 11:
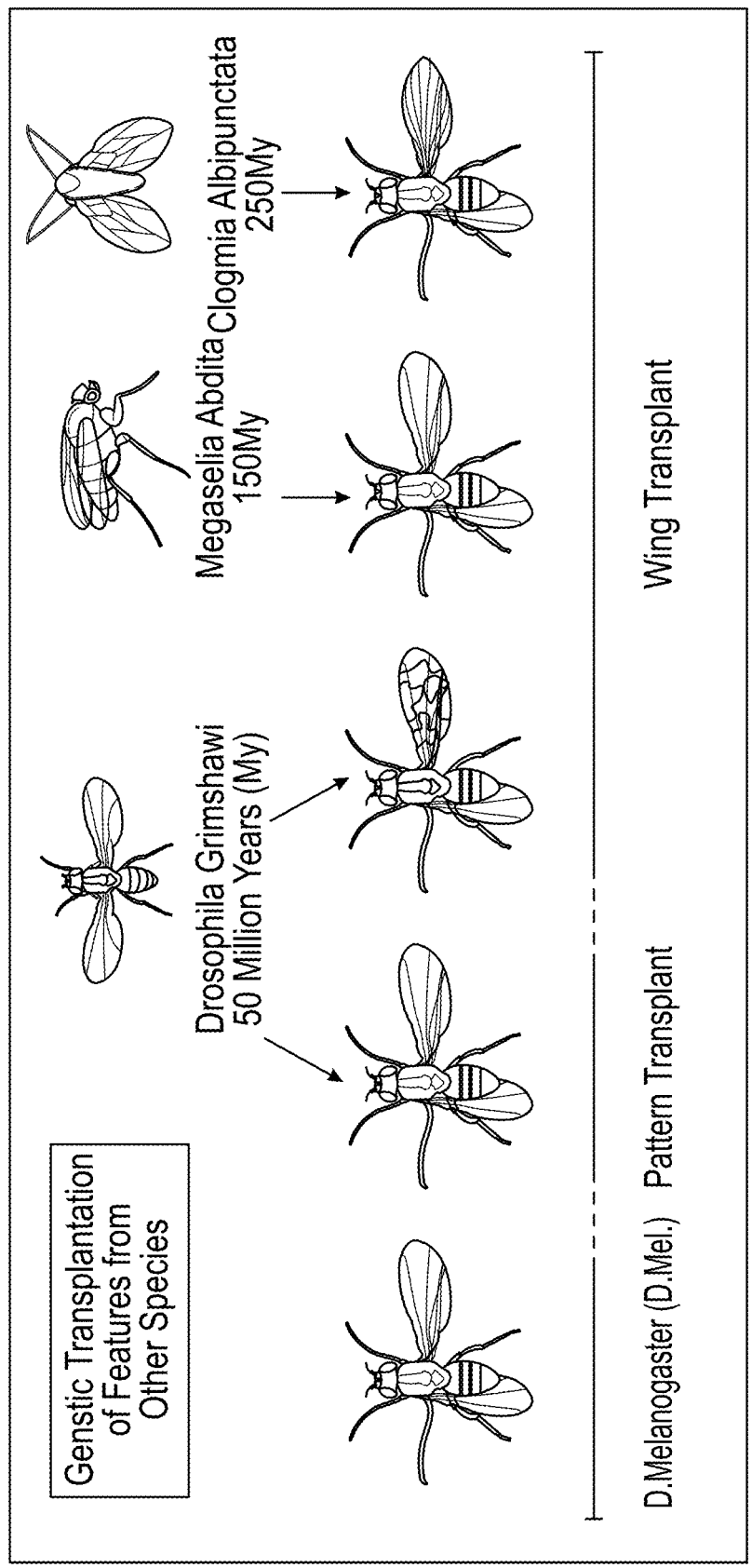
FIG. 11 illustrates potential application of the present disclosure. Methods of the disclosure can be used to transplant the genetic circuitry controlling whole body pigmentation (e.g., *D. grimshawi*) or wing patterning (e.g., *M. abdita, C. albipunctata*) from other fly species into *D. melanogaster*.

In some embodiments, the present disclosure is used to replace large genomic segments in the context of genes controlling developmental traits (e.g., body pigmentation and wing development in the fruit fly (*Drosophila melanogaster*=D. mel.) with the corresponding loci from other fly species differing in pigmentation and wing pattern, as shown in FIG. 11).

In some embodiments, methods of the disclosure are used for multiplex engineering of large chromosome segments encompassing a panel of complex loci—e.g., drought resistance, use of alternative food sources, increased longevity, changes in shape and/or size of organisms, humanization of organisms for purposes such as research or milk production, autonomous growth of organs for transplantation or meat production, or genome/phenotype engineering.

In some embodiments, methods of the disclosure are used to treat a disease or disorder. In some embodiments, the disease is cancer.

In some embodiments, the genome engineering produced using the methods of the disclosure is reversed or neutralized.

Genome editing using methods of the disclosure can be used to combat pathogens, viruses, bacteria, pathogens, insects, diseases such as insect borne disease (e.g., malaria). Methods of the disclosure can be used for selectively adding, deleting, inserting, or mutating genes.

In some cases, a virus is a retrovirus or lentivirus. In some cases, the virus is a member of Group I, Group II, Group III, Group IV, Group V, Group VI, or Group VII in the Baltimore virus classification system. In some cases, a virus is a member of the family Adenoviridae, Anelloviridae, Arenaviridae, Astroviridae, Bunyaviridae, Caliciviridae, Coronaviridae, Filoviridae, Flaviviridae, Hepadnaviridae, Hepeviridae, Herpesviridae, Orthomyxoviridae, Papillomaviridae, Papovaviridae, Paramyxoviridae, Parvoviridae, Picornaviridae, Polyomaviridae, Poxviridae, Reoviridae, Retroviridae, Rhabdoviridae, or Togaviridae. In some cases, a virus is Adenovirus, Amur virus, Andes virus, Animal virus, Astrovirus, Avian nephritis virus, Avian orthoreovirus, Avian Reovirus, Banna virus, Bas-Congo virus, Bat-borne virus, BK virus, Blueberry shock virus, Chicken anaemia virus, Bovine adenovirus, Bovine coronavirus, Bovine herpesvirus 4, Bovine parvovirus, Bulbul coronavirus HKU11, Carrizal virus, Catacamas virus, Chandipura virus, Channel catfish virus, Choclo virus, Coltivirus, Coxsackievirus, Cricket paralysis virus, Crimean-Congo hemorrhagic fever virus, Cytomegalovirus, dengue virus, Dobrava-Belgrade virus, Ebola virus, Ebolavirus, El Moro Canyon virus, Elephant endotheliotropic herpesvirus, Epstein-Barr virus, Feline leukemia virus, Foot-and-mouth disease virus, Gou virus, Guanarito virus, Hantaan River virus, Hantavirus, HCoV-EMC/2012, Hendra virus, Henipavirus, Hepatitis A virus, Hepatitis B virus, Hepatitis C virus, Hepatitis D, Hepatitis E virus, Herpes simplex type 1, Herpes simplex type 2, Herpes simplex virus type 1, Herpes simplex virus type 2, HIV, Human astrovirus, Human bocavirus, Human cytomegalovirus, Human herpesvirus type 8, Human herpesvirus type 8, Human immunodeficiency virus (HIV), Human metapneumovirus, Human papillomavirus, Imjin virus, Influenza virus, Isla Vista virus, JC virus, Junin virus, Khabarovsk virus, Koi herpes virus, Kunjin virus, Lassa virus, Limestone Canyon virus, Lloviu cuevavirus, Lloviu virus, Lujo virus, Machupo virus, Magboi virus, Marburg marburgvirus, Marburg virus, Marburgvirus, Measles virus, Melaka virus, Menangle virus, Middle East respiratory syndrome coronavirus, Miniopterus Bat coronavirus 1, Miniopterus Bat coronavirus HKU8, Monkeypox virus, Monongahela virus, Muju virus, Mumps virus, Nipah virus, Norwalk virus, Orbivirus, Parainfluenza virus, Parvovirus B19, Phytoreovirus, Pipistrellus bat coronavirus HKU5, Poliovirus, Porcine adenovirus, Prospect Hill virus, Qalyub virus, Rabies virus, Ravn virus, Respiratory syncytial virus, Reston virus, Reticuloendotheliosis virus, Rhinolophus Bat coronavirus HKU2, rhinovirus, Roseolovirus, Ross River virus, Rotavirus, Rousettus bat coronavirus HKU9, Rubella virus, Saaremaa virus, Sabiá virus, Sangassou virus, Scotophilus Bat coronavirus 512, Serang virus, Severe acute respiratory syndrome virus, Shope papilloma virus, Simian foamy virus, Sin Nombre virus, Smallpox, Soochong virus, Sudan ebolavirus, Sudan virus, Tai Forest ebolavirus, Tai Forest virus, Tanganya virus, Thottapalayam virus, Topografov virus, Tremovirus, Tula virus, Turkey coronavirus, Turkeypox virus, Tylonycteris bat coronavirus HKU4, Varicella zoster virus, Varicella-zoster virus, West Nile virus, Woodchuck hepatitis virus, yellow fever virus, or Zaire ebolavirus.

Some non-limiting examples of a pathogen include a virus, bacterium, prion, fungus, parasite, protozoan, and microbe. Some non-limiting examples of pathogens include *Acanthamoeba*, *Acari*, *Acinetobacter baumannii*, *Actinomyces israelii*, *Actinomyces gerencseriae*, *Propionibacterium propionicus*, *Actinomycetoma*, *Eumycetoma*, Adenoviridae, Alphavirus, Anaplasma genus, *Anaplasma phagocytophilum*, *Ancylostoma braziliense*, *Ancylostoma duodenale*, *Necator americanus*, *Angiostrongylus costaricensis*, *Anisakis*, *Arachnida Ixodidae*, *Argasidae*, *Arcanobacterium haemolyticum*, *Archiacanthocephala*, *Moniliformis moniliformis*, Arenaviridae, *Ascaris lumbricoides*, *Ascaris* sp. *Ascaris lumbricoides*, *Aspergillus* genus, Astroviridae, *Babesia B. divergens*, *B. bigemina*, *B. equi*, *B. microfti*, *B. duncani*, *Babesia* genus, *Bacillus anthracis*, *Bacillus cereus*, *Bacteroides* genus, *Balamuthia mandrillaris*, *Balantidium coli*, *Bartonella henselae*, *Baylisascaris* genus, *Baylisascaris*

*procyonis, Bertiella mucronata, Bertiella studeri,* BK virus, *Blastocystis, Blastocystis hominis, Blastomyces dermatitidis, Bordetella pertussis, Borrelia burgdorferi, Borrelia* species, *Borrelia genus, Brucella genus, Brugia malayi, Brugia timori, Bunyaviridae, Burkholderia cepacia, Burkholderia* species, *Burkholderia mallei, Burkholderia pseudomallei, Caliciviridae, Campylobacter genus, Candida albicans, Candida* species, *Cestoda, Taenia multiceps, Chlamydia trachomatis, Chlamydia trachomatis, Neisseria gonorrhoeae, Chlamydophila pneumoniae, Chlamydophila psittaci, Cimicidae Cimex lectularius, Clonorchis sinensis; Clonorchis viverrini, Clostridium botulinum, Clostridium difficile, Clostridium perfringens, Clostridium perfringens, Clostridium* species, *Clostridium tetani, Coccidioides immitis, Coccidioides posadasii, Cochliomyia hominivorax*, Colorado tick fever virus (CTFV), Coronaviridae, *Corynebacterium diphtheriae, Coxiella burnetii*, Crimean-Congo hemorrhagic fever virus, *Cryptococcus neoformans, Cryptosporidium, Cryptosporidium* genus, *Cyclospora cayetanensis*, Cytomegalovirus, *Demodex folliculorum/brevis/canis*, Dengue viruses (DEN-1, DEN-2, DEN-3 and DEN-4), Flaviviruses, *Dermatobia hominis, Dicrocoelium dendriticum, Dientamoeba fragilis, Dioctophyme renale, Diphyllobothrium, Diphyllobothrium latum, Dracunculus medinensis*, Ebolavirus (EBOV), *Echinococcus* genus, *Echinococcus granulosus, Echinococcus multilocularis, E. vogeli, E. oligarthrus, Ehrlichia chaffeensis, Ehrlichia ewingii, Ehrlichia genus, Entamoeba histolytica, Entamoeba histolytica, Enterobius vermicularis, Enterobius gregorii, Enterococcus* genus, *Enterovirus* genus, Enteroviruses, Coxsackie A virus, *Enterovirus* 71 (EV71), *Epidermophyton floccosum, Trichophyton rubrum, Trichophyton mentagrophytes*, Epstein-Barr Virus (EBV), *Escherichia coli* O157:H7, O111 and O104:H4, *Fasciola hepatica, Fasciola gigantica, Fasciolopsis buski*, Filarioidea superfamily, Filoviridae, Flaviviridae, *Fonsecaea pedrosoi, Francisella tularensis, Fusobacterium genus, Geotrichum candidum, Giardia intestinalis, Giardia lamblia, Gnathostoma spinigerum, Gnathostoma hispidum*, Group A *Streptococcus, Staphylococcus*, Guanarito virus, *Haemophilus ducreyi, Haemophilus influenzae, Halicephalobus gingivalis, Heartland virus, Helicobacter pylori*, Hepadnaviridae, Hepatitis A Virus, Hepatitis B Virus, Hepatitis C Virus, Hepatitis D Virus, Hepatitis E Virus, Hepeviridae, Herpes simplex virus 1 and 2 (HSV-1 and HSV-2), Herpesviridae, *Histoplasma capsulatum*, HIV (Human immunodeficiency virus), *Hortaea werneckii*, Human bocavirus (HBoV), Human herpesvirus 6 (HHV-6), Human herpesvirus 7 (HHV-7), Human metapneumovirus (hMPV), Human papillomavirus (HPV), Human parainfluenza viruses (HPIV), *Hymenolepis nana, Hymenolepis diminuta, Isospora belli*, JC virus, Junin virus, *Kingella kingae, Klebsiella granulomatis*, Lassa virus, *Legionella pneumophila, Leishmania, Leptospira* genus, *Linguatula serrata, Listeria monocytogenes, Loa loa filaria, Lymphocytic choriomeningitis* virus (LCMV), Machupo virus, *Malassezia* genus, *Mansonella streptocerca*, Marburg virus, Measles virus, *Metagonimus yokagawai*, Microsporidia phylum, Middle East respiratory syndrome coronavirus, *Molluscum contagiosum* virus (MCV), Monkeypox virus, Mucorales order (Mucormycosis), Entomophthorales order (Entomophthoramycosis), Mumps virus, *Mycobacterium leprae, Mycobacterium lepromatosis, Mycobacterium tuberculosis, Mycobacterium ulcerans, Mycoplasma pneumoniae, Naegleria fowleri, Neisseria gonorrhoeae, Neisseria meningitidis, Nocardia asteroides, Nocardia* species, *Oestroidea, Calliphoridae, Sarcophagidae, Onchocerca volvulus, Opisthorchis viverrini, Opisthorchis felineus, Clonorchis sinensis*, Orthomyxoviridae, Papillomaviridae, *Paracoccidioides brasiliensis, Paragonimus africanus; Paragonimus caliensis; Paragonimus kellicotti; Paragonimus skrjabini; Paragonimus uterobilateralis, Paragonimus westermani, Paragonimus* species, Paramyxoviridae, parasitic dipterous fly larvae, Parvoviridae, Parvovirus B19, *Pasteurella* genus, *Pediculus humanus, Pediculus humanus capitis, Pediculus humanus corporis, Phthirus pubis, Picornaviridae, Piedraia hortae, Plasmodium falciparum, Plasmodium vivax, Plasmodium ovale curtisi, Plasmodium ovale wallikeri, Plasmodium malariae, Plasmodium knowlesi, Plasmodium genus, Pneumocystis jirovecii*, Poliovirus, Polyomaviridae, Poxviridae, *Prevotella* genus, PRNP, *Pthirus pubis, Pulex irritans*, Rabies virus, Reoviridae, Respiratory syncytial virus (RSV), Retroviridae, Rhabdoviridae, *Rhinosporidium seeberi*, Rhinovirus, rhinoviruses, coronaviruses, *Rickettsia akari, Rickettsia genus, Rickettsia prowazekii, Rickettsia rickettsii, Rickettsia typhi*, Rift Valley fever virus, Rotavirus, Rubella virus, Sabia, *Salmonella enterica* subsp. *enterica, Serovar typhi, Salmonella genus, Sarcocystis bovihominis, Sarcocystis suihominis, Sarcoptes scabiei*, SARS coronavirus, *Schistosoma* genus, *Schistosoma haematobium, Schistosoma japonicum, Schistosoma mansoni* and *Schistosoma intercalatum, Schistosoma mekongi, Schistosoma* sp., *Shigella* genus, Sin Nombre virus, *Spirometra erinaceieuropaei, Sporothrix schenckii, Staphylococcus genus, Streptococcus agalactiae, Streptococcus pneumoniae, Streptococcus pyogenes, Strongyloides stercoralis, Taenia genus, Taenia saginata, Taenia solium*, the bacterial family Enterobacteriaceae, *Thelazia californiensis, Thelazia callipaeda*, Togaviridae, *Toxocara canis, Toxocara cati, Toxoplasma gondii, Treponema pallidum, Trichinella spiralis, Trichinella britovi, Trichinella nelsoni, Trichinella nativa, Trichobilharzia regenti*, Schistosomatidae, *Trichomonas vaginalis, Trichophyton* genus, *Trichophyton rubrum, Trichophyton tonsurans, Trichosporon beigelii, Trichuris trichiura, Trichuris trichiura, Trichuris vulpis, Trypanosoma brucei, Trypanosoma cruzi, Tunga penetrans, Ureaplasma urealyticum*, Varicella zoster virus (VZV), Variola major, Variola minor, Venezuelan equine encephalitis virus, *Vibrio cholerae*, West Nile virus, *Wuchereria bancrofti, Wuchereria bancrofti, Brugia malayi*, Yellow fever virus, *Yersinia enterocolitica, Yersinia pestis*, and *Yersinia pseudotuberculosis.*

Insects that carry insect borne diseases include, but are not limited to, the mosquito, tick, flea, lice, Culicoid midge, sandfly, Tsetse fly, and bed bug. Insect borne diseases include, but are not limited to, mosquito borne diseases, tick borne diseases, flea borne diseases, lice borne diseases, Culicoid midge borne diseases, sandfly borne diseases, Tsetse fly borne diseases, bed bug borne diseases, and any combination thereof. Examples of insect borne diseases include, but are not limited to, African horse sickness, babesiosis, bluetongue disease, tick-borne encephalitis, Rickettsial diseases (e.g., typhus, rickettsialpox, Boutonneuse fever, African tick bite fever, Rocky Mountain spotted fever), Crimean-Congo hemorrhagic fever, ehrlichiosis, Southern tick-associated rash illness, tick-borne relapsing fever, tularemia, lice infestation, heartland virus, plague, Trypanosomiasis, sleeping sickness, leishmaniasis, Chagas disease, and Lyme disease. Mosquito borne diseases include, but are not limited to, malaria, dengue fever, yellow fever, chikungunya, dog heartworm, Eastern equine encephalitis, epidemic polyarthritis, filariasis, Rift Valley fever, Ross River fever, St. Louis encephalitis, Japanese encephalitis, pogosta disease, LaCrosse encephalitis, Western equine encephalitis, and West Nile virus.

Pests that may also be targeted include, but are not limited to, the Medfly (≈$1.2 billion damage/yr), olive fly (can reduce oil production by as much as 80%), pea leaf miner (a fly causing over $1.5 billion of crop damage), and Asian tiger mosquito (a vector for encephalitis, dengue fever, yellow fever and dog heartworm). Pests or weeds that are resistant to pesticides or herbicides (e.g., glyphosate), respectively, may also be targeted by MCRs and/or NCRs. For example, MCRs may replace resistant alleles to restore susceptibility to a pesticide or herbicide. Resistant pests that may be targeted include, but are not limited to, the western corn rootworm, horseweed, pigweed, *Amaranthus hybridus* (syn: quitensis) (Smooth Pigweed); *Amaranthus palmeri* (Palmer Amaranth); *Amaranthus spinosus* (Spiny Amaranth); *Amaranthus tuberculatus* (=*A. rudis*) (Tall Waterhemp); *Ambrosia artemisiifolia* (Common Ragweed); *Ambrosia trifida* (Giant Ragweed); *Bidens pilosa* (Hairy Beggarticks); *Brachiaria eruciformis* (Sweet Summer Grass); *Bromus diandrus* (Ripgut Brome); *Bromus rubens* (Red Brome); Chloris *elata* (Tall Windmill Grass); Chloris *truncata* (Windmill Grass); *Conyza bonariensis* (Hairy Fleabane); *Conyza canadensis* (Horseweed); *Conyza sumatrensis* (Sumatran Fleabane); *Cynodon hirsutus* (Gramilla mansa); *Digitaria insularis* (Sourgrass); *Echinochloa colona* (Junglerice); *Eleusine indica* (Goosegrass); *Hedyotis verticillata* (Woody borreria); *Kochia scoparia* (Kochia); *Leptochloa virgata* (Tropical Sprangletop, Juddsgrass); *Lolium perenne* (Perennial Ryegrass); *Lolium perenne* ssp. *multiflorum* (Italian Ryegrass); *Lolium rigidum* (Rigid Ryegrass); *Parthenium* hysterophorus (Ragweed *Parthenium*); *Plantago lanceolata* (Buckhorn Plantain); *Poa annua* (Annual Bluegrass); *Raphanus raphanistrum* (Wild Radish); *Sonchus oleraceus* (Annual Sowthistle); *Sorghum halepense* (Johnsongrass); *Urochloa panicoides* (Liverseedgrass); and any combination thereof. By reducing resistance or reversing it, a pesticide or herbicide may be used for a longer period of time and/or in lower concentrations or amounts.

Agriculture pests include, but are not limited to, agriculture pest insects, agriculture pest mites, agriculture pest nematodes, grape pests, pest molluscs, strawberry pests, Western honey bee pests, insect pests of ornamental plants, insect vectors of plant pathogens, plant pathogenic nematodes, invasive species, and any combination thereof.

Agriculture pest insects include, but are not limited to, Acalymma, *Acrythosiphon kondoi*, *Acyrthosiphon gossypii*, *Acyrthosiphon pisum*, African armyworm, Africanized bee, *Agrilus planipennis* (Emerald ash borer), Agromyzidae, *Agrotis ipsilon*, *Agrotis munda*, *Agrotis porphyricollis*, *Akkaia taiwana*, *Aleurocanthus woglumi*, *Aleyrodes proletella*, *Alphitobius diaperinus*, *Alsophila aescularia*, *Altica chalybea*, *Ampeloglypter ater*, *Anasa tristis*, *Anisoplia austriaca*, *Anthonomus pomorum*, *Anthonomus signatus*, *Aonidiella aurantii*, *Apamea apamiformis*, *Apamea niveivenosa*, Aphid, *Aphis gossypii*, *Aphis nasturtii*, Apple maggot, Argentine ant, Army cutworm, *Arotrophora arcuatalis*, *Astegopteryx bambusae*, *Astegopteryx insularis*, *Astegopteryx minuta*, *Asterolecanium coffeae*, *Atherigona reversura*, *Athous haemorrhoidalis*, *Aulacophora*, *Aulacorthum solani*, Australian plague locust, *Bactericera cockerelli*, *Bactrocera*, *Bactrocera correcta*, *Bagrada hilaris*, Beet armyworm, Black bean aphid, *Blepharidopterus chlorionis*, Bogong moth, Boll weevil, Bollworm, Brassica pod midge, *Brevicoryne brassicae*, Brown locust, Brown marmorated stink bug, Brown planthopper, Cabbage moth, Cabbage worm, *Callosobruchus maculatus*, Cane beetle, Carrot fly, *Cerataphis brasiliensis*, *Ceratitis capitata*, *Ceratitis* rosa, *Ceratoglyphina bambusae*, *Ceratopemphigus zehntneri*, *Ceratovacuna lanigera*, Cereal leaf beetle, *Chaetosiphon tetrarhodum*, *Chlorops pumilionis*, *Chrysophtharta bimaculata*, Citrus flatid planthopper, Citrus long-horned beetle, *Coccus hesperidum*, *Coccus viridis*, Codling moth, Coffee borer beetle, Colorado potato beetle, Confused flour beetle, Crambus, Cucumber beetle, *Curculio nucum*, *Curculio occidentis*, Cutworm, *Cyclocephala borealis*, Date stone beetle, *Delia* (genus), *Delia antiqua*, *Delia floralis*, *Delia radicum*, Desert locust, *Diabrotica*, *Diabrotica balteata*, *Diabrotica speciosa*, Diamondback moth, *Diaphania indica*, *Diaphania nitidalis*, *Diaphorina citri*, *Diaprepes abbreviatus*, *Diatraea saccharalis*, Differential grasshopper, *Dociostaurus maroccanus*, *Drosophila suzukii*, *Dryocosmus kuriphilus*, *Dysaphis crataegi*, *Earias perhuegeli*, *Epicauta vittata*, *Epilachna varivestis*, *Erionota thrax*, *Eriosoma lanigerum*, Eriosomatinae, *Euleia heraclei*, *Eumetopina flavipes*, *Eupoecilia ambiguella*, European corn borer, *Eurydema oleracea*, *Eurygaster integriceps*, *Ferrisia virgata*, Forest bug, *Frankliniella tritici*, *Galleria mellonella*, Garden Dart, *Geoica lucifuga*, Glassy-winged sharpshooter, Great French Wine Blight, Greenhouse whitefly, *Greenidea artocarpi*, *Greenidea formosana*, *Greenideoida ceyloniae*, *Gryllotalpa orientalis*, Gypsy moths in the United States, *Helicoverpa armigera*, *Helicoverpa gelotopoeon*, *Helicoverpa punctigera*, *Helicoverpa zea*, *Heliothis virescens*, *Henosepilachna vigintioctopunctata*, Hessian fly, *Hyalopterus pruni*, *Hysteroneura setariae*, *Ipuka dispersum*, *Jacobiasca formosana*, Japanese beetle, *Kaltenbachiella elsholtriae*, *Kaltenbachiella japonica*, Khapra beetle, Knulliana, *Lampides boeticus*, Leaf miner, Leek moth, *Lepidiota consobrina*, *Lepidosaphes beckii*, *Lepidosaphes ulmi*, Leptocybe, *Leptoglossus zonatus*, *Leptopterna dolabrata*, Lesser wax moth, *Leucoptera* (moth), *Leucoptera caffeina*, Light brown apple moth, Light brown apple moth controversy, *Lipaphis erysimi*, *Lissorhoptrus oryzophilus*, Long-tailed skipper, *Lygus*, *Lygus hesperus*, *Maconellicoccus hirsutus*, *Macrodactylus subspinosus*, *Macrosiphoniella pseudoartemisiae*, *Macrosiphoniella sanborni*, *Macrosiphum euphorbiae*, Maize weevil, *Manduca sexta*, *Matsumuraja capitophoroides*, *Mayetiola hordei*, Mealybug, *Megacopta cribraria*, *Melanaphis sacchari*, *Micromyzus judenkoi*, *Micromyzus kalimpongensis*, *Micromyzus niger*, Moth, *Myzus ascalonicus*, *Myzus boehmeriae*, *Myzus cerasi*, *Myzus obtusirostris*, *Myzus ornatus*, *Myzus persicae*, *Neomyzus circumflexus*, *Neotoxoptera oliveri*, *Nezara viridula*, *Nomadacris succincta*, Oak processionary, *Oebalus pugnax*, Olive fruit fly, *Ophiomyia simplex*, *Opisina arenosella*, *Opomyza*, *Opomyza florum*, Opomyzidae, *Oscinella frit*, *Ostrinia furnacalis*, *Oxycarenus hyalinipennis*, *Papilio demodocus*, *Paracoccus marginatus*, *Paralobesia viteana*, *Paratachardina pseudolobata*, *Pentalonia nigronervosa*, Pentatomoidea, *Phorodon humuli*, *Phthorimaea operculella*, Phyllophaga, Phylloxeridae, Phylloxeroidea, *Pieris brassicae*, Pink bollworm, *Planococcus citri*, *Platynota idaeusalis*, Plum curculio, *Prionus californicus*, *Pseudococcus maritimus*, *Pseudococcus viburni*, *Pseudoregma bambucicola*, *Pyralis farinalis*, Red imported fire ant, Red locust, *Rhagoletis cerasi*, *Rhagoletis indifferens*, *Rhagoletis mendax*, *Rhodobium porosum*, *Rhopalosiphoninus latysiphon*, *Rhopalosiphum maidis*, *Rhopalosiphum padi*, *Rhopalosiphum rufiabdominale*, *Rhyacionia frustrana*, *Rhynchophorus ferrugineus*, *Rhynchophorus palmarum*, Rhyzopertha, Rice moth, Russian wheat aphid, San Jose scale, Scale insect, *Schistocerca americana*, *Schizaphis graminum*, *Schizaphis hypersiphonata*, *Schizaphis minuta*, *Schizaphis rotundiventris*, *Schoutedenia lutea*, Sciaridae, *Scirtothrips dorsalis*, Scutelleridae, *Scutiphora pedicellata*, Serpentine leaf miner, Setaceous Hebrew character, *Shivaphis celti*, Silver Y, Silverleaf whitefly, *Sinomegoura citricola*, *Sipha flava*, *Sitobion avenae*, *Sitobion lambersi*, *Sitobion leelamaniae*, *Sitobion miscanthi*, *Sitobion pauliani*, *Sitobion phyllanthi*, *Sitobion wikstroemiae*, Small hive beetle, Southwestern corn borer, Soybean aphid, *Spodoptera cilium*, *Spodoptera litura*, Spotted cucumber beetle, Squash vine borer, Stemborer, *Stenotus binotatus*, *Strauzia longipennis*, Striped flea beetle, Sunn pest, Sweetpotato bug, *Synanthedon exitiosa*, Tarnished plant bug, *Tetraneura nigriabdominalis*, *Tetraneura yezoensis*, Thrips, *Thrips angusticeps*, *Thrips palmi*, *Tinocallis kahawaluokalani*, *Toxoptera aurantii*, *Toxoptera citricida*, *Toxoptera odinae*, *Trioza erytreae*, Turnip moth, *Tuta absoluta*, *Uroleucon minutum*, Varied carpet beetle, *Vesiculaphis caricis*, *Virachola isocrates*, Waxworm, Western corn rootworm, Western flower thrips, Wheat fly, Wheat weevil, Whitefly, Winter moth, *Xylotrechus quadripes*, and any combination thereof.

Agriculture pest mites include, but are not limited to, *Abacarus hystrix*, *Abacarus sacchari*, *Acarapis woodi*, *Aceria guerreronis*, *Aceria tosichella*, *Brevipalpus phoenicis*, *Dermanyssus gallinae*, *Eriophyes padi*, Eriophyidae, Flour mite, *Oligonychus sacchari*, *Panonychus ulmi*, *Polyphagotarsonemus latus*, Redberry mite, *Steneotarsonemus spinki*, *Tetranychus urticae*, Tuckerella, *Varroa destructor*, *Varroa jacobsoni*, *Varroa* sensitive hygiene, and any combination thereof.

Agriculture pest nematodes include, but are not limited to, *Achlysiella williamsi*, Anguina (nematode), *Anguina agrostis*, *Anguina amsinckiae*, *Anguina australis*, *Anguina balsamophila*, *Anguina funesta*, *Anguina graminis*, *Anguina spermophaga*, *Anguina tritici*, Aphelenchoides, *Aphelenchoides arachidis*, *Aphelenchoides besseyi*, *Aphelenchoides fragariae*, *Aphelenchoides parietinus*, *Aphelenchoides ritzemabosi*, *Aphelenchoides subtenuis*, Belonolaimus, *Belonolaimus gracilis*, *Belonolaimus longicaudatus*, Cereal cyst nematode, Coffee root-knot nematode, Ditylenchus, *Ditylenchus africanus*, *Ditylenchus angustus*, *Ditylenchus destructor*, *Ditylenchus dipsaci*, *Dolichodorus heterocephalus*, Fig Pin Nematode, Foliar nematode, *Globodera pallida*, *Globodera rostochiensis*, *Globodera tabacum*, *Helicotylenchus dihystera*, *Hemicriconemoides kanayaensis*, *Hemicriconemoides mangiferae*, *Hemicycliophora arenaria*, *Heterodera avenae*, *Heterodera cajani*, *Heterodera carotae*, *Heterodera ciceri*, *Hoplolaimus galeatus*, *Hoplolaimus indicus*, *Hoplolaimus magnistylus*, *Hoplolaimus seinhorsti*, *Hoplolaimus uniformis*, *Longidorus africanus*, *Longidorus maximus*, *Longidorus sylphus*, *Meloidogyne acronea*, *Meloidogyne arenaria*, *Meloidogyne artiellia*, *Meloidogyne brevicauda*, *Meloidogyne chitwoodi*, *Meloidogyne enterolobii*, *Meloidogyne incognita*, *Meloidogyne javanica*, *Meloidogyne naasi*, *Meloidogyne partityla*, *Meloidogyne thamesi*, *Merlinius brevidens*, *Mesocriconema xenoplax*, *Nacobbus aberrans*, Northern root-knot nematode, *Paralongidorus maximus*, *Paratrichodorus minor*, *Paratylenchus curvitatus*, *Paratylenchus elachistus*, *Paratylenchus macrophallus*, *Paratylenchus microdorus*, *Paratylenchus projectus*, *Paratylenchus tenuicaudatus*, Potato cyst nematode, *Pratylenchus alleni*, *Quinisulcius acutus*, *Quinisulcius capitatus*, *Radopholus similis*, Soybean cyst nematode, Tylenchorhynchus, *Tylenchorhynchus brevilineatus*, *Tylenchorhynchus claytoni*, *Tylenchorhynchus dubius*, *Tylenchorhynchus maximus*, *Tylenchorhynchus nudus*, *Tylenchorhynchus phaseoli*, *Tylenchorhynchus vulgaris*, *Tylenchorhynchus zeae*, *Tylenchulus semipenetrans*, Xiphinema, *Xiphinema americanum*, *Xiphinema bakeri*, *Xiphinema brevicolle*, *Xiphinema diversicaudatum*, *Xiphinema insigne*, *Xiphinema rivesi*, *Xiphinema vuittenezi*, and any combination thereof.

Grape pests include, but are not limited to, *Ampeloglypter ater*, *Ampeloglypter sesostris*, *Eriophyes vitis*, *Eupoecilia ambiguella*, Fig Pin Nematode, Great French Wine Blight, Japanese beetle, List of Lepidoptera that feed on grapevines, *Maconellicoccus hirsutus*, *Mesocriconema xenoplax*, *Otiorhynchus cribricollis*, *Paralobesia viteana*, *Paratrichodorus minor*, Phylloxera, *Pseudococcus maritimus*, *Pseudococcus viburni*, *Tetranychus urticae*, *Xiphinema index*, *Zenophassus*, and any combination thereof.

Pest molluscs include, but are not limited to, *Cornu aspersum*, Deroceras, Grove snail, Limax, *Milax gagates*, *Theba pisana*, and any combination thereof.

Strawberry pests include, but are not limited to, *Anthonomus rubi*, *Anthonomus signatus*, *Aphelenchoides fragariae*, *Otiorhynchus ovatus*, *Pratylenchus coffeae*, *Xiphinema diversicaudatum*, and any combination thereof.

Western honey bee pests include, but are not limited to, *Acarapis woodi*, American foulbrood, Braula, Deformed wing virus, List of diseases of the honey bee, *Nosema apis*, Small hive beetle, *Varroa destructor*, Waxworm, and any combination thereof.

Insect pests of ornamental plants include, but are not limited to, *Acleris variegana*, *Acyrthosiphon pisum*, *Alsophila aescularia*, Aphid, Bird-cherry ermine, *Coccus hesperidum*, *Coccus viridis*, *Contarinia quinquenotata*, Grapeleaf skeletonizer, Gypsy moths in the United States, Japanese beetle, *Macrodactylus subspinosus*, Mealybug, Mullein moth, Orchidophilus, *Otiorhynchus sulcatus*, *Paratachardina pseudolobata*, *Paysandisia archon*, Sawfly, Scale insect, Scarlet lily beetle, Sciaridae, *Spodoptera cilium*, *Stephanitis takeyai*, *Tenthredo scrophulariae*, *Yponomeuta malinellus*, *Yponomeuta padella*, and any combination thereof.

Insect vectors of plant pathogens include, but are not limited to, *Acyrthosiphon pisum*, Agromyzidae, Anthomyiidae, Aphid, Bark beetle, Beet leafhopper, *Brevicoryne brassicae*, *Cacopsylla melanoneura*, *Chaetosiphon fragaefolii*, Cicadulina, *Cicadulina mbila*, Common brown leafhopper, *Cryptococcus fagisuga*, Curculionidae, *Diabrotica balteata*, *Empoasca decedens*, *Eumetopina flavipes*, *Euscelis plebejus*, *Frankliniella tritici*, Glassy-winged sharpshooter, *Haplaxius crudus*, *Hyalesthes obsoletus*, *Hylastes ater*, Jumping plant louse, Leaf beetle, Leafhopper, *Macrosteles quadrilineatus*, Mealybug, Melon fly, Molytinae, *Pegomya hyoscyami*, Pissodes, *Pissodes strobi*, Pissodini, Planthopper, *Pseudococcus maritimus*, *Pseudococcus viburni*, *Psylla pyri*, *Rhabdophaga rosaria*, *Rhynchophorus palmarum*, *Scaphoideus titanus*, *Scirtothrips dorsalis*, Silverleaf whitefly, Tephritidae, Thripidae, *Thrips palmi*, *Tomicus piniperda*, *Toxoptera citricida*, Treehopper, Triozidae, Western flower thrips, *Xyleborus glabratus*, and any combination thereof.

Plant pathogenic nematodes include, but are not limited to, Helicotylenchus, Heterodera, *Heterodera amygdali*, *Heterodera arenaria*, *Heterodera aucklandica*, *Heterodera bergeniae*, *Heterodera bifenestra*, *Heterodera cacti*, *Heterodera canadensis*, *Heterodera cardiolata*, *Heterodera cruciferae*, *Heterodera delvii*, *Heterodera elachista*, *Heterodera filipjevi*, *Heterodera gambiensis*, *Heterodera goettingiana*, *Heterodera hordecalis*, *Heterodera humuli*, *Heterodera latipons*, *Heterodera medicaginis*, *Heterodera oryzae*, *Heterodera oryzicola*, *Heterodera rosii*, *Heterodera sacchari*, *Heterodera schachtii*, *Heterodera tabacum*, *Heterodera trifolii*, Heteroderidae, *Hirschmanniella oryzae*, Hoplolaimidae, *Hoplolaimus columbus, Hoplolaimus pararobustus, Meloidogyne fruglia, Meloidogyne gajuscus, Nacobbus dorsalis, Pratylenchus brachyurus, Pratylenchus coffeae, Pratylenchus crenatus, Pratylenchus dulscus, Pratylenchus fallax, Pratylenchus flakkensis, Pratylenchus goodeyi, Pratylenchus hexincisus, Pratylenchus loosi, Pratylenchus minutus, Pratylenchus mulchandi, Pratylenchus musicola, Pratylenchus neglectus, Pratylenchus penetrans, Pratylenchus pratensis, Pratylenchus reniformia, Pratylenchus scribneri, Pratylenchus thornei, Pratylenchus vulnus, Pratylenchus zeae, Punctodera chalcoensis*, Root gall nematode, Root invasion (parasitic), Root-knot nematode, *Rotylenchulus, Rotylenchulus parvus, Rotylenchulus reniformis, Rotylenchus brachyurus, Rotylenchus robustus, Scutellonema brachyurum, Scutellonema cavenessi, Subanguina radicicola, Subanguina wevelli*, and any combination thereof.

Invasive species include, but are not limited to, *Acacia mearnsii, Achatina fulica, Acridotheres tristis, Aedes albopictus, Anopheles quadrimaculatus, Anoplolepis gracilipes, Anoplophora glabripennis, Aphanomyces astaci, Ardisia elliptica, Arundo donax, Asterias amurensis*, Banana bunchy top virus (BBTV), *Batrachochytrium dendrobatidis, Bemisia tabaci, Boiga irregularis, Bufo marinus=Rhinella marina, Capra hircus, Carcinus maenas, Caulerpa taxifolia, Cecropia peltata, Cercopagis pengoi, Cervus elaphus, Chromolaena odorata, Cinara cupressi, Cinchona pubescens, Clarias batrachus, Clidemia hirta, Coptotermes formosanus, Corbula amurensis, Cryphonectria parasitica, Cyprinus carpio, Dreissena polymorpha, Eichhornia crassipes, Eleutherodactylus coqui, Eriocheir sinensis, Euglandina rosea, Euphorbia esula, Fallopia japonica=Polygonum cuspidatum, Felis catus, Gambusia affinis, Hedychium gardnerianum, Herpestes javanicus, Hiptage benghalensis, Imperata cylindrica, Lantana camara, Lates niloticus, Leucaena leucocephala, Ligustrum robustum, Linepithema humile, Lymantria dispar, Lythrum salicaria, Macaca fascicularis, Melaleuca quinquenervia, Miconia calvescens, Micropterus salmoides, Mikania micrantha, Mimosa pigra, Mnemiopsis leidyi, Mus musculus, Mustela erminea, Myocastor coypus, Morella faya, Mytilus galloprovincialis, Oncorhynchus mykiss, Ophiostoma ulmi sensu lato, Opuntia stricta, Oreochromis mossambicus, Oryctolagus cuniculus, Pheidole megacephala, Phytophthora cinnamomi, Pinus pinaster, Plasmodium relictum, Platydemus manokwari, Pomacea canaliculata, Prosopis glandulosa, Psidium cattleianum, Pueraria montana* var. *lobata, Pycnonotus cafer, Rana catesbeiana, Rattus rattus, Rubus ellipticus, Salmo trutta, Salvinia molesta, Schinus terebinthifolius, Sciurus carolinensis, Solenopsis invicta, Spartina anglica, Spathodea campanulata, Sphagneticola trilobata, Sturnus vulgaris, Sus scrofa, Tamarix ramosissima, Trachemys scripta elegans, Trichosurus vulpecula, Trogoderma granarium, Ulex europaeus, Undaria pinnatifida, Vespula vulgaris, Vulpes vulpes, Wasmannia auropunctata*, and any combination thereof.

Methods of the disclosure can be used to generate libraries of model organisms; generate specific strains, breeds, or mutants of a model organism; for one-step mutagenesis schemes to generate scoreable recessive mutant phenotypes in a single generation; facilitate basic genetic manipulations in diverse experimental and agricultural organisms (e.g., accelerating the generation of combinatorial mutants and facilitating mutagenesis in polyploid organisms); accelerate genetic manipulations in animals (e.g., primates) or plants (e.g., trees) with a long generation time; and for gene therapy.

Model organisms include, but are not limited to, viruses, prokaryotes, eukaryotes, protists, fungi, plants, invertebrate animals, vertebrate animals, and any combination thereof. A model organism may include, but is not limited to, a mammal, human, non-human mammal, a domesticated animal (e.g., laboratory animals, household pets, or livestock), non-domesticated animal (e.g., wildlife), dog, cat, rodent, mouse, hamster, cow, bird, chicken, fish, pig, horse, goat, sheep, rabbit, and any combination thereof.

Virus model organisms include, but are not limited to, Phage lambda; Phi X 174; SV40; T4 phage; Tobacco mosaic virus; Herpes simplex virus; and any combination thereof.

Prokaryotic model organisms include, but are not limited to, *Escherichia coli; Bacillus subtilis; Caulobacter crescentus; Mycoplasma genitalium; Aliivibrio fischeri; Synechocystis; Pseudomonas fluorescens*; and any combination thereof.

Protist model organisms include, but are not limited to, *Chlamydomonas reinhardtii; Dictyostelium discoideum; Tetrahymena thermophila; Emiliania huxleyi; Thalassiosira pseudonana*; and any combination thereof.

Fungal model organisms include, but are not limited to, *Ashbya gossypii; Aspergillus nidulans; Coprinus cinereus; Cryptococcus neoformans; Cunninghamella elegans; Neurospora crassa; Saccharomyces cerevisiae; Schizophyllum commune; Schizosaccharomyces pombe; Ustilago maydis*; and any combination thereof.

Plant model organisms include, but are not limited to, *Arabidopsis thaliana*; Boechera; *Selaginella moellendorffii; Brachypodium distachyon; Setaria viridis; Lotus japonicus; Lemna gibba*; Maize (*Zea mays* L.); *Medicago truncatula; Mimulus guttatus; Nicotiana benthamiana; Nicotiana tabacum*; Rice (*Oryza sativa*); *Physcomitrella patens; Marchantia polymorpha*; Populus; and any combination thereof.

Invertebrate animal model organisms include, but are not limited to, *Amphimedon queenslandica; Arbacia punctulata; Aplysia; Branchiostoma floridae; Caenorhabditis elegans; Caledia captiva* (Orthoptera); *Callosobruchus maculatus; Chorthippus parallelus; Ciona intestinalis; Daphnia* spp.; Coelopidae; Diopsidae; *Drosophila* (e.g., *Drosophila melanogaster*); *Euprymna scolopes; Galleria mellonella; Gryllus bimaculatus*; Hydra; *Loligo pealei; Macrostomum lignano; Mnemiopsis leidyi; Nematostella vectensis; Oikopleura dioica; Oscarella carmela; Parhyale hawaiensis; Platynereis dumerilii; Podisma* spp.; *Pristionchus pacificus; Scathophaga stercoraria; Schmidtea mediterranea*; Stomatogastric ganglion; *Strongylocentrotus purpuratus; Symsagittifera roscoffensis; Tribolium castaneum; Trichoplax adhaerens; Tubifex tubifex*; and any combination thereof.

Vertebrate animal model organisms include, but are not limited to, Laboratory mice; *Bombina bombina, Bombina variegata*; Cat (*Felis sylvestris catus*); Chicken (*Gallus gallus domesticus*); Cotton rat (*Sigmodon hispidus*); Dog (*Canis lupus familiaris*); Golden hamster (*Mesocricetus auratus*); Guinea pig (*Cavia porcellus*); Little brown bat (*Myotis lucifugus*); Medaka (*Oryzias latipes*, or Japanese ricefish); Mouse (*Mus musculus*); *Poecilia reticulata*; Rat (*Rattus norvegicus*); Rhesus macaque (or Rhesus monkey) (*Macaca* mulatta); Sea lamprey (*Petromyzon marinus*); Takifugu (*Takifugu rubripes*); *Xenopus tropicalis; Xenopus laevis*; Zebra finch (*Taeniopygia guttata*); Zebrafish (*Danio rerio*); African Killifish (*Nothobranchius furzeri*); Human (*Homo sapiens*); and any combination thereof.

Disease model organisms can include, for example, aging (e.g., African killifish), neurodegeneration, cancer, unique models for infectious disease (e.g., macaques for HIV, armadillos for leprosy, chinchillas or the hispid cotton rat for various viral infections), and specialized behaviors (e.g., genetically tractable primate models such as mouse lemurs, pigmy marmosets).

Traditional CRISPR application can use NHEJ, which can have a ~5-20% efficiency. The methods of the disclosure can use HDR (~90-100% efficiency). CopyCat elements can be referred to as examples of active genetic elements. Active genetic-based applications can be more efficient than traditional CRISPR in generating precise genome edits. In some embodiments, the efficiency of the disclosed methods for genome engineering is about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some embodiments, the efficiency of cc element integrating into a genome is at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, or 99.9%. In some embodiments, the efficiency of a cc element integrating into a genome is up to about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100%. In some embodiments, the efficiency of allelic conversion is about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some embodiments, the efficiency of allelic conversion is at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, or 99.9%. In some embodiments, the efficiency of allelic conversion is up to about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100%.

Nucleic acid of any suitable size can be integrated into a genome. In some embodiments, the element integrated into a genome is about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 kilobases (kb) in length. In some embodiments, the element integrated into a genome is at least about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 (kb) in length. In some embodiments, the element integrated into a genome is up to about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 (kb) in length.

Methods of the disclosure can be targeted to any locus in a genome. They can generate null or tissue-specific mutations in a target.

In some embodiments, the methods of the system form a gene drive for spreading beneficial genes or exogenous DNA fragments through a population of an organism (e.g., insects such as vectors for human disease or agricultural pests).

Figure 18:
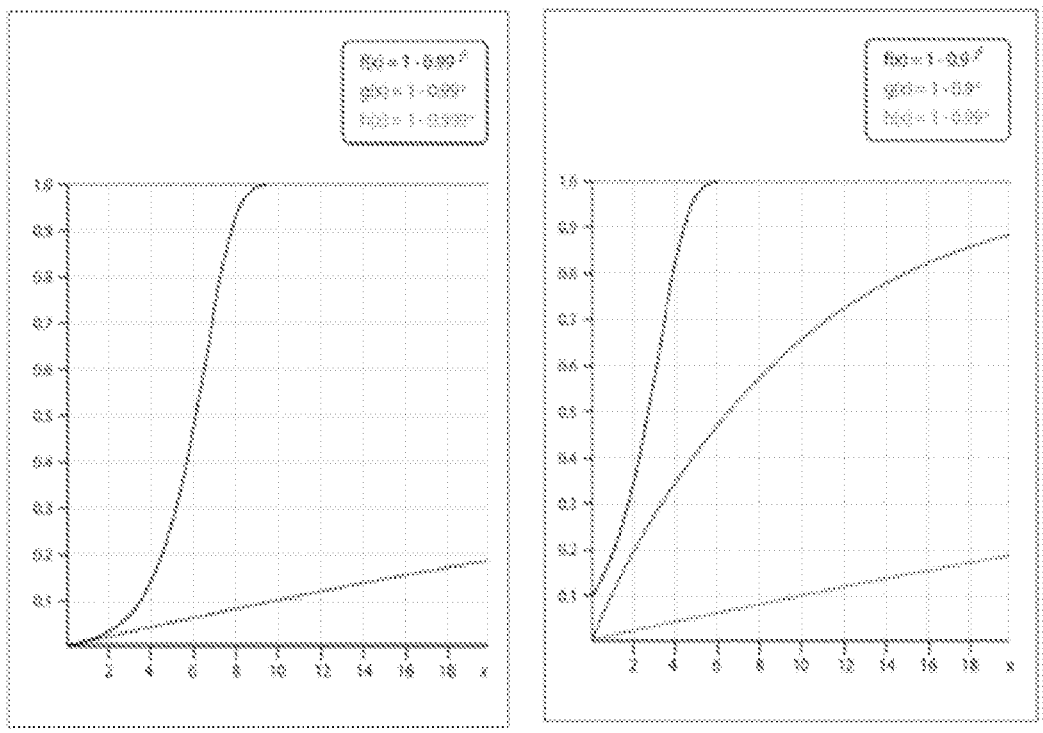
FIG. 18 illustrates gene drive via allelic pump. Left Panel: Time course of accumulated mutant alleles resulting from 1:100 seeding of an MCR (blue curve), a cas9; <gRNA> allelic pump (red curve), and a standard cas9; gRNA encoding transgenes green curve (buried in the baseline). Right Panel: Same as in Left Panel but with a seeding ratio of 1:10. Note that the allelic pump in Left Panel (red curve) has precisely the same behavior as the standard cas9; gRNA combination in Right Panel (green curve).
Figure 19:
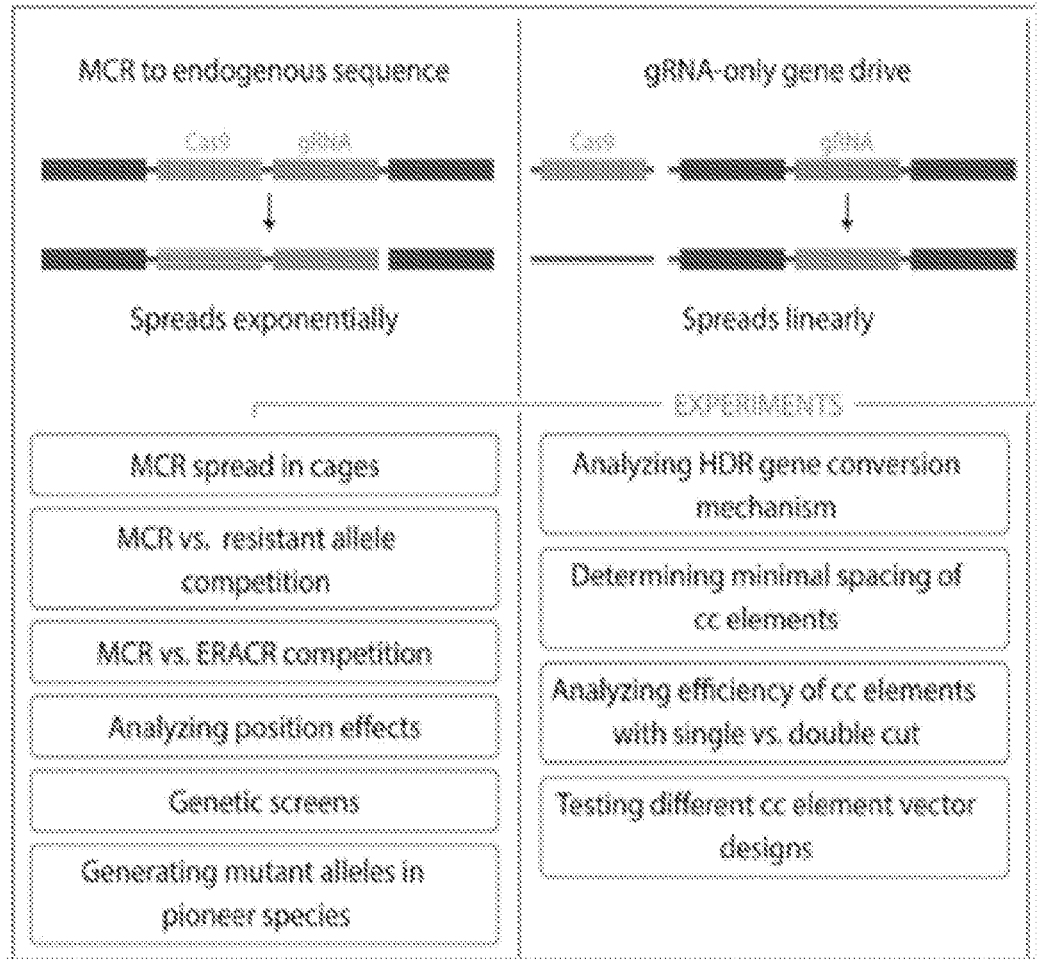
FIG. 19 illustrates schemes depicting an MCR targeting an endogenous sequence (left), a split cas9; <gRNA> allelic pump (right).
Figure 23:
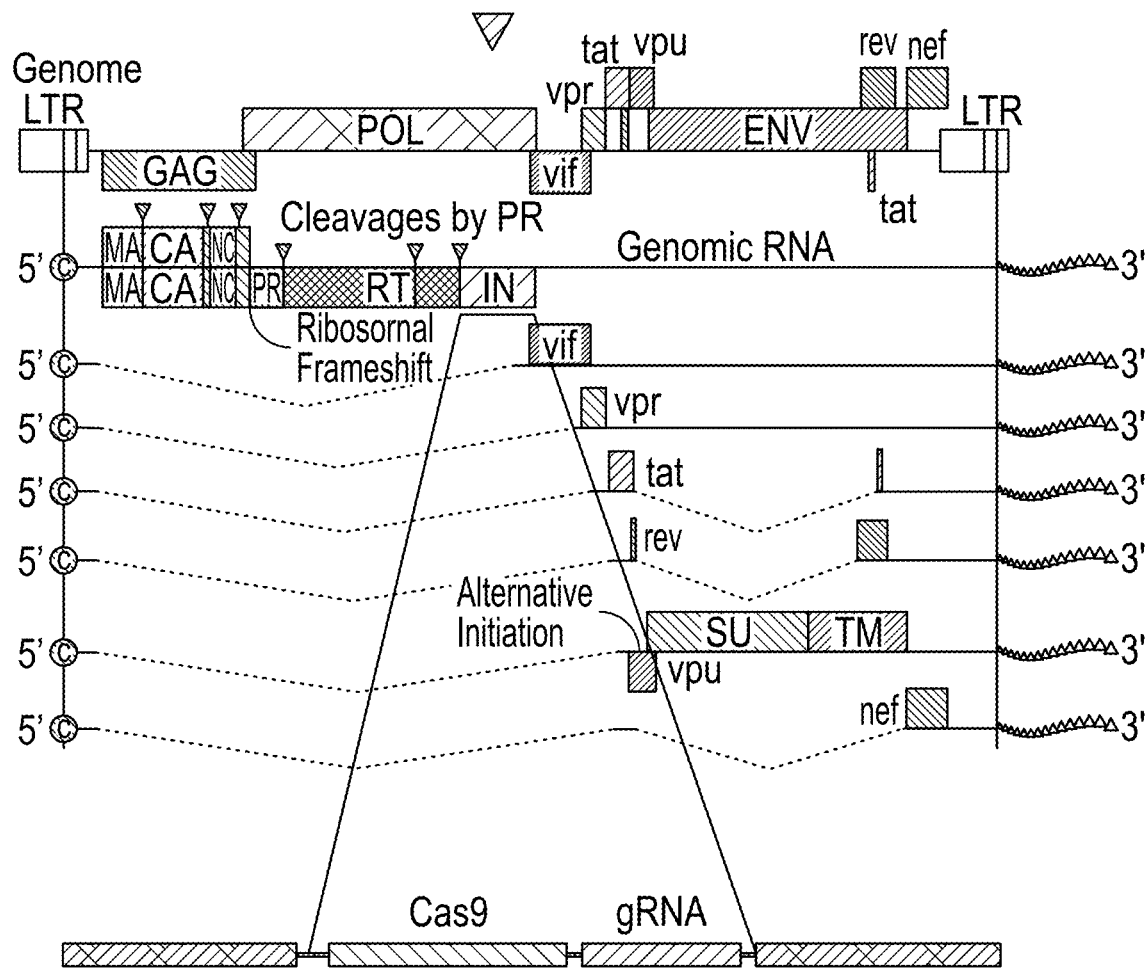
FIG. 23 illustrates a potential application of the methods of the disclosure to treat HIV. Figure discloses "AAAAAAAAAAAA" as SEQ ID NO: 36.
Figure 24:
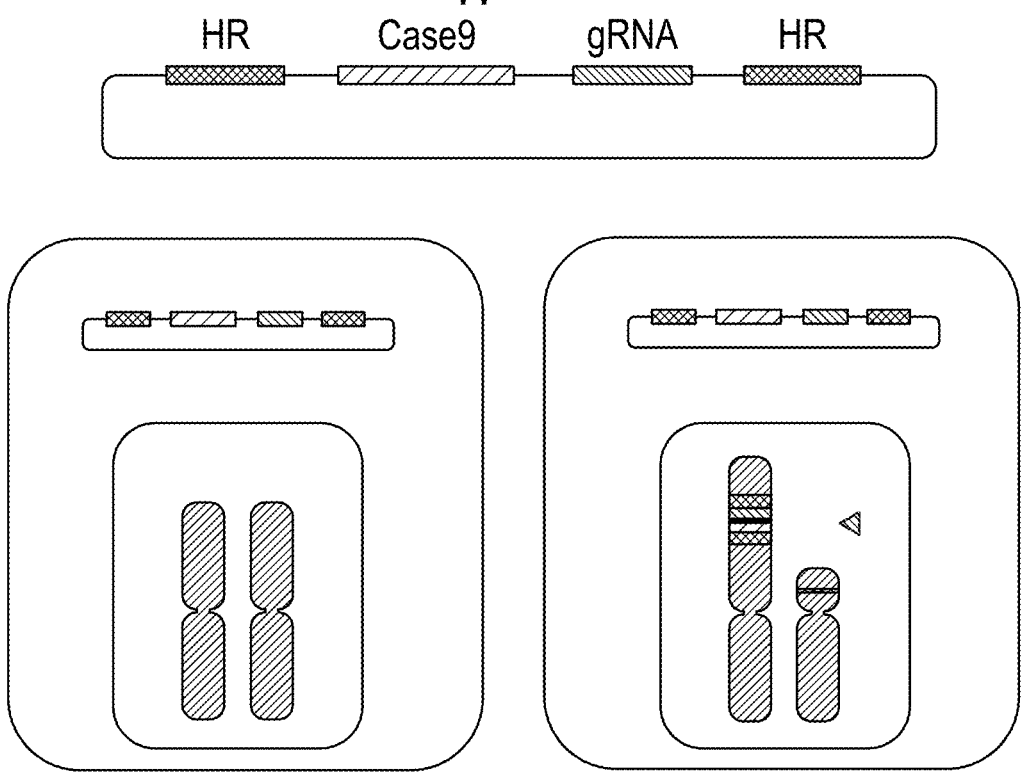
FIG. 24 illustrates a potential application of the methods of the disclosure to treat cancer.

Genomically encoded split cas9; <gRNA> configurations can create a gene drive by virtue of the fact that the cas9 encoding gene cannot segregate away from the <gRNA>, assuming the gRNA is faithfully copied to the other allele 100% of the time. However, the reciprocal event can take place 50% of the time (i.e., one of the two <gRNA> copies can segregate from the cas9 source). The enforced association of cas9 with one copy of the <gRNA> can result in a constant production of new <gRNA> alleles at each generation. This system can be referred to as an "allelic pump". This type of coupled allelic pump can be modeled by the first order recursion formula: $f_n = f_{n-1} + c_0(1 - f_{n-1})$ where $c_0 = g_0$ (initial fractions of cas9 and gRNAs in the population). The closed form solution for this equation is $f(n) = 1 - (1 - c_0)^n$, which for low values of $c_0 = g_0$ can be approximated by the linear equation $f(n) = c_0(n)$. For this scenario, an initial seeding at 1% can require more than 100 generations for mutant cas9/<gRNA> alleles to introgress completely into a population (FIG. 18—Left Panel). If seeded at 10%, however, it can spread to about 65% of the population in 10 generations (as compared to about 4 generations for an MCR to spread through 90% of the population) (FIG. 18—Right Panel). Thus, at high seeding frequencies allelic pumps can spread through much of the population.

Genomically-encoded sources of Cas9 and gRNAs can result in a very weak mutational drive since each time the two elements encounter each other by random assortment, a new allele could be generated at the gRNA cut site. The recursion formula for this type of mutational drive is given by $f_n = f_{n-1} + c_0 g_0(1 - f_{n-1})$, which has the closed form solution $f(n) = 1 - (1 - c_0 g_0)^n$ ($\approx c_0 g_0(n)$ for $c_0$ and $g_0 \ll 1$). For values of $c_0 = g_0 = 1\%$, this would amount to adding only 0.01% alleles/generation. However, if seeded at $c_0 = g_0 = 10\%$ it can produce a drive of identical strength to an allelic pump seeded at $c_0 = g_0 = 1\%$ (compare red curve in FIG. 18—Left Panel with green curve in FIG. 18—Right Panel).

Methods and compositions of the disclosure can be used to spread genotypic or phenotypic in offspring via the germline. The dissemination of constructs can also be achieved between cells within an individual by coupling these elements to a viral delivery system. In such cases, the somatic spread of a genetic element can be exploited by targeting its insertion into such unique sequences. In principle, this approach can be used to fight any disease that results in specific alterations in genome sequence.

Methods of the disclosure can be used for a broad variety of purposes such as designing novel system for transgenesis, inducing mutations that can be rapidly combined to test for cumulative or interacting effects, assembling complex arrays of transgenes and traditional Mendelian alleles, combinatorial testing of allelic variants contributing to complex traits, generating potent drive systems to disseminate effector transgenes through populations to combat insect-borne diseases and invasive species, and dispersal of gene therapy vectors throughout the human body targeting them to diseased cells.

In some embodiments, the methods of the disclosure are used for custom design of new chimeric organisms with traits combined from different species or de novo characteristics designed from first principles.

Large scale genome engineering methods described herein can be used to replace, delete, insert, or modify contiguous or discontiguous segments of a genome. The size of the segments can be about 100, 200, 300, 400, 500, 600, 700, 800, 900, 1000, or more kilobases.

Autocatalytic Genome Editing Using Trans-Complementation

The term "MCR elements" can refer to DNA constructs consisting of a Cas9/gRNA cassette flanked by homology arms that precisely abut the gRNA cut site. A shorthand for a given MCR can be denoted <cas9; gRNA> wherein the brackets denote the flanking homology arms.

A single-unit MCR can refer to a system in which both the Cas9 source and the gRNA are carried on a common cassette flanked by homology arms that directly abut the gRNA cut site (denoted <cas9; gRNA1>). Such single-unit MCRs can require a high level of confinement since they can spread exponentially through wild populations upon escaping because they automatically copy themselves (i.e., generate a gene-drive). Further, the combination of Cas9 and the gRNA in the germline can lead to persistent low level mutagenesis on off target loci that can accumulate over time. A trans-complementing MCR described herein can mitigate problems associated with single-unit MCR since the two separate elements (i.e., <cas9> and <gRNA1; gRNA2> each can be propagated safely as neither alone can create a gene-drive. Also, neither element alone can create a significant level of off-target mutagenesis since both elements must be combined. Thus, the two separate components of the trans-complementing MCR can be kept separately until the time they were to be used at which point the two stocks could be crossed. The resulting progeny of this cross can then carry both elements which can propagate as a unit like a single-unit MCR (e.g., to spread a desired transgene carried on one or the other single element).

In some embodiments, the disclosure provides for a split Cas protein and gRNA configuration. In this system only the gRNA can be inserted at the cut site. Since persistent low-level cas9 mutagenesis can reduce the fitness of individuals, such <gRNA> constructs can only be copied to the other chromosome when a source of cas9 is provided in trans.

In some embodiments, a trans-complementing MCR (mutagenic chain reaction) element is used for genome engineering. An illustrative scheme for trans-complementing MCR is shown in FIG. 20. A trans-complementing MCR can be based on two separate trans-complementing drives for the cas9<cas9> and gRNAs <gRNA1; gRNA2>. gRNA1 can direct cleavage at the site of cas9 genomic insertion. gRNA2 can cut at the integration site of the <gRNA1; gRNA2> element (FIG. 20). Since neither of the two constructs alone can constitute a drive, each single element can be propagated safely as a separate stock. The two stocks can be crossed, for example, after amplification of each of the stocks for release purposes. This crossing can then result in a full gene drive. A progeny of a cross resulting from this <cas9>; <gRNA1; gRNA2> can combine to create a drive that can behave thereafter as a linked <cas9; gRNA> MCR. This method can offer husbandry advantages.

A trans-complementing MCR provides a split system, which can consist of two separate transgenic elements which when combined can lead to autocatalytic copying of both elements to their sister chromosomes (FIG. 20). One element expresses the Cas9 endonuclease and the other element, which can be inserted elsewhere on the same chromosome as the Cas9-bearing construct or on a different chromosome, can carry two gRNAs, one of which cuts at the genomic site of insertion of the Cas9 element and the other can cut at the site of genomic insertion of the gRNA-bearing construct. When these two elements are carried in the same individual (e.g., in progeny resulting from a cross of two individuals carrying the different two elements to each other) both can get copied onto their sister chromosomes.

In some embodiments, one or both of the trans-complementing constructs carry an effector cassette of interest. For example, when both constructs carry an effector cassette of interest, this can result in expression of four copies of such cassettes thereby doubling the levels of transgene expression as compared to that provided by a single cis-linked <cas9; gRNA> MCR element. Thus, an advantage of the trans-complementing MCR configuration can be the propagation of two different transgene effectors (one carried by the <cas9> element and another by the <gRNA1; gRNA2> element) thus increasing the payload that can be propagated throughout the population.

In some embodiments, a trans-complementing MCR consists of two components: 1) a DNA fragment, in any form (e.g., plasmid or linear DNA fragments), including a cDNA encoding the Cas9 endonuclease (or homologs) under control of regulatory sequences that direct its expression in the germline (and possibly also in somatic cells), which is flanked by genomic sequences acting as homology arms precisely abutting the site at which a first gRNA-1 directs cutting in the host (e.g., *Drosophila*) genome, (denoted here as "<cas9>" where the symbols "< >" represent the homology arms flanking gRNA-1 cut site; and 2) a DNA fragment, in any form, encoding two gRNA genes each under the control promoters regulating their expression (e.g., ubiquitously-expressed U6 polymerase-III promoter), one of which (gRNA-1) cuts at the previously mentioned site of Cas9 insertion in the genome, while the other (gRNA-2) cuts at the site of insertion of the two-gRNA gene cassette. The two-gRNA gene cassette can be precisely abutted by host homology arms flanking the gRNA-2 cut site in the genome and can be denoted as <gRNA1; gRNA2>. Each of these constructs can be inserted into the genome independently (i.e., by co-injecting a plasmid containing the construct described in point (1) with a plasmid encoding only the gRNA-1 transcript, and by injecting a plasmid containing the construct described in point (2) with a plasmid encoding cas9, purified Cas9 protein, or into the germline of transgenic individuals expressing Cas9). Each of these two constructs if integrated into the genome of germline cells at their respective gRNA sites can be inherited in a standard Mendelian fashion. When individuals separately carrying these two elements are crossed to each other, the two elements can propagate like a standard MCR element in that the two parts (i.e., the Cas9 transgene inserted at gRNA cut-site1, and the gRNA cassette inserted at gRNA cut-site 2, can copy themselves from one chromosome to the sister chromosome). Because both elements can copy themselves onto the opposing chromosome, all (or nearly all) progeny from such a parent can inherit constructs and thus can pass on both constructs to their progeny.

A trans-complementing MCR can be used for generating genetic drive systems in organisms in which Cas9 is toxic and levels of the enzyme must fall within a narrow window of concentrations that can produce sufficient enzyme to power a gRNA drive but yet do not create significant toxicity. In such organisms (some species of mosquitoes being possible examples), one can conduct initial genetic screens to identify Cas9 insertions that satisfy the restrictive criteria for expression and then this stock can be used to generate gRNA drive elements that carry two gRNAs cutting both at the site of Cas9 insertion and at the site of gRNA cassette insertion. This can allow targeting of the gRNA (plus effector cassettes) to a wide variety of loci that may not be amenable for insertion of a full single-unit MCR.

A trans-complementing MCR can have the same high efficiency observed for a single-unit MCR (e.g., one in which the Cas9 source and a gRNA are carried as a single cassette inserted into the site cut by the gRNA=95% conversion efficiency).

Non-limiting examples of application of the methods and compositions of the disclosure include elimination of pathogens (e.g., malaria), targeted suppression of crop pests to those actively attacking a crop of interest, weed control, strategies to combat HIV and other diseases caused by retroviruses, strategies to combat DNA viruses that accumulate multiple copies of their genomes within cells (e.g., Herpes viruses), generalized strategies to combat cancer that can be independent of the type of cancer or stage of cancer progression, powerful one-step mutagenesis schemes to generate scoreable recessive mutant phenotypes in a single generation, facilitate basic genetic manipulations in diverse experimental and agricultural organisms (e.g., accelerating the generation of combinatorial mutants and facilitating mutagenesis in polyploid organisms), accelerate genetic manipulations in animals (e.g., primates, humans) or plants (e.g., trees) with a long generation time, and gene therapy.

In some embodiments, the method generates identifiable homozygous mutations in G1 progeny. In some cases, mutations are generated in a single step bypassing any need for other transgenesis methods. In some embodiments, it takes two steps (i.e., first getting transformants expressing a source of Cas9 using either CRISPR or traditional transgenesis methods coupled with dominant marker genes, e.g., GFP) and then injecting the <gRNA> construct into such backgrounds.

Methods of the disclosure can be employed in species for which there is a concern of escape into wild populations. Another important advantage of mutations induced by the systems is that the <gRNA>-induced mutation can be segregated away from the source of cas9 at which point it would behave as a simple Mendelian allele that can be used for traditional genetic studies. Classic Mendelian alleles also should be possible to generate as a byproduct of using full MCR elements as mutagens since they should induce standard indel alleles of the locus via NHEJ at an appreciable rate (e.g., >5%).

In some embodiments, methods of the disclosure are used to facilitate basic genetic manipulations in diverse experimental and agricultural organisms (e.g., accelerating the generation of combinatorial mutants and facilitating mutagenesis in polyploid organisms). In some embodiments, methods of the disclosure are used to accelerate genetic manipulations in animals (e.g., primates) or plants (e.g., trees) with a long generation time.

In some embodiments, methods of the disclosure are used to treat a disease or disorder. In some embodiments, the disease is cancer.

In some embodiments, the genome engineering produced using the methods of the disclosure is reversed or neutralized.

Genome editing using methods of the disclosure can be used to combat pathogens, viruses, bacteria, pathogens, insects, diseases such as insect borne disease (e.g., malaria). Methods of the disclosure can be used for selectively adding, deleting, inserting, or mutating genes.

Methods of the disclosure can be used to generate libraries of model organisms; generate specific strains, breeds, or mutants of a model organism; for one-step mutagenesis schemes to generate scoreable recessive mutant phenotypes in a single generation; facilitate basic genetic manipulations in diverse experimental and agricultural organisms (e.g., accelerating the generation of combinatorial mutants and facilitating mutagenesis in polyploid organisms); accelerate genetic manipulations in animals (e.g., primates) or plants (e.g., trees) with a long generation time; and for gene therapy.

Traditional CRISPR application can use NHEJ, which can have a ~5-20% efficiency. The methods of the disclosure can use HDR (~90-100% efficiency). Active genetic-based applications described herein can be more efficient than traditional CRISPR in generating precise genome edits. In some embodiments, the efficiency of the disclosed methods for genome engineering is about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some embodiments, the efficiency of disclosed methods is at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, or 99.9%. In some embodiments, the efficiency of the disclosed methods is up to about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100%. In some embodiments, the efficiency of allelic conversion is about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some embodiments, the efficiency of allelic conversion is at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, or 99.9%. In some embodiments, the efficiency of allelic conversion is up to about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100%.

Nucleic acid of any suitable size can be integrated into a genome. In some embodiments, the element integrated into a genome is about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 kilobases (kb) in length. In some embodiments, the element integrated into a genome is at least about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 (kb) in length. In some embodiments, the element integrated into a genome is up to about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 or more than 500 (kb) in length.

Methods of the disclosure can be targeted to any locus in a genome. They can generate null or tissue-specific mutations in a target.

In some embodiments, the methods of the system form a gene drive for spreading beneficial genes or exogenous DNA fragments through a population of an organism (e.g., insects such as vectors for human disease or agricultural pests).

Methods and compositions of the disclosure can be used to spread genotypic or phenotypic in offspring via the germline. The dissemination of constructs can also be achieved between cells within an individual by coupling these elements to a viral delivery system. In such cases, the somatic spread of a genetic element can be exploited by targeting its insertion into such unique sequences. In principle, this approach can be used to fight any disease that results in specific alterations in genome sequence.

Methods of the disclosure can be used for a broad variety of purposes such as designing novel system for transgenesis, inducing mutations that can be rapidly combined to test for cumulative or interacting effects, assembling complex arrays of transgenes and traditional Mendelian alleles, combinatorial testing of allelic variants contributing to complex traits, generating potent drive systems to disseminate effector transgenes through populations to combat insect-borne diseases and invasive species, and dispersal of gene therapy vectors throughout the human body targeting them to diseased cells.

Biochemical Autocatalytic Genome Conversion and Neutralization of the Autocatalytic Mutagenic Chain Reaction Classic rules of Mendelian inheritance impose several significant constraints on genetic manipulation of organisms (e.g., random segregation of distant loci and coinheritance of closely linked loci). These "passive" rules of inheritance can in principle be superseded by a new form of "active genetics" based on a new CRISPR method referred to as the Mutagenic Chain Reaction (MCR). Although other forms of active genetics can also bypass Mendelian inheritance (e.g., transposable elements), MCR-related strategies offer an array of new programmable functions in the field of genetics.

CRISPR/Cas9 Based Genome Editing

Figure 25A:
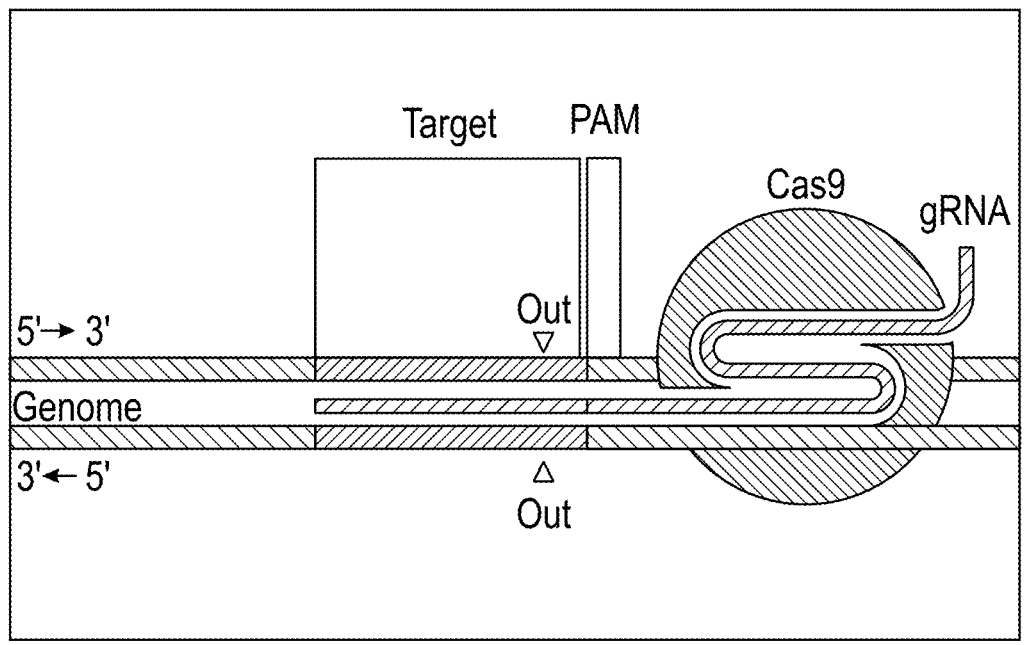
FIGS. 25A-25D depict an exemplary scheme outlining CRISPR and Mutagenic Chain Reaction (MCR) methods.
Figure 25B:
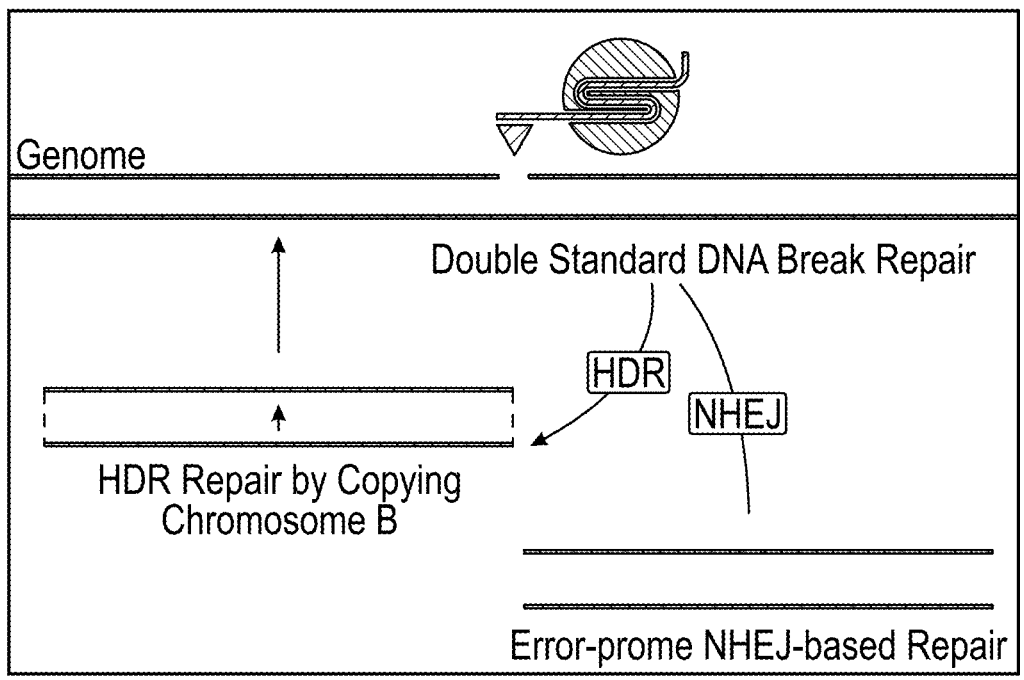

The CRISPR/Cas9 system is an effective genome editing tool in a wide variety of organisms including diverse animals, plants and yeast (FIGS. 25A, 25B). This system can include two entities, the Cas9 endonuclease, which cleaves DNA templates on both strands, and a guide-RNA (gRNA), the first 20 nucleotides of which direct the Cas9 cleavage of a complementary target DNA at a site three nucleotides upstream the 3'-end of the gRNA target sequence (FIG. 25A). Following cleavage of a targeted genomic sequence by a Cas9/gRNA complex, one of two alternative DNA repair mechanisms restores chromosomal integrity: 1) non-homologous end joining (NHEJ), which typically generates insertions and/or deletions of a few base-pairs (bp) of DNA near the gRNA cut site, or 2) homology-directed repair (HDR), which can correct the lesion via a DNA template with sequence homology spanning the gRNA cut site (FIG. 25B). In D. melanogaster, individuals carrying sources of genomically-encoded germline Cas9 and gRNAs (or embryos injected with plasmid encoded sources of gRNAs) efficiently mutate the target sequence via NHEJ in the great majority of somatic and germline cells. In addition, when a DNA template containing homologous sequences is coinjected into the polar plasm, these standard CRISPR components can trigger HDR-mediated repair in the germline. The autocatalytic mutagenesis method described herein combines features of the CRISPR/Cas9 system in a novel configuration, exploiting the cell's endogenous repair mechanism to generate self-homozygosing alleles.

Figure 25C:
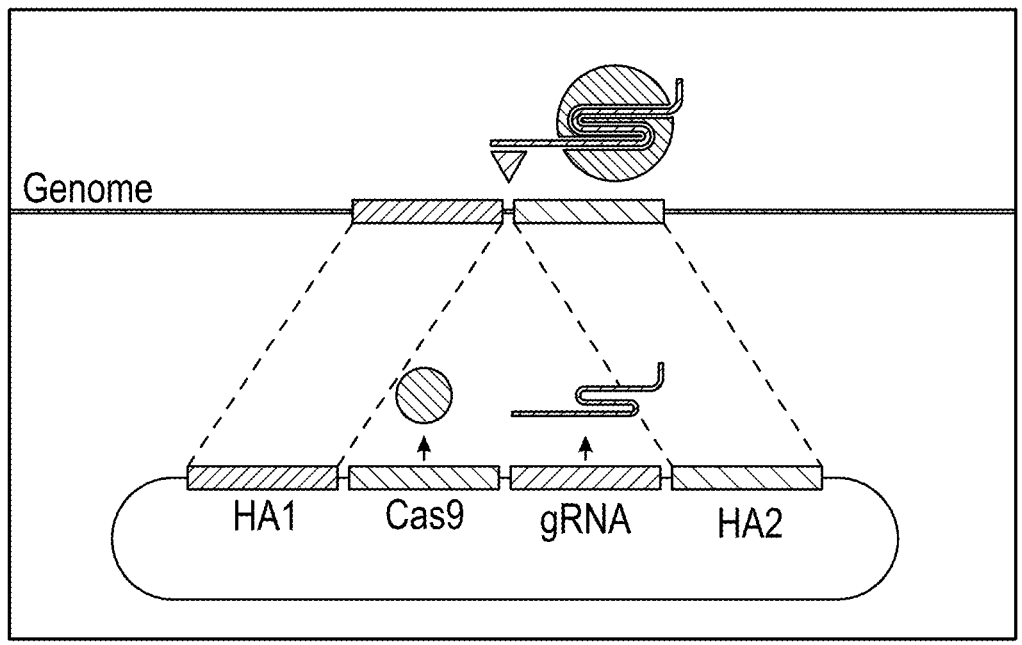
Figure 25D:
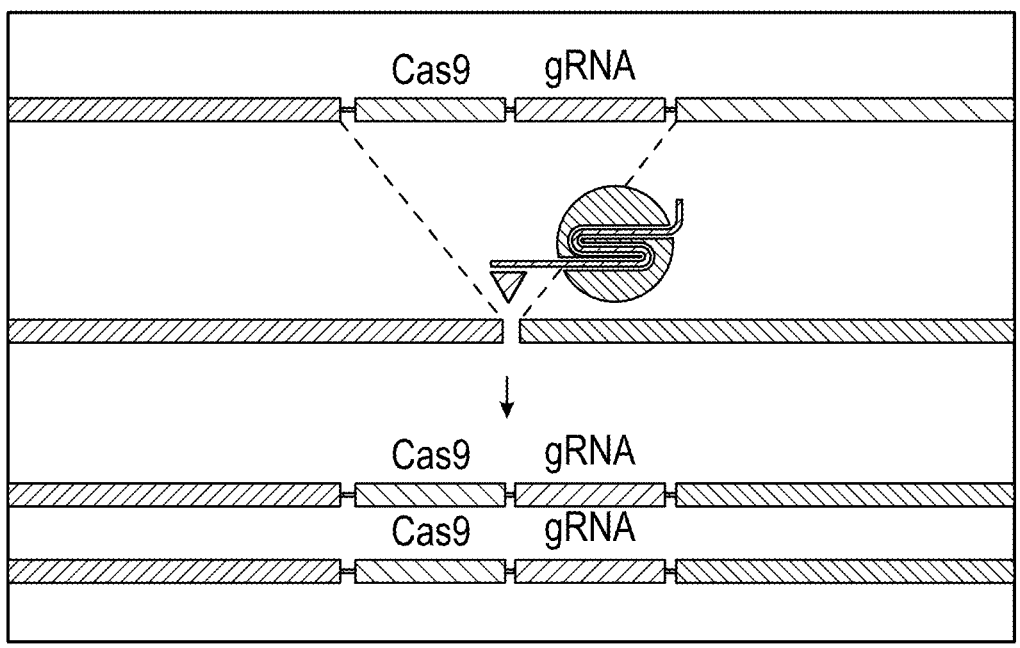

FIGS. 25A-25D are an exemplary scheme outlining CRISPR and Mutagenic Chain Reaction (MCR) methods. The CRISPR/Cas9 genome editing system can include two elements, the Cas9 endonuclease, which generates blunt ended double stranded DNA breaks, and a 20 nucleotide guide RNA (gRNA) that binds to Cas9 and targets it to complementary genomic sequences, which in addition must have a so-called PAM sequence (e.g., NGG) recognized by Cas9 that lies immediately 3' to the 20 nucleotides of gRNA match (FIG. 25A). Double stranded chromosomal breaks caused by targeted cas9/gRNA cleavage can be repaired by either the Rad51-dependent Homology Directed Repair (HDR) pathway, which faithfully copies information from the sister chromosome into the cut site, or the Ku70/80-dependent Non-homologous End-Joining (NHEJ) pathway, which typically results in short insertions/deletions (indels) at the cut site (FIG. 25B). MCR mutagenesis scheme: MCR constructs can comprise three components: 1) a transgene encoding an endonuclease (e.g., nuclear targeted form of Cas9 endonuclease), 2) a guide polynucleotide (e.g., gRNA) directing cleavage to a desired genomic site, and 3) homology arms (e.g., HA1 and HA2) from the targeted locus that directly abut the guide polynucleotide (e.g., gRNA) cut site (FIG. 25C). An injected MCR construct inserts into the genome at the site of guide polynucleotide (e.g., gRNA) directed cleavage. Once integrated into the genome, the MCR element can act on the opposing allele and can insert itself to generate a homozygous insertional mutation (FIG. 25D).

The Mutagenic Chain Reaction

Based on the CRISPR/Cas9 system or similar polynucleotide guided endonuclease system, an autocatalytic genetic behavior can be achieved in which insertional mutants are generated by a construct having three components: 1) a central segment encoding an endonuclease (e.g., Cas9) (expressed in both somatic cells and the germline), 2) a ubiquitously expressed gene encoding a guide polynucleotide (e.g., gRNA) targeted to a genomic sequence of interest, and 3) homology arms flanking the endonuclease/guide polynucleotide (e.g., Cas9/gRNA) cassette matching the two genomic sequences immediately adjacent to either side of the target cut site (FIG. 25C). Such a tripartite construct can result in the endonuclease (e.g., Cas9) cutting the genomic target at the site determined by the guide polynucleotide (e.g., gRNA) followed by insertion of the endonuclease/guide polynucleotide (e.g., Cas9/gRNA)-bearing cassette into that locus via HDR directed by the flanking sequences. Expression of the endonuclease (e.g., Cas9) and the guide polynucleotide (e.g., gRNA) from the insertion allele then can lead to cleavage of the opposing allele (FIG. 25D) followed by HDR-driven insertion of the endonuclease/guide polynucleotide (e.g., Cas9/gRNA) cassette into the companion chromosome. Analogously to the polymerase chain reaction (PCR), which doubles the number of DNA templates each cycle, this trans-acting autocatalytic mutagenesis scheme is referred to as the Mutagenic Chain Reaction (MCR), since it accomplishes the same end by in vivo DNA amplification each generation.

Targeting Elements for Tethered HDR Reactions (TETHR) and Oligo-Clamps

Figure 26:
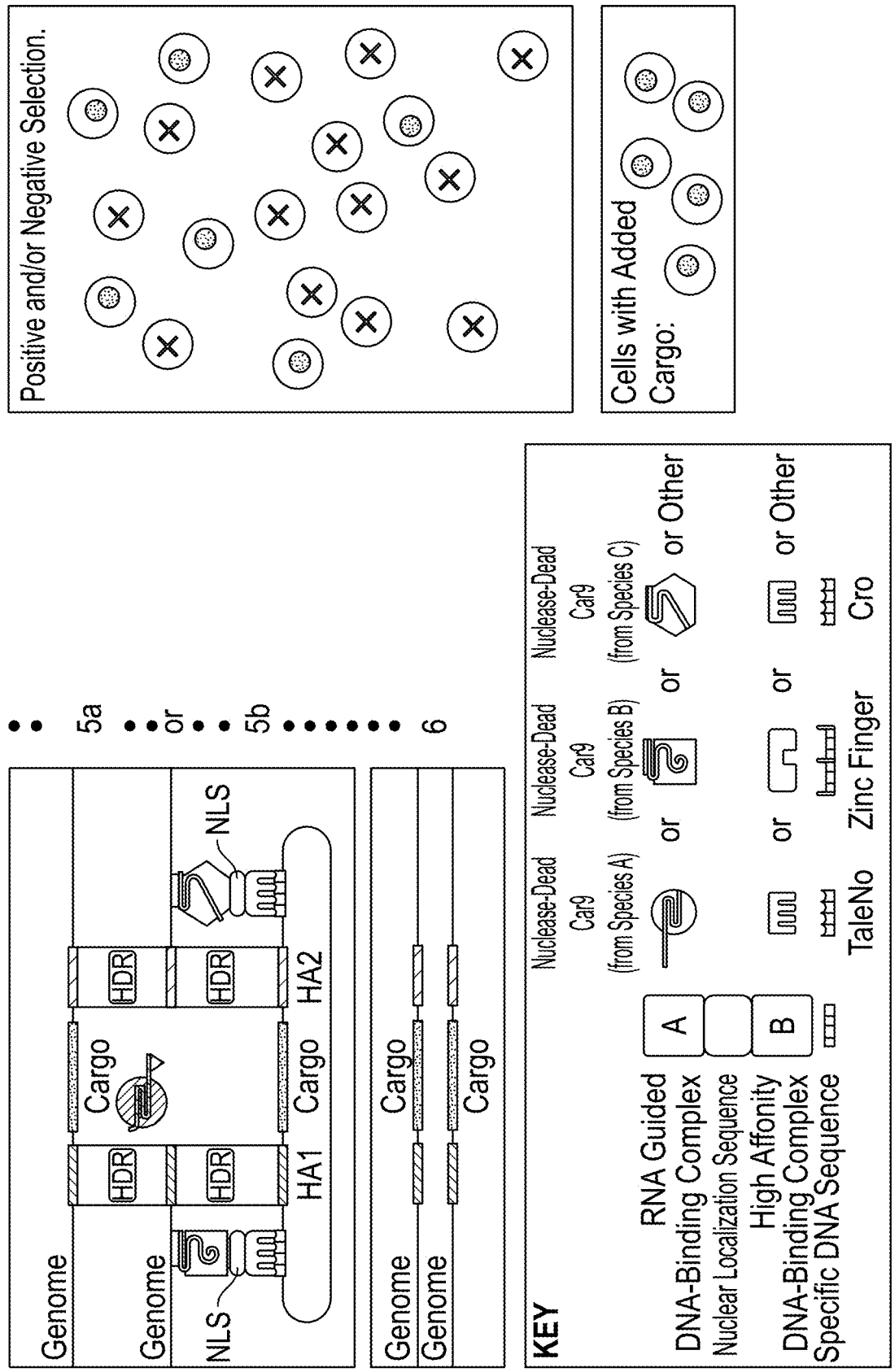
FIG. 26 depicts an exemplary scheme outlining Targeting Elements for Tethered HDR Reactions (TETHR) methods.

Targeting Elements for Tethered HDR Reactions (TETHR) and Oligo-Clamps can increase the efficiency of HDR-mediated transgene insertion into the genome of cells (e.g., in culture or other systems that might require an increase in HDR biased DNA repair). TETHR or an Oligo-Clamp can mimic using biochemical means the inter-allelic alignment between sister chromosomes that can be essential for the high efficiency of inter-chromosomal gene conversion mediated in gene conversion schemes such as the mutagenic chain reaction (MCR), ERACR, CHACR, or e-CHACR. Bivalent nucleic acid binding proteins (e.g., sequence-specific DNA binding proteins) can tether (e.g., noncovalently bind) a cargo donor vector (e.g., plasmid DNA, linear DNA, or viral DNA) containing a nucleic acid cargo sequence to a nucleic acid target sequence (e.g., site targeted for insertion such as a chromosomal site). A bivalent nucleic acid binding protein can contain two nucleic acid binding domains. One of the two nucleic acid binding domains can be designed to bind sequences in the cargo donor vector (e.g., plasmid) near a homology arm on the cargo donor vector, and the other nucleic acid binding domain (e.g., a catalytically inactive or nuclease-deficient form of Cas9 denoted as Cas9*) can target a sequence in the nucleic acid target sequence (e.g., chromosome) that lies at a similar distance from the homology arm (FIG. 26). The donor cargo vector (e.g., transfection vector) carrying a nucleic acid cargo sequence can align closely with the nucleic acid target sequence (e.g., chromosomal target sequence). In the presence of an enzymatically active endonuclease (e.g., endonuclease/guide polynucleotide complex such as Cas9/gRNA) (e.g., provided as a purified ribonuclear protein complex, on plasmids encoding the Cas9* and gRNA, or encoded on the transfection vector itself or TALEN-Fok1, etc.), the donor cargo vector can be in a configuration to serve as a substrate for homology directed repair (HDR). HDR can then efficiently insert the nucleic acid cargo sequence into the nucleic acid target sequence (e.g., at the guide polynucleotide (e.g., gRNA) cut site).

FIG. 26 is an exemplary scheme depicting the steps using TETHR (Targeting Elements for Tethered HDR Reactions). Biological events are indicated on the left and corresponding experimental steps are shown on the right. Step 1: A genome target site for Homology Directed Repair (HDR)-mediated vector insertion is selected. Step 2: A transfection vector sequence carrying cargo of interest to be inserted into the genome (top line) is flanked by inner homology arms (e.g., HA1 and HA2) and outer DNA binding sites recognized by high affinity DNA binding domains (e.g., a zinc finger, TALEN, or lambda Cro proteins—see key) of bivalent nucleic acid binding proteins that can also contain nuclear localization signals (NLS) and programmable domains for interaction with specific genomic target sequences (e.g., nuclease dead CRISPR associated proteins—Cas*). Two such chimeric DNA binding proteins fused to different enzyme-defective Cas* proteins (e.g., Cas9 from two different bacterial strains or Cpf1) can form complexes in vitro with distinct types of guide RNAs and can then assemble onto the DNA vector template to generate a tripartite complex, which is transfected into cells. Upon entry into the cell, the chimeric tethering complexes guided by the Cas*/gRNAs tether the vector DNA template to the desired genomic site such that the homology arms on the vector line up with the genomic target sequences. Step 3: An enzymatically active Cas9/gRNA is co-transfected into the same cells, which can cleave the genome at a site flanked by the homology arms carried on the transfection vector. The Cas9 protein can also be fused to a protein domain that promotes HDR over NHEJ-mediated DNA repair such as Exonuclease 1 (Exo1) that can resect DNA at the cut site to permit association of the Rad51 protein, which can then initiate HDR. Selection using positive and/or negative markers carried on the vector can enhance efficiency of precise gene insertions. Steps 4: High efficiency HDR mediated gene conversion (Step 4) can lead to insertion of the vector sequence with its cargo into the genome at the gRNA cut site. Step 5: Cas9/gRNA can then lead to cleavage of the sister chromosome and copying of the cargo via HDR using either the chromosome (a) or tethered vector (b) as the homologous template to generate a biallelic insertion (Step 6).

Transfection of cells with constructs carrying homology-flanked inserts generally use Cas9 protein and gRNA provided as a purified ribonuclear protein complex or as plasmids encoding the Cas9* and gRNA components which are synthesized upon cellular uptake of the plasmids. These traditional methods may provide the template for HDR in a random orientation with respect to the chromosomal target sequence. This random localization may result in a bias toward NHEJ repair over HDR. TETHR or an Oligo-Clamp can direct the template to the target cleavage site. The clamped proximity to the double stranded DNA break provided by TETHR or an Oligo-Clamp can increase the rate of DNA repair of double stranded DNA breaks by HDR over NHEJ.

In some embodiments, a TETHR complex (e.g., a nucleoprotein complex described herein) or an Oligo-Clamp can be used to increase the efficincy of transgenesis. These complexes can be injected into an embryo (e.g., regions from which the germline derives or the pronucleus of a ferterilzed mammalian embryo). Upon injection, the chimeric tethering complex guided by the Cas*/gRNA tether the donor cargo vector to the desired nucleic acid target sequence (e.g., a genomic site) such that the homology arms on the vector line up with the target sequence. FIG. 26 Steps 3-6 are an exemplary scheme depicting the steps of cleavage of the nucleic acid target sequence (e.g., genomic locus) at a site of cassette insertion (e.g., nucleic acid cargo sequence insertion) (Step 3—shown as a single cut here for simplicity, although more than one cut site can be used) can lead to high efficiency HDR mediated gene conversion (Step 4) and insertion of the nucleic acid cargo sequence into the genome at the gRNA cut site (Step 5), which can then become homozygous to generate a biallelic insertion (Step 6). Such transgenesis applications may be of particular utility for efforts in large scale genomic engineering.

In some embodiments, one moeity of the bivalent tethering complex could bind to a cell surface protein thereby targeting a DNA substrate for selective entry (e.g., via endocytosis) into specific cell types.

HDR generally occurs most efficiently at late S or G2 phases of the cell cycle, presumably because co-linear sister chromatids are held together in a cohesion complex. Here, the chromatids may be aligned, and double-stranded breaks, mediated by an endonuclease (e.g., Cas9-ribonucleoprotein), can be preferentially repaired by HDR. However, in female fruit flies carrying an MCR targeting the X-linked yellow (y) locus, the y−MCR construct was observed to be transmitted to their progeny at ≈97% efficiency. The MCR reaction may have occurred subsequent to fertilization, e.g., in one of the first embryonic cell divisions. Since the resulting y− females are yellow and the MCR alleles were transmitted as expected, the insertion may have occurred in the somatic cell lineage as well as the germline. HDR may occur not just between sister chromatids, but between homologous chromosomes once a double-stranded break exists. A plasmid-based repair event can be similarly efficient.

A biochemical-DNA tethering method that mimics the feature responsible for the high efficiency of MCR may increase the probability of HDR being used in cases where the homologous template is aligned with the target sequence. Once the non-converted allele is cleaved by the endonuclease (e.g., Cas9/gRNA nuclease), the proximity and long regions of homology can favor HDR. In contrast, free plasmids carrying homology sequences may not be concentrated at the cleavage site in the nucleus where they are needed to serve as templates. The MCR-dependent HDR reaction can be mimicked by overcoming the rate-limiting step of template pairing. The donor cargo vector (e.g., MCR plasmid) can be tethered to the nucleic acid target sequence (e.g., chromatin region-of-interest, sequence adjacent to the site of endonuclease cleavage) via at least one or two bridging bivalent nucleic acid binding proteins (FIG. 26). Complexes of the bivalent nucleic acid binding protein with the donor cargo vector can be assembled prior to transfection and can help target the homology arms to the genomic site where they can mediate insertion of the nucleic acid cargo sequence. This targeting strategy can be referred to as Biochemical-MCR or Biochemical autocatalytic gene conversion.

The bivalent nucleic acid binding protein (e.g., bridging chimeric protein) can comprise two nucleic acid binding domains (e.g., two DNA binding domains such as a nuclease-deficient Cas9*/gRNA attached to a zinc finger protein, Talen, or the Lambda-phage Cro protein) (FIG. 26). The Cas9* protein has been shown to bind DNA when expressed as a chimeric DNA sequence targeting protein to regulate transcription. Cro is the smallest known DNA binding protein at 66 amino acids in length; it can bind to three related 17 mer sequences of Lambda OR1, OR2, and OR3 at an affinity of $\sim 10^{10}$-$10^{12}$ M$^{-1}$. These sequences are not found in the human or mouse genomes, and they can be easily engineered into the template plasmid. Cro has also been expressed as a functional chimeric protein and remains bound to plasmid DNA as it localizes to the nucleus of human cells. In some cases, a bivalent nucleic acid binding protein is a Cas9*-Cro protein (e.g., one nucleic acid binding domain is a nuclease-deficient Cas9*/gRNA and another nucleic acid binding domain is a Cro protein).

A bivalent nucleic acid binding protein can include a nuclear localization sequence or nuclear localization signal (NLS). An NLS can be an amino acid sequence that tags a protein for import into the cell nucleus by nuclear transport. An NLS can comprise one or more short sequences of positively charged lysines or arginines. An NLS includes, but is not limited to, a classical NLS and non-classical NLS. In some cases, an NLS can be recognized by an importin protein (also known as karyopherin protein) (e.g., importin α, importin β, importin β1, importin β2 (also known as transportin or karyopherin β2), an importin α-like protein, or an importin β-like protein). In some cases, a classical NLS can be monopartite or bipartite. A classical NLS includes, but is not limited to, SV40 Large T-Antigen (SEQ ID NO: 1 PKKKRKV), Nucleoplasmin (SEQ ID NO: 2 KRPAATK-KAGQAKKKK or SEQ ID NO: 3 AVKRPAATKK-AGQAKKKKLD), EGL-13 (SEQ ID NO: 4 MSRRR-KANPTKLSENAKKLAKEVEN), c-Myc (SEQ ID NO: 5 PAAKRVKLD), and TUS-protein (SEQ ID NO: 6 KLKIKRPVK). In some cases, a monopartite NLS has the consensus sequence SEQ ID NO: 7 K(K/R)X(K/R). In some cases, a bipartite NLS has the consensus sequence SEQ ID NO: 8 (K/R)(K/R)X$_{10-12}$(K/R)$_{3/5}$, where (K/R)$_{3/5}$ represents at least three of either lysine or arginine of five consecutive amino acids. A non-classical NLS includes, but is not limited to, the acidic M9 domain of hnRNP A1, the sequence KIPIK (SEQ ID NO: 18) in yeast transcription repressor Mata2, and the complex signals of U snRNPs. In some cases, an NLS is a PY-NLS motif (named because of the proline-tyrosine amino acid pairing in it).

By targeting a transfection construct DNA (e.g., donor cargo vector) to the site of endonuclease (e.g., Cas9/gRNA) cleavage, the proximity and alignment can increase the rate of HDR-mediated insertion of the construct. One or two tether sites can align the plasmid and chromosomes at one or two sites adjacent to or flanking the insertion site. As an example, the following components can be used: 1) nuclease (e.g., gRNA-Cas9 ribonucleoprotein) targeting the nucleic acid target sequence (e.g., locus of interest) for cleavage; 2) donor cargo vector (e.g., transfection vector DNA) including the binding site(s) for the bivalent nucleic acid binding protein(s); 3) one or more bivalent nucleic acid binding proteins (FIG. 26). In some cases, a nuclease and/or bivalent nucleic acid binding protein can be assembled with appropriate guide polynucleotide(s) (e.g., gRNAs) that target programmed genomic target site(s). In some cases, a bivalent nucleic acid binding protein includes a Cas9*-Cro protein that has been preloaded with a gRNA that targets upstream of the target cleavage site.

A high efficiency is observed for copying of a single-unit MCR (e.g., one in which the Cas9 source and a gRNA are carried as a single cassette inserted into the site cut by the gRNA=95% conversion efficiency for published y–MCR in fruit flies (Gantz and Bier, 2015), Science 348, 442-4) and a 99.5% conversion for a MCR carrying a ~17 kb cargo insert in mosquitoes (Gantz et al., 2015). By mimicking the alignment of sister chromosomes achieved in germline cells by tethering the initial transfection template (or injection template for introducing MCR or CopyCat elements into the germline to establish transgenic lines or organisms), greater efficiencies of primary insertion into the genome target site via HDR may be achieved.

Figure 39:
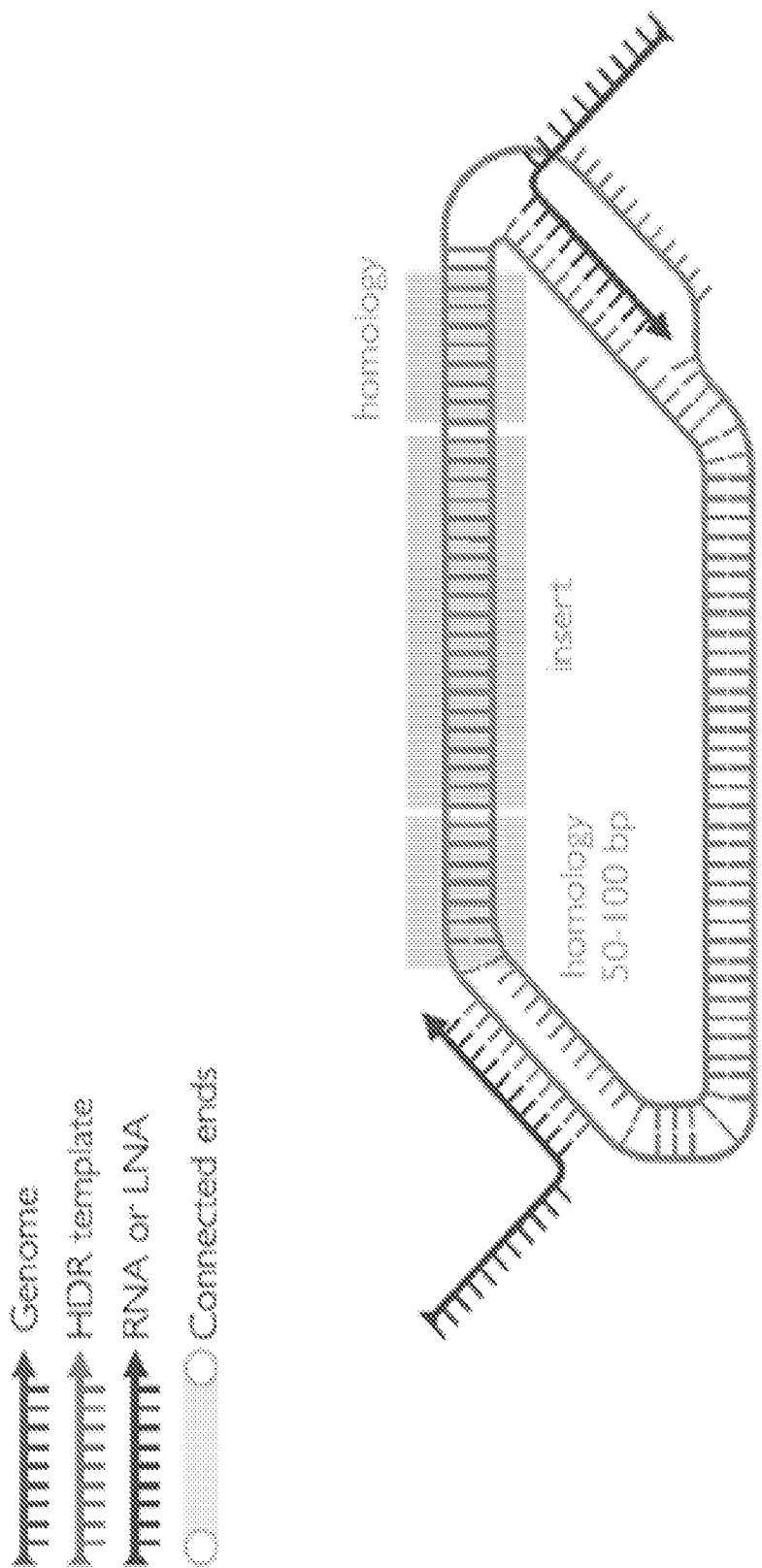
FIG. 39 is a scheme outlining treating the HDR template with two nucleic acid probes.
Figure 40:
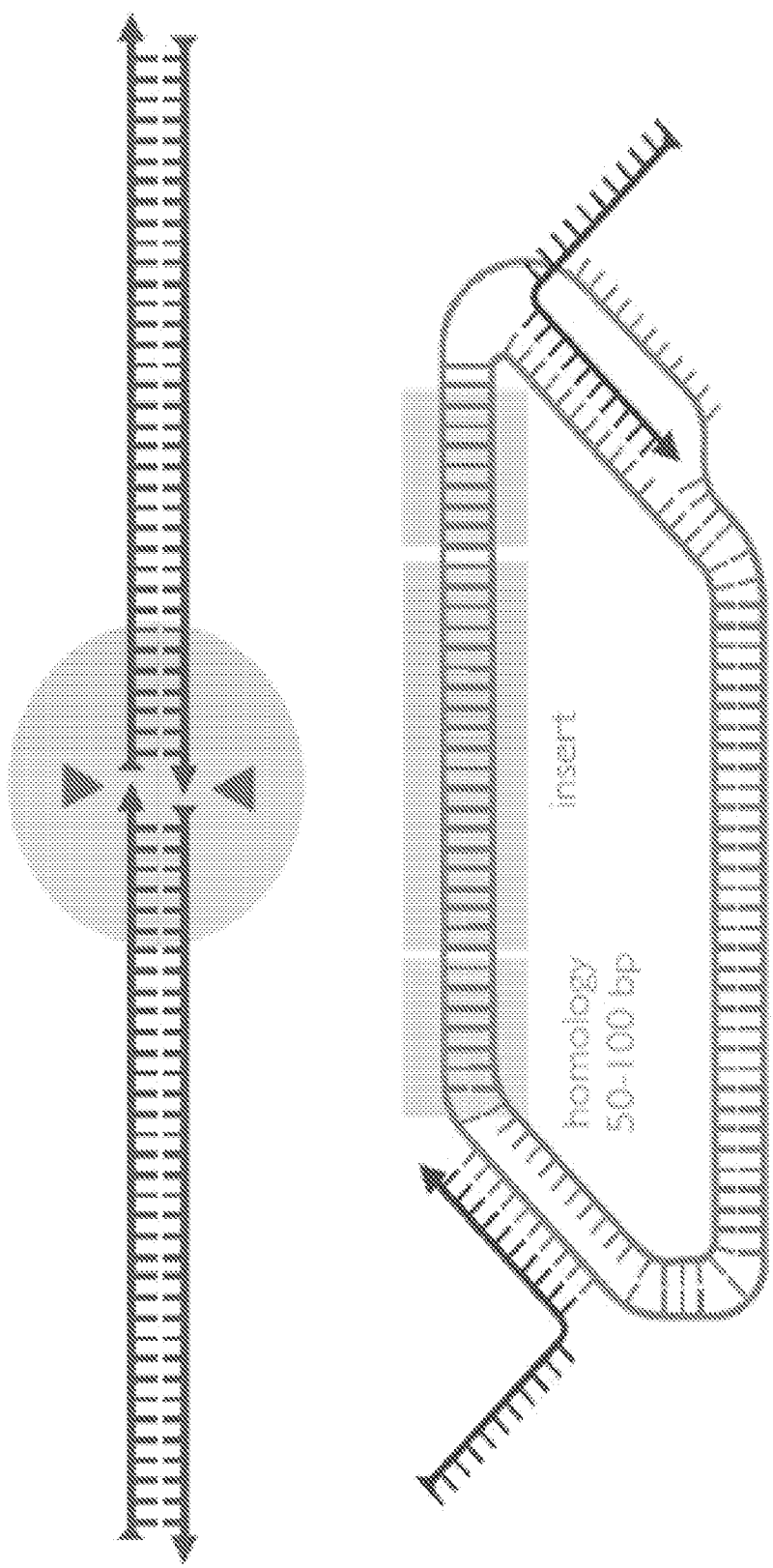
FIG. 40 is a scheme outlining transfection or injection with CRISPR components and the HDR template/nucleic acid probe complex.
Figure 41:
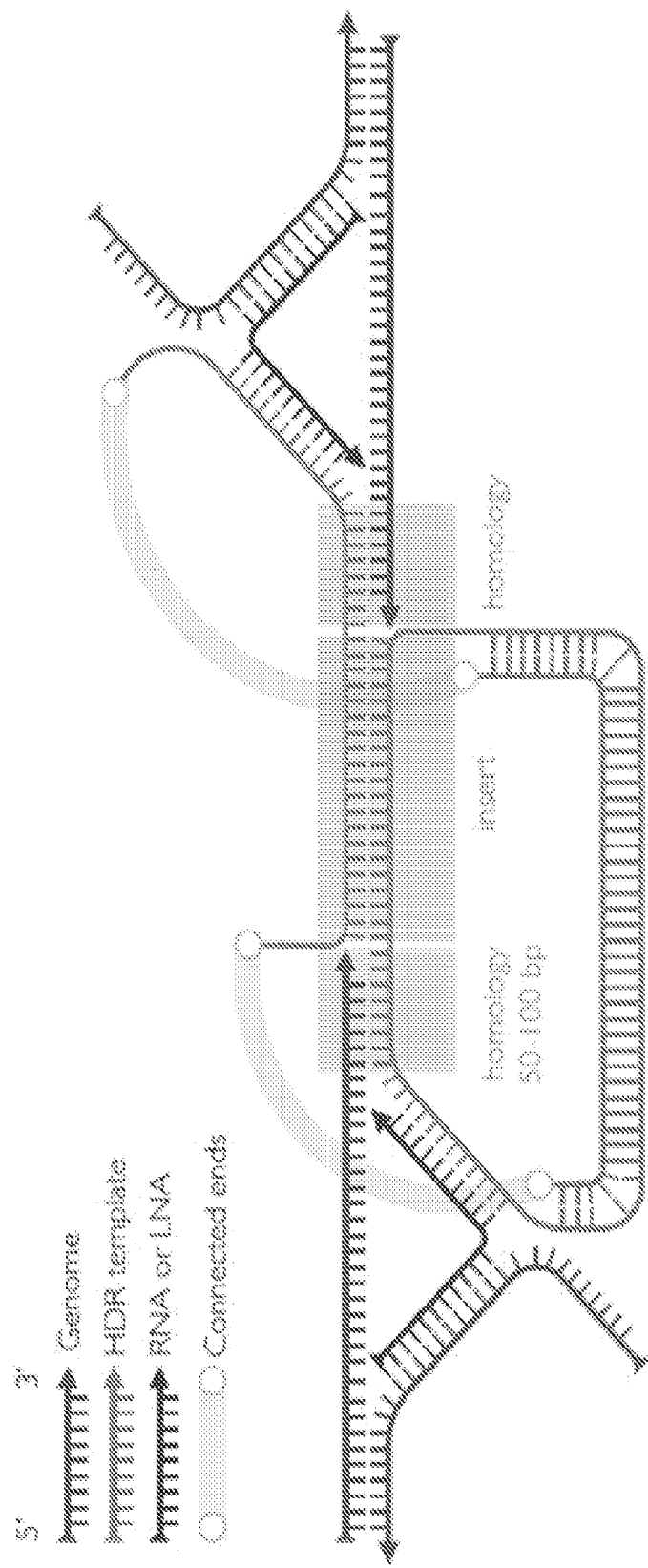
FIG. 41 is a scheme outlining complex formation promoting HCR at a targeted locus using an Oligo-Clamp.

An alternative to a protein TETHR is an Oligo-Clamp as shown in FIGS. 39-41 which can serve a similar purpose of a protein TETHR by increasing the local concentration of the donor plasmid in the vicinity of its genome target and optimizing the orientation of the donor plasmid for serving as a template for HDR. The Oligo-Clamp comprises an oligonucleotide (or paired oligonucleotides) that has sequences complementary to the genomic target on one end and sequences complementary to the donor plasmid on the other end. Such Oligo-Clamps can serve as a bridge between the genome target and donor plasmid in the similar manner to a TETHR construct. The sequences to which the Oligo-Clamp can hybridize with in the genome and donor plasmid could be the same as those bound by the TETHR or any other unique sequences present in the donor vector and genome that result in accurate alignment of the homology arms on the donor plasmid with corresponding genome sequences. Oligo-Clamps could be designed to sequences flanking either of the two homology arms carried on the donor vector and could either be used separately or together.

FIGS. 39-41 show HDR template docking using nucleic acid addressing probes. FIG. 39 shows treating the donor plasmid (e.g., HDR template) with two nucleic acid probes. The donor plasmid contains an insert sequence (e.g., cargo sequence) to be inserted into the genome and homology arms flanking the insert. In some cases, the homology arms are 50-100 bp in length. In some cases, the two nucleic acid probes are RNA or LNA. In some cases, the two nucleic acid probes comprise a sequence complementary to the donor plasmid on one end and can hybridize to the donor plasmid. In some cases, the two nucleic acid probes are single stranded. FIG. 40 shows transfection or injection with CRISPR components and the HDR template/nucleic acid probe complex. The CRISPR components can specifically cleave at a targeted locus on the genome. FIG. 41 shows complex formation promoting HCR at a targeted locus using an Oligo-Clamp. After the targeted locus is cleaved, each of the nucleic acid probes can hybridize to the genome through the sequence complementary to the genomic target. In addition, the homology arms on the donor plasmid can hybridize to the genome. A complex of the genomic locus, donor plasmid, and nucleic acid probes can be formed, allowing for HDR mediated insertion of the insert on the donor plasmid into the genome.

TETHR or an Oligo-Clamp may be used to increase the efficiency of HDR mediated insertion of a nucleic acid cargo sequence into a nucleic acid target sequence (e.g., genome of cells). In some cases, HDR mediated insertion is accomplished via Cas9/gRNA targeting. In some cases, efficiency is increased relative to a control construct without the tethering interaction mediated by the one or more bivalent nucleic acid binding proteins by about or at least about 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 5000, or 10000 fold.

TETHR or an Oligo-Clamp may be used to accelerate personalized ex-vivo cell therapies to treat a disease or condition such as cancer.

TETHR or an Oligo-Clamp may be used to increase frequencies of biallelic insertion of transfection constructs into a target site. In some cases, biallelic insertion is accomplished via Cas9/gRNA targeting.

TETHR or an Oligo-Clamp may be used to increase frequencies of germline transgenesis of an organism, including invertebrate and vertebrate animals and plants. In some cases, germline transgenesis is mediated by Cas9/gRNA.

A donor cargo vector can be physically tethered to a specific chromosomal location via a bivalent nucleic acid binding protein that binds to the homology arms on the DNA vector and to the target sequence on the chromosome. The proximity to the target location can increase homology-directed repair triggered by a double-stranded DNA break (e.g., at a nuclease cut site). In some cases, a donor cargo vector comprises a nucleic acid cargo sequence, MCR (e.g., MCR element or MCR construct), ERACR (e.g., ERACR element or ERACR construct), CHACR (e.g., CHACR element or CHACR construct), e-CHACR (e.g., e-CHACR element or e-CHACR construct), and/or CopyCat element, construct, or vector.

In some cases, a tether site is a location on a donor cargo vector and/or a nucleic acid target sequence where a bivalent nucleic acid binding protein binds. In some cases, about or at least about 1, 2, 3, 4, 5, 6, 7, 8, 9, or 10 tether sites are used. In some cases, each tether site comprises a different nucleic acid sequence.

In some cases, a tether site is about or at least about 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1100, 1200, 1300, 1400, 1500, 2000, 2500, 3000, 4000, or 5000 nucleotides away from the DNA break site, nuclease cut site, or homology arm.

A bivalent nucleic acid binding protein can contain two nucleic acid-binding domains and/or nucleic acid-binding proteins. In some cases, a bivalent nucleic acid binding protein also contains an NLS. In some cases, the nucleic-acid binding domain is a DNA-binding domain. In some cases, the nucleic-acid binding protein is a DNA-binding protein. In some cases, at least one DNA-binding domain of a bivalent nucleic acid binding protein is a nuclease-deficient or inactivated nuclease (e.g., Cas protein, Cas9).

A DNA-binding domain includes, but is not limited to, helix-turn-helix motif, zing finger, leucine zipper, basic leucine zipper (bZIP) domain, winged helix domain, winged helix turn helix domain, helix-loop-helix domain, HMG box domain, Wor3 domain, OB-fold domain, immunoglobulin fold, B3 domain, TAL effector DNA-binding domain, and RNA-guided DNA-binding domain. In some cases, the DNA-binding domain is a sequence specific DNA-binding domain.

A DNA-binding protein includes, but is not limited to, zinc finger protein, Talen, Lambda-phage Cro protein, nuclease (e.g., endonuclease, nuclease-deficient nuclease, nuclease-deficient endonuclease), transcription factor, and repressor. In some cases, the DNA-binding protein is a sequence specific DNA-binding protein. In some cases, the DNA-binding protein contains a DNA-binding domain.

In some cases, a nucleic acid-binding domain (e.g., DNA-binding domain) or nucleic acid-binding protein (e.g., DNA-binding protein) binds to its nucleic acid (e.g., DNA) target sequence with a $K_d$ of about or at least about 1 pM, 5 pM, 10 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, 900 pM, 1 nM, 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, or 500 nM.

In some embodiments, the nucleic acid cargo sequence is about or at least about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, or more than 50 kilobases (kb) in length. In some embodiments, the nucleic acid cargo sequence is up to about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, or more than 50 kilobases (kb) in length. In some cases, the nucleic acid cargo sequence encodes an MCR (e.g., MCR element or MCR construct), ERACR (e.g., ERACR element or ERACR construct), CHACR (e.g., CHACR element or CHACR construct), e-CHACR (e.g., e-CHACR element or e-CHACR construct), and/or CopyCat element, construct, or vector. In some cases, the nucleic acid cargo sequence is located on a donor cargo vector. In some cases, the donor cargo vector is a plasmid.

In some embodiments, a nucleic acid cargo sequence comprises about or at least about 1, 2, 3, 4, 5, 6, 7, 8, 9, 10, 15, 20, 25, 30, 40, or 50 genes, sequences encoding a protein (e.g., enzyme, endonuclease, fluorescent protein, transcription factor, cell signaling protein, signal transduction protein, membrane protein, transmembrane protein, receptor protein, structural protein, fibrous protein, globular protein, motor protein, antibody, ligand transport protein, transport protein, chaperone protein, hormone, growth factor, hemoprotein, plasma protein, cytoskeletal protein, extracellular matrix protein, DNA binding protein, DNA repair protein), guide polynucleotides, coding regions and/or regulatory regions, or regulatory elements (e.g., promoter, terminator, enhancer, silencer, operator, 5' untranslated region, 3' untranslated region, ribosome binding site, intron).

In some cases, a nuclease, endonuclease, bivalent nucleic acid binding protein, DNA-binding domain, or DNA-binding protein is covalently or noncovalently linked to a protein involved in HDR, homologous recombination, or DNA repair. In some cases, a protein involved in HDR, homologous recombination, or DNA repair is tethered. Proteins involved in HDR, homologous recombination, or DNA repair include, but are not limited to, BRCA2, Cdc28, Dmc1, DMC1/Lim15, DNA polymerase, Dna2, ExoI, helicase, ligase, Mre11, MRN complex, MRX complex, Nbs1, nicking endonuclease, nuclease, PALB2, Rad1, Rad10, Rad50, Rad51, Rad51B, Rad51C, Rad51D, Rad51L1/B, Rad51L2/C, Rad51L3/D, RAD52, Rad54, RadA, RadB, RecA, RecA1, RecA-like NTPase, RecB, RecBCD, RecC, RecD, RecF, RecO, RecQ, RecR, restriction endonuclease, RPA, RPA, RuvA, RuvAB, RuvABC, RuvB, RuvC, Sae2, Saw1, SbcCD, Sgs1, Six4, Spo11, UvsX, XRCC2, XRCC3, and Xrs2. Proteins involved in HDR, homologous recombination, or DNA repair can bias DNA repair toward HDR over the NHEJ pathway.

An MCR Element Efficiently Converts its Sister Chromosome in Flies

Figures 27A, 27B, 27C:
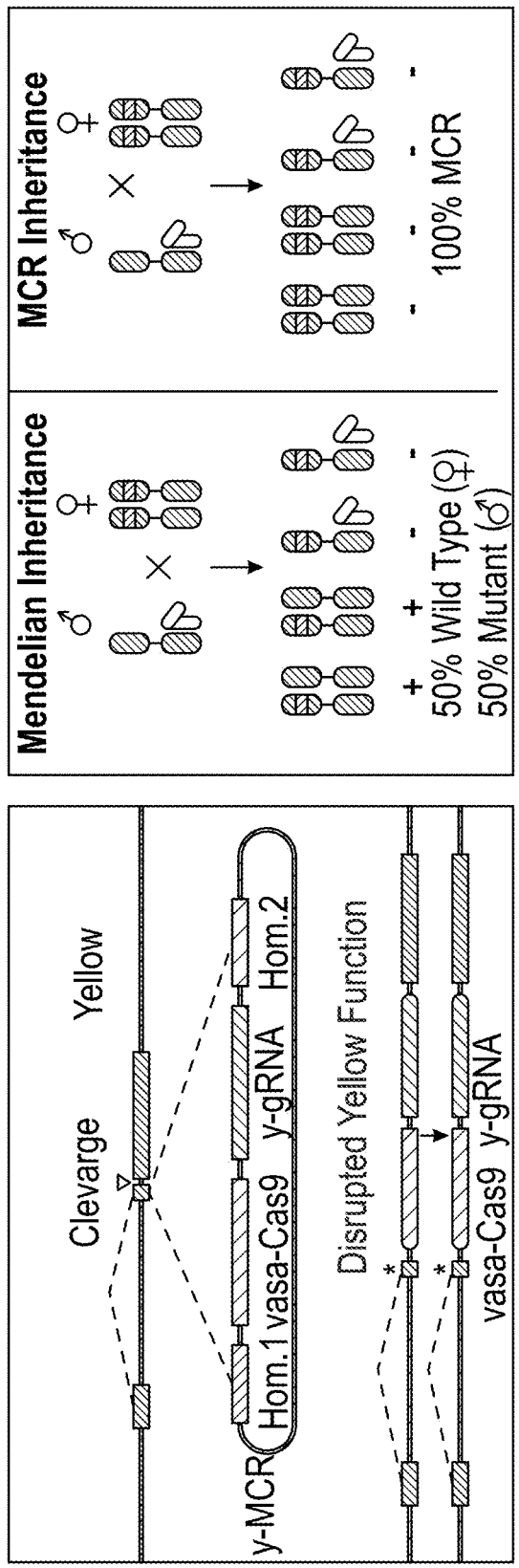
FIGS. 27A-27C depict an exemplary scheme outlining transmission of a y-MCR element.

The MCR concept has been tested in *Drosophila*. Similar high frequencies of transmission of a significantly larger MCR in mosquitoes has also been observed, and related constructs have been reported to efficiently bias inheritance in yeast. In an initial study in flies, known efficient CRISPR/Cas9 components were used, and two flanking homology arms of ~1 kb that precisely abut the gRNA-directed cut site (FIG. 27A). This y-MCR element converted the opposing allele in the female germline ≈95% of the time, deviating significantly from the predicted 50% Mendelian transmission rate (FIG. 27B, 27C). In addition, somatic cells were converted to full body yellow mutant phenotype in the great majority of individuals (96%). PCR analysis confirmed the precise expected gRNA-driven genomic insertion of the y-MCR construct in such individuals indicating that the y-MCR element copied itself to the sister chromosome with high efficiency in the female germline and the yellow mutant phenotype was widespread in the vast majority of pigmented somatic cells of most individuals. However, molecular analysis revealed the presence of both MCR and wild-type size y locus PCR products in MCR females, indicating that allelic conversion was incomplete. Sequencing of the few exceptions in which the MCR did not convert or mutate the sister chromosome revealed NHEJ events. Rare non-converted y+ alleles had synonymous nucleotide changes at the gRNA directed cut site or small in-frame insertion/deletions (indels). Such mutations, although rare, are potentially important in certain contexts (e.g., reducing the efficiency of gene drives) because they constitute ~wild-type MCR-resistant alleles. MCR alleles acting in both germline and in somatic cells (which may induce mutations via either HDR or NHEJ) can only be used to generate viable alleles. Targeting essential loci for the purposes of suppressive gene drive systems is also possible if Cas9-dependent mutagenesis is strictly confined to the germline.

FIGS. 27A-27C are an exemplary scheme outlining transmission of a y-MCR element. Structure of the y-MCR construct and its insertion into the genome at the yellow locus on the X chromosome (FIG. 27A). Mendelian versus MCR inheritance of a yellow (y) allele (FIG. 27B). Summary of results of 8 crosses between F1 y- heterozygous flies and y+ flies (2 male MCR and 6 female MCR crosses) yielding a total of 527 F2 progeny (FIG. 27C). The MCR transmission rate in the experiments was 97%, which translates into a 95% rate of the MCR allele converting the opposite allele in the germline (conversion %=2(X−0.5N)/N where N=total number of flies and X=number of y flies with a y- phenotype or y mosaic phenotype).

Accessory Elements can Recall MCRs or Expand their Functionality

MCR elements can carry both a source of endonuclease (e.g., Cas9) and a guide polynucleotide (e.g., gRNA) inserted at the guide polynucleotide (e.g., gRNA) cut site. For example, an MCR arrangement with Cas9 and a gRNA is denoted as: <cas9; gRNA> wherein the symbols < > represent the homology sequences flanking the gRNA cut site. Since persistent low-level endonuclease (e.g., Cas9) mutagenesis might reduce the fitness of individuals carrying such constructs and because it can be prudent to have methods for neutralizing MCRs, two types of constructs are devised in which only the guide polynucleotide(s) (e.g., gRNA(s)) are flanked by homology arms (denoted <gRNA> elements for a gRNA). Such <gRNA> constructs can only be copied to the other chromosome when a source of endonuclease (e.g., cas9) is provided in trans. For example, two categories of <gRNA> constructs can be used in conjunction with MCRs: 1) ERACRs (Elements for Reversing the Autocatalytic Chain Reaction), which upon encountering an MCR deletes and replaces it (FIG. 28A), and 2) CHACRs (Constructs for Hitchhiking on the Autocatalytic Chain Reaction) are targeted to other chromosomal loci and copied in parallel with the MCR. This strategy can be extended to devising <gRNA> active "copy-cat" cloning vectors.

Figure 28A:
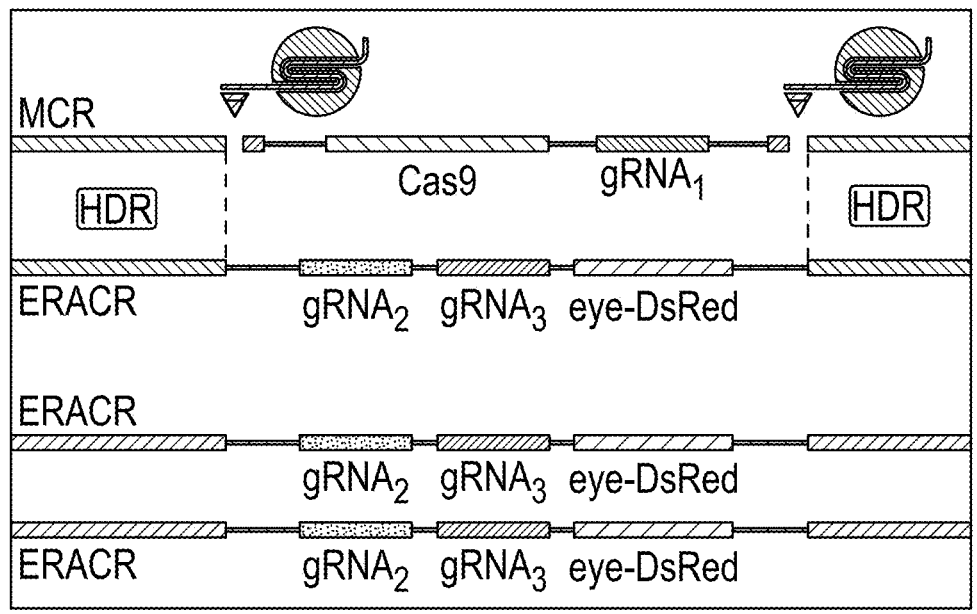
Figure 28B:
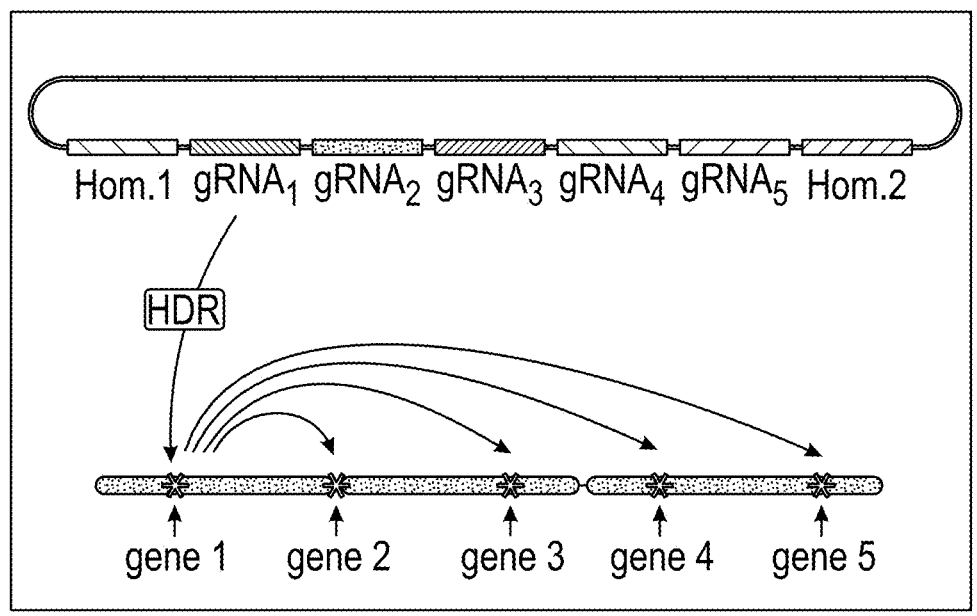
Figure 28F:
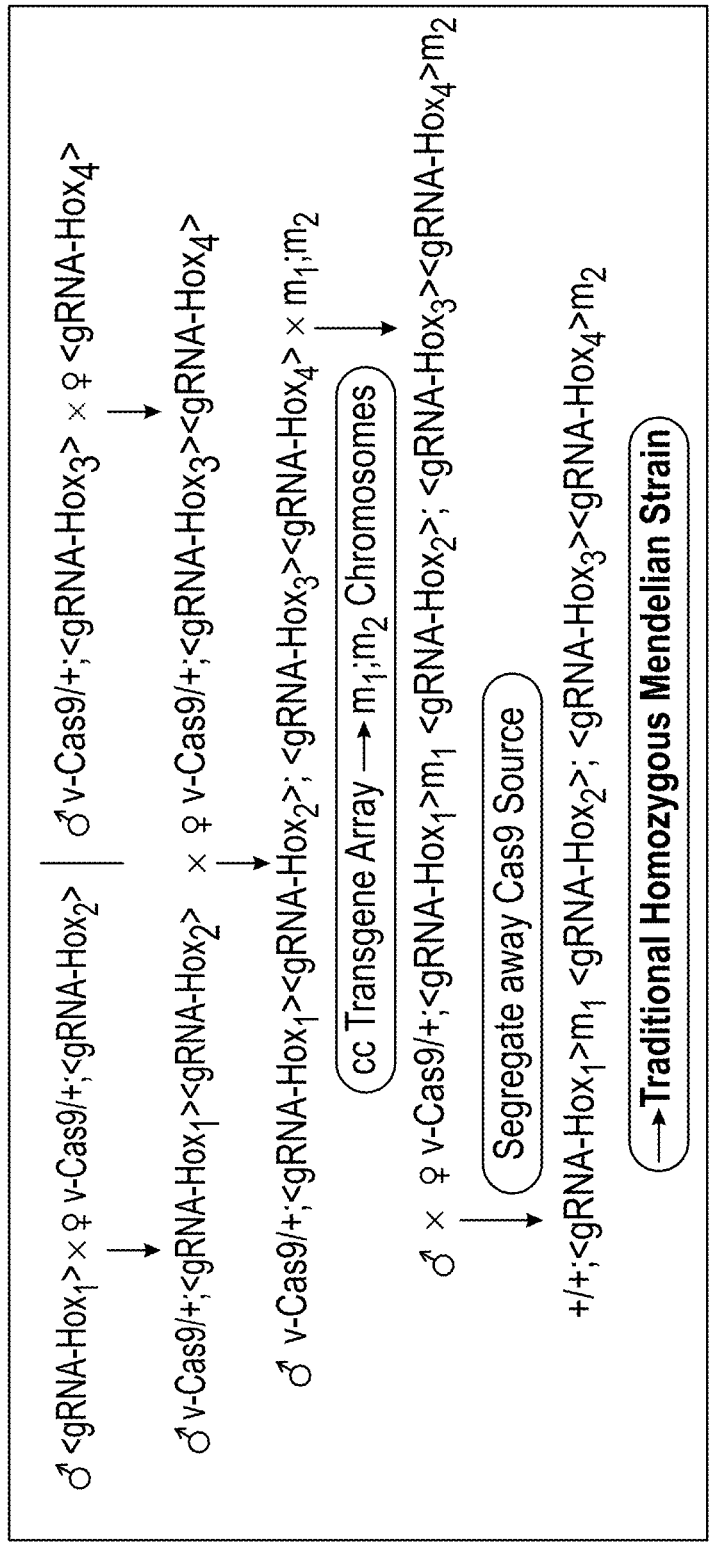

FIGS. 28A-28F are an exemplary scheme outlining ERACRs, CHACRs, and copy-cat <gRNA> constructs. ERACRs: "Elements to Reverse the Autocatalytic Chain Reaction" or NCRs delete MCR elements (FIG. 28A). In flies carrying both an MCR and an ERACR allele, Cas9 produced by the MCR cuts at sites directed by gRNA-2 and gRNA-3. eye-DsRed=dominant marker. The MCR inserted at a cut site determined by gRNA-1 lying within the deleted segment leading to the ERACR element becoming homozygous. CHACRs: "Constructs Hitchhiking on the Autocatalytic Chain Reaction" target other genomic targets (FIG. 28B). For example, a CHACR can serve as a platform to launch an array of guide polynucleotides (e.g., gRNAs) to multiple or diverse targets (e.g., one or more locations on a gene; one or more genes) where they can induce standard NHEJ-dependent mutations. An MCR element (top left panel) can be neutralized by CHACR elements used as second-site ERACRs (e-CHACR—inserted at site determined by gRNA2—top second panel) that can carry multiple guide polynucleotides (e.g., gRNAs such as gRNA3 and gRNA4) targeting an endonuclease (e.g., Cas9) in the MCR (FIG. 28C). CHACRs can be used to drive the spread of unlinked auxiliary elements. A CHACR element (top right panel) can carry multiple guide polynucleotides (e.g., 3 gRNAs) inserted into the cut site of one of these guide polynucleotides (e.g., gRNAs such as gRNA5), which is in a different location in the genome than the MCR (inserted at a site defined by gRNA1). Like an ERACR, in the presence of an MCR carrying an endonuclease (e.g., Cas9) source, the CHACR cuts the opposing chromosome (via cleavage induced by gRNA5) and inserts itself into the resulting DNA gap. The depicted CHACR carries gRNA6 and gRNA7, which cut at adjacent sites flanking an edited genomic locus (or existing natural allelic variant—top right panel). The resulting small deletion (e.g., region between the gRNA6 and gRNA7 cut sites) can then be repaired via HDR using an edited sequence. The lower panel shows a magnified view of the top right panel indicating the gene edited residues as asterisks and the two cleavage sites for gRNA6 and gRNA7 relative to the sequences of perfect homology mediating HDR repair. "Copy-cat" or cc vectors allow the cloning of transgenes into multiple cloning sites (MCS) as well as matched sets of gRNA(s) flanked by both 5' (U6p) and 3' (U6-3') U6-RNA regulatory elements, and homology arms (HA-L=left, HA-R=right), standard features of cloning vectors such as a bacterial origin of replication (Ori), a gene providing Ampicillin resistance (AmpR), as well as optional use cassettes such as a UAS promoter, an attB 031C recombinase donor site allowing for alternative recombinase-driven insertion of the construct into a genomic recipient site (attP), or instead, an attP recipient site to allow recombinase-mediated insertion into the genomically inserted copy-cat element, and an FRT-flanked transcriptional stop cassette (<Stop<) (FIG. 4D). cc elements can insert at various loci along a chromosome (D. melanogaster X-chromosome shown as example) which are determined by their particular matched sets of gRNAs and homology arms (FIG. 4E). In the presence of an endonuclease (e.g., cas9) source, these elements can be copied to the sister chromosome, thereby homozygosing the element with the inserted transgene. For example, copy-cat elements can be used in a model vertebrate organism such as a mouse or fish to create an endonuclease (e.g., cas9)-dependent viable quadruple knock-out of a set of target genes (e.g., redundantly acting Hox gene paralogs) (FIG. 28F). Not shown here for simplicity are various transgene constructs that also can be carried by each of the cc-elements (e.g., CRE/LOX components and fluorescent markers appropriate for expressing and analyzing the ability of a single Hox gene to substitute for the normal sets of genes in a given tissue). These cc elements/mutant alleles can be assembled in two generations. Next, in the maintained presence of endonuclease (e.g., cas9), they can be combined with two traditional Mendelian alleles (m1 and m2) by cc-ing the Hox mutant alleles into the mutant background. The source of endonuclease (e.g., cas9) then can be removed by segregation, resulting in the complex assembly of mutant alleles and transgenes which can now behave according to standard Mendelian rules.

ERACR Elements can Recall MCRs

ERACRs or NCRs are designed to delete and replace MCR elements, thereby eliminating endonuclease (e.g., cas9) from the genome. These elements can carry two guide polynucleotides (e.g., gRNAs) that target sequences flanking the genomic integration site of a specific MCR element (denoted: <$gRNA_1$; $gRNA_2$>), but differ from other so-called reversal constructs that have been proposed in that they do not carry a source of endonuclease (e.g., Cas9) (FIG. 28A). ERACRs can be inserted into the genome by providing an exogenous source of endonuclease (e.g., Cas9) at the time of injection. When ERACR and MCR stocks are crossed, the guide polynucleotides (e.g., gRNAs) provided by the ERACR element combine with the endonuclease (e.g., Cas9) provided in trans by the MCR element to both delete the MCR and replace it with the ERACR. Importantly, ERACRs cannot spread through wild populations since they lack an endonuclease (e.g., Cas9) source, nor do they subject genomes to any endonuclease (e.g., Cas9)-based mutagenesis. ERACRs also can include dominant markers (e.g., eye-DsRed), recoded gene cassettes that restore gene functions disrupted by insertion of the MCR element, or effector cassettes such as anti-malarial factors. ERACRs can be employed to eliminate an MCR that might inadvertently spread to an unintended population (e.g., from a pest population into a neighboring or distant indigenous population). In addition, the ability of ERACRs to delete the endonuclease (e.g., Cas9) source carried by MCRs can limit the accumulation of unwanted off-target mutations that might accompany the long term presence of an MCR in a population. ERACRs, like MCRs, can generate a small fraction of NHEJ generated lesions, and some such events can destroy the guide polynucleotide (e.g., gRNA) cut site and prevent clean deletion of the MCR. Since subsequent HDR-mediated copying of the ERACR-resistant MCR can also include adjacent ERACR-induced mutations, such closely linked NHEJ mutations can spread along with MCR into the population. One way to prevent such a scenario can be to target the ERACR cut sites far enough from the MCR (e.g., ~at least 500 bp, 600 bp, 700 bp, 800 bp, 900 bp, or 1 kb) to prevent or greatly reduce HDR mediated copying of the ERACR-derived NHEJ mutations (e.g., via DNA resection, which typically extends <500 bp from the double stranded break).

MCRs can Target Secondary Loci in Combination with CHACR Elements

CHACRs are <gRNA> constructs that can carry one or two or more than two gRNAs targeting non-MCR loci. For example, if a prominent off-target MCR site were identified in a population, a CHACR can be designed that clips out the mutation when crossed to the MCR and replaces the altered site with a recoded version of that sequence to repair damage caused by the MCR and to prevent subsequent mutagenesis at that site. After the CHACR had spread throughout the population and performed its reparative task, an ERACR can then be deployed to delete the MCR and restore the genome to a nearly wild-type condition. Although this chain of events may not always proceed with ideal frequencies (e.g., 95-100%), correcting off-target effects and deleting MCR elements need occur in only a fraction of individuals in order to permit regeneration of a healthy population from a "rescued" minority population via natural selection. CHACRs can also be used as second-site ERACRs or e-CHACRs (erasing-Construct Hitchhiking on the Autocatalytic Chain Reaction) by carrying guide polynucleotides (e.g., gRNAs) targeting the gene encoding an endonuclease (e.g., Cas9) (FIG. 28C). Such elements can be used to inactive multiple or all MCRs carrying a given endonuclease (e.g., Cas9) isoform, in contrast to ERACRs, which are MCR-specific. Another variation can be to incorporate additional guide polynucleotides (e.g., gRNAs) in an MCR or CHACR that cuts at sites where desired gene edits are to be made. Such gRNAs can be used to perform standard CRISPR edits of target genes in one strain and then crossed to the MCR strain. In subsequent generations, the gRNAs carried by an MCR or CHACR can cut the unedited alleles and HDR can efficiently repair the lesions using the edited locus as a homology template (FIG. 28C). Such edits can then hitchhike with the MCR leading to their linked spread in the population. CHACRs can also carry a gRNA driving its insertion into a locus encoding a component in one pathway and a set of gRNAs targeting other genes acting redundantly in that same pathway or in parallel acting pathways to ensure that the desired process was knocked out (FIG. 28B).

An e-CHACR (erasing-Construct Hitchhiking on the Autocatalytic Chain Reaction) is a type of guide polynucleotide (e.g., gRNA) drive (also known as a copy-cat element) that can use a trans-acting source of an endonuclease (e.g., Cas9) to copy itself to the opposing chromosome at a site determined by a guide polynucleotide (e.g., gRNA2) (FIG. 28C). This particular type of CHACR element can carry multiple guide polynucleotides (e.g., gRNAs, such as gRNA3 and gRNA4 in FIG. 28C) targeting a gene encoding an endonuclease (e.g., Cas9) present in a Mutagenic Chain Reaction (MCR) element, thereby inactivating the enzyme and immobilizing the resulting crippled MCR. e-CHACR elements can also carry additional guide polynucleotides (e.g., gRNAs) targeting other gene sequences contained either within the MCR or elsewhere in the genome. e-CHACRs can be used in conjunction with ERACR elements (also referred to as Neutralizing Chain Reaction—NCR elements).

The guide polynucleotide (e.g., gRNA) mediating copying of the e-CHACR is unaffected by alterations at the MCR locus. Non-copying events such as the generation of insertion/deletion (indel) mutations caused by endonuclease (e.g., Cas9/gRNA1) cleavage of the opposing chromosome and repair of that double stranded DNA break via non-homologous end joining (NHEJ) can segregate freely away from the inactivated MCR. Such alleles should not provide effective protection to other MCR elements in a population that have not yet encountered the e-CHACR. The e-CHACR can eliminate active MCR elements from a population given sufficient time. In some cases, an ERACR can be fallible at some low rate to NHEJ destruction (e.g., of its gRNA cleavage sites on either side of the MCR) creating ERACR-resistant MCR constructs. e-CHACRs can work to inactivate any MCR using a given form of endonuclease (e.g., Cas9 or related enzyme such as cpf1). ERACRs are MCR specific as they are inserted at the same chromosomal site as the targeted MCR. An additive functionality can result from combining ERACRs and e-CHACRs since they act by independent mechanisms.

The ERACR and e-CHACR elements can lack a source of endonuclease (e.g., Cas9). The presence of endonucleases (e.g., Cas9) in reversal elements can present a significant problem in that there can remain an active mutagenic agent (e.g., Cas9±gRNAs) in the population even once the gene drive element (MCR-like) is inactivated. ERACRs and e-CHACRs stop propagation of MCR elements and also eliminate endonuclease (e.g., Cas9) from a population, so that a persistent source of potentially mutagenic endonuclease (e.g., Cas9) does not remain in the population.

The concept of the e-CHACR is diagrammed in FIG. 28C. The MCR (top left panel) can copy itself from one chromosome to the other via the autocatalytic mutagenic chain reaction wherein the endonuclease (e.g., Cas9) and guide polynucleotide (e.g., gRNA1) encoded by the MCR assemble to form an endonuclease complex that cleaves the opposing chromosome at the same site that the MCR is inserted. Repair of the resulting double stranded DNA break via the homology dependent repair (HDR) pathway leads to copying of the MCR into the gap. This HDR-mediated copying has been shown to be highly efficient in the germline of fruit flies and mosquitoes and also occurs efficiently in yeast. The e-CHACR (top middle left panel) is inserted at a genomic site cut by a guide polynucleotide (e.g., gRNA2) that it carries. Like the MCR, it can be copied to the other chromosome via HDR in the presence of a source of endonuclease (e.g., Cas9) provided in-trans. In this example, the endonuclease (e.g., Cas9) source is provided by the MCR element. Also carried on the e-CHACR can be multiple guide polynucleotides (e.g., gRNAs (only two are shown in this diagram for simplicity—gRNA3, gRNA4)) that target sequences in the endonuclease (e.g., Cas9) transgene (e.g., coding region and/or regulatory region) in the MCR for cleavage. When an individual carrying an MCR element mates with an individual carrying an e-CHACR the following can occur: 1) a Cas9/gRNA2 complex forms and cleaves the opposing chromosome leading to HDR-mediated copying of the e-CHACR element to that chromosome, and 2) Cas9/gRNA3 and Cas9/gRNA4 complexes form leading to cleavage and inactivation of the Cas9 transgene mediated by the error-prone NHEJ DNA repair pathway. Hence, the frequency of the e-CHACR doubles, leading to its spread in the population, while the MCR is inactivated. Iterations of such a cycle can lead to the reduction or elimination of active MCR elements from the population.

e-CHACRs can be used for the reduction, elimination, or neutralization of gene drive systems such as MCRs that are designed to combat vector-borne diseases, pest species, or invasive species. These reversal systems can provide a means of recalling an MCR should it become necessary for ecological or safety reasons to do so. e-CHACRs could also be used in combination with ERACRs or NCRs to increase the efficiency of neutralizing MCRs or gene-drive elements.

e-CHACRs could also be designed to target mutagenesis and disruption of other nucleases or enzymes used to create gene drive elements including Cpf1.

Active Genetics can Enhance Research in Model and Pioneer Organisms

MCRs or split cas9; <gRNA> constructs can be used for a wide variety of applications in both traditional animal and plant model systems as well as in "pioneer organisms" currently lacking genetic tools. In addition, active genetic tools such as versatile "copy-cat"<gRNA> plasmid cloning vectors, which once inserted into the genome can be homozygosed in the presence of a separate cas9 source, can significantly accelerate the assembly of complex arrays of transgenes bypassing Mendelian rules of inheritance in well-developed models. These strategies can permit genetic shortcuts enabling combinatorial genetic studies that are infeasible with currently available methods.

Active Genetics Provides an Entry Point for Functional Genomics in Pioneer Organisms MCRs can conduct functional genomic studies in pioneer organisms. The number of such species with sequenced genomes is growing, but development and mastery of genetic tools in some novel organisms remains difficult. Pioneer organisms are generally chosen for sequencing based on their informative position in phylogenetic trees or because they offer particular advantages in a specific area of biology such as aging (e.g., African killifish), neurodegeneration, cancer, unique models for infectious disease (e.g., macaques for HIV, armadillos for leprosy, chinchillas or the hispid cotton rat for various viral infections), specialized behaviors (e.g., genetically tractable primate models such as mouse lemurs, pigmy marmosets) or other adaptations.

Active genetic approaches offer an obvious avenue for gaining a genetic foothold in these species. Although in many cases it may be possible to employ basic CRISPR/Cas9 technology to generate mutations in the germline of pioneer species, such endeavors can be very challenging, particularly in species without existing transgenesis methods. Thus, MCRs or split cas9; <gRNA> elements, offer potential advantages in generating identifiable homozygous mutations in G1 progeny. For full MCR elements, mutations can be generated in a single step bypassing any need for other transgenesis methods, while in the case of split cas9; <gRNA> configurations it can take two steps (e.g., first obtaining strains expressing a source of Cas9) and then injecting the <gRNA> construct into such backgrounds. The split cas9; <gRNA> option can be a preferred method to employ in species for which there is a serious concern of escape into wild populations. Another important advantage of mutations induced by split cas9; <gRNA> systems is that the <gRNA>-induced mutation can be segregated away from the source of cas9 at which point it can behave as a simple Mendelian allele that can be used for traditional genetic studies. Full MCR elements may also create standard indel alleles of the locus at an appreciable rate (e.g., ~5%) via NHEJ that can similarly be segregated away from the MCR.

"Copy-Cat" Transgenesis Vectors can Bypass Constraints of Mendelian Inheritance

The ability to homozygose <gRNA> constructs in a single step in the presence of an endonuclease (e.g., Cas9) source opens up fundamental new possibilities for genetically manipulating transgenic constructs and combining them with traditional Mendelian alleles. For example, one application can be to create a set of cloning vectors referred to as "copy-cat" (cc) elements. These vectors can harbor a guide polynucleotide (e.g., gRNA) and flanking homology sequences to guide its insertion into a desired genomic (e.g., chromosomal) location and can include other standard features such as multiple cloning sites (MCS) and a dominant marker gene (Mrk) for identifying transgenic individuals (FIG. 28D). A modular kit of cc vectors can be generated for any given organism that target sequences spaced along the various chromosomes to permit the flexible assembly of complex combinations of transgenes (FIG. 28E). cc elements can insert into coding regions of non-essential visible marker genes (e.g., pigment or bristle markers in *Drosophila*), into regulatory regions of essential genes that direct expression in a non-vital cell type (e.g., a wing specific cis-regulatory sequence of an essential *Drosophila* gene), or into fitness neutral sites (e.g., rosa26 in mice) to avoid effects of the transgene insertion site on the sensitive biological systems (e.g., complex neuronal-based behaviors).

Short-Cutting Classical Genetics in Model Organisms=Active Genetics cc elements mobilized by an endonuclease (e.g., cas9) can insert a variety of different transgenes at defined loci (FIG. 28E), which can then be combined by crossing strains carrying insertions at different sites. The progeny can inherit both transgenes, and then transmit them together to their progeny. cc-elements can also be tailored to insert into loci of interest and generate mutant phenotypes, combining transgenesis with mutagenesis. Once assembled, an array of cc-transgenic elements can be launched onto another set of chromosomes (e.g., that carried traditional sets of Mendelian alleles) in the maintained presence of an endonuclease (e.g., cas9) source, by a process that can be referred to as cc-ing (e.g., example of targeting four Hox genes in FIG. 28F). One can then segregate away the source of endonuclease (e.g., cas9) and settle back into the traditional stable Mendelian realm for experimental analysis of the resulting mutant phenotypes. This facilitated ability to assemble complex arrays of transgenic constructs and traditional alleles can greatly enable research in diverse fields (e.g., optogenetics in neuroscience or drought or pest resistance in polyploid crop plants). For these types of applications, cc elements would not have to be copied with exceptional efficiency as allelic conversion rates greater than 50% can be more than adequate for recovering the desired allelic combinations.

Active genetics can also facilitate identification of modifier loci for a given trait or phenotype that encode missing components of a pathway. Such loci are typically identified in screens for dominant alleles that alter a reference homozygous mutant phenotype. Thus, a set of candidate interacting strains (which may have been generated in specific genetic backgrounds) can be crossed into the reference mutant background to identify alterations (suppressed or enhanced) in that phenotype. If the reference homozygous mutant were generated using cas9 and a <gRNA> allele in the gene of interest, it can be possible to screen F1 progeny directly for an altered mutant phenotype. To illustrate this strategy, a cas9<gRNA> stock can be crossed to a genome-wide collection of isogenic deletions and the progeny can be screened for alterations of the <gRNA> phenotype based on heterozygosity for the deleted interval. In contrast, existing genetic strategies can require intercrossing the F1 progeny to generate homozygous recessive mutants, which can necessarily assort the genetic background from the interacting strains in the ensuing F2 progeny, thus confounding interacting effects.

Employing MCR Elements for Genetic Drives

An autosomal allele is defined as being under genetic drive if more than 50% of the progeny inherit the allele from an individual carrying a single copy of that allele. A wide variety of genetic elements or symbiotic/parasitic organisms have been identified that generate drive, and are often referred to as selfish genes because they can spread through a population and become fixed. Well-studied examples of such selfish elements or organisms include: chromosomal rearrangements, transposons, Medea elements, homing endonuclease genes (HEGs), maternal-effect lethal underdominant elements, and the bacterial endosymbiont/parasite *Wolbachia*. CRISPR-based self-propagating elements such as MCRs or similar constructs are newcomers to this established selfish DNA realm.

Figure 29A:
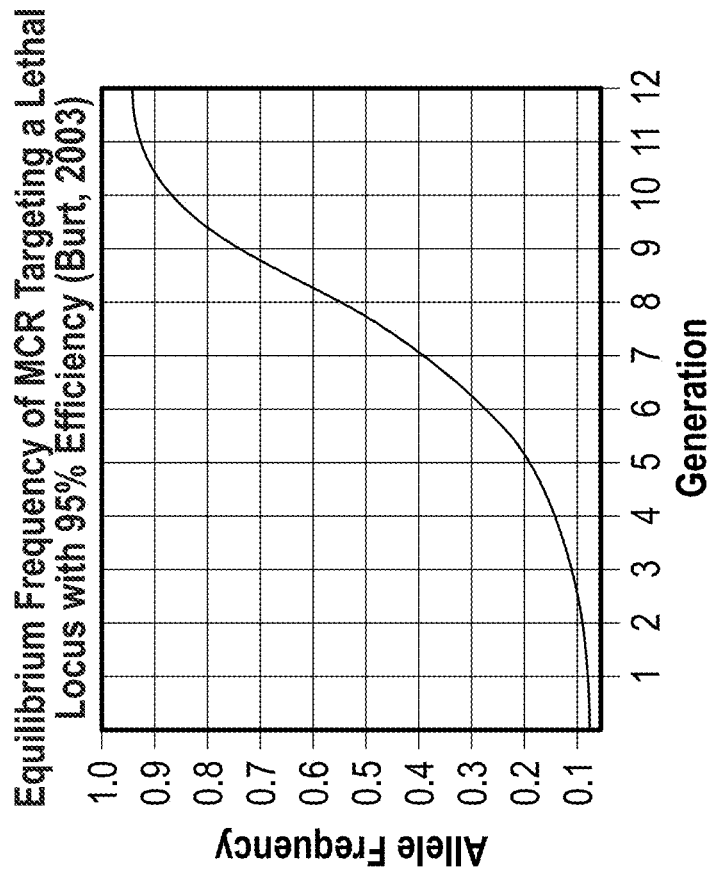
FIGS. 29A-29H depict an exemplary scheme outlining modeling of MCRs, ERACRs, and other <gRNA> elements.

Gene-Converting Drives can Suppress or Modify Disease Vector or Pest Populations HEGs act much like MCRs in cutting chromosomes at a specific site and inserting themselves into the break via HDR. HEGs can be a potential drive mechanism for suppressing insect populations such as mosquitoes (FIG. 29A) that serve as vectors of diseases such as malaria, dengue fever, and chikungunya. Based on data from the World Health Organization and other sources, the Gates Foundation recently estimated that mosquitoes are responsible for more human deaths than any other animal. Burt and collaborators modeled the spread of HEGs targeting essential genes or various classes of genes required for fertility under conditions where the endonuclease was expressed in a germline-specific fashion. They showed that an HEG seeded at a frequency of 1% can rapidly spread through the population until it reaches a stable equilibrium in 12-14 generations. Thus, individuals carrying an HEG transgenic targeting an essential locus can initially breed by chance most often with wild-type individuals. Their progeny carry only a single targeted mutant allele in their somatic cells and hence are viable. However, as the HEG allele frequency increases due to gene drive HEG carriers can begin mating with each other. When such unions arise, a quarter of the offspring can inherit two mutant copies of the insertion, and die. Eventually, a balance is struck between the HEG-mediated gene drive and the fitness cost of carrying a lethal allele such that an equilibrium frequency for the HEG allele is reached equal to the efficiency (e) with which the HEG converts the opposing allele (FIG. 29A). If e is close enough to one, an HEG drive can cause effective suppression (or in more extreme cases, elimination) of a population.

FIGS. 29A-29H are an exemplary scheme outlining modeling of MCRs, ERACRs, and other <gRNA> elements. Modeling of an MCR powered by a germline specific source of cas9 that targets an essential gene is based on the modeling of HEGs by Austin Burt (FIG. 29A). The example assumes that the MCR has a 95% efficiency of conversion (like the y–MCR in *Drosophila*)=the equilibrium frequency of the MCR allele in that population.

Figure 29B:
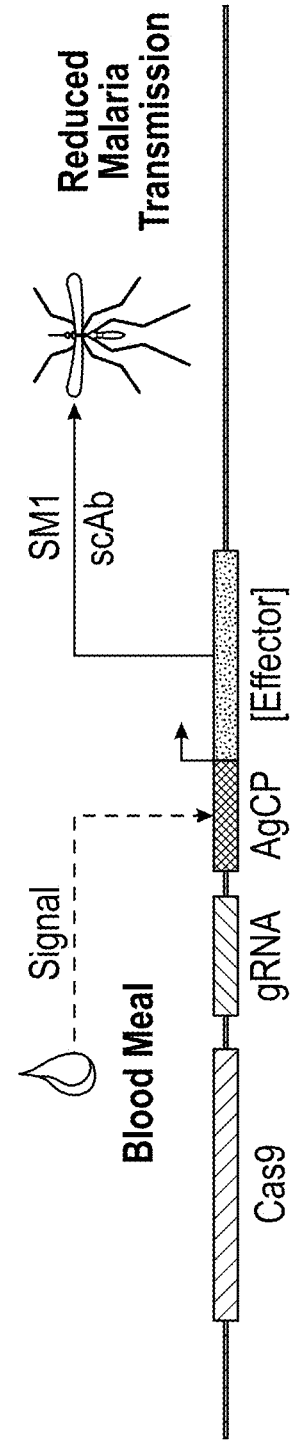

Application of MCR to attenuate mosquito borne malaria in which an effector cassette encoding the SM1 peptide, which is conditionally activated by a blood meal (e.g., AgCP promoter) or a single chain antibody (e.g., scFvs) directed against the malarial agent *P. falciparum*, is inserted along with core MCR components (e.g., Cas9 and gRNA) into a non-coding region of the mosquito genome (FIG. 29B). Such a construct has been inserted into the genome of the malarial vector *Anopheles stephensi* and has been shown to propagate with 99.5% efficiency to progeny via the germline (Gantz et al., 2015). The antimalarial gene casettes are transcrptionally induced upon feeding female mosquitoes a blood meal. As another example, the SM1 peptide limits passage of *P. falciparum* through the gut, a required step in its exploitation of that vector host.

Figure 29C:
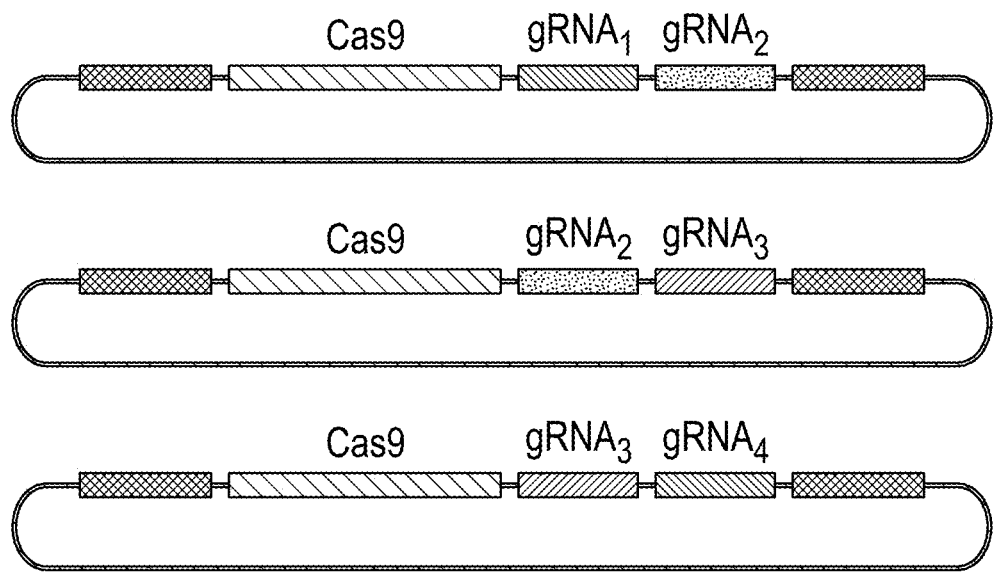

A set of three mutually reinforcing MCRs is shown in FIG. 29C. Each MCR can carry two gRNAs, one targeting its own insertion site and a second gRNA targeting the cut site a companion MCR. If each of these elements behave as in the example shown in panel A, when integrated into the genome and released together they can create a sufficient genetic load to drive the population to extinction. Flanking homology regions and gRNAs in the depicted plasmid constructs are matched to indicate which gRNAs direct cleavage at different genomic sites. Arrows summarize redundant patterns of gRNA cleavage that result in two gRNAs from different MCRs cutting at each chromosomal site.

Figure 29D:
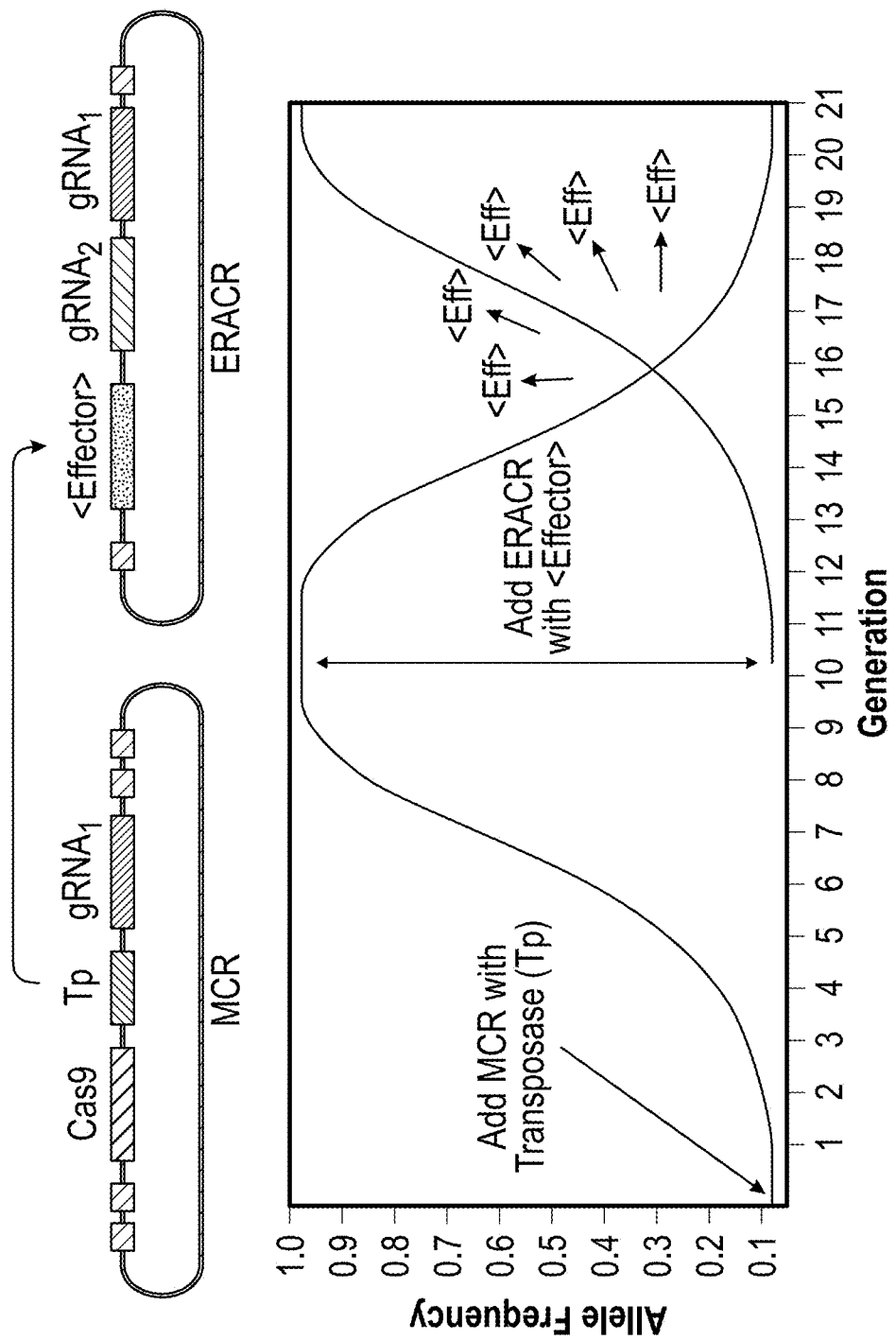

Top: A coupled pair of MCR and ERACR constructs designed to launch a transposon burst (FIG. 29D). The MCR carries a Transposase gene (Tp), while the ERACR carries an effector gene cassette <EF> flanked by inverted transposon ends. Bottom: The MCR (first curve) seeded at 1:100 spreads through the target population following a logistic growth curve in ≈10 generations whereupon the ERACR is added. The ERACR (second curve) then spreads with the same dynamics through the MCR population. In individuals carrying both the MCR and ERACR (maximal in gray zone) the Transposase provided by the MCR mobilizes the transposon born effector cassette to new chromosomal sites. This mobilization is restricted to single generation since the ERACR also deletes the MCR. The result is an amplification of the number of effector cassettes in the population and their dispersion to potentially advantageous new genomic locations.

Trans-complementing <cas9>; <gRNA> which together create a drive system equivalent to that of a single coupled <cas9; gRNA> MCR element (FIG. 5E). In this scheme, gRNA1 cleaves at the cas9 insertion site and gRNA2 cleaves at the <gRNA1,2> insertion site.

Figure 29E:
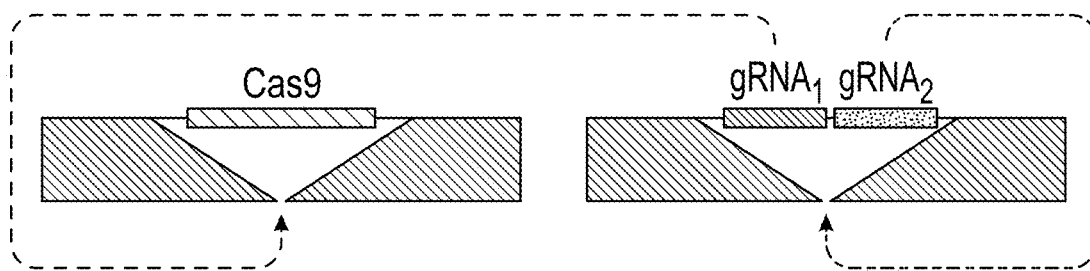
Figure 29F:
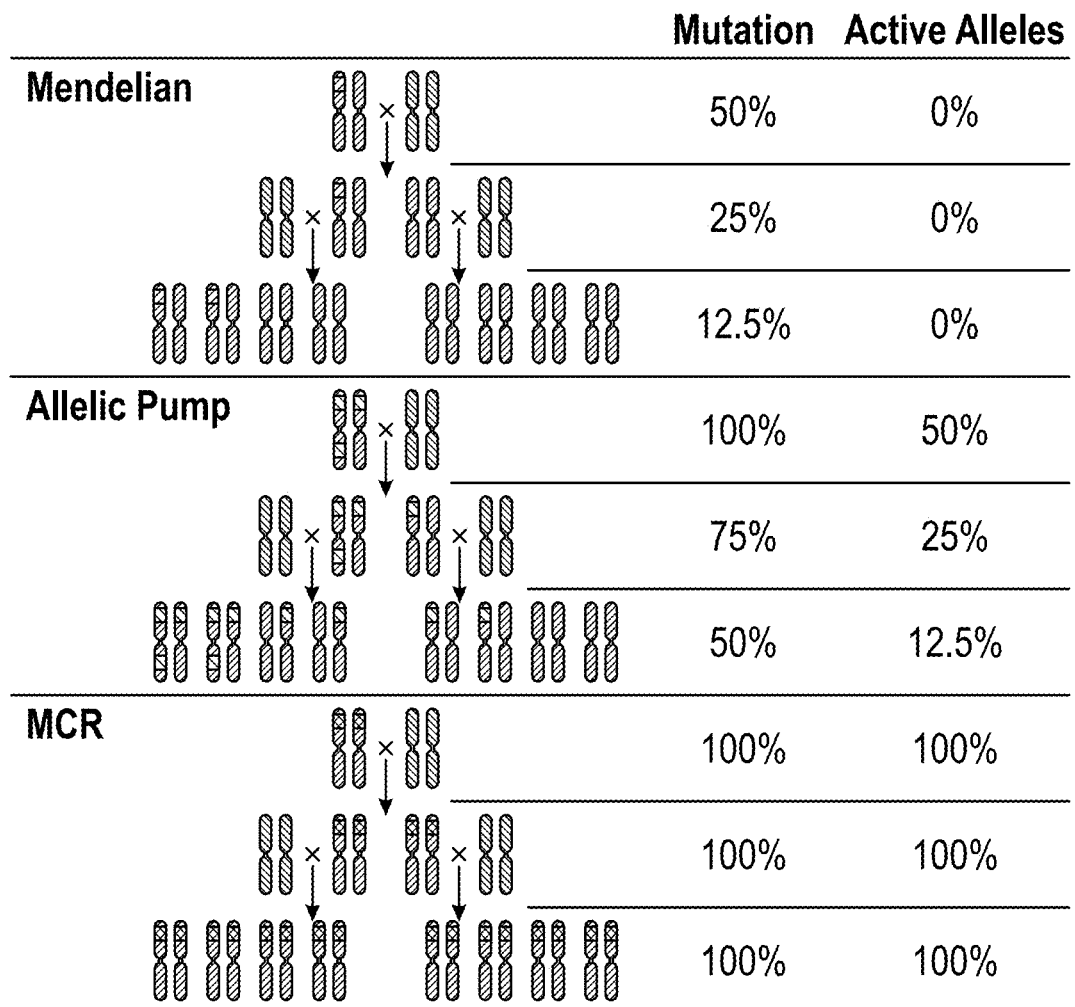
Figure 29G:
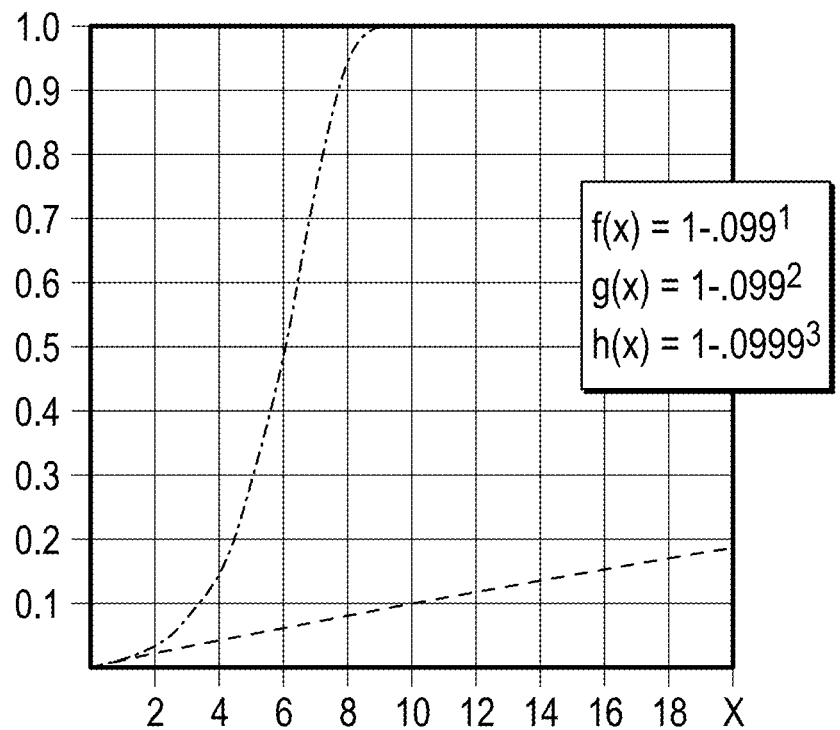
Figure 29H:
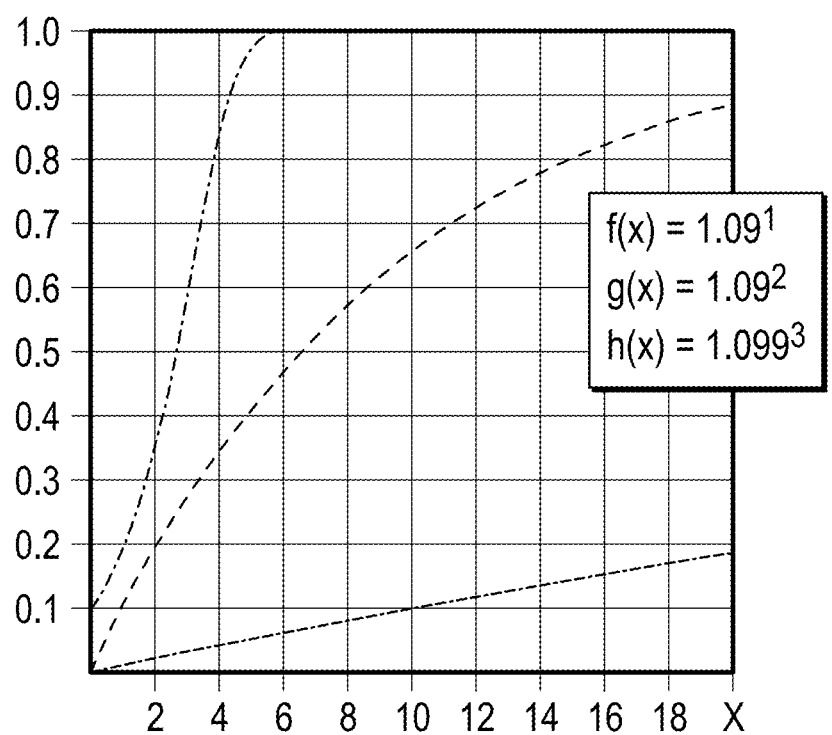

Exemplary scheme depicting two generations of inheritance for a classic Mendelian allele (top), a copy-cat allelic pump including a separated source of cas9 and a <gRNA> (middle), and an MCR (bottom) (FIG. 29F). This logistic growth curve is defined by the second order recursion formula: $f_{n+1}=f_n+f(1-f_n)=2f_n-f_n^2$, where $f_n$ is the frequency of the MCR in the population at generation n. This formula has the closed form solution $f(n)=1-(1-c_0)^{(2^n)}$, where $c_0$=the seeding frequency of the MCR, which for low values of $c_0$ can be approximated as expected, by the exponential equation $f(n)=c_0 2^n$. Time course of accumulated mutant alleles resulting from 1:100 seeding of an MCR, a cas9; <gRNA> allelic pump, and a standard cas9; gRNA encoding transgenes (buried in the baseline) (FIG. 29G). The additive copy-cat drive can be modeled by the first order recursion formula: $f_n=f_{n-1}+c_0(1-f_{n-1})$ where $c_0=g_0$ (initial fractions of cas9 and gRNAs in the population). The closed form solution for this equation is $f(n)=1-(1-c_0)^n$, which for low values of $c_0=g_0$ can be approximated by the linear equation $f(n)=c_0(n)$. For comparison, the standard mutational drive can be represented by $f_n=f_{n-1}+c_0 g_0(1-f_{n-1})$, which has the closed form solution $f(n)=1-(1-c_0 g_0)^n$ ($\approx c_0 g_0(n)$ for $c_0$ and $g_0 \ll 1$). FIG. 29H shows the same as in FIG. 29G but with a seeding ratio of 1:10. Note that the allelic pump in FIG. 29G has precisely the same behavior as the standard cas9; gRNA combination in FIG. 29H. Note that the growth curve for the copy-cat allelic pump seeding at $c_0=g_0=1\%$ is identical to that of the standard non-drive mutagenesis scheme seeded at $c_0=g_0=10\%$ (asterisks indicate equal endpoints).

Burt, colleagues, and others have since modeled a wide variety of scenarios for HEG-mediated gene drives and reached several interesting conclusions, including: 1) targeting genes causing female sterility or grandchildless phenotypes is more effective than targeting essential genes for eradicating a population, 2) targeting multiple sites with HEGs can provide more reliable suppression than a single element, 3) low density populations are more prone to suppression than high density populations (fortunately many mosquito species carrying malaria are found in relatively low density), and 4) an aggressive HEG can lead to local elimination of an isolated pocket of a population before it can spread to the full population and thereby burn itself out (e.g., like highly-virulent forms of Ebola virus).

Advantages of MCR-Mediated Gene Drives

An MCR element in which the endonuclease (e.g., cas9) source is expressed in a germline specific fashion can behave exactly as an HEG drive. Thus, the modeling of HEG dynamics by Burt and colleagues can be directly applied to MCRs. MCRs can be targeted to virtually any locus to generate either null or tissue-specific mutations in a target gene. In addition, guide polynucleotides (e.g., gRNA) target sequences can be selected that are unique to a species within a closely related clade to greatly reduce the risk of inadvertent horizontal gene transfer. Since mosquitoes, like flies, are dipteran (two winged) insects, it is perhaps not surprising that MCRs can spread efficiently through mosquito populations as observed in *Drosophila*. Likewise, MCRs can be expected to function efficiently in various invasive fly species to help restore ecologies to their native state and reduce associated agriculture damage.

The feasibility of a gene drive strategy in mosquitoes was tested by generating an MCR that carries one of several well-studied effector gene cassettes capable of blocking transmission of the malarial parasite *Plasmodium falciparum* (FIG. 29B). This kh-MCR targets insertion into an eye pigmentation locus (kynurenine hydroxylase=kh=cinnabar in *Drosophila*) in the Asian vector, *Anopheles stephensi*. The blood-meal inducible gene cassette carried by the ~17 kb kh-MCR expresses two single-chain antibodies that block different steps of the parasite life cycle and are 100% effective in preventing propagation of *P. falciparum* in mosquitoes. Since the kh-MCR propagates to 99.5% of progeny via both the male and female germline, a similar MCR targeted to one of several characterized fitness neutral loci can provide a strategy for sustainable malaria control. A potential add-on to this system can be for the MCR to carry an additional gRNA(s) targeting one of several host loci required for parasite transmission for either mutagenesis or editing.

There are several advantages to using effector-bearing MCRs that target fitness neutral sites. First, such strategies can have the smallest possible ecological impact because their only effect is to block parasite transmission and not to harm the mosquito population. Second, the absence of a fitness handicap can allow isolated pockets of MCR mosquitoes to persist until they can disperse and mate with adjacent connected populations. Modeling of lethal HEGs indicated that aggressive elements were subject to elimination in this type of scenario, particularly when the mosquito population density is low. In contrast, MCR-effector vectors, in principle, can be more likely to spread smoothly through areas with uneven or locally disconnected population distributions.

Coupled MCR/ERACR/Transposon Systems can Reinforce Drive or Amplify Effector Delivery As Burt and colleagues pointed out with regard to suppression of target populations with HEGs, deploying more than one such element can greatly increase the probability of success. This same strategy can help complement MCRs that are designed to target fitness neutral loci because such elements are likely to generate MCR-resistant alleles via NHEJ at some frequency (~5% in experiments with the y–MCR in *Drosophila*). Also, mutations can arise in MCR components that eliminate either endonuclease (e.g., Cas9) or guide polynucleotide (e.g., gRNA) function. One multiplicative strategy can be to generate a series of several reinforcing MCRs, each carrying two guide polynucleotides (e.g., gRNAs): one that targets the site at which the MCR integrates and the other targeting the insertion site of a companion MCR (FIG. 29C). Such mutually reinforcing MCRs should virtually never fail to propagate through a population because at least one of them can propagate into nearly all progeny of every cross of an MCR parent with a wild-type individual. In addition, because of cross-reinforcement, such multiplicative MCRs can be relatively invulnerable to mutations in either endonuclease (e.g., cas9) (normally present at three different genomic sites) or the guide polynucleotides (e.g., gRNAs) (present at two distinct genomic sites).

It can also be possible to make use of a combination of MCRs, ERACRs, and transposons to broadly disseminate multiple copies of effector gene cassettes. For example, in the exemplary scheme depicted in FIG. 29D, an MCR carries a copy of a transposase gene (e.g., P-transposase Δ2-3) while a matched ERACR carries a desired effector cassette flanked by corresponding transposon ends. The MCR can first be released and allowed to spread broadly throughout the population. These animals do not express the effector genes. Subsequently animals carrying the ERACR, which allows the expression of the effector gene, can be released. When an ERACR encounters an MCR, the transposase encoded by the MCR can mobilize transposition of the effector cassette carried between the transposon ends. Because the ERACR also deletes the MCR, transposition can take place for one generation, thereby creating a singular burst of transposon mobilization peaking at the point where the frequencies of the ERACR and MCR are equal. While this idealized scenario makes several assumptions, such as a higher relative rate of transposition versus deletion of the transposon, in principle, it can increase the copy number of effector cassettes in the genome. In addition, transposon insertions can sample new loci for effective transgene expression, while deleterious insertions can be eliminated by natural selection.

Trans-Complementing MCR Drives Offer Advantages Over Single-Unit Elements

Another variation on the theme of endonuclease (e.g., Cas9) drives, which offers potential husbandry advantages, is to have two separate trans-complementing drives for the cas9<cas9> and gRNAs <gRNA$_1$; gRNA$_2$> wherein gRNA$_1$ directs cleavage at the site of cas9 genomic insertion while gRNA$_2$ cuts at the integration site of the <gRNA$_1$; gRNA$_2$> element (FIG. 29E). Since neither of the two constructs alone constitutes a drive, each single element can be propagated safely as a separate stock. When the two stocks are crossed (possibly after amplification of each of the stocks for release purposes) to test (or release) a full drive can result. In progeny of this cross the resulting <cas9>; <gRNA$_1$; gRNA$_2$> can combine to create a drive that can behave thereafter as a linked <cas9; gRNA> MCR. One additional advantage of such trans-complementing MCR drives is that each of the two constructs can carry the same or different effector cassette, resulting in the former case to expression of four copies of a cassette, thereby doubling the levels of transgene expression as compared to that provided by a single cis-linked <cas9; gRNA> MCR element.

Modeling CRISPR Drives

Introduction of a few MCR-bearing individuals into a wild-type population can initially result in doubling of the frequency the MCR allele at each generation (FIG. 29F). However, as this process continues, MCR individuals can begin mating with others carrying the allele, and the rate of increase can decline following a logistical growth curve. For an initial seeding frequency ($c_0$)=1%, an ideal MCR (100% allele conversion) can spread through a population in only 10 generations, increasing from 10% to 90% in just over four generations (FIG. 29G,H). Idealized ERACR elements can spread in exactly the same fashion within a uniform population of MCR bearing organisms, resulting in concomitant reduction and elimination of the MCR (FIG. 29C).

Genomically encoded split cas9; <gRNA> configurations can also create a gene drive by virtue of the fact that the cas9 encoding gene cannot segregate away from the <gRNA>, assuming the gRNA is faithfully copied to the other allele 100% of the time (FIG. 29F). However, the reciprocal event can take place 50% of the time (i.e., one of the two <gRNA> copies can by necessity segregate from the cas9 source). The enforced association of cas9 with one copy of the <gRNA> results in a constant production of new <gRNA> alleles at each generation. Such a copy-cat system can be referred to as an "allelic pump", since it pumps out a constant percentage of new alleles at each generation. For this scenario, an initial seeding at 1% can require more than 100 generations for mutant cas9/<gRNA> alleles to introgress completely into a population (FIG. 29G). If seeded at 10%, however, it can spread to ≈65% of the population in 10 generations (as compared to ≈4 generations for an MCR to spread through 90% of the population) (FIG. 29H). Thus, at high seeding frequencies allelic pumps can spread significantly through a population if unopposed by any form of negative selection.

Even standard non-driving forms of genomically-encoded of Cas9 and gRNAs can result in a very weak mutational drive because each time the two elements encounter each other by random assortment, a new allele can be generated at the gRNA cut site. For initial seeding values $c_0=g_0=1\%$, this can amount to adding only 0.01% alleles/generation. However, if seeded at $c_0=g_0=10\%$ it can produce a drive of identical strength to an allelic pump seeded at $c_0=g_0=1\%$ (compare curve in FIG. 29G with curve in FIG. 29H). Thus, it may make sense to consider coupled allelic pumps in the same general category as standard CRISPR mutagenesis configurations because they differ only in the effective seeding frequency, which is a quantitative not qualitative distinction. In contrast, MCRs or trans-complementing MCRs represent an entirely different category.

Potential Applications of "Active Genetics" to Human Gene Therapy

The examples of active genetics or gene drives discussed herein involve the spread of an MCR construct to offspring via the germline. The dissemination of MCR constructs can also be achieved between cells within an individual by coupling these elements to a viral delivery system. In such cases, the somatic spread of an MCR element can be exploited by targeting its insertion into such unique sequences. This approach can be used to fight any disease that results in specific alterations in genome sequence. Two such examples include using MCRs to target the HIV reservoir pool and selectively targeting cancer cells marked by distinguishing DNA sequence signatures.

An MCR Strategy can be Used to Target the HIV Reservoir

Figure 30A:
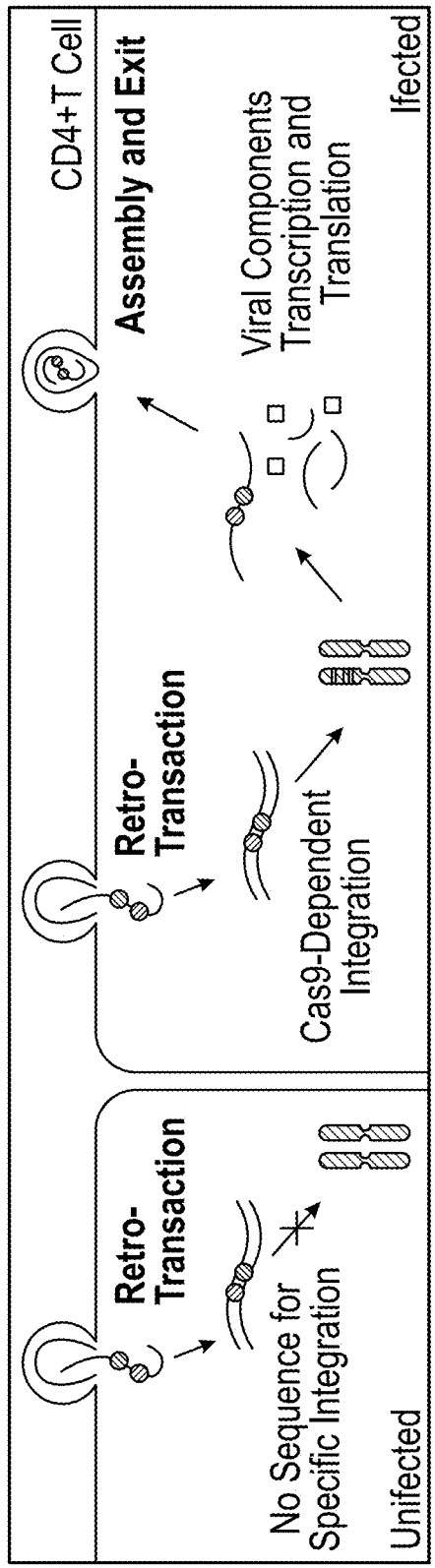
FIGS. 30A-30B describe some exemplary applications of MCR technology to gene therapy.

Retroviruses such as HIV insert into the host genome. An MCR element can be engineered that directs its insertion into the HIV Integrase gene and replaces its function with CRISPR/Cas9-mediated insertion (FIG. 30A). If a construct of this kind were designed such that the Cas9 and gRNAs can be packaged within HIV viral particles, then the virus can infect CD4+ cells, but only integrate into those carrying an HIV provirus in the genome. Virus produced by such targeted MCR elements can then replicate and spread to other helper T-cells, but would only integrate into those with a proviral insertion. This process can continue until cells carrying the provirus in their genome were neutralized. HIV reservoir cells are thought to be quiescent while HDR-mediated allelic conversion most likely requires DNA replication. However, there are methods for inducing reservoir cells to re-enter the cell cycle, which then may allow the conceptual chain of events described above to proceed. MCR mediated allelic conversion may be significantly less efficient in somatic cells than in the germline. NHEJ generated alleles once generated often destroy the gRNA target site thereby precluding subsequent HDR-mediated gene conversion. Nonetheless, NHEJ generated mutations in an integrase gene can at least neutralize that particular proviral element. Efficient propagation of such viruses, however, may require development of methods to increase HDR-mediated gene copying such as suppression of NHEJ via silencing of key pathway components (e.g., Ku70-RNAi) or the use of alternative Cas9-related enzymes such as the recently characterized Cpf1, which cuts at a distance from its DNA recognition sequence thereby potentially permitting iterative rounds of NHEJ mutagenesis without destroying the gRNA-recognition sequence required for HDR.

Figure 30B:
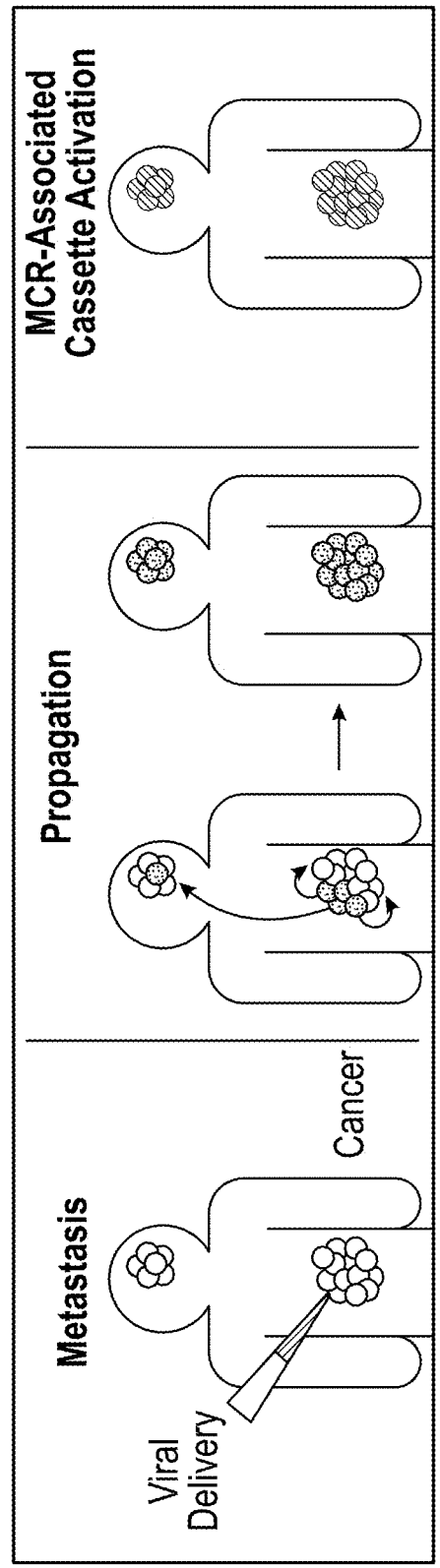

FIGS. 30A-30B describe some exemplary applications of MCR technology to gene therapy. MCR-based spread of an Integrase-deficient Cas9/gRNA-dependent retroviral (e.g., HIV) construct directing its insertion into a chromosomal inserted provirus thereby rendering that proviral element inactive (e.g., reference) (FIG. 30A). Induction and maturation of such targeted proviruses can lead to the production of assembled viruses which can then infect other CD4+ helper T-cells but only integrates into the genomes of cells carrying proviral insertions. This within-organism spread of the MCR construct can eventually incapacitate proviruses leading to the eventual clearance of the HIV infection.

MCR Vectors Might Selectively Target Cancer Cells

MCRs designed to spread between cells in the body might also be developed that target nucleotide differences between the cancer cell and normal cells, which can now be rapidly detected by deep sequencing. While this approach may not be feasible for all types of cancer, those in which cancer-cell specific sequences can be identified, (e.g., chromosomal rearrangements) can be targeted by a construct comprising a cancer-specific guide polynucleotide (e.g., gRNA) carried by an MCR packaged in an Integrase-deficient retrovirus or adenovirus. Such an MCR-viral construct can infect both normal and cancer cells in the patient, but can only insert into the genome of cancer cells (FIG. 30B). If such an element were engineered to replicate and spread from cell-to-cell, an initial infection of only a small subset of cancer cells can result in spread of the MCR-virus until the great majority of cancer cells contained the construct even if the primary tumor had metastasized. Once MCR-viral delivery had become widespread among cancer cells, drug-inducible effectors (e.g., toxins, agents triggering apoptosis, or cellular antigens flagging cells for immune recognition) carried by the MCR can be activated. Again, as mentioned above, for these types of applications it may first be necessary to develop methods to increase the frequency of HDR-mediated gene copying in somatic cells. For such applications, it can also be important to use various means (e.g., careful gRNA target selection or nickase forms of Cas9) to reduce off-target effects to the lowest possible levels to avoid unintended secondary consequences of the therapy, particularly when the strategy is not to kill targeted cells.

A retro-virally propagated MCR element directs its insertion into a cancer-specific genomic sequence (FIG. 30B). Infection and spread of this element throughout the body can lead to its selective insertion in cancer cells (in primary and metastatic tumors). When testing of patient cells indicates that the MCR has spread effectively to cancer cells, an effector cassette carried by the MCR can be activated (e.g., by a hormone) to induce apoptosis or flag cells for destruction by the immune system.

Active genetic holds enormous promise to improving human welfare by accelerating research, combating disease, restoring the environment, and improving agriculture.

Many applications of active genetic methods can employ various split cas9; <gRNA> copy-cat systems. These elements can be used for a broad variety of purposes such as: a novel system for transgenesis, inducing and combining mutations to test for cumulative or interacting effects, or assembling complex arrays of transgenes and traditional Mendelian alleles. Also, full MCR-related elements can serve as potent drive systems to disseminate effector transgenes through populations to combat insect-borne diseases or invasive species, and potentially allowing dispersal of gene therapy vectors throughout the human body targeting them to diseased cells.

Combining components from distinct CRISPR systems and other existing tools (e.g., transposons, φ31C, FLP/FRT, CRE/LOX, GAL4/UAS, LexA, Q-systems, and the wealth of such compounded tools in *Drosophila*) can stimulate a flurry of innovation in genome engineering. Fusion of genome engineering with synthetic biology can allow transplantation or replacement of large chromosome segments from one organism into another.

The term "active genetics" can refer to genetic manipulations in which a genetic element is copied from one chromosome to the identical insertion site on the sister chromosome using endonuclease (e.g., Cas9) and guide polynucleotide (e.g., gRNA) elements (e.g., MCRs or split cas9; <gRNA> drives).

The term "mutagenic Chain Reaction" or "MCR" can refer to a method by which a cassette encoding an endonuclease (e.g., Cas9) and a guide polynucleotide (e.g., gRNA) is inserted precisely into the guide polynucleotide (e.g., gRNA) cut site.

The term "MCR construct" can refer to a DNA construct including an endonuclease/guide polynucleotide (e.g., Cas9/gRNA) cassette flanked by homology arms that precisely abut the guide polynucleotide (e.g., gRNA) cut site. A shorthand for a given MCR can be denoted <cas9; gRNA> wherein the brackets denote the flanking homology arms.

The term "element for Reversing the Autocatalytic Chain Reaction" or "ERACR" can refer to a DNA construct comprising two guide polynucleotides (e.g., gRNAs) that cut genomic sequences flanking an MCR element. The guide polynucleotide (e.g., gRNA) construct can be flanked by chromosomal homology arms that respectively abut the two guide polynucleotide (e.g., gRNA) cut sites. An important feature of the ERACR can be that is does not carry a source of Cas9. When a stock carrying an ERACR is crossed to one carrying the targeted MCR, the Cas9 provided by the MCR results in the ERACR deleting the MCR and copying itself in place of the MCR. An ERACR can be denoted as <gRNA1; gRNA2> wherein gRNA1 cuts on one side of the MCR and gRNA2 cuts on the other side.

The term "Construct for Hitchhiking on the Autocatalytic Chain Reaction" or "CHACR" can refer to a DNA construct similar to an ERACR in that it carries guide polynucleotides (e.g., gRNAs) flanked by precisely abutting homology arms. It can differ from an ERACR in that the guide polynucleotides (e.g., gRNAs) target insertion (e.g., a single gRNA) or insertion/deletion (e.g., two gRNAs) into a genomic site distinct from that of the MCR. In addition, CHACRs can carry gRNAs that drive edited genetic changes at a given genomic site or target loci for mutagenesis by NHEJ.

The term "split cas9; <gRNA>" can refer to a configuration in which a cas9 transgene inherited in a standard Mendelian fashion is combined with a gRNA flanked by homology arms (denoted as <gRNA>). In this situation, only the <gRNA> element is actively copied to the other chromosome.

The term "allelic pump" can refer to a configuration resulting from the combination of a traditional Mendelian source of an endonuclease (e.g., cas9) and a <gRNA> that results in the production of a constant new number of <gRNA> alleles at each generation.

The term "copy-cat" or "cc" cloning vectors can refer to plasmid cloning vectors that in addition to having standard features (e.g., origin of replication, antibiotic resistance genes, multiple cloning sites) also carry a guide polynucleotide (e.g., gRNA) flanked by homology arms that direct insertion of the element into defined locations. Transgenes inserted into cc vectors can be readily rendered homozygous by providing a source of endonuclease (e.g., cas9) in trans.

The term "genetic drive" can refer to an allele of a diploid gene that experiences genetic drive if it is inherited more than 50% of the time (e.g., more than by random chance alone).

The term "effector gene cassette" can refer to a transgene encoding a protein that when expressed exerts a desired effect (e.g., anti-malarial peptides expressed following a blood meal in mosquitoes or a drug inducible cell lethal gene in a cancer cell).

As used herein, the term "about" when referring to a number or a numerical range means that the number or numerical range referred to is an approximation within experimental variability (or within statistical experimental error), and thus the number or numerical range may vary from, for example, between 1% and 15% of the stated number or numerical range. In examples, the term "about" refers to ±10% of a stated number or value.

The terms "polynucleotide", "nucleotide", "nucleotide sequence", "nucleic acid", and "oligonucleotide" are used interchangeably. They refer to a polymeric form of nucleotides of any length, including deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, expression vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a detectable label.

"Expression" refers to the process by which a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide", and "protein" are used interchangeably herein to refer to polymers of amino acids of any length. The polymer may be linear or branched, may comprise modified amino acids, and may be interrupted by non amino acids. The terms also encompass an amino acid polymer that has been modified, for example, by disulfide bond formation, glycosylation, lipidation, acetylation, phosphorylation, or any other manipulation, such as conjugation with a detectable label.

As used herein the term "amino acid" includes natural and/or unnatural or synthetic amino acids, including glycine, cysteine, and both the D or L optical isomers, and amino acid analogs and peptidomimetics. In some embodiments, an amino acid is a proteinogenic, natural, standard, non-standard, non-canonical, essential, non-essential, or non-natural amino acid. In some embodiments, an amino acid has a positively charged side chain, a negatively charged side chain, a polar uncharged side chain, a non-polar side chain, a hydrophobic side chain, a hydrophilic side chain, an aliphatic side chain, an aromatic side chain, a cyclic side chain, an acyclic side chain, a basic side chain, or an acidic side chain. In some embodiments, an amino acid has a nucleophilic or electrophilic side chain.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 96%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

A polynucleotide described herein can be obtained using chemical synthesis, molecular cloning or recombinant methods, DNA or gene assembly methods, artificial gene synthesis, PCR, or any combination thereof. Methods of chemical polynucleotide synthesis are well known in the art and need not be described in detail herein. One of skill in the art can use the sequences provided herein and a commercial DNA synthesizer to produce a desired DNA sequence. For preparing polynucleotides using recombinant methods, a polynucleotide comprising a desired sequence can be inserted into a suitable cloning or expression vector, and the cloning or expression vector in turn can be introduced into a suitable host cell for replication and amplification, as further discussed herein. Polynucleotides may be inserted into host cells by any means known in the art. Cells may be transformed by introducing an exogenous polynucleotide, for example, by direct uptake, endocytosis, transfection, F-mating, PEG-mediated protoplast fusion, Agrobacterium tumefaciens-mediated transformation, biolistic transformation, chemical transformation, or electroporation. Once introduced, the exogenous polynucleotide can be maintained within the cell as a non-integrated expression vector (such as a plasmid) or integrated into the host cell genome. The polynucleotide so amplified can be isolated from the host cell by methods well known within the art. Alternatively, nucleic acid amplification methods (e.g., PCR) allow reproduction of DNA sequences.

RNA can be obtained by using the isolated DNA in an appropriate expression vector and inserting it into a suitable host cell (e.g., through transfection or genomic integration). When the DNA is transcribed into RNA, the RNA can be used or isolated using methods well known to those of skill in the art. Alternatively, RNA can be obtained by transcribing the isolated DNA, for example, by an in vitro transcription reaction using an RNA polymerase. Alternatively, RNA can be obtained using chemical synthesis.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the expression vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

A polynucleotide may be located in an expression vector. A nucleic acid cargo sequence may be located in an expression vector. A donor cargo vector, MCR construct, ERACR construct, CHACR construct, e-CHACR construct, or CopyCat construct or vector may be an expression vector. An expression vector may be a construct, which is capable of delivering, and preferably expressing, one or more gene(s) or sequence(s) of interest in a host cell. Examples of expression vectors include, but are not limited to, viral vectors (e.g., adenoviruses, adeno-associated viruses, and retroviruses), naked DNA or RNA expression vectors, plasmids, cosmids, phage vectors, DNA or RNA expression vectors associated with cationic condensing agents, DNA or RNA expression vectors encapsulated in liposomes, and certain eukaryotic cells, such as producer cells. An expression vector may allow easy and efficient replication, cloning, and/or selection. An expression vector, nucleic acid target sequence, donor cargo vector, MCR construct or element, ERACR construct or element, CHACR construct or element, e-CHACR construct or element, or CopyCat element, construct, or vector may additionally include nucleic acid sequences that permit it to replicate in the host cell (e.g., an origin of replication), one or more therapeutic genes and/or selectable marker genes, or other genetic elements known in the art such as regulatory elements directing transcription, translation and/or secretion of the encoded protein. Components of an expression vector, donor cargo vector, MCR construct, ERACR construct, CHACR construct, e-CHACR construct, or CopyCat construct or vector may include, but are not limited to, one or more of the following: a signal sequence; an origin of replication; one or more marker genes; and suitable transcriptional controlling elements (such as promoters, enhancers and terminator). For expression (e.g., translation), one or more translational controlling elements are also usually required, such as ribosome binding sites, translation initiation sites, internal ribosome entry site, and stop codons. The expression vector may be used to transduce, transform or infect a cell, thereby causing the cell to express nucleic acids and/or proteins other than those native to the cell. The expression vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such expression vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining cloning and expression vectors are well-known (see, e.g., Green and Sambrook, Molecular Cloning: A Laboratory Manual, 4th edition, Cold Spring Harbor Laboratory Press, New York (2012)).

An expression vector, nucleic acid target sequence, donor cargo vector, MCR construct or element, ERACR construct or element, CHACR construct or element, e-CHACR construct or element, or CopyCat element, construct, or vector may further comprise a promoter. Promoters include, but are not limited to, a constitutive promoter, inducible promoter, and hybrid promoter. Promoters include, but are not limited to, acu-5, adh1+, alcohol dehydrogenase (ADH1, ADH2, ADH4), AHSB4m, AINV, alcA, α-amylase, alternative oxidase (AOD), alcohol oxidase I (AOX1), alcohol oxidase 2 (AOX2), AXDH, B2, CaMV, cellobiohydrolase I (cbh1), ccg-1, cDNA1, cellular filament polypeptide (cfp), cpc-2, ctr4+, CUP1, dihydroxyacetone synthase (DAS), enolase (ENO, ENO1), formaldehyde dehydrogenase (FLD1), FMD, formate dehydrogenase (FMDH), G1, G6, GAA, GAL1, GAL2, GAL3, GAL4, GAL5, GAL6, GAL7, GAL8, GAL9, GAL10, GCW14, gdhA, gla-1, α-glucoamylase (glaA), glyceraldehyde-3-phosphate dehydrogenase (gpdA, GAP, GAPDH), phosphoglycerate mutase (GPM1), glycerol kinase (GUT1), HSP82, inv1+, isocitrate lyase (ICL1), acetohydroxy acid isomeroreductase (ILV5), KAR2, KEX2, β-galactosidase (lac4), LEU2, melO, MET3, methanol oxidase (MOX), nmt1, NSP, pcbC, PET9, peroxin 8 (PEX8), phosphoglycerate kinase (PGK, PGK1), pho1, PHO5, PHO89, phosphatidylinositol synthase (PIS1), PYK1, pyruvate kinase (pki1), RPS7, sorbitol dehydrogenase (SDH), 3-phosphoserine aminotransferase (SER1), SSA4, SV40, TEF, translation elongation factor 1 alpha (TEF1), THI11, homoserine kinase (THR1), tpi, TPS1, triose phosphate isomerase (TPI1), XRP2, and YPT1.

An expression vector, nucleic acid target sequence, donor cargo vector, MCR construct or element, ERACR construct or element, CHACR construct or element, e-CHACR construct or element, or CopyCat element, construct, or vector may further comprise an auxotrophic marker (e.g., ade1, arg4, his4, ura3, met2). An expression vector, nucleic acid target sequence, donor cargo vector, MCR construct or element, ERACR construct or element, CHACR construct or element, e-CHACR construct or element, or CopyCat element, construct, or vector may further comprise a selectable marker (e.g., a resistance gene). In some cases, a resistance gene may confer resistance to zeocin, ampicillin, blasticidin, kanamycin, nurseothricin, chloroamphenicol, tetracycline, triclosan, or ganciclovir. An expression vector, donor cargo vector, MCR construct, ERACR construct, CHACR construct, e-CHACR construct, or CopyCat construct or vector may comprise a plasmid.

DNA cuts generated by an endonuclease such as Cas9 can be corrected using different cellular repair mechanisms, including: error-prone Non-homologous End Joining ("NHEJ") and/or Homology Directed Repair ("HDR"). In some embodiments, a nucleic acid cargo sequence, MCR element, ERACR element, CHACR element, e-CHACR element, or CopyCat element is integrated into a genome using HDR.

In general, traditional CRISPR applications use NHEJ (which has about 5-20% efficiency). TETHR, an Oligo-Clamp, MCR, ERACR, CHACR, e-CHACR, or CopyCat can use HDR (which has about 90-100% efficiency). The broader term active genetics can apply to the use of any construct in which a Cas9 source drives the insertion of a DNA cassette into a particular locus using a gRNA encoded within that cassette. MCR, ERACR, CHACR, e-CHACR, and CopyCat elements are examples of active genetic elements. Active genetic-based applications are more efficient than traditional CRISPR in generating precise genome edits. In some embodiments, the efficiency of a nucleic acid cargo sequence, MCR element, ERACR element, CHACR element, e-CHACR element, or CopyCat element integrating into a genome is about or at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some embodiments, the efficiency of a nucleic acid cargo sequence, MCR element, ERACR element, CHACR element, e-CHACR element, or CopyCat element integrating into a genome is up to about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100%. In some embodiments, the efficiency of allelic conversion of a nucleic acid cargo sequence, MCR element, ERACR element, CHACR element, e-CHACR element, or CopyCat element into a genome is about or at least about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%. In some embodiments, the efficiency of allelic conversion of a nucleic acid cargo sequence, MCR element, ERACR element, CHACR element, e-CHACR element, or CopyCat element into a genome is up to about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or 100%.

TETHR, an Oligo-Clamp, MCR, ERACR, CHACR, e-CHACR, or CopyCat may be used to copy DNA fragments of varying size. In some embodiments, a nucleic acid cargo sequence, MCR, ERACR, CHACR, or e-CHACR may be used to copy large DNA fragments, for example, DNA fragments of about 10 kb in length, or DNA fragments of about 17 kb in length. The nucleic acid cargo sequence, TETHR, an Oligo-Clamp, MCR, ERACR, CHACR, or e-CHACR allows for flexibility in size of DNA of such when engineering applications from environmental pathogens, to plants, to human therapies. In some embodiments, the nucleic acid cargo sequence, MCR element, ERACR element, CHACR element, e-CHACR element, or CopyCat element integrated into a genome is about or at least about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, or more than 50 kilobases (kb) in length. In some embodiments, the nucleic acid cargo sequence, MCR element, ERACR element, CHACR element, e-CHACR element, or CopyCat element integrated into a genome is up to about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, or more than 50 kilobases (kb) in length. In one non-limiting example, recent experiments have shown that a ~17 kb MCR propagates via the germline in male and female mosquitoes (*Anopheles stephensi*) with 99.5% transmission efficiency. In addition, this MCR carries an effector gene cassette previously shown to block the propagation of the malarial parasite *Plasmodium falciparum*. This gene cassette is inducible by a female mosquito feeding on a blood meal and this induction is also observed for the gene cassette carried by the MCR. See Gantz V, Jasinskiene N, Tatarenkova O, Fazekas A, Macias V M, Bier E, James A A. Highly efficient Cas9-mediated gene drive for population modification of the malaria vector mosquito, Anohpeles stepensi. Proc Natl Acad Sci 2015; In Press, incorporated herein by reference.

MCR elements may nearly double their frequency in a population at each generation, as they may convert chromosomes derived from non-MCR parents to the MCR condition. This results in potent gene drive systems for spreading beneficial genes or exogenous DNA fragments through a population of an organism (e.g., insects that can be as vectors for human disease or insects that are agricultural pests). The same autocatalytic property can be engineered to spread effector transgenes among specific cell populations within an individual (e.g., cancerous cells). This property enables new gene therapy approaches. In some embodiments, the frequency of a nucleic acid cargo sequence, MCR element, ERACR element, CHACR element, e-CHACR element, or CopyCat element increases in a population in a generation by a factor of about or at least about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, or more than 3. In some embodiments, the frequency of a nucleic acid cargo sequence, MCR element, ERACR element, CHACR element, e-CHACR element, or CopyCat element increases in a population in a generation by a factor of up to about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, or more than 3.

Nucleases are enzymes that cleave the phosphodiester bond within a polynucleotide chain. Endonucleases include, but are not limited to, Cas proteins, RNA-guided endonucleases (e.g., Cpf1), restriction endonucleases, meganucleases, homing endonucleases, TAL effector nucleases, and Zinc finger nucleases. Endonucleases include, but are not limited to, Type I, Type II, Type III, Type IV, and Type V endonucleases, any one of which may further include subtypes. Cas proteins include, but are not limited to, Cas1, Cas1B, Cas2, Cas3, Cas3' (Cas3-prime), Cas3" (Cas3-double prime), Cas4, Cas5, Cas6, Cas6e (formerly referred to as CasE, Cse3), Cas6f (i.e., Csy4), Cas7, Cas8, Cas8a1, Cas8a2, Cas8b, Cas8c, Cas9 (also known as Csn1 and Csx12), Cas10, Cas10d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, and modified versions thereof. One skilled in the art could choose a nuclease based on various factors, including size, stability, ability to bind to a guide nucleic acid, ability to recognize a target sequence, etc. In some embodiments, the nuclease may be further optimized (e.g., to have a longer half-life, to be codon-optimized for the organism, to further comprise a nuclear localization signal, etc.). In some embodiments, the nuclease can be fused to other functional groups, for example a GFP domain, to visualize the protein.

In some embodiments, the nuclease may be Cas9. In some embodiments, the nuclease may be a Cas9 cloned or derived from a bacteria (e.g., *S. pyogenes, S. pneumoniae, S. aureus,* or *S. thermophilus*). One skilled in the art can recognize there are many Cas9 nucleases derived from bacteria. One skilled in the art could choose a Cas9 nuclease based on various factors, including size, stability, ability to bind to a guide nucleic acid, ability to recognize a protospacer adjacent motif (i.e., PAM) etc. In some embodiments, the Cas9 nuclease may be further optimized (e.g., to have a longer half-life, to be codon-optimized for the organism, to further comprise a nuclear localization signal, etc.). In some embodiments, the Cas9 nuclease can be fused to other functional groups, for example a GFP domain, to visualize the protein.

In some embodiments, a donor cargo vector, nucleic acid cargo sequence, MCR construct or element, ERACR construct or element, CHACR construct or element, e-CHACR construct or element, or CopyCat element, construct, or vector comprises about or at least about 1, 2, 3, 4, 5, 6, 7, 8, 9, 10, 15, 20, 25, 30, 35, 40, 45, 50, or more than 50 guide polynucleotides. In some embodiments, a donor cargo vector, nucleic acid cargo sequence, MCR construct or element, ERACR construct or element, CHACR construct or element, e-CHACR construct or element, or CopyCat element, construct, or vector comprises up to about 1, 2, 3, 4, 5, 6, 7, 8, 9, 10, 15, 20, 25, 30, 35, 40, 45, 50, or more than 50 guide polynucleotides.

In some embodiments, a CHACR or e-CHACR element comprises a sequence encoding one guide polynucleotide directing cleavage on both sides or a gene encoding an endonuclease or an MCR element or a sequence encoding two guide polynucleotides directing cleavage on either side of a gene encoding an endonuclease or an MCR element. In some embodiments, the guide polynucleotides direct cleavage at sites flanking the gene encoding an endonuclease or the MCR element.

In some embodiments, a cleavage site directed by a guide polynucleotide is about or at least about 100 bp, 200 bp, 300 bp, 400 bp, 500 bp, 600 bp, 700 bp, 800 bp, 900 bp, 1 kb, or 1.5 kb away from a gene encoding an endonuclease or an MCR element. In some embodiments, the cleavage site distance is chosen to prevent resection-mediated copying of potential guide polynucleotide-resistant NHEJ alleles that can be generated at a low frequency and can be copied with the gene encoding an endonuclease or the MCR element if located in close proximity.

A homology arm may be about or at least about 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 600, 700, 800, 900, 1000, 1100, 1200, 1300, 1400, or 1500 nucleotides in length. In some embodiments, homology arms on a donor cargo vector, MCR construct, ERACR construct, CHACR construct, e-CHACR construct, CopyCat construct or vector, or any vector or construct described herein are the same length, similar lengths, or different lengths. In some embodiments, the degree of complementarity between a homology arm and its corresponding target sequence, when optimally aligned using a suitable alignment algorithm, is about or at least about 50%, 55%, 60%, 65%, 70%, 75%, 80%, 85%, 90%, 95%, 96%, 97%, 98%, 99%, 99.5%, 99.9%, or 100%. In some instances, the homology arms directly abut the endonuclease cleavage sites. In some embodiments of any one of the methods, vectors, or constructs described herein, the homology arms directly abut the endonuclease cut site(s) determined by the at least one guide polynucleotide, or are separated by up to 100, 75, 50, 40, 30, 20, 10, 9, 8, 7, 6, 5, 4, 3, 2, or 1 nucleotides.

In some embodiments, an e-CHACR element comprises:
(a) a sequence encoding a first guide polynucleotide directing cleavage within the gene encoding an endonuclease; and
(b) a second guide polynucleotide directing cleavage outside the gene encoding an endonuclease.

In some embodiments, an e-CHACR construct comprises:
(a) an e-CHACR element; and
(b) homology arms flanking the sequence that directly abut an endonuclease cut site determined by a guide polynucleotide (e.g., second guide polynucleotide).

In some embodiments, an MCR element comprises:
(a) a sequence encoding a guide polynucleotide that is genomically integrated in a cell or organism; and
(b) a gene encoding an endonuclease.

In some embodiments, an MCR element comprises:
(a) a genomically integrated sequence encoding a guide polynucleotide; and
(b) a gene encoding an endonuclease.

In some embodiments, an MCR construct comprises:
(a) an MCR element; and
(b) homology arms flanking the sequence that directly abut an endonuclease cut site determined by a guide polynucleotide.

In some embodiments, an MCR element comprises:
(a) a gene encoding an endonuclease,
(b) at least one sequence encoding at least one guide polynucleotide, and
(c) an effector cassette.

In some embodiments, an MCR construct comprises:
(a) an MCR element; and
(b) homology arms flanking the MCR element, wherein the homology arms directly abut an endonuclease cut site(s) determined by at least one guide polynucleotide.

In some embodiments, a CopyCat element comprises:
(a) at least one sequence encoding at least one guide polynucleotide, and
(b) an effector cassette.

In some embodiments, a CopyCat element is introduced by a CopyCat construct, wherein the CopyCat construct comprises:
(a) the CopyCat element;
(b) homology arms flanking the CopyCat element, wherein the homology arms directly abut the endonuclease cut site(s) determined by the at least one guide polynucleotide;
(c) a multiple cloning site;
(d) a selectable marker;
(e) a bacterial origin of replication; and
(f) a gene conferring antibiotic resistance.

Methods of the disclosure can be targeted to any locus in a genome. They can generate null or tissue-specific mutations in a target.

Methods and compositions of the disclosure can be used to spread genotypic or phenotypic in offspring via the germline. The dissemination of constructs can also be achieved between cells within an individual by coupling these elements to a viral delivery system. In such cases, the somatic spread of a genetic element can be exploited by targeting its insertion into such unique sequences. In principle, this approach can be used to fight any disease that results in specific alterations in genome sequence.

Methods of the disclosure can be used for a broad variety of purposes such as designing novel system for transgenesis, inducing mutations that can be rapidly combined to test for cumulative or interacting effects, assembling complex arrays of transgenes and traditional Mendelian alleles, combinatorial testing of allelic variants contributing to complex traits, generating potent drive systems to disseminate effector transgenes through populations to combat insect-borne diseases and invasive species, and dispersal of gene therapy vectors throughout the human body targeting them to diseased cells.

In some embodiments, the methods of the disclosure are used for custom design of new chimeric organisms with traits combined from different species or de novo characteristics designed from first principles.

Large scale genome engineering methods described herein can be used to replace, delete, insert, or modify contiguous or discontinuous segments of a genome. The size of the segments can be about 100, 200, 300, 400, 500, 600, 700, 800, 900, 1000, or more kilobases.

A cell has been "genetically modified" or "transformed" or "transfected" by exogenous DNA, e.g., a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication.

Methods of introducing a nucleic acid into a host cell are known in the art, and any known method can be used to introduce a nucleic acid (e.g., an expression construct) into a cell. Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, direct micro injection, nanoparticle-mediated nucleic acid delivery (see, e.g., Panyam et. al Adv Drug Deliv Rev. 2012 Sep. 13. pii: S0169-409X(12)00283-9. doi: 10.1016/j.addr.2012.09.023), and the like.

MCR constructs may be used to disperse (or drive) transgenes into animal or plant pest populations to combat propagation of insect borne pathogens or diseases (e.g., Malaria), to selectively inhibit propagation of insect pests in crop fields, or to help control weeds (FIG. 29B). An MCR construct supplied to somatic cells within an individual via a replicating vector (e.g., a virus) could insert into diseased cells carrying specific sequences (e.g., retroviral insertions or cancer cell specific mutations) and then spread to other cells within that organism (FIG. 30). Such constructs by virtue of carrying effector cassettes could then be engineered to combat the disease by killing the diseased cells (e.g., by inducing production of a toxin or a cell surface molecule to alert the host immune system) or by altering them in some other way (e.g., by repairing a gene or restoring a necessary cellular function). In addition, MCR elements may be used for gene therapy purposes to either fix mutant genes or eliminate gene functions contributing to a disease state.

Other applications involve getting the mutation to spread within cells of a single individual afflicted with a disease such as HIV or cancer. The disclosure targets insertion of the construct into DNA sequences that are specific to diseased cells and then carry some type of cassette that could kill, fix, or reprogram the diseased cells.

In some embodiments, methods of the disclosure are used to treat a disease or disorder. In some embodiments, the disease is cancer.

Targeting microorganisms. An MCR element may direct its insertion into one or more genes of a microorganism, for example, to treat an disease or illness, decrease pathogenicity, decrease virulence, decrease or reverse resistance to an antimicrobial (e.g., antibacterial, antifungal, antiviral, antiparasitic), decrease colonization, decrease transmission, decrease persistence, decrease replication, and/or kill a microorganism. Some non-limiting examples of a microorganism or microbe include bacteria, archaea, protozoa, protists, fungus, algae, virus, retrovirus, pathogen, or parasite. In some cases, the microorganism or microbe is a prokaryote. In some cases, the microorganism or microbe is a eukaryote. Some non-limiting examples of bacteria include *Bacillus, Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Staphyloccus Aures, Streptococcus, Treponema, Vibrio,* and *Yersinia*. Some non-limiting examples of fungi include *Candida, Aspergillus, Cryptococcus, Histoplasma, Pneumocystis,* and *Stachybotrys*. In some instances, the microbe or microorganism detected by the methods provided herein is a drug-resistant microbe or multi-drug resistant pathogen. Non-limiting examples of drug-resistant or multi-drug resistant pathogens include: In some cases, drug-resistant strains of resistant *Neisseria, gonorrhoeae* (cephalosporin resistant), multi-drug-resistant *Acinetobacter*, drug-resistant *Campylobacter*, fluconazole-resistant *Candida* (a fungus), extended spectrum β-lactamase producing Enterobacteriaceae (ESBLs), vancomycin-resistant *Enterococcus* (VRE), multidrug-resistant *Pseudomonas aeruginosa*, drug-resistant non-typhoidal *Salmonella*, drug-resistant *Salmonella Typhi*, drug-resistant *Shigella*, methicillin-resistant *Staphylococcus aureus* (MRSA), drug-resistant *Streptococcus pneumonia*, drug-resistant tuberculosis (MDR and XDR), multi-drug resistant *Staphylococcus aureus*, vancomycin-resistant *Staphylococcus aureus* (VRSA), erythromycin-resistant *Streptococcus* Group A, or clindamycin-resistant *Streptococcus* Group B. Some examples of parasites include those causing malaria (*Plasmodium* sp.), Chagas disease or sleeping sickness (trypanosomes). Some examples of viruses include those causing Dengue fever, chikungunya, and Zika.

Combatting Insect Borne Diseases:

MCR elements can be designed that block disease transmission. In the case of malaria, for example, MCR elements may be designed to carry anti-malarial effector cassettes, which encode factors that may prevent the malarial parasite from completing its life cycle, but may not harm the mosquito and hence may have a neutral effect on the environment. Mosquitoes carrying such a construct may be released into an area where malaria is endemic. Mosquitoes may then mate with indigenous mosquitoes and spread the MCR construct exponentially through the population in as few as 10 generations. This goal may be accomplished in a single season since it is estimated that mosquitoes complete 10-20 reproductive cycles per year. As more mosquitoes in the treated area carry the construct, propagation of malaria should be greatly reduced or eliminated. Similar strategies could be devised to combat other insect borne diseases.

Treating Diseases or Conditions:

MCR elements can be designed that treat diseases or conditions by selectively adding, deleting, or mutating genes. For example, genes that encode immunogenic proteins may be targeted to reduce or eliminate immunogenicity. Allergens in food may be reduced by targeting the genes encoding the allergen in the organism (e.g., peanut, tree nut, cow (or other source of milk), chicken (or other source of egg), wheat, soy, fish, shellfish) from which the food was derived. Specific cells may be targeted, such as beta cells (role in diabetes) or cells and/or genes involved in autoimmune disorders.

Controlling Agriculture Pest Species: Agriculture pests and invasive species cause over $3 billion of damage to crops per year. A nucleic acid cargo sequence, MCR, ERACR, CHACR, e-CHACR, and/or CopyCat targeting one or more genes, for example those required for female fertility or survival, may reduce the damage caused by many of these pests.

For instance, MCRs can suppress crop pests actively attacking a crop of interest or be used for weed control. This strategy closely parallels that illustrated above for combating malaria. For example, the spotted wing fly (*Drosophila suzukii*), which is related to the laboratory fruit fly (*Drosophila melanogaster*), may be targeted. *D. suzukii* entered the U.S. in 2008 and in 2010 was estimated to cause over $500 million of damage to soft fruits (strawberries, other berries, grapes, cherries) in Pacific coast states, amounting to nearly 20% of this $2.5 billion industry. The genome sequence of *D. suzukii* has been determined, and MCR constructs can be generated to test for control and eradication of this invasive pest. Other pests that may also be targeted include, but are not limited to, the Medfly (≈$1.2 billion damage per year), olive fly (can reduce oil production by as much as 80%), pea leaf miner (a fly causing over $1.5 billion of crop damage), and Asian tiger mosquito (a vector for encephalitis, dengue fever, yellow fever and dog heartworm). Pests or weeds that are resistant to pesticides or herbicides (e.g., glyphosate), respectively, may also be targeted by a nucleic acid cargo sequence, MCR, ERACR, CHACR, e-CHACR, and/or CopyCat.

Accelerating Genetic Manipulations and Genome Engineering.

An active MCR drive may provide faster propagation of a genetic trait compared to passive Mendelian inheritance. A set of copycat cloning vectors may be generated to be used for active genetics into which a transgene may be cloned, targeted for genomic insertion at a desired site, and then homozygosed in the presence of an unlinked source of cas9.

Similar methods may be used to generate libraries of model organisms; generate specific strains, breeds, or mutants of a model organism; for one-step mutagenesis schemes to generate scoreable recessive mutant phenotypes in a single generation; facilitate basic genetic manipulations in diverse experimental and agricultural organisms (e.g., accelerating the generation of combinatorial mutants and facilitating mutagenesis in polyploid organisms); accelerate genetic manipulations in animals (e.g., primates) or plants (e.g., trees) with a long generation time; and for gene therapy.

Responsible Use of Active Genetic Systems

Currently available sequence data are consistent with no bacterially-derived CRISPR system having been mobilized horizontally into a plant or animal genome in nature. Thus, constructs such as MCRs that are inherently capable of rapid dispersion throughout naïve wild populations of plant and animal species are unprecedented. While it is clear that many other selfish genetic systems have appeared, driven themselves to fixation, and then responded as all fixed genes do to natural selection, prudence can be employed to insure that Cas9-based drives do not gain access to wild populations of organisms that have never adapted to this system. Recently, a consensus set of interim suggestions was published for safe use of active genetic elements in the laboratory in which researchers are urged to consider the implications of using active genetic elements and to use all reasonable precautions when embarking on their experiments (FIG. 31).

Figure 31:
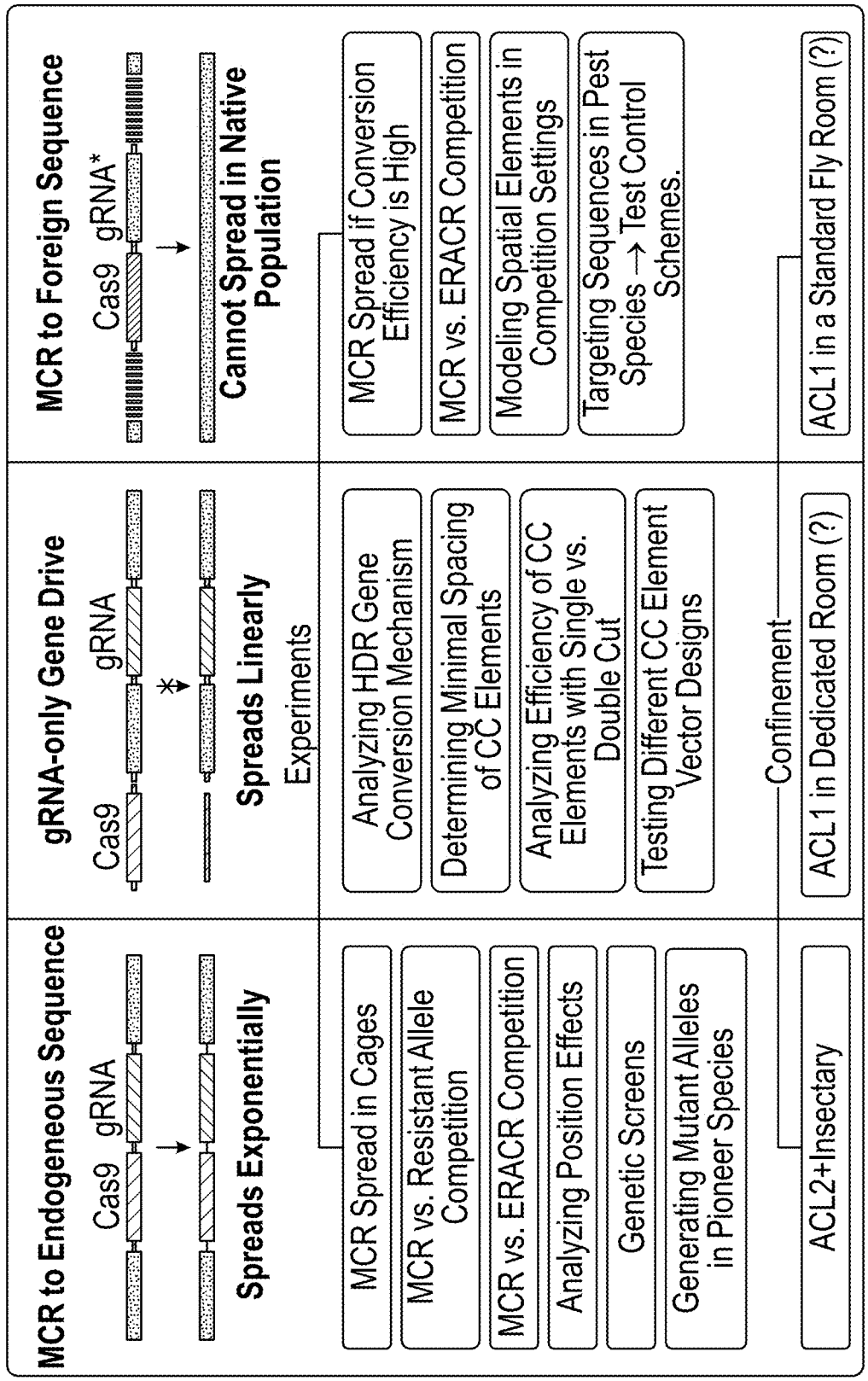
FIG. 31 is a scheme outlining biosafety options for sample experiments for different active genetic elements.

FIG. 31 is a scheme outlining biosafety options for sample experiments for different active genetic elements. Top: Schemes depicting an MCR targeting an endogenous sequence (left), a split cas9; <gRNA> allelic pump (middle), and an MCR targeting an exogenous sequence (right). Bottom: Types of experiments and recommended physical confinement strategies suitable for each type of active element. ACL=Arthropod Containment Levels. ACL1 corresponds to containment of arthropods judged to present a BioSafety Level 1 (BSL1) concern, which applies to standard laboratory organisms (e.g., flies or harmless strains of *E. coli* used for cloning) while ACL2 applies to insect vectors carrying BSL2 rated pathogens (e.g., mosquitoes carrying malarial parasites or tsetse flies carrying trypanosomes). Question marks indicate tentative suggested levels of confinement for the different drive configurations.

EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, make and utilize the compounds of the present disclosure and practice the claimed methods. The following working examples specifically point out various embodiments of the present disclosure, and are not to be construed as limiting in any way the remainder of the disclosure.

Example 1

An MCR construct (y–MCR) targeting the *Drosophila* yellow (y) locus are generated. Transgenic flies carrying this construct are recovered. The y–MCR construct is transmitted via the germline with an efficiency of 97% indicating that, within the germ cell lineage, MCR is highly efficient at converting the second allele to the sequence of the MCR allele. PCR and DNA sequence analysis of flies carrying the y–MCR construct confirm that MCR flies carry the expected precise insertion of the construct at the cleavage site dictated by the guide RNA.

TABLE 1

| F0 progenitor | Sex of F1 | Total F2 offspring | F2 y- ♂ | F2 y+ ♂ | F2 y- ♀ | F2 y+ ♀ | Mosaic ♀ | % ♀ Mosaic | Tot. F2 ♀ | Tot. HDR ♀ | % y-MCR ♀ | HDR germline conversion rate (%) |
|---|---|---|---|---|---|---|---|---|---|---|---|---|
| M3 | f1 | 55 | 30 | 0 | 22 | 0 | 3 | 12 | 25 | 25 | 100 | 100 |
| M3 | f2 | 73 | 39 | 0 | 33 | 0 | 1 | 3 | 34 | 34 | 100 | 100 |
| M3 | f3 | 74 | 35 | 1*‡ | 35 | 2 | 1 | 3 | 38 | 36 | 94.7 | 89 |
| M3 | f4 | 69 | 31 | 1* | 34 | 2 | 1 | 3 | 37 | 35 | 94.6 | 89 |
| M3 | f5 | 66 | 28 | 0 | 33 | 1 | 4 | 11 | 38 | 37 | 97.4 | 95 |
| M3 | f6 | 99 | 51 | 0 | 46 | 1 | 1 | 2 | 48 | 47 | 97.9 | 96 |
| F5 | m1 | 30 | — | 15 | 15 | 0 | 0 | 0 | 15 | 15 | 100 | 100 |
| F5 | m2 | 61 | — | 35 | 25 | 1 | 0 | 0 | 26 | 25 | 96.2 | 92 |
| Total/Ave. | — | 527 | 214 | 52 | 243 | 7 | 11 | 4.2 | 261 | 254 | 97.3 | 94.5 |

Table 1 shows propagation of the y− phenotype among progeny of y−MCR parents. Summary of the genetic transmission of the y− phenotype through two generations carrying the y−MCR construct. Two F0 parents were selected for this analysis, one male (M3) and one female (F5) which when mated to y+ flies gave rise to y− female F1 progeny, and hence were scored as carrying the y−MCR construct. For M3 (who had no male y− F1 progeny as expected), 6 of his 37 y− F1 female progeny (f1-6) were then crossed to y+ males to generate an F2 generation. Female F5 gave rise to 14 y-females and 18 y− males, of which two males (m1, m2) were tested for potential inheritance and propagation of the y−MCR construct by crossing them to y+ females and scoring the F2 generation for the y− phenotype. Female F2 y− progeny were each examined closely for mosaicism. The percent of y−MCR progeny was calculated by dividing the number of y− F2 progeny (including mosaics) by the total number of female progeny. The percent of germline cells that were converted by the MCR construct via HDR (homology directed repair) was estimated in female progeny from F1 crosses by assuming that half would be expected to inherit the MCR element directly by Mendelian segregation and would thus give rise to 100% y− progeny (perhaps with some mosaicism) while the other half would bear a y+ chromosome unless it had been converted in the germline of the F1 parent via HDR. This is likely to be an underestimate of the actual germline conversion rate since some females inheriting the F1 y−MCR allele might not give rise to y− progeny. Indeed, as indicated in the male crosses, where all female progeny would be expected to inherit the MCR construct by simple Mendelian transmission, one y+ female (from m2) was found, suggesting that the y+ allele inherited from the female F1 parent somehow evaded HDR conversion.

Figure 7:
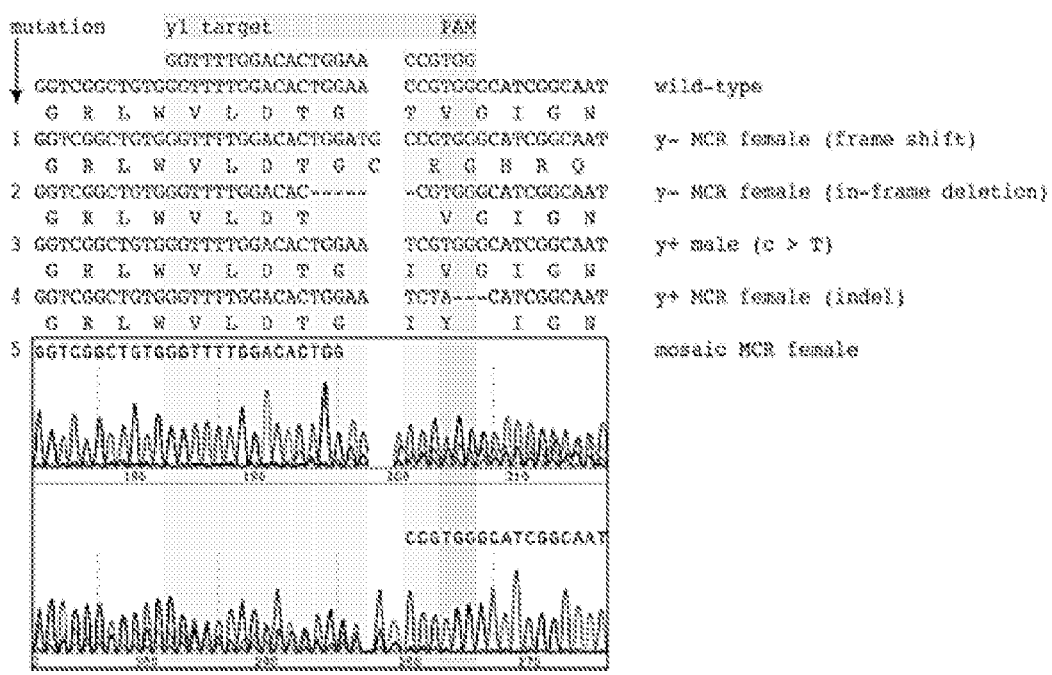
FIG. 7 is an experimental demonstration of MCR in *Drosophila*. Figure discloses SEQ ID NOS 20-32, respectively, in order of appearance.

Two instances were observed in which male progeny inherited y+ alleles from y−MCR carrying females (asterisks). These alleles may either have escaped MCR conversion altogether or perhaps were the result of non-homologous end-joining repair that generated in frame deletions that carry out y gene function but that are protected from further gRNA directed cleavage. The latter embodiment is strongly suggested by the y+ male derived from the female f3, which sequence analysis revealed carries a single nucleotide change at the gRNA cut site within the y locus resulting a T→I substitution. FIG. 7. This guide-resistant allele is not often a rare sequence polymorphism, since if it were, it should have resulted in 50% of the F2 offspring being y+.

The sequence of one of the two y+ females derived from the same MCR parent (f3) was analyzed and a combined in-frame deletion (7 nucleotides) and insertion (4 nucleotides) was identified, the net effect of which is the substitution of three amino acids (TVG) with two residues (IY) FIG. 7. The percent of y− males among total male progeny (2%) is less than that for y+ females (6%) raising the possibility that y+ females consist of both y−(guide-cleaved mutant)/+ and y+(guide-resistant mutant)/+ genotypes. PCR data for entries indicated in bold red text are shown in FIG. 2D. F2 progeny from male m2 (bold blue text) are shown in FIG. 2E. Green text indicates averages of % y−MCR and % HDR germline conversion for all lines tested in this table.

Example 2

Generation of Genetically Engineered T Cells Lacking PD-1 Signaling, Comprising Inducible Expression of a Toxin Under Negative Transcriptional Control of a Tetracycline Promoter and Auxotrophic for Arginine The compositions and methods described herein are useful for generating genetically engineered immune cells. FIG. 6A. In this example, it is understood that the genetic approaches described herein, including the CRISPR/Cas9 system comprising gRNA sequences, expression cassettes and the like, could be used to generate genetically engineered immune cells described herein. The CRISPR/Cas9 system may be an active genetics system comprising a vector (e.g., CopyCat) that may be transfected or transformed into immune cells, such as T cells, so as to genetically modify the immune cells to perform a plurality of integrated functions. The vector would be introduced together with purified TAT-tagged form of Cas9 into T-cells (e.g., primary, isolated and purified) resulting in biallelic chromosomal insertion of an integrated set of effector molecules. FIG. 6B.

Hypothetical CopyCat elements, such as gRNA1, gRNA2 and a Tetracycline OFF promoter, would be used to transfect or transduce T cells with a gRNA1 that targets its own Cas9-mediated insertion into a locus required for arginine biosynthesis (e.g., ASS1) thereby rendering the T-cells auxotrophic for arginine by abolishing ASS1 function. FIG. 6B. In addition, insertion of the hypothetical CopyCat elements could be targeted for insertion into other gene loci where the genes encode proteins for synthesis of arginine (e.g., ASL, OTC), or for synthesis of other amino acids (e.g., asparagine synthetase—ASY, or serine biosynthetic enzymes) or of enzymes required for production of cell non-autonomous metabolites.

Expression cassettes of the present example includes polypeptides encoding any number of polypeptides useful for T cell mediated killing tumor cells FIG. 6A. There are three different types of expression cassettes depicted herein by way of example. First, by expression of a specific TCR, presentation of a peptide fragment of a tumor antigen by MHCI engages the specific TCR, which then signals via CD3 and downstream kinases to phosphorylate and activate transcription factors (TF) that in turn activate genes required for killing the recognized tumor cells. Second, because T cell activation, and subsequently, cancer cell killing, is attenuated by a set of negative regulatory pathways including PD-1 (also CTLA-4, BTLA, TIM3, LAIR-1, Siglecs, TIGIT, LAG-3), elimination of signaling through negative regulatory pathways may prevent, or at least attenuate, inhibitory signals against T cell activation. In this example, an expression cassette comprising polynucleotides which encode a signal inactivated engineered negative regulatory molecule such that upon binding of a cognate antigen, the signal inactivated engineered negative regulatory molecule is unable to transmit inhibitory signals to the T cell, or to any other cells. Third, an artificial means for achieving T-cell activation against tumors bearing known cell-specific markers is to generate Chimeric Antigen Receptors (CARs) that signal in response to binding to the tumor antigen (e.g., the CD19 B-cell antigen in the embodiment of B-cell acute lymphoblastic leukemia). In addition to the three different expression cassettes, T cell activation may be enhanced by deleting inhibitory inputs to T cells (e.g., PD-1) so as to respond in a prolonged fashion to antigen presented via MHCI. Such deletion of inhibitory inputs may be achieved by targeting insertion of some of the CopyCat elements to the PD-1 gene locus of the T cell. In order to prevent unregulated growth of such genetically engineered T cells, use of a drug inducible toxin gene cassette may provide a means to kill these genetically engineered T cells after they have successfully eliminated the target tumor cells in order to prevent off target effects, and/or autoimmune responses.

Endogenous antigen-specific T-cell activation could be enhanced by deleting inhibitory inputs native to T cells (e.g., PD-1) while simultaneously rendering such T cells auxotrophic for arginine. FIG. 6B. T cells may be transfected with a CopyCat plasmid encoding two guide RNAs (gRNA$_1$, gRNA2), an effector cassette (e.g., TET-off-Toxin), and genomic sequences flanking the site at which gRNA$_1$ directs Cas9-mediated cleavage of the Argininosuccinate synthase 1 (ASS1) gene. FIG. 6B—top. In addition, the T cells may also be co-transfected with a TAT-tagged form of a Cas9 protein. FIG. 6B—top. Upon entering the T-cell, the Cas9/gRNA$_1$ endonuclease complex may cleave one allele of the ASS1 gene leading to insertion of the Toxin/gRNA$_1$/gRNA2 cassette via homology directed repair (HDR) FIG. 6B—top. If the CopyCat cassette is integrated into one allele of ASS1, then the same Cas9/gRNA$_1$ endonuclease may cleave the other (e.g., sister) allele, leading to the potential insertion of the same expression cassette via HDR to generate a potential biallelic insertional mutation into ASS1 (ASS1*) which renders the cell auxotrophic for arginine. gRNA2 may direct Cas9 cleavage of the PD-1 gene at a catalytic residue, which may be repaired by the alternative error prone Non-Homologous End-Joining (NHEJ) pathway, resulting in a potential biallelic mutation of the PD-1 gene (PD-1*) which may relieve inhibition of endogenous TCR signaling mediated by the PD-1 receptor. FIG. 6B—middle. CopyCat insertion may result in a genetically engineered T cell auxotrophic for arginine, where the T cell conditionally expresses the Toxin transgene and lacks PD-1 mediated inhibition of endogenous TCR signaling. FIG. 6B—bottom. The drug inducible toxin gene cassette may provide a means for killing the genetically engineered T cells as described herein after the genetically engineered T cells have eliminated the target tumor cells. FIG. 6B—bottom. By genetically engineering T cells as described herein, the genetically engineered T cell should respond in a prolonged fashion to an antigen presented by MHCI (e.g., presented by a tumor cell MHCI). As a backup strategy for eliminating the genetically engineering T cells, an ASS1 inhibitor (e.g., arginine deiminase—ADI, or arginase I) could be administered to the subject which should selectively kill the genetically engineered T-cells unable to synthesize arginine.

As described herein, this example is efficient at generating biallelic insertions of cargo effector genes (e.g., CARs) and because CopyCat vectors integrate larger inserts into the genome with high efficiency and fidelity, this example should provide larger multifunctional effector cassettes (e.g., CARs, gRNAs targeting other loci such as receptors for inhibitory pathways, or conditional cis-regulatory sequences that could be targeted for insertion adjacent to endogenous genes one wished to place under regulatory control by agents such as drugs) for transfer into T cells. In this way, the example provides for an integrated set of T-cell effectors that may be produced in a single round of ex vivo treatment so as to reduce both the number of cell divisions that take place in culture conditions as well as minimizing the time from cell retrieval from a patient to re-delivery of cells targeting the tumor.

Example 3

Generation of Genetically Engineered T Cells Auxotrophic for Arginine

The compositions and methods described herein are useful for generating genetically engineered immune cells. FIG. 6A. In this example, it is understood that the genetic approaches described herein, including the CRISPR/Cas9 system comprising gRNA sequences, expression cassettes and the like, could be used to generate genetically engineered immune cells described herein. The CRISPR/Cas9 system may be an active genetics system comprising a vector (e.g., CopyCat) that may be transfected or transformed into immune cells, such as T cells, so as to genetically modify the immune cells to perform a plurality of integrated functions. The vector would be introduced together with purified TAT-tagged form of Cas9 into T-cells (e.g., primary, isolated and purified) resulting in biallelic chromosomal insertion of an integrated set of effector molecules. FIG. 6B.

Expression cassettes of the present example includes polypeptides encoding any number of polypeptides useful for T cell mediated killing tumor cells FIG. 6A such as achieving T-cell activation against tumors bearing known cell-specific markers is to generate Chimeric Antigen Receptors (CARs) that signal in response to binding to the tumor antigen (e.g., the CD19 B-cell antigen in the embodiment of B-cell acute lymphoblastic leukemia). The CAR may induce genetically engineered T cells to become activated (e.g., for cell killing) when binding to a tumor antigen recognized by the single-chain antibody portion of the CAR or for drug-regulated expression of a Toxin gene. FIG. 6C. For example, the CopyCat vector may carry a CAR targeted for biallelic insertion in the Asparagine Synthetase 1 (ASS1) gene rendering the genetically engineered T cells auxotrophic for arginine. FIG. 6C. Following administration of the auxotrophic genetically engineered CAR expressing T cells to a cancer patient and the tumor was cleared, the patient could be treated with an ASS1 inhibitor (e.g., arginine deiminase—ADI, or arginase I) to selectively kill the auxotrophic genetically engineered CAR expressing T cells that may not be able to synthesize arginine. FIG. 6C.

In addition, T cell activation may be enhanced by deleting inhibitory inputs to T cells (e.g., PD-1) so as to respond in a prolonged fashion to antigen presented via MHCI. Such deletion of inhibitory inputs may be achieved by targeting insertion of some of the CopyCat elements to the PD-1 gene locus of the T cell. In order to prevent unregulated growth of such genetically engineered T cells, use of a drug inducible toxin gene cassette may provide a means to kill these genetically engineered T cells after they have successfully eliminated the target tumor cells in order to prevent off target effects, and/or autoimmune responses.

As described herein, this example is efficient at generating biallelic insertions of cargo effector genes (e.g., CARs) and because CopyCat vectors integrate larger inserts into the genome with high efficiency and fidelity, this example should provide larger multifunctional effector cassettes (e.g., CARs, gRNAs targeting other loci such as receptors for inhibitory pathways, or conditional cis-regulatory sequences that could be targeted for insertion adjacent to endogenous genes one wished to place under regulatory control by agents such as drugs) for transfer into T cells. In this way, the example provides for an integrated set of T-cell effectors that may be produced in a single round of ex vivo treatment so as to reduce both the number of cell divisions that take place in culture conditions as well as minimizing the time from cell retrieval from a patient to re-delivery of cells targeting the tumor.

Example 4

Generation of Genetically Engineered T Cells Lacking PD-1 Signaling and Inducibly Auxotrophic for Arginine Under Transcriptional Control of a Tetracycline Promoter The compositions and methods described herein are useful for generating genetically engineered immune cells. FIG. 6A. In this example, it is understood that the genetic approaches described herein, including the CRISPR/Cas9 system comprising gRNA sequences, expression cassettes and the like, could be used to generate genetically engineered immune cells described herein. The CRISPR/Cas9 system may be an active genetics system comprising a vector (e.g., CopyCat) that may be transfected or transformed into immune cells, such as T cells, so as to genetically modify the immune cells to perform a plurality of integrated functions. The vector would be introduced together with purified TAT-tagged form of Cas9 into T-cells (e.g., primary, isolated and purified) resulting in biallelic chromosomal insertion of an integrated set of effector molecules.

Hypothetical CopyCat elements, such as gRNA1 and gRNA2 could target the biallelic insertion of a CopyCat vector carrying drug responsive cis-regulatory sequences so as to insert the drug responsive cis-regulatory elements adjacent to a gene of interest to either silence or activate expression of that gene by providing or withdrawing the drug. FIG. 6D. In this example, the hypothetical CopyCat vector would be used to transfect or transduce T cells with a gRNA1 that targets its own Cas9-mediated insertion upstream of a locus required for arginine biosynthesis (e.g., the ASS1 gene) thereby disassociating the endogenous promoter from the ASS1 gene and inserting an expression cassette comprising an inducible promoter operably linked to the ASS1 gene. In this way, T cells would transcribe and translate the ASS1 gene in the presence of tetracycline. In the absence of tetracyline, the T cells would not survive. FIG. 6D. In addition, insertion of the hypothetical CopyCat elements could be targeted by gRNA2 for insertion into other gene loci, such as those comprising inhibitory signaling pathways in T cells, such as PD-1, where the genes encode proteins for synthesis of PD-1.

The hypothetical CopyCat vector inserts biallelically upstream of the ASS1 gene by gRNA1 targeting so as to inactivate the endogenous cis-regulation of ASS1 and replacing endogenous cis-regulation with a drug responsive promoter, such as the Tet ON promoter. A second gRNA2 may be designed to target the PD-1 gene to relieve inhibitory signals that lead to T cell exhaustion. Under this example, tetracycline could initially be administered to the subject together with the genetically engineered T cells in order to maintain expression of the ASS1 locus under Tet ON promoter control in the subject. FIG. 6D—top. Following clearance of the tumor in the subject, tetracycline could be withdrawn so as to result in death of the genetically engineered T cells. As mentioned in Example 2, genetically engineered T cells with a disruption at or near the ASS1 locus could also be eliminated by treating the subject with an ASS1 inhibitor (e.g., arginine deiminase—ADI, or arginase I). As an alternative, or as an addition to targeting ASS1 and PD-1, a gene inducing apoptosis (e.g., Bax) or an anti-apoptotic gene (e.g., Bcl-2) could be targeted by the hypothetical CopyCat vector As described herein, this example is efficient at generating biallelic insertions of cargo effector genes (e.g., CARs) and because CopyCat vectors integrate larger inserts into the genome with high efficiency and fidelity, this example should provide larger multifunctional effector cassettes (e.g., CARs, gRNAs targeting other loci such as receptors for inhibitory pathways, or conditional cis-regulatory sequences that could be targeted for insertion adjacent to endogenous genes one wished to place under regulatory control by agents such as drugs) for transfer into T cells. In this way, the example provides for an integrated set of T-cell effectors that may be produced in a single round of ex vivo treatment so as to reduce both the number of cell divisions that take place in culture conditions as well as minimizing the time from cell retrieval from a patient to re-delivery of cells targeting the tumor.

Expression cassettes of the present example includes, in addition to drug responsive cassettes, polypeptides encoding any number of polypeptides useful for T cell mediated killing tumor cells FIG. 6A. There are three different types of expression cassettes depicted herein by way of example. First, by expression of a specific TCR, presentation of a peptide fragment of a tumor antigen by MHCI engages the specific TCR, which then signals via CD3 and downstream kinases to phosphorylate and activate transcription factors (TF) that in turn activate genes required for killing the recognized tumor cells. Second, because T cell activation, and subsequently, cancer cell killing, is attenuated by a set of negative regulatory pathways including PD-1 (also CTLA-4, BTLA, TIM3, LAIR-1, Siglecs, TIGIT, LAG-3), elimination of signaling through negative regulatory pathways may prevent, or at least attenuate, inhibitory signals against T cell activation. In this example, an expression cassette comprising polynucleotides which encode a signal inactivated engineered negative regulatory molecule such that upon binding of a cognate antigen, the signal inactivated engineered negative regulatory molecule is unable to transmit inhibitory signals to the T cell, or to any other cells. Third, an artificial means for achieving T-cell activation against tumors bearing known cell-specific markers is to generate Chimeric Antigen Receptors (CARs) that signal in response to binding to the tumor antigen (e.g., the CD19 B-cell antigen in the embodiment of B-cell acute lymphoblastic leukemia). In addition to the three different expression cassettes, T cell activation may be enhanced by deleting inhibitory inputs to T cells (e.g., PD-1) so as to respond in a prolonged fashion to antigen presented via MHCI. Such deletion of inhibitory inputs may be achieved by targeting insertion of some of the CopyCat elements to the PD-1 gene locus of the T cell. In order to prevent unregulated growth of such genetically engineered T cells, use of a drug inducible toxin gene cassette may provide a means to kill these genetically engineered T cells after they have successfully eliminated the target tumor cells in order to prevent off target effects, and/or autoimmune responses. Alternative strategies for eliminating genetically engineered immune cells following therapeutic benefit include, but are not limited to, conditional expression of a toxin, condition expression of a pro-apoptotic factor (e.g., Bax), or conditional expression of a protein targeting the immune cell for recognition and clearance by the subject's immune system.

Example 5

As shown in FIG. 32, CopyCat (CC) elements can be a cloning vehicle for introducing sequences of interest into targeted sites of the genome (e.g., serving as an efficient site-specific transgenesis vector) which can then be rendered homozygous in the germline in the presence of a separately supplied source of Cas9. The CopyCat elements can carry guide-RNAs (gRNAs (black and blue carets) that can direct Cas9 cleavage to the site on CC insertion into the genome, but do not carry a linked source of Cas9. When these CC elements are combined with a separate Cas9 source, the gRNAs can cut the homologous chromosome leading to copying of the CC element into that gap. The CopyCat vector can be inherited by most or all progeny while the Cas9 element can be passed on as a traditional Mendelian locus to only 50% of progeny. An advantage of CopyCat elements is that they bypass standard constraints of Mendelian inheritance such as independent assortment of chromosomes and linkage of nearby loci on the same chromosome. This property can form the basis for active genetics.

Example 6

As shown in FIG. 33, efficient propagation of a two-cut CopyCat vector (kniCC) is demonstrated that carries two gRNAs cutting ~2.0 Kb apart to generate a deletion of the cis-regulatory module (CRM) that drives expression of the Knirps (Kni) transcription factor in the primordium of the second longitudinal wing vein (L2). The kniCC element is crossed to a y–MCR construct, crossed males carrying both constructs to wild-type females, and then in nine separate crosses tested for propagation of the kniCC element (marked with DS-Red) to progeny. In 4 of the nine crosses 100% of the progeny inherited the kniCC element and in three 89% of the progeny inherited the DS-Red element. In two crosses, the element did not copy and was only inherited in a Mendelian fashion by 50% of the progeny. Independent of the frequency of germline inheritance of the element, however, approximately 70% of individuals were observed to display somatic vein loss phenotypes indicating that somatic and germline activity of the kniCC elements are likely to be independent events. The efficient active genetic propagation of the kniCC element is observed and supports the use of double-cut strategies such as those that can be used for large-scale genome engineering.

Example 7

Figure 34:
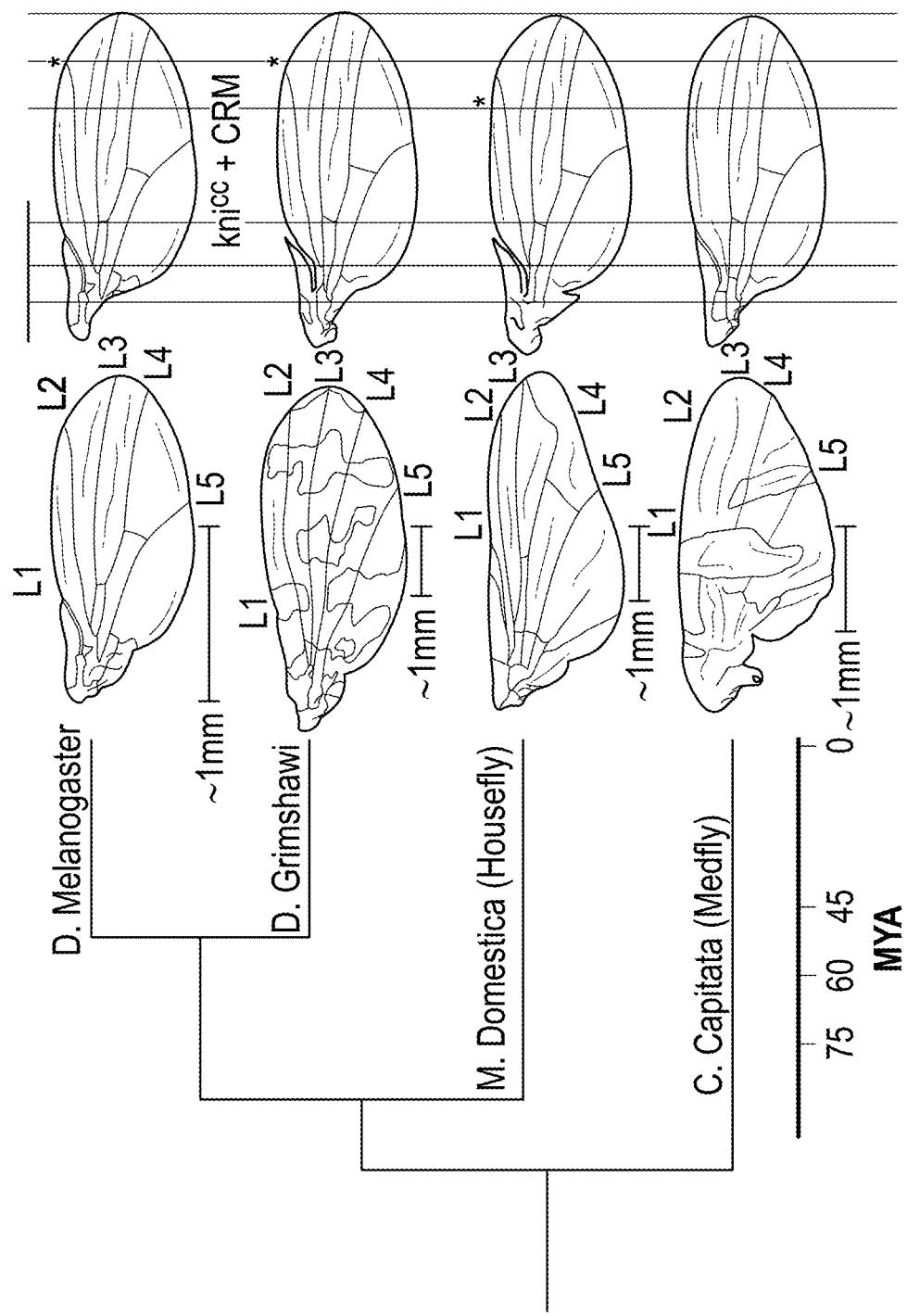
FIG. 34 is a scheme outlining use of CopyCat elements to compare.

As shown in FIG. 34, an inserted L2-CRM sequence is added to a modified version of the kniCC element. In the upper left is the control experiment in which the endogenous L2-CRM from *Drosophila melanogaster* is added back (e.g., the endogenous element is cut out, and then is added back). This manipulation leads to reinstatement of the L2 vein (asterisk). Next, the endogenous L2-CRM sequence from *D. melanogaster* is replaced with that of the distantly related Drosophild *D. grimsawi* (e.g., the D. mel sequence is cut out and the *D. grimshawi* sequence is added back in its place). This manipulation results in full restoration of the L2 vein in its normal location (asterisk—note its equivalent position to that in the control wing above as indicated by the vertical gray lines). In the third case, the D. mel. L2-CRM is replaced with corresponding sequences from the more diverged housefly (*M. domestica*). In this case, formation of the L2 is fully rescued but its position is significantly shifted anteriorly relative to wild-type D. mel. (asterisk—note how the intersection with the margin is shifted proximally as a consequence of the anterior displacement of the rescued vein). The substantial anterior shift of the rescued L2 vein reflects the relatively more anterior position of the L2 vein as it forms in *M. domestica*. Finally, in the last case of the medfly (*C. capitata*), the CRM replacement results in only a partial rescue of the L2, but that rescued centrals segment of the vein is shifted far anteriorly so that is lies just barely separated from the marginal vein. This experiment has two important consequences. First, it demonstrates the feasibility of using CopyCat elements as efficient means of transgenesis allowing in a single step for the targeted replacement of sequences. Indeed, the high frequency with which transgenic flies carrying the precise CC replacement were recovered is on the same order of that obtained with transposon or phi-31C mediated transgenesis vectors. Second, this experiment demonstrates the degree to which replacement of a single CRM can alter the wing developmental program. This argues strongly against the potential concern that one might have to change many (10s to 100s) of genes to see any effect of wing morphology. Presumably, the balance of transcription factor inputs to the L2-CRM in the housefly and medfly have shifted sufficiently (e.g., possibly favoring central activators versus peripheral repressors) so that the readout results in a marked anterior shift in resulting kni gene expression. The sequences responsible for the altered CRM output can then be identified.

Example 8: yl-MCR Construct Transgeneis Efficiency

CRISPR components can be used to trigger homology directed repair events at efficiencies as high or higher than regular P-element transgenesis in fruit flies. The numbers in the following table represent vials that were positive for an MCR construct insertion. When injected males or females crossed a wild-type coupterpart and yielded y-F1 progeny, the vial was considered positive for insertion. High transgeneis efficiency ranging from 11% to 25% was observed in both male and females, with an overall average of 19%.

TABLE 2

| | MCR construct insetion event | | | |
|---|---|---|---|---|
| | YES (yields y– females) | NO (yields no > y– females) | TOTAL | |
| Male injected | 2 | 17 | 19 | 11% |
| Female | 7 | 21 | 28 | 25% |
| Total | 9 | 38 | 47 | 19% |

Example 9: Testing of a GFP-Marked CHACR Construct Disrupting the Wing Vein L2 Knirps Cis-Regulatory Module (CRM)

The following table shows the F2 progeny of 9 independent single pair crosses between a female heterozygous for both a yl-MCR construct and a GFP-marked CopyCat Element and wild type males. The CopyCat Element targets for disruption the previously characterized L2 vein knirps Cis-Regulatory Module (CRM). This CopyCat element carries two gRNA that cut on each side of the L2 CRM, and promotes the substitution of the wild type sequence with the GFP reporter which drives expression of the fluorescent marker in the eyes under the control of a 3×P3 promoter. For simplicity, the following table does not report the resulting knirpsri phenotype, but only the presence of GFP which is indicative of the presence of the copy element. While the expected Medelian inheritance ratio of the GFP marker is 50%, a 94% transmission efficiency is observed (when omitting two outliers marked with ***). This transmission efficiency corresponds to the conversion efficiency at the knirps locus of 88% by action of the CopyCat element. From the female progeny, it is observed that the MCR at the yellow locus can convert at high frequencies (~99%) indicated by the ration of the y-females observed.

Figure 35A:
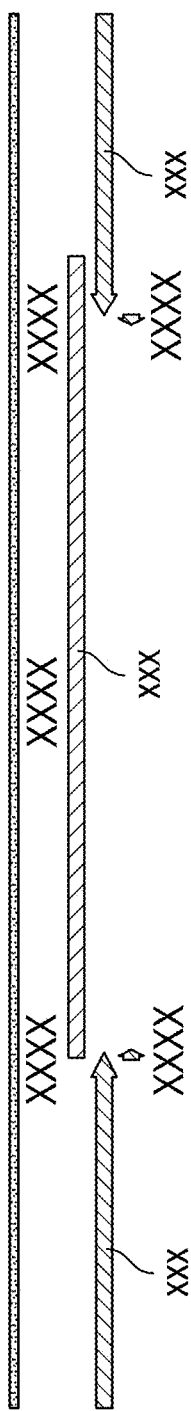
FIG. 35A is a scheme outlining the endogenous knirps locus and the knirps L2 CRM target.
Figure 35B:
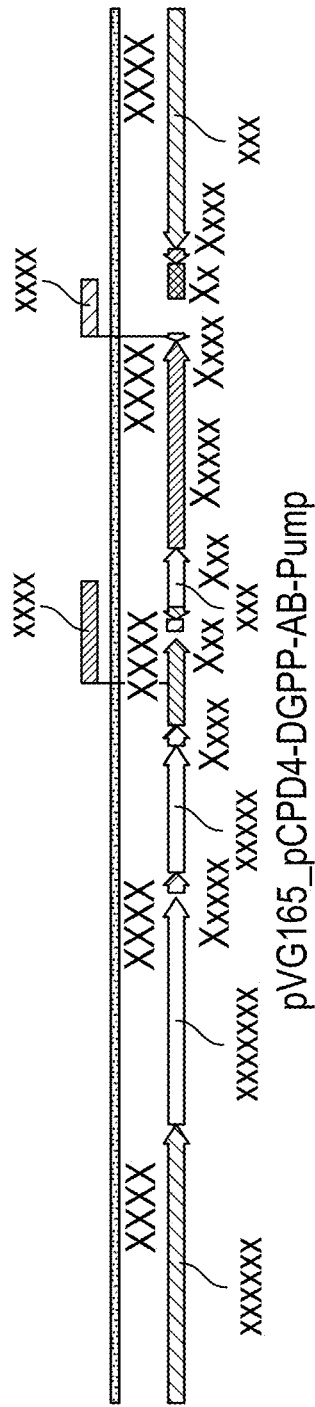
FIG. 35B is a scheme outlining the structure of the CopyCat or allelic pump including two gRNAs (gRNA-A and gRNA-B) targeting insertion of the construct in place of the knirps CRM.

FIG. 35A shows the endogenous knirps locus and the knirps L2 CRM target (EV fragment). FIG. 35B shows the structure of the CopyCat or allelic pump, which includes two gRNAs (gRNA-A and gRNA-B) targeting insertion of the construct in place of the knirps CRM; the two homology arms used (HA-A and HA-B); and the 3×P3-GFP reporter construct.

TABLE 3

| F1CROSS Parents: FEMALE y-MCR/GFP (knirps-ri) MALE (wild type) CopyCat (C y-MCR/+;; +/riAB-CC-GFP +/+;; +/Y | | | | | | | | | | | | | |
|---|---|---|---|---|---|---|---|---|---|---|---|---|---|
| | M (F2 progeny) | | | | F (F2 progeny) | | | | Male + Females (GFP marked CopyCat) | | | Transmission | Conversion |
| | y– | | y+ | | y– | | y+ | | | | | | |
| CROSS ID | GFP+ | GFP– | GFP+ | GFP– | GFP+ | GFP– | GFP+ | GFP– | GFP+ | GFP– | TOTAL (F2) | efficiency | efficiency |
| 1-1 | 0 | 0 | 29 | 0 | 43 | 0 | 0 | 0 | 72 | 0 | 72 | 100% | 100% |
| 2-1 | 2 | 0 | 7 | 5 | 13 | 8 | 0 | 0 | 22 | 13 | 35 | 63% | 26% |
| 3-1 | 0 | 0 | 23 | 0 | 27 | 0 | 0 | 0 | 50 | 0 | 56 | 160% | 100% |
| 4-1 | 1 | 0 | 14 | 15 | 12 | 15 | 0 | 0 | 27 | 30 | 57 | 47% | –5% |
| 5-3 | 0 | 0 | 21 | 0 | 30 | 0 | 0 | 0 | 51 | 0 | 51 | 100% | 100% |
| 7-3 | 0 | 0 | 27 | 1 | 30 | 0 | 0 | 0 | 57 | 1 | 58 | 98% | 97% |
| 8-3 | 0 | 0 | 18 | 8 | 29 | 3 | 0 | 0 | 47 | 11 | 58 | 81% | 62% |
| S-5 | 0 | 0 | 27 | 1 | 22 | 2 | 0 | 0 | 49 | 3 | 52 | 94% | 88% |
| 10-5 | 1 | 0 | 28 | 2 | 32 | 5 | 0 | 2 | 61 | 9 | 70 | 87% | 74% |
| Total | 4 | 0 | 194 | 32 | 238 | 33 | 0 | 2 | 436 | 67 | 563 | 87% | 73% |
| Total (without Crosses 2-1 and | 1 | 0 | 173 | 12 | 213 | 10 | 0 | 2 | 387 | 24 | 411 | 94% | 88% |

***= in these two cases the germline of the femal was majorly affected by an inpreise conversion event early on, leading to close-to-mendelian inheritance

Example 10

The following table shows the F2 progeny of several independent single pair crosses between a female heterozygous for both a yl-MCR construct and a DsRed-marked ERACR element and a wild-type male. Phenotypes observed in the F2 progeny of such crosses are reported in separate columns and classified by the M/F Yy Rr code (M=male, F=female, R=DsRed positive, r=DsRed negative, Y=Wild-Type/Yellow+, y=yellow− phenotype). The top (ERACR-1) and middle (ERACR-2) tables collect data from different experiments performed using a first version (ERACR-1) and a second version (ERACR-2) of the ERACR construct built to reverse the Mutagenic Chain Reaction at the yellow locus by the yl-MCR construct. The bottom table summarizes, collects, and compares the data from the two constructs. The MYR and FYR correspond to individuals that inherited the ERACR construct. The ERACR-1 and ERACR-2 constructs are capable of chromosomal conversion of 21% and 58%, respectively, resulting in a biased inheritance of 61% and 79%, respectively, which deviate from the expected Mendelian 50%. A lower conversion rate is observed than one previously observed with the yl-MCR construct (~96%, Gantz and Bier, Science 2015). In the individuals that were not converted (DsRed negative), an absence of MCR activity is observed (observable in females only, FYr class) suggesting that the MCR, even if not converted, is successfully disrupted (e.g., probably by excision). By looking at total MCR neutralization events (conversion/FYR+disruption/FYr), an efficiency above 90% is observed. Parital sequence homology between the MCR construct and the ERACR-1 construct may have impaired a proper Homology-Directed Repair process contributing to the low conversion efficiency observed and the presence of the unexpected phenotypical classes (MyR, MYr, FyR, Fyr). ERACR-2 is designed to avoid homology between the two sequences by replacing the yellow sequence with a recoded version, and the yellow 3'UTR and U6 promoters from the distantly related (~45 million years of separation) *Drosophila grimshawi*.

Figure 36:
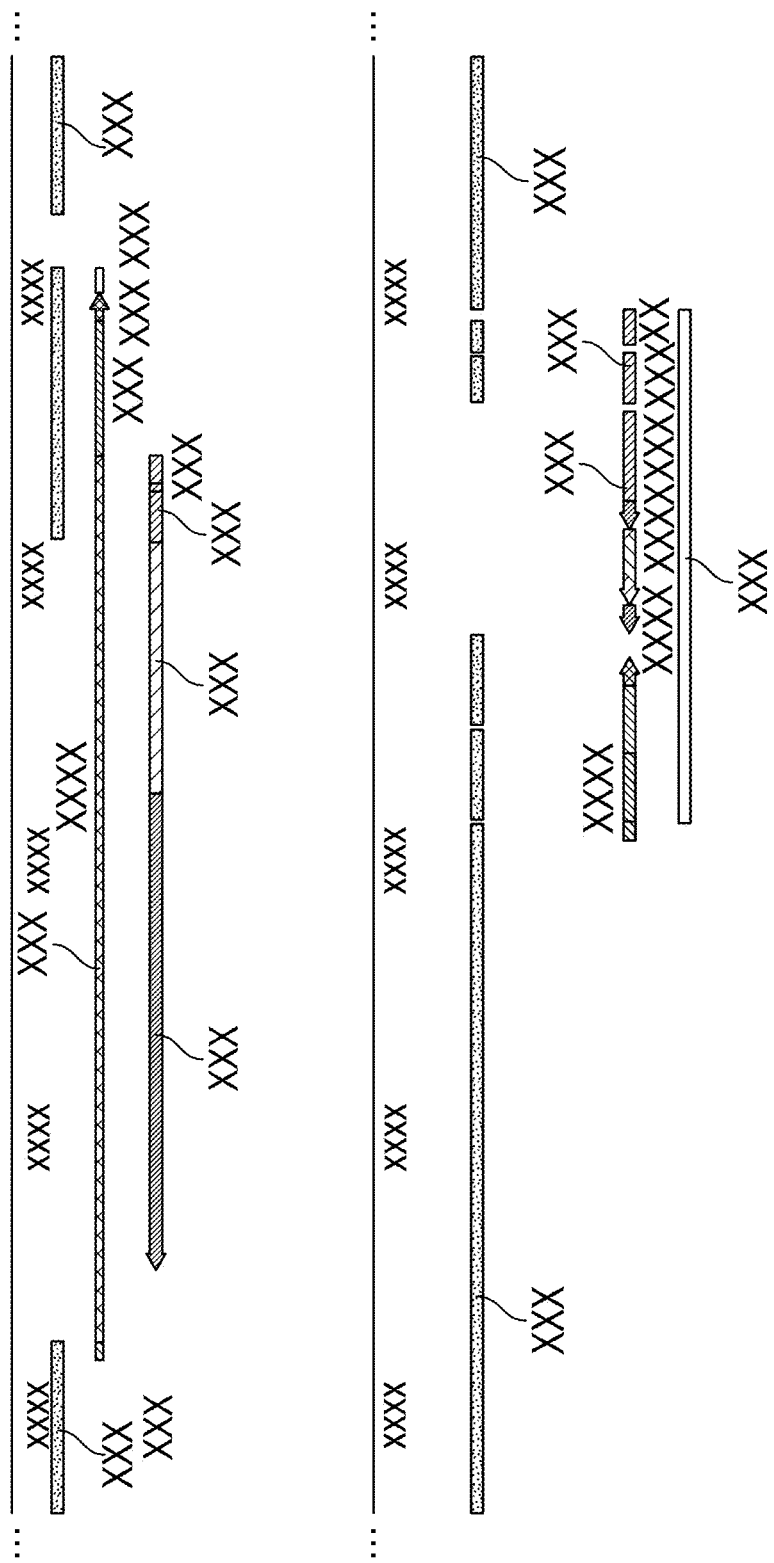
FIG. 36 is a scheme outlining homology between yl-MCR and ERACR-1 constructs inserted in the yellow locus.
Figure 37:
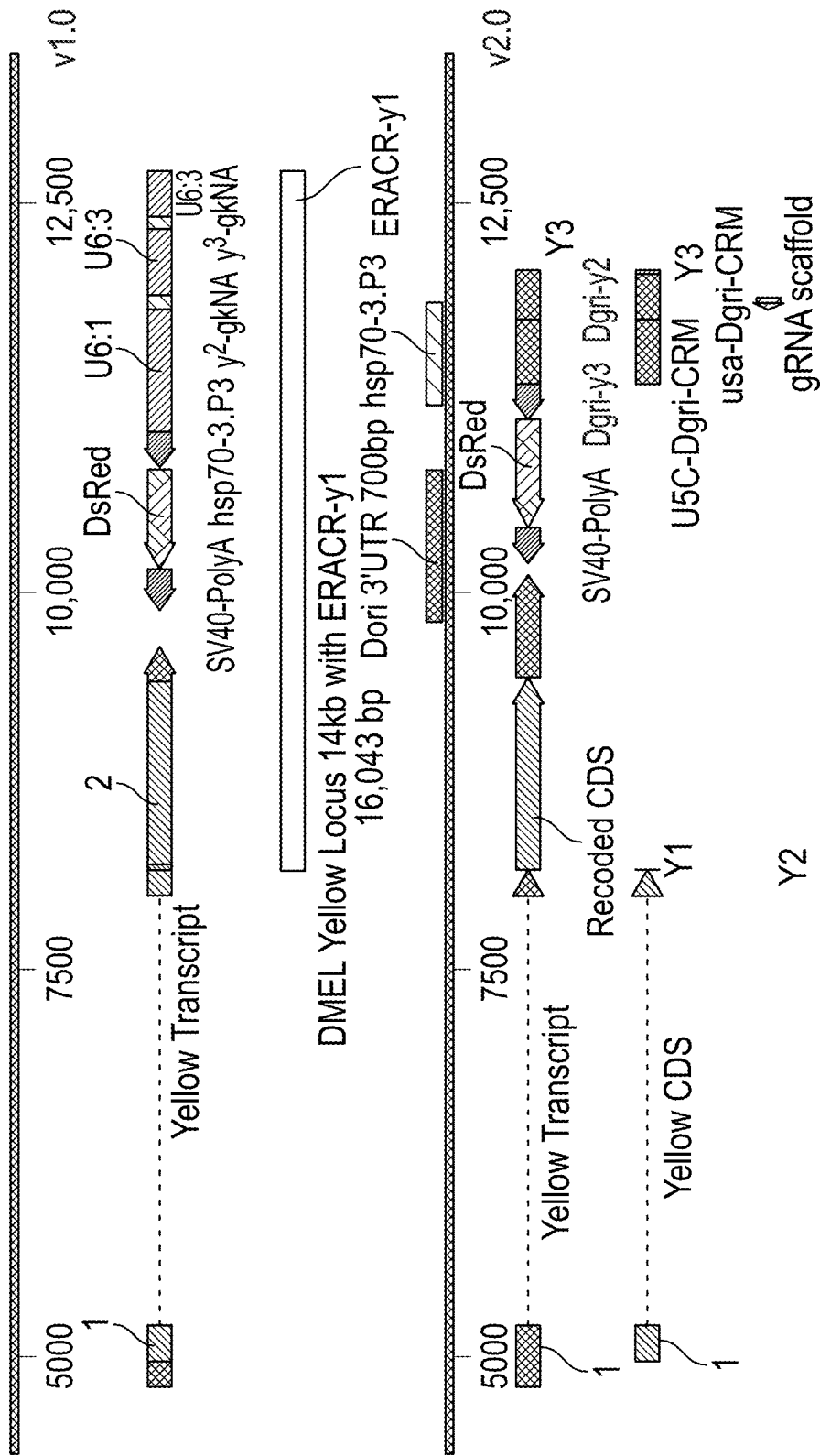
FIG. 37 is a scheme outlining an exemplary ERACR-1 and exemplary ERACR-2.
Figure 38A:
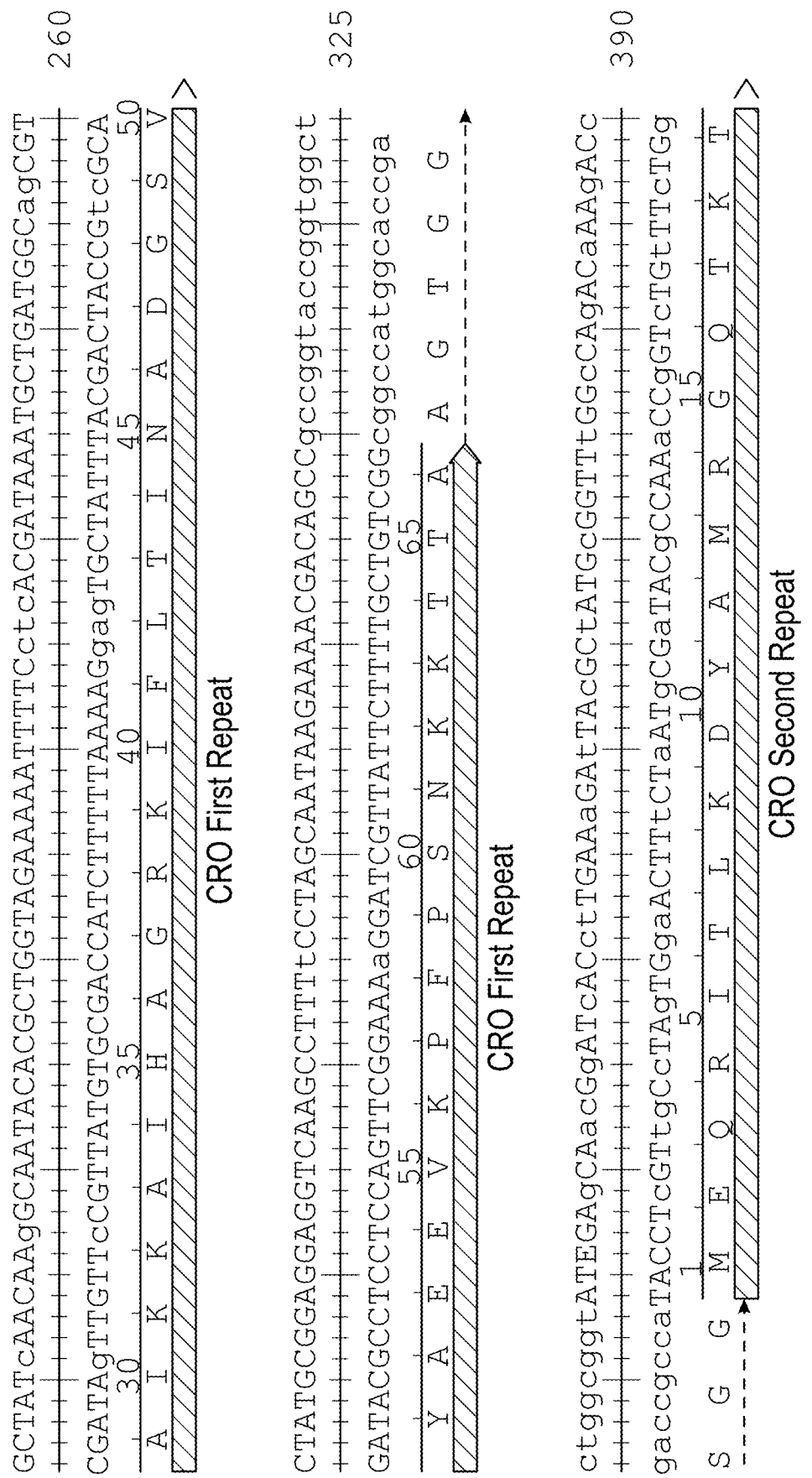
Figure 38B:
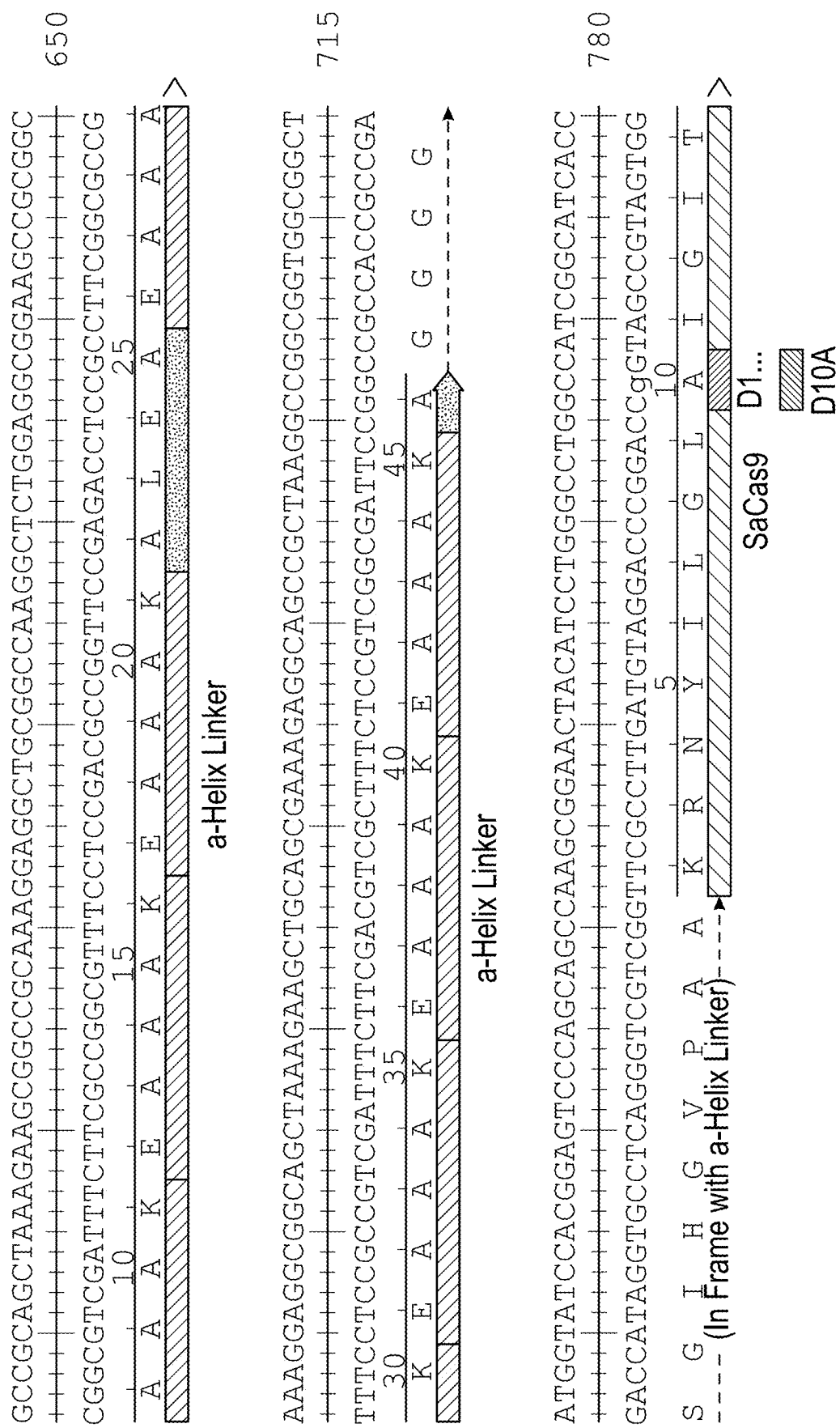

FIG. 36 shows homology between yl-MCR and ERACR-1 constructs inserted in the yellow locus. FIG. 37 shows an exemplary ERACR-1 and exemplary ERACR-2. The yellow sequence was completely recoded, and the 3'UTR was taken from a different species, the Hawaiian picture wing *Drosophila grimshawi* as well as the U6 promoter and 3' regions which were also taken from the same species.

TABLE 4

Testing of the ERACR 1 Construct

| | M (F2 Progeny) | | | | | F (F2 Progeny) | | | | | ERACR 1 efficiency: | | |
|---|---|---|---|---|---|---|---|---|---|---|---|---|---|
| | y+ | | y− | | Total | | | | | Total | | | MCR |
| CROSS | M Y R | M Y r | M y R | M y r | M | F Y R | F Y r | F y R | F y r | F | Transmission | Conversion | Neutralization |
| ME 1-1 | 38 | | | | 38 | 38 | 33 | | | 71 | 54% | 7% | 100% |
| ME 1-2 | 39 | 1 | | | 40 | 34 | 43 | | | 77 | 44% | −12% | 100% |
| ME 1-3 | 29 | 1 | 1 | | 31 | 44 | 18 | | | 62 | 71% | 42% | 100% |
| ME 1-4 | 41 | 6 | | | 47 | 45 | 7 | | 4 | 56 | 80% | 61% | 93% |
| ME 1-5 | 37 | | 1 | 12 | 50 | 30 | 19 | | 10 | 59 | 51% | 2% | 83% |
| ME 1-6 | 32 | | | 15 | 47 | 32 | 16 | 1 | 12 | 61 | 52% | 5% | 79% |
| ME 1-7 | 14 | | | | 14 | 20 | 3 | | 1 | 24 | 83% | 67% | 96% |
| ME 1-8 | 15 | 5 | | 1 | 21 | 15 | 3 | 1 | 3 | 22 | 68% | 36% | 82% |
| ME 1-9 | 42 | 16 | | | 58 | 52 | 11 | | 1 | 64 | 81% | 63% | 98% |
| ME 2-1 | 27 | 11 | | 2 | 40 | 28 | 22 | | 2 | 52 | 54% | 8% | 96% |
| ME 2-2 | 42 | 6 | | 1 | 49 | 33 | 30 | | 2 | 65 | 51% | 2% | 97% |
| ME 3-1 | 24 | 7 | | 2 | 33 | 20 | 19 | | 2 | 41 | 49% | −2% | 95% |
| ME 3-2 | 44 | 6 | 1 | | 51 | 43 | 23 | | 1 | 67 | 64% | 28% | 99% |
| ME 3-3 | 32 | | 2 | 3 | 37 | 45 | 24 | | 1 | 70 | 64% | 29% | 99% |
| ME 3-4 | 38 | 10 | | 3 | 51 | 33 | 18 | | 1 | 52 | 63% | 27% | 98% |
| Total | 494 | 69 | 5 | 39 | 607 | 512 | 289 | 2 | 40 | 843 | 61% | 21% | 95% |
| Total % | 81.38% Converted | 11.37% Other (7) | 0.82% Other (7) | 6.43% Other (7) | 100% | 60.74% NOT Converted NOT MCR | 34.28% Excised | 0.24% Other (7) | 4.74% NOT Converted MCR | 100% | | | |

TABLE 5

Testing of the ERACR 2 Construct

| MCR Isolate us | CROSS | M | | | | Total | F | | | | Total | ERACR 2 efficiency: | | |
|---|---|---|---|---|---|---|---|---|---|---|---|---|---|---|
| | | y+ | | y− | | | y+ | | y− | | | Trans- mission | Conver- sion | Neutral- ization |
| | | M Y R | M Y r | M y R | M y r | M | F Y R | F Y r | F y R | F y r | F | | | |
| yll-1 | 2-1 | 21 | 0 | 0 | 0 | 21 | 29 | 21 | 0 | 8 | 58 | 50% | 0% | 86% |
| | 2-3 | 31 | 1 | 0 | 0 | 32 | 26 | 0 | 0 | 0 | 26 | 100% | 100% | 100% |
| | 2-4 | 44 | 0 | 0 | 0 | 44 | 44 | 0 | 0 | 0 | 44 | 100% | 100% | 100% |

TABLE 5-continued

Testing of the ERACR 2 Construct

| MCR Isolatus | CROSS | M | | | | Total M | F | | | | Total F | ERACR 2 efficiency: Transmission | Conversion | Neutralization | MCR |
|---|---|---|---|---|---|---|---|---|---|---|---|---|---|---|---|
| | | y+ | | y- | | | y+ | | y- | | | | | | |
| | | M Y R | M Y r | M y R | M y r | | F Y R | F Y r | F y R | F y r | | | | | |
| | 2-6 | 46 | 0 | 0 | 0 | 46 | 48 | 0 | 0 | 0 | 48 | 100% | 100% | 100% | |
| | 3-1 | 0 | 0 | 0 | 1 | 1 | 2 | 2 | 0 | 0 | 4 | 50% | 0% | 100% | |
| | 3-2 | 35 | 0 | 0 | 0 | 35 | 42 | 12 | 0 | 1 | 55 | 76% | 53% | 98% | |
| | 3-4 | 22 | 1 | 0 | 0 | 23 | 61 | 12 | 0 | 2 | 75 | 81% | 63% | 97% | |
| | 3-5 | 19 | 2 | 0 | 0 | 21 | 27 | 10 | 0 | 2 | 39 | 69% | 38% | 95% | |
| | 3-6 | 26 | 1 | 0 | 0 | 27 | 44 | 6 | 1 | 3 | 54 | 81% | 63% | 93% | |
| | 4-1 | 40 | 1 | 0 | 9 | 50 | 25 | 0 | 1 | 14 | 40 | 63% | 25% | 63% | |
| F5 line (Cas9 2/ mutaton) | 6-1 | 17 | 0 | 0 | 6 | 23 | 33 | 4 | 1 | 6 | 44 | 75% | 50% | 84% | |
| | 6-3 | 11 | 0 | 0 | 0 | 11 | 9 | 18 | 0 | 0 | 27 | 33% | -33% | 100% | |
| | 6-4 | 2 | 1 | 0 | 0 | 3 | 1 | 1 | 0 | 0 | 2 | 50% | 0% | 100% | |
| | 6-5 | 53 | 1 | 2 | 2 | 58 | 49 | 5 | 0 | 2 | 56 | 88% | 75% | 96% | |
| | Total | 315 | 7 | 2 | 18 | 342 | 385 | 70 | 3 | 30 | 488 | 79% | 58% | 93% | |
| | Total % | 92.11% Converted | 2.05% Other (7) | 0.58% Other (7) | 5.26% Other (7) | 100% | 78.89% Converted NOT MCR | 14.34% Excised | 0.61% Other (7) | 6.15% NOT Converted MCR | 100% | | | | |

TABLE 6

Comparison of ERACR 1 vs. ERACR 2

| | | M (F2 Pogeny) | | | | Total M | F (F2 Pogeny) | | | | Total F | ERACR 2 efficiency: Transmission | Conversion | Neutralization | MCR |
|---|---|---|---|---|---|---|---|---|---|---|---|---|---|---|---|
| | | y+ | | y- | | | y+ | | y- | | | | | | |
| | | M Y R | M Y r | M y R | M y r | | F Y R | F Y r | F y R | F y r | | | | | |
| ERACR 1 | Total | 494 | 69 | 5 | 39 | 607 | 512 | 289 | 2 | 40 | 843 | 60.7% | 21.5% | 95.0% | ERACR 1 |
| | Total % | 81.4% | 11.4% | 0.8% | 6.4% | 100.0% | 60.7 | 34.3% | 0.2% | 4.7% | 100.0% | | | | |
| ERACR 2 | Total | 315 | 7 | 2 | 18 | 342 | 385 | 70 | 3 | 30 | 488 | 78.9% | 57.8% | 93.2% | ERACR 2 |
| | Total % | 92.1% | 2.0% | 0.6% | 5.3% | 100.0% | 78.9% | 14.3% | 14.3% | 6.1% | 100.0% | | | | |
| | | Converted | Other (7) | Other (7) | Other (7) | | Converted NOT MCR | Excised | Other (7) | NOT Converted MCR | | | | | |

Example 11

```
TETHR protein sequenve (SEQ ID NO: 19):
>TETHR ORF
MDYKDHDGDYKDHDIDYKDDDDKGAPKKKRKVGGGGSGEQRITLKDYAMR

FGQTKTAKDLGVYQSAINKAIHAGRKIFLTNADGSVYAEEKPFPSNKKTT

AAGTGGSGGMEQRITKDYAMRFGQTKTAKDLGVYQSAINKAIHAGRKIFL

TINADGSVYAEEVKPFPSNKKTTAGGGGSGGGGSGAEAAAKEAAAKEAAA

KEAAAKALEAEAAAKEAAAKEAAAKEAAAKAGGGGSGIHGVPAAKRNYIL

GLAIGITSVGYGIIDYETRDVIDAGVRLFKEANVENNEGRRSKRGARRLK

RRRRHHIQRVKKLLFDYNLLTDHSELSGINPYEARVKGLSQKLSEEEFSA

ALLHLAKRRGVHNYNVEEDTGNELSTKEQISRNSKALEEKYVAEELQLER

LKKDGEVRGSINRFKTSDYVKEAKQLLKVQKAYHQLDQSFIDTYIDLLET

RRTYYEGPGEGSPFGWKDIKEWYEMLMGHCTYFPEELRSVKYAYNADLYN

ALNDLNNLVITRDENEKLEYYEKFQIIENVFKQKKKPTLKQIAKEILVNE

EDIKGYRVTSTGKPEFTNLKVYHDIKDITARKEIIENAELLDQIAKILTI

YQSSEDIQEELTNLNSELTQEEIEQISNLKGYTGTHNLSLKAINLILDEL

WHTNDNQIAIFNRLKLVPKKVDLSQQKEIPTTLVDDFILSPVVKRSFIQS

IKVINAIIKKYGLPNDIIIELAREKNSKDAQKMINEMQKRNRQTNERIEE

EIRTTGKENAKYLIEKIKLHDMQEGKCLYSLEAIPLEDLLNNPFNYEVDH

IIPRSVSFDNSFNNKVLVKQEEASKKGNRTPFQYLSSSDSKISYETFKKH

ILNLAKGKGRISKTKKEYLLEERDINRFSVQKDFINRNLVDTRYATRGLM

NLLRSYFVRNNLDVKVKSINGGFTSFLRRKWKFKKERNKGYKHHAEDALI

IANADFIFKEWKKLDKAKKVMENQMFEEKQAESMPEIETEQEYKEIFITP
```

-continued

HQIKHIKDFKDYKYSHRVDKKPNAELINDTLYSTRKDDKGNTLIVNNLNG

LYDKDNDKLKKLINKSPEKLLMYHHDPQTYQKLKLIMEQYGDEKNPLYKY

YEETGNYLTKYSKKDNGPVIKKIKYYGNKLNAHLDITDDYPNSRNKVVKL

SLKPYRFDVYLDNGVYKFVTVKNLDVIKKENYYEVNSKCYEEAKKLKKIS

NQAEFIAFYNNDLIKINGELRVIGVNNDLLNRIEVNMIDITYREYLENMN

DKRPPRIIKTIASKTQSIKKYSTDILGNLYEVKSKKHPQIIKKGKRPAAT

KKAGQAKKKKGSYPYDVPDYAYPYDVPDYAYPYDVPDYA*

The TETHR protein is expressed as a single peptide in human cells. Detection of both Flag (N-terminus) and HA (C-terminus) tags with respective antibodies shows successful expression of a protein of the expected molecular weight.

FIGS. 38A-H show an exemplary TETHR open reading frame.

Unless defined otherwise, all technical and scientific terms used herein have the same meaning as commonly understood by one of ordinary skill in the art to which the disclosure pertains. Other specifically defined terms are to be construed in a manner consistent with the definition provided herein. Although any methods and materials similar or equivalent to those described herein is often used in the practice for testing of the present disclosure, the preferred materials and methods are described herein. In describing and claiming the present disclosure, the following terminology will be used.

As used in this specification and the appended claims, the singular forms "a", "an" and "the" include plural referents unless the content clearly dictates otherwise. Thus, for example, reference to "a construct" includes a combination of two or more nucleic acid constructs, and the like.

Other embodiments and uses are apparent to one skilled in the art in light of the present disclosures. Those skilled in the art will appreciate that numerous changes and modifications can be made to the embodiments of the disclosure and that such changes and modifications can be made without departing from the spirit of the disclosure. It is, therefore, intended that the appended claims cover all such equivalent variations as fall within the true spirit and scope of the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

```
<160> NUMBER OF SEQ ID NOS: 40

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 16
<212> TYPE: PRT
<213> ORGANISM: Unknown
<220> FEATURE:
<223> OTHER INFORMATION: Description of Unknown:
      Nucleoplasmin peptide

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 20
<212> TYPE: PRT
<213> ORGANISM: Unknown
<220> FEATURE:
<223> OTHER INFORMATION: Description of Unknown:
      Nucleoplasmin peptide

<400> SEQUENCE: 3

Ala Val Lys Arg Pro Ala Ala Thr Lys Lys Ala Gly Gln Ala Lys Lys
1               5                   10                  15

Lys Lys Leu Asp
            20
```

```
<210> SEQ ID NO 4
<211> LENGTH: 25
<212> TYPE: PRT
<213> ORGANISM: Unknown
<220> FEATURE:
<223> OTHER INFORMATION: Description of Unknown:
      EGL-13 peptide

<400> SEQUENCE: 4

Met Ser Arg Arg Arg Lys Ala Asn Pro Thr Lys Leu Ser Glu Asn Ala
1               5                   10                  15

Lys Lys Leu Ala Lys Glu Val Glu Asn
            20                  25

<210> SEQ ID NO 5
<211> LENGTH: 9
<212> TYPE: PRT
<213> ORGANISM: Unknown
<220> FEATURE:
<223> OTHER INFORMATION: Description of Unknown:
      c-Myc peptide

<400> SEQUENCE: 5

Pro Ala Ala Lys Arg Val Lys Leu Asp
1               5

<210> SEQ ID NO 6
<211> LENGTH: 9
<212> TYPE: PRT
<213> ORGANISM: Unknown
<220> FEATURE:
<223> OTHER INFORMATION: Description of Unknown:
      TUS-protein peptide

<400> SEQUENCE: 6

Lys Leu Lys Ile Lys Arg Pro Val Lys
1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys or Arg

<400> SEQUENCE: 7

Lys Xaa Xaa Xaa
1

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
      consensus peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(14)
<223> OTHER INFORMATION: Any amino acid
<220> FEATURE:
<221> NAME/KEY: MISC_FEATURE
<222> LOCATION: (3)..(14)
<223> OTHER INFORMATION: This region may encompass 10-12 residues
<220> FEATURE:
<221> NAME/KEY: MOD_RES
<222> LOCATION: (15)..(19)
<223> OTHER INFORMATION: Any amino acid
<220> FEATURE:
<221> NAME/KEY: MISC_FEATURE
<222> LOCATION: (15)..(19)
<223> OTHER INFORMATION: This region must include at least three of
      either lysine or arginine
<220> FEATURE:
<223> OTHER INFORMATION: See specification as filed for detailed
      description of substitutions and preferred embodiments

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 9
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 'Gly Gly Gly
      Gly Ser' repeating units
<220> FEATURE:
<223> OTHER INFORMATION: See specification as filed for detailed
      description of substitutions and preferred embodiments

<400> SEQUENCE: 9

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
        35                  40                  45

Gly Ser
    50

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
```

```
<223> OTHER INFORMATION: This sequence may encompass 1-10 'Gly Gly Gly
      Ser' repeating units
<220> FEATURE:
<223> OTHER INFORMATION: See specification as filed for detailed
      description of substitutions and preferred embodiments

<400> SEQUENCE: 10

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Ser Gly Gly Ser
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Ser Gly Gly Gly Ser
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser Gly Gly Gly Gly Ser
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Gly Ser
1

<210> SEQ ID NO 15
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 15

Gly Gly Ser Gly Gly Ser Gly Gly Ser Gly Gly Ser
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Ser Gly Gly Gly Ser Gly Gly Gly Ser Gly Gly Gly Ser
1               5                   10                  15

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Gly Ser Gly Gly Gly Gly Ser Gly
1               5                   10                  15

Gly Gly Gly Ser
            20

<210> SEQ ID NO 18
<211> LENGTH: 5
<212> TYPE: PRT
<213> ORGANISM: Unknown
<220> FEATURE:
<223> OTHER INFORMATION: Description of Unknown:
      Yeast transcription repressor Mat-alpha-2 peptide

<400> SEQUENCE: 18

Lys Ile Pro Ile Lys
1               5

<210> SEQ ID NO 19
<211> LENGTH: 1344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Asp Tyr Lys Asp His Asp Gly Asp Tyr Lys Asp His Asp Ile Asp
1               5                   10                  15

Tyr Lys Asp Asp Asp Asp Lys Gly Ala Pro Lys Lys Arg Lys Val
            20                  25                  30

Gly Gly Gly Gly Ser Gly Glu Gln Arg Ile Thr Leu Lys Asp Tyr Ala
            35                  40                  45

Met Arg Phe Gly Gln Thr Lys Thr Ala Lys Asp Leu Gly Val Tyr Gln
        50                  55                  60

Ser Ala Ile Asn Lys Ala Ile His Ala Gly Arg Lys Ile Phe Leu Thr
65                  70                  75                  80

-continued

```
Ile Asn Ala Asp Gly Ser Val Tyr Ala Glu Val Lys Pro Phe Pro
                 85                  90                  95
Ser Asn Lys Lys Thr Thr Ala Ala Gly Thr Gly Ser Gly Gly Met
            100                 105                 110
Glu Gln Arg Ile Thr Leu Lys Asp Tyr Ala Met Arg Phe Gly Gln Thr
            115                 120                 125
Lys Thr Ala Lys Asp Leu Gly Val Tyr Gln Ser Ala Ile Asn Lys Ala
130                 135                 140
Ile His Ala Gly Arg Lys Ile Phe Leu Thr Ile Asn Ala Asp Gly Ser
145                 150                 155                 160
Val Tyr Ala Glu Glu Val Lys Pro Phe Pro Ser Asn Lys Lys Thr Thr
                165                 170                 175
Ala Gly Gly Gly Gly Ser Gly Gly Gly Ser Gly Ala Glu Ala Ala
                180                 185                 190
Ala Lys Glu Ala Ala Lys Glu Ala Ala Lys Glu Ala Ala Ala
            195                 200                 205
Lys Ala Leu Glu Ala Glu Ala Ala Lys Glu Ala Ala Lys Glu
210                 215                 220
Ala Ala Ala Lys Glu Ala Ala Lys Ala Gly Gly Gly Ser Gly
225                 230                 235                 240
Ile His Gly Val Pro Ala Ala Lys Arg Asn Tyr Ile Leu Gly Leu Ala
                245                 250                 255
Ile Gly Ile Thr Ser Val Gly Tyr Gly Ile Ile Asp Tyr Glu Thr Arg
            260                 265                 270
Asp Val Ile Asp Ala Gly Val Arg Leu Phe Lys Glu Ala Asn Val Glu
            275                 280                 285
Asn Asn Glu Gly Arg Arg Ser Lys Arg Gly Ala Arg Arg Leu Lys Arg
290                 295                 300
Arg Arg Arg His Arg Ile Gln Arg Val Lys Lys Leu Leu Phe Asp Tyr
305                 310                 315                 320
Asn Leu Leu Thr Asp His Ser Glu Leu Ser Gly Ile Asn Pro Tyr Glu
                325                 330                 335
Ala Arg Val Lys Gly Leu Ser Gln Lys Leu Ser Glu Glu Phe Ser
            340                 345                 350
Ala Ala Leu Leu His Leu Ala Lys Arg Arg Gly Val His Asn Val Asn
            355                 360                 365
Glu Val Glu Glu Asp Thr Gly Asn Glu Leu Ser Thr Lys Glu Gln Ile
                370                 375                 380
Ser Arg Asn Ser Lys Ala Leu Glu Glu Lys Tyr Val Ala Glu Leu Gln
385                 390                 395                 400
Leu Glu Arg Leu Lys Lys Asp Gly Glu Val Arg Gly Ser Ile Asn Arg
                405                 410                 415
Phe Lys Thr Ser Asp Tyr Val Lys Glu Ala Lys Gln Leu Leu Lys Val
            420                 425                 430
Gln Lys Ala Tyr His Gln Leu Asp Gln Ser Phe Ile Asp Thr Tyr Ile
            435                 440                 445
Asp Leu Leu Glu Thr Arg Arg Thr Tyr Tyr Glu Gly Pro Gly Glu Gly
            450                 455                 460
Ser Pro Phe Gly Trp Lys Asp Ile Lys Glu Trp Tyr Glu Met Leu Met
465                 470                 475                 480
Gly His Cys Thr Tyr Phe Pro Glu Glu Leu Arg Ser Val Lys Tyr Ala
                485                 490                 495
Tyr Asn Ala Asp Leu Tyr Asn Ala Leu Asn Asp Leu Asn Asn Leu Val
```

-continued

```
                500                 505                 510
Ile Thr Arg Asp Glu Asn Glu Lys Leu Glu Tyr Tyr Glu Lys Phe Gln
            515                 520                 525
Ile Ile Glu Asn Val Phe Lys Gln Lys Lys Pro Thr Leu Lys Gln
            530                 535                 540
Ile Ala Lys Glu Ile Leu Val Asn Glu Glu Asp Ile Lys Gly Tyr Arg
545                 550                 555                 560
Val Thr Ser Thr Gly Lys Pro Glu Phe Thr Asn Leu Lys Val Tyr His
                565                 570                 575
Asp Ile Lys Asp Ile Thr Ala Arg Lys Glu Ile Ile Glu Asn Ala Glu
                580                 585                 590
Leu Leu Asp Gln Ile Ala Lys Ile Leu Thr Ile Tyr Gln Ser Ser Glu
            595                 600                 605
Asp Ile Gln Glu Glu Leu Thr Asn Leu Asn Ser Glu Leu Thr Gln Glu
            610                 615                 620
Glu Ile Glu Gln Ile Ser Asn Leu Lys Gly Tyr Thr Gly Thr His Asn
625                 630                 635                 640
Leu Ser Leu Lys Ala Ile Asn Leu Ile Leu Asp Glu Leu Trp His Thr
                645                 650                 655
Asn Asp Asn Gln Ile Ala Ile Phe Asn Arg Leu Lys Leu Val Pro Lys
                660                 665                 670
Lys Val Asp Leu Ser Gln Gln Lys Glu Ile Pro Thr Thr Leu Val Asp
            675                 680                 685
Asp Phe Ile Leu Ser Pro Val Val Lys Arg Ser Phe Ile Gln Ser Ile
            690                 695                 700
Lys Val Ile Asn Ala Ile Ile Lys Lys Tyr Gly Leu Pro Asn Asp Ile
705                 710                 715                 720
Ile Ile Glu Leu Ala Arg Glu Lys Asn Ser Lys Asp Ala Gln Lys Met
                725                 730                 735
Ile Asn Glu Met Gln Lys Arg Asn Arg Gln Thr Asn Glu Arg Ile Glu
                740                 745                 750
Glu Ile Ile Arg Thr Thr Gly Lys Glu Asn Ala Lys Tyr Leu Ile Glu
            755                 760                 765
Lys Ile Lys Leu His Asp Met Gln Glu Gly Lys Cys Leu Tyr Ser Leu
            770                 775                 780
Glu Ala Ile Pro Leu Glu Asp Leu Leu Asn Asn Pro Phe Asn Tyr Glu
785                 790                 795                 800
Val Asp His Ile Ile Pro Arg Ser Val Ser Phe Asp Asn Ser Phe Asn
                805                 810                 815
Asn Lys Val Leu Val Lys Gln Glu Glu Ala Ser Lys Lys Gly Asn Arg
                820                 825                 830
Thr Pro Phe Gln Tyr Leu Ser Ser Ser Asp Ser Lys Ile Ser Tyr Glu
            835                 840                 845
Thr Phe Lys Lys His Ile Leu Asn Leu Ala Lys Gly Lys Gly Arg Ile
            850                 855                 860
Ser Lys Thr Lys Lys Glu Tyr Leu Leu Glu Glu Arg Asp Ile Asn Arg
865                 870                 875                 880
Phe Ser Val Gln Lys Asp Phe Ile Asn Arg Asn Leu Val Asp Thr Arg
                885                 890                 895
Tyr Ala Thr Arg Gly Leu Met Asn Leu Leu Arg Ser Tyr Phe Arg Val
                900                 905                 910
Asn Asn Leu Asp Val Lys Val Lys Ser Ile Asn Gly Gly Phe Thr Ser
            915                 920                 925
```

```
Phe Leu Arg Arg Lys Trp Lys Phe Lys Lys Glu Arg Asn Lys Gly Tyr
    930             935             940

Lys His His Ala Glu Asp Ala Leu Ile Ile Ala Asn Ala Asp Phe Ile
945             950             955             960

Phe Lys Glu Trp Lys Lys Leu Asp Lys Ala Lys Lys Val Met Glu Asn
            965             970             975

Gln Met Phe Glu Glu Lys Gln Ala Glu Ser Met Pro Glu Ile Glu Thr
        980             985             990

Glu Gln Glu Tyr Lys Glu Ile Phe Ile Thr Pro His Gln Ile Lys His
    995             1000            1005

Ile Lys Asp Phe Lys Asp Tyr Lys Tyr Ser His Arg Val Asp Lys
    1010            1015            1020

Lys Pro Asn Arg Glu Leu Ile Asn Asp Thr Leu Tyr Ser Thr Arg
    1025            1030            1035

Lys Asp Asp Lys Gly Asn Thr Leu Ile Val Asn Asn Leu Asn Gly
    1040            1045            1050

Leu Tyr Asp Lys Asp Asn Asp Lys Leu Lys Lys Leu Ile Asn Lys
    1055            1060            1065

Ser Pro Glu Lys Leu Leu Met Tyr His His Asp Pro Gln Thr Tyr
    1070            1075            1080

Gln Lys Leu Lys Leu Ile Met Glu Gln Tyr Gly Asp Glu Lys Asn
    1085            1090            1095

Pro Leu Tyr Lys Tyr Tyr Glu Glu Thr Gly Asn Tyr Leu Thr Lys
    1100            1105            1110

Tyr Ser Lys Lys Asp Asn Gly Pro Val Ile Lys Lys Ile Lys Tyr
    1115            1120            1125

Tyr Gly Asn Lys Leu Asn Ala His Leu Asp Ile Thr Asp Asp Tyr
    1130            1135            1140

Pro Asn Ser Arg Asn Lys Val Val Lys Leu Ser Leu Lys Pro Tyr
    1145            1150            1155

Arg Phe Asp Val Tyr Leu Asp Asn Gly Val Tyr Lys Phe Val Thr
    1160            1165            1170

Val Lys Asn Leu Asp Val Ile Lys Lys Glu Asn Tyr Tyr Glu Val
    1175            1180            1185

Asn Ser Lys Cys Tyr Glu Glu Ala Lys Lys Leu Lys Lys Ile Ser
    1190            1195            1200

Asn Gln Ala Glu Phe Ile Ala Ser Phe Tyr Asn Asn Asp Leu Ile
    1205            1210            1215

Lys Ile Asn Gly Glu Leu Tyr Arg Val Ile Gly Val Asn Asn Asp
    1220            1225            1230

Leu Leu Asn Arg Ile Glu Val Asn Met Ile Asp Ile Thr Tyr Arg
    1235            1240            1245

Glu Tyr Leu Glu Asn Met Asn Asp Lys Arg Pro Pro Arg Ile Ile
    1250            1255            1260

Lys Thr Ile Ala Ser Lys Thr Gln Ser Ile Lys Lys Tyr Ser Thr
    1265            1270            1275

Asp Ile Leu Gly Asn Leu Tyr Glu Val Lys Ser Lys Lys His Pro
    1280            1285            1290

Gln Ile Ile Lys Lys Gly Lys Arg Pro Ala Ala Thr Lys Lys Ala
    1295            1300            1305

Gly Gln Ala Lys Lys Lys Lys Gly Ser Tyr Pro Tyr Asp Val Pro
    1310            1315            1320
```

Asp Tyr Ala Tyr Pro Tyr Asp Val Pro Asp Tyr Ala Tyr Pro Tyr
    1325                1330                1335

Asp Val Pro Asp Tyr Ala
    1340

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggttttggac actggaaccg tgg                                            23

<210> SEQ ID NO 21
<211> LENGTH: 45
<212> TYPE: DNA
<213> ORGANISM: Drosophila sp.
<220> FEATURE:
<221> NAME/KEY: CDS
<222> LOCATION: (1)..(45)

<400> SEQUENCE: 21 ggt cgg ctg tgg gtt ttg gac act gga acc gtg ggc atc ggc aat        45
Gly Arg Leu Trp Val Leu Asp Thr Gly Thr Val Gly Ile Gly Asn
1               5                   10                  15

<210> SEQ ID NO 22
<211> LENGTH: 15
<212> TYPE: PRT
<213> ORGANISM: Drosophila sp.

<400> SEQUENCE: 22

Gly Arg Leu Trp Val Leu Asp Thr Gly Thr Val Gly Ile Gly Asn
1               5                   10                  15

<210> SEQ ID NO 23
<211> LENGTH: 46
<212> TYPE: DNA
<213> ORGANISM: Drosophila sp.
<220> FEATURE:
<221> NAME/KEY: CDS
<222> LOCATION: (1)..(45)

<400> SEQUENCE: 23 ggt cgg ctg tgg gtt ttg gac act gga tgc cgt ggg cat cgg caa t      46
Gly Arg Leu Trp Val Leu Asp Thr Gly Cys Arg Gly His Arg Gln
1               5                   10                  15

<210> SEQ ID NO 24
<211> LENGTH: 15
<212> TYPE: PRT
<213> ORGANISM: Drosophila sp.

<400> SEQUENCE: 24

Gly Arg Leu Trp Val Leu Asp Thr Gly Cys Arg Gly His Arg Gln
1               5                   10                  15

<210> SEQ ID NO 25
<211> LENGTH: 39
<212> TYPE: DNA
<213> ORGANISM: Drosophila sp.
<220> FEATURE:
<221> NAME/KEY: CDS
<222> LOCATION: (1)..(39)

<400> SEQUENCE: 25

| ggt | cgg | ctg | tgg | gtt | ttg | gac | acc | gtg | ggc | atc | ggc | aat | | 39 |
| Gly | Arg | Leu | Trp | Val | Leu | Asp | Thr | Val | Gly | Ile | Gly | Asn | | |
| 1 | | | | 5 | | | | | 10 | | | | | |

<210> SEQ ID NO 26
<211> LENGTH: 13
<212> TYPE: PRT
<213> ORGANISM: Drosophila sp.

<400> SEQUENCE: 26

Gly Arg Leu Trp Val Leu Asp Thr Val Gly Ile Gly Asn
1               5                   10

<210> SEQ ID NO 27
<211> LENGTH: 45
<212> TYPE: DNA
<213> ORGANISM: Drosophila sp.
<220> FEATURE:
<221> NAME/KEY: CDS
<222> LOCATION: (1)..(45)

<400> SEQUENCE: 27

| ggt | cgg | ctg | tgg | gtt | ttg | gac | act | gga | atc | gtg | ggc | atc | ggc | aat | 45 |
| Gly | Arg | Leu | Trp | Val | Leu | Asp | Thr | Gly | Ile | Val | Gly | Ile | Gly | Asn | |
| 1 | | | | 5 | | | | | 10 | | | | | 15 | |

<210> SEQ ID NO 28
<211> LENGTH: 15
<212> TYPE: PRT
<213> ORGANISM: Drosophila sp.

<400> SEQUENCE: 28

Gly Arg Leu Trp Val Leu Asp Thr Gly Ile Val Gly Ile Gly Asn
1               5                   10                  15

<210> SEQ ID NO 29
<211> LENGTH: 42
<212> TYPE: DNA
<213> ORGANISM: Drosophila sp.
<220> FEATURE:
<221> NAME/KEY: CDS
<222> LOCATION: (1)..(42)

<400> SEQUENCE: 29

| ggt | cgg | ctg | tgg | gtt | ttg | gac | act | gga | atc | tac | atc | ggc | aat | 42 |
| Gly | Arg | Leu | Trp | Val | Leu | Asp | Thr | Gly | Ile | Tyr | Ile | Gly | Asn | |
| 1 | | | | 5 | | | | | 10 | | | | | |

<210> SEQ ID NO 30
<211> LENGTH: 14
<212> TYPE: PRT
<213> ORGANISM: Drosophila sp.

<400> SEQUENCE: 30

Gly Arg Leu Trp Val Leu Asp Thr Gly Ile Tyr Ile Gly Asn
1               5                   10

<210> SEQ ID NO 31
<211> LENGTH: 26
<212> TYPE: DNA
<213> ORGANISM: Drosophila sp.

<400> SEQUENCE: 31
ggtcggctgt gggttttgga cactgg                                      26

<210> SEQ ID NO 32
<211> LENGTH: 17
<212> TYPE: DNA
<213> ORGANISM: Drosophila sp.

<400> SEQUENCE: 32
ccgtgggcat cggcaat                                                  17

<210> SEQ ID NO 33
<211> LENGTH: 31
<212> TYPE: DNA
<213> ORGANISM: Drosophila sp.

<400> SEQUENCE: 33
tgtgggtttt ggacactgga accgtgggca t                                  31

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gguuuuggac acuggaaccg                                               20

<210> SEQ ID NO 35
<211> LENGTH: 33
<212> TYPE: DNA
<213> ORGANISM: Drosophila sp.

<400> SEQUENCE: 35
ggatgcccac ggttccagtg tccaaaaccc aca                                33

<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaaaaaaaaa aa                                                       12

<210> SEQ ID NO 37
<211> LENGTH: 32
<212> TYPE: DNA
<213> ORGANISM: Drosophila sp.

<400> SEQUENCE: 37
tgtgggtttt ggacactgga accgtgggca tc                                 32

<210> SEQ ID NO 38
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other -continued

```
<220> FEATURE:
<221> NAME/KEY: modified_base
<222> LOCATION: (24)..(39)
<223> OTHER INFORMATION: a, c, t, g, unknown or other
<220> FEATURE:
<221> NAME/KEY: modified_base
<222> LOCATION: (42)..(62)
<223> OTHER INFORMATION: a, c, t, g, unknown or other

<400> SEQUENCE: 38
nnnnnnnnnn nnnnnnnnnn nggnnnnnnn nnnnnnnnnc cnnnnnnnnn nnnnnnnnnn    60 nn                                                                   62

<210> SEQ ID NO 39
<211> LENGTH: 4035
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (4)..(4032)

<400> SEQUENCE: 39 atg gac tat aag gac cac gac gga gac tac aag gat cat gat att gat        48
    Asp Tyr Lys Asp His Asp Gly Asp Tyr Lys Asp His Asp Ile Asp
    1               5                  10                  15 tac aaa gac gat gac gat aag gga gcc cca aag aag aag cgg aag gtc        96
Tyr Lys Asp Asp Asp Asp Lys Gly Ala Pro Lys Lys Lys Arg Lys Val
                20                  25                  30 ggc ggt ggg ggg tca ggc gaa cag aga att aca ctc aag gac tat gcc       144
Gly Gly Gly Gly Ser Gly Glu Gln Arg Ile Thr Leu Lys Asp Tyr Ala
            35                  40                  45 atg aga ttc ggg caa act aaa aca gca aaa gac ttg ggt gtt tac caa       192
Met Arg Phe Gly Gln Thr Lys Thr Ala Lys Asp Leu Gly Val Tyr Gln
        50                  55                  60 tcc gct atc aac aag gca ata cac gct ggt aga aaa att ttc ctc acg       240
Ser Ala Ile Asn Lys Ala Ile His Ala Gly Arg Lys Ile Phe Leu Thr
    65                  70                  75 ata aat gct gat ggc agc gtc tat gcg gag gag gtc aag cct ttt cct       288
Ile Asn Ala Asp Gly Ser Val Tyr Ala Glu Glu Val Lys Pro Phe Pro
80                  85                  90                  95 agc aat aag aaa acg aca gcc gcc ggt acc ggt ggc tct ggc ggt atg       336
Ser Asn Lys Lys Thr Thr Ala Ala Gly Thr Gly Gly Ser Gly Gly Met
                100                 105                 110 gag caa cgg atc acc ttg aaa gat tac gct atg cgg ttt ggc cag aca       384
Glu Gln Arg Ile Thr Leu Lys Asp Tyr Ala Met Arg Phe Gly Gln Thr
            115                 120                 125 aag acc gct aag gat ctc ggc gtg tat cag agc gcc att aat aaa gct       432
Lys Thr Ala Lys Asp Leu Gly Val Tyr Gln Ser Ala Ile Asn Lys Ala
        130                 135                 140 atc cat gcc ggc cgg aag atc ttt ttg aca atc aac gca gac gga tcc       480
Ile His Ala Gly Arg Lys Ile Phe Leu Thr Ile Asn Ala Asp Gly Ser
    145                 150                 155 gtg tac gcc gaa gaa gtg aaa cca ttc cca tcc aac aaa aag acc act       528
Val Tyr Ala Glu Glu Val Lys Pro Phe Pro Ser Asn Lys Lys Thr Thr
160                 165                 170                 175 gct ggc gga ggt ggt tct gga ggc ggg ggt tca ggc gct gaa gca gct       576
Ala Gly Gly Gly Gly Ser Gly Gly Gly Gly Ser Gly Ala Glu Ala Ala
                180                 185                 190 gcg aaa gag gcc gca gct aaa gaa gcg gcc gca aag gag gct gcg gcc       624
Ala Lys Glu Ala Ala Ala Lys Glu Ala Ala Ala Lys Glu Ala Ala Ala
```

```
                195                 200                 205
aag gct ctg gag gcg gaa gcc gcg gca aag gag gcg gca gct aaa gaa    672
Lys Ala Leu Glu Ala Glu Ala Ala Ala Lys Glu Ala Ala Ala Lys Glu
            210                 215                 220 gct gca gcg aaa gag gca gcc gct aag gcc ggc ggt ggc ggc tct ggt    720
Ala Ala Ala Lys Glu Ala Ala Ala Lys Ala Gly Gly Gly Gly Ser Gly
        225                 230                 235 atc cac gga gtc cca gca gcc aag cgg aac tac atc ctg ggc ctg gcc    768
Ile His Gly Val Pro Ala Ala Lys Arg Asn Tyr Ile Leu Gly Leu Ala
240                 245                 250                 255 atc ggc atc acc agc gtg ggc tac ggc atc atc gac tac gag aca cgg    816
Ile Gly Ile Thr Ser Val Gly Tyr Gly Ile Ile Asp Tyr Glu Thr Arg
                260                 265                 270 gac gtg atc gat gcc ggc gtg cgg ctg ttc aaa gag gcc aac gtg gaa    864
Asp Val Ile Asp Ala Gly Val Arg Leu Phe Lys Glu Ala Asn Val Glu
            275                 280                 285 aac aac gag ggc agg cgg agc aag aga ggc gcc aga agg ctg aag cgg    912
Asn Asn Glu Gly Arg Arg Ser Lys Arg Gly Ala Arg Arg Leu Lys Arg
        290                 295                 300 cgg agg cgg cat aga atc cag aga gtg aag aag ctg ctg ttc gac tac    960
Arg Arg Arg His Arg Ile Gln Arg Val Lys Lys Leu Leu Phe Asp Tyr
305                 310                 315 aac ctg ctg acc gac cac agc gag ctg agc ggc atc aac ccc tac gag   1008
Asn Leu Leu Thr Asp His Ser Glu Leu Ser Gly Ile Asn Pro Tyr Glu
320                 325                 330                 335 gcc aga gtg aag ggc ctg agc cag aag ctg agc gag gaa gag ttc tct   1056
Ala Arg Val Lys Gly Leu Ser Gln Lys Leu Ser Glu Glu Glu Phe Ser
            340                 345                 350 gcc gcc ctg ctg cac ctg gcc aag aga aga ggc gtg cac aac gtg aac   1104
Ala Ala Leu Leu His Leu Ala Lys Arg Arg Gly Val His Asn Val Asn
        355                 360                 365 gag gtg gaa gag gac acc ggc aac gag ctg tcc acc aaa gag cag atc   1152
Glu Val Glu Glu Asp Thr Gly Asn Glu Leu Ser Thr Lys Glu Gln Ile
    370                 375                 380 agc cgg aac agc aag gcc ctg gaa gag aaa tac gtg gcc gaa ctg cag   1200
Ser Arg Asn Ser Lys Ala Leu Glu Glu Lys Tyr Val Ala Glu Leu Gln
385                 390                 395 ctg gaa cgg ctg aag aaa gac ggc gaa gtg cgg ggc agc atc aac aga   1248
Leu Glu Arg Leu Lys Lys Asp Gly Glu Val Arg Gly Ser Ile Asn Arg
400                 405                 410                 415 ttc aag acc agc gac tac gtg aaa gaa gcc aaa cag ctg ctg aag gtg   1296
Phe Lys Thr Ser Asp Tyr Val Lys Glu Ala Lys Gln Leu Leu Lys Val
            420                 425                 430 cag aag gcc tac cac cag ctg gac cag agc ttc atc gac acc tac atc   1344
Gln Lys Ala Tyr His Gln Leu Asp Gln Ser Phe Ile Asp Thr Tyr Ile
        435                 440                 445 gac ctg ctg gaa acc cgg cgg acc tac tat gag gga cct ggc gag ggc   1392
Asp Leu Leu Glu Thr Arg Arg Thr Tyr Tyr Glu Gly Pro Gly Glu Gly
    450                 455                 460 agc ccc ttc ggc tgg aag gac atc aaa gaa tgg tac gag atg ctg atg   1440
Ser Pro Phe Gly Trp Lys Asp Ile Lys Glu Trp Tyr Glu Met Leu Met
465                 470                 475 ggc cac tgc acc tac ttc ccc gag gaa ctg cgg agc gtg aag tac gcc   1488
Gly His Cys Thr Tyr Phe Pro Glu Glu Leu Arg Ser Val Lys Tyr Ala
            480                 485                 490                 495 tac aac gcc gac ctg tac aac gcc ctg aac gac ctg aac aat ctc gtg   1536
Tyr Asn Ala Asp Leu Tyr Asn Ala Leu Asn Asp Leu Asn Asn Leu Val
                500                 505                 510 atc acc agg gac gag aac gag aag ctg gaa tat tac gag aag ttc cag   1584
Ile Thr Arg Asp Glu Asn Glu Lys Leu Glu Tyr Tyr Glu Lys Phe Gln
```

```
                Ile Thr Arg Asp Glu Asn Glu Lys Leu Glu Tyr Tyr Glu Lys Phe Gln
                                515                 520                 525 atc atc gag aac gtg ttc aag cag aag aag aag ccc acc ctg aag cag        1632
Ile Ile Glu Asn Val Phe Lys Gln Lys Lys Lys Pro Thr Leu Lys Gln
            530                 535                 540 atc gcc aaa gaa atc ctc gtg aac gaa gag gat att aag ggc tac aga        1680
Ile Ala Lys Glu Ile Leu Val Asn Glu Glu Asp Ile Lys Gly Tyr Arg
545                 550                 555 gtg acc agc acc ggc aag ccc gag ttc acc aac ctg aag gtg tac cac        1728
Val Thr Ser Thr Gly Lys Pro Glu Phe Thr Asn Leu Lys Val Tyr His
560                 565                 570                 575 gac atc aag gac att acc gcc cgg aaa gag att att gag aac gcc gag        1776
Asp Ile Lys Asp Ile Thr Ala Arg Lys Glu Ile Ile Glu Asn Ala Glu
                580                 585                 590 ctg ctg gat cag att gcc aag atc ctg acc atc tac cag agc agc gag        1824
Leu Leu Asp Gln Ile Ala Lys Ile Leu Thr Ile Tyr Gln Ser Ser Glu
            595                 600                 605 gac atc cag gaa gaa ctg acc aat ctg aac tcc gag ctg acc cag gaa        1872
Asp Ile Gln Glu Glu Leu Thr Asn Leu Asn Ser Glu Leu Thr Gln Glu
        610                 615                 620 gag atc gag cag atc tct aat ctg aag ggc tat acc ggc acc cac aac        1920
Glu Ile Glu Gln Ile Ser Asn Leu Lys Gly Tyr Thr Gly Thr His Asn
625                 630                 635 ctg agc ctg aag gcc atc aac ctg atc ctg gac gag ctg tgg cac acc        1968
Leu Ser Leu Lys Ala Ile Asn Leu Ile Leu Asp Glu Leu Trp His Thr
640                 645                 650                 655 aac gac aac cag atc gct atc ttc aac cgg ctg aag ctg gtg ccc aag        2016
Asn Asp Asn Gln Ile Ala Ile Phe Asn Arg Leu Lys Leu Val Pro Lys
                660                 665                 670 aag gtg gac ctg tcc cag cag aaa gag atc ccc acc acc ctg gtg gac        2064
Lys Val Asp Leu Ser Gln Gln Lys Glu Ile Pro Thr Thr Leu Val Asp
            675                 680                 685 gac ttc atc ctg agc ccc gtc gtg aag aga agc ttc atc cag agc atc        2112
Asp Phe Ile Leu Ser Pro Val Val Lys Arg Ser Phe Ile Gln Ser Ile
        690                 695                 700 aaa gtg atc aac gcc atc atc aag aag tac ggc ctg ccc aac gac atc        2160
Lys Val Ile Asn Ala Ile Ile Lys Lys Tyr Gly Leu Pro Asn Asp Ile
705                 710                 715 att atc gag ctg gcc cgc gag aag aac tcc aag gac gcc cag aaa atg        2208
Ile Ile Glu Leu Ala Arg Glu Lys Asn Ser Lys Asp Ala Gln Lys Met
720                 725                 730                 735 atc aac gag atg cag aag cgg aac cgg cag acc aac gag cgg atc gag        2256
Ile Asn Glu Met Gln Lys Arg Asn Arg Gln Thr Asn Glu Arg Ile Glu
                740                 745                 750 gaa atc atc cgg acc acc ggc aaa gag aac gcc aag tac ctg atc gag        2304
Glu Ile Ile Arg Thr Thr Gly Lys Glu Asn Ala Lys Tyr Leu Ile Glu
            755                 760                 765 aag atc aag ctg cac gac atg cag gaa ggc aag tgc ctg tac agc ctg        2352
Lys Ile Lys Leu His Asp Met Gln Glu Gly Lys Cys Leu Tyr Ser Leu
        770                 775                 780 gaa gcc atc cct ctg gaa gat ctg ctg aac aac ccc ttc aac tat gag        2400
Glu Ala Ile Pro Leu Glu Asp Leu Leu Asn Asn Pro Phe Asn Tyr Glu
785                 790                 795 gtg gac cac atc atc ccc aga agc gtg tcc ttc gac aac agc ttc aac        2448
Val Asp His Ile Ile Pro Arg Ser Val Ser Phe Asp Asn Ser Phe Asn
800                 805                 810                 815 aac aag gtg ctc gtg aag cag gaa gaa gcc agc aag aag ggc aac cgg        2496
Asn Lys Val Leu Val Lys Gln Glu Glu Ala Ser Lys Lys Gly Asn Arg
                820                 825                 830
```

|  |  |
|---|---|
| acc cca ttc cag tac ctg agc agc agc gac agc aag atc agc tac gaa<br>Thr Pro Phe Gln Tyr Leu Ser Ser Ser Asp Ser Lys Ile Ser Tyr Glu<br>835            840            845 | 2544 |
| acc ttc aag aag cac atc ctg aat ctg gcc aag ggc aag ggc aga atc<br>Thr Phe Lys Lys His Ile Leu Asn Leu Ala Lys Gly Lys Gly Arg Ile<br>850            855            860 | 2592 |
| agc aag acc aag aaa gag tat ctg ctg gaa gaa cgg gac atc aac agg<br>Ser Lys Thr Lys Lys Glu Tyr Leu Leu Glu Glu Arg Asp Ile Asn Arg<br>865            870            875 | 2640 |
| ttc tcc gtg cag aaa gac ttc atc aac cgg aac ctg gtg gat acc aga<br>Phe Ser Val Gln Lys Asp Phe Ile Asn Arg Asn Leu Val Asp Thr Arg<br>880            885            890            895 | 2688 |
| tac gcc acc aga ggc ctg atg aac ctg ctg cgg agc tac ttc aga gtg<br>Tyr Ala Thr Arg Gly Leu Met Asn Leu Leu Arg Ser Tyr Phe Arg Val<br>            900            905            910 | 2736 |
| aac aac ctg gac gtg aaa gtg aag tcc atc aat ggc ggc ttc acc agc<br>Asn Asn Leu Asp Val Lys Val Lys Ser Ile Asn Gly Gly Phe Thr Ser<br>915            920            925 | 2784 |
| ttt ctg cgg cgg aag tgg aag ttt aag aaa gag cgg aac aag ggg tac<br>Phe Leu Arg Arg Lys Trp Lys Phe Lys Lys Glu Arg Asn Lys Gly Tyr<br>930            935            940 | 2832 |
| aag cac cac gcc gag gac gcc ctg atc att gcc aac gcc gat ttc atc<br>Lys His His Ala Glu Asp Ala Leu Ile Ile Ala Asn Ala Asp Phe Ile<br>945            950            955 | 2880 |
| ttc aaa gag tgg aag aaa ctg gac aag gcc aaa aaa gtg atg gaa aac<br>Phe Lys Glu Trp Lys Lys Leu Asp Lys Ala Lys Lys Val Met Glu Asn<br>960            965            970            975 | 2928 |
| cag atg ttc gag gaa aag cag gcc gag agc atg ccc gag atc gaa acc<br>Gln Met Phe Glu Glu Lys Gln Ala Glu Ser Met Pro Glu Ile Glu Thr<br>            980            985            990 | 2976 |
| gag cag gag tac aaa gag atc ttc atc acc ccc cac cag atc aag cac<br>Glu Gln Glu Tyr Lys Glu Ile Phe Ile Thr Pro His Gln Ile Lys His<br>            995            1000          1005 | 3024 |
| att aag gac ttc aag gac tac aag tac agc cac cgg gtg gac aag<br>Ile Lys Asp Phe Lys Asp Tyr Lys Tyr Ser His Arg Val Asp Lys<br>            1010           1015           1020 | 3069 |
| aag cct aat aga gag ctg att aac gac acc ctg tac tcc acc cgg<br>Lys Pro Asn Arg Glu Leu Ile Asn Asp Thr Leu Tyr Ser Thr Arg<br>            1025           1030           1035 | 3114 |
| aag gac gac aag ggc aac acc ctg atc gtg aac aat ctg aac ggc<br>Lys Asp Asp Lys Gly Asn Thr Leu Ile Val Asn Asn Leu Asn Gly<br>            1040           1045           1050 | 3159 |
| ctg tac gac aag gac aat gac aag ctg aaa aag ctg atc aac aag<br>Leu Tyr Asp Lys Asp Asn Asp Lys Leu Lys Lys Leu Ile Asn Lys<br>            1055           1060           1065 | 3204 |
| agc ccc gaa aag ctg ctg atg tac cac cac gac ccc cag acc tac<br>Ser Pro Glu Lys Leu Leu Met Tyr His His Asp Pro Gln Thr Tyr<br>            1070           1075           1080 | 3249 |
| cag aaa ctg aag ctg att atg gaa cag tac ggc gac gag aag aat<br>Gln Lys Leu Lys Leu Ile Met Glu Gln Tyr Gly Asp Glu Lys Asn<br>            1085           1090           1095 | 3294 |
| ccc ctg tac aag tac tac gag gaa acc ggg aac tac ctg acc aag<br>Pro Leu Tyr Lys Tyr Tyr Glu Glu Thr Gly Asn Tyr Leu Thr Lys<br>            1100           1105           1110 | 3339 |
| tac tcc aaa aag gac aac ggc ccc gtg atc aag aag att aag tat<br>Tyr Ser Lys Lys Asp Asn Gly Pro Val Ile Lys Lys Ile Lys Tyr<br>            1115           1120           1125 | 3384 |
| tac ggc aac aaa ctg aac gcc cat ctg gac atc acc gac gac tac<br>Tyr Gly Asn Lys Leu Asn Ala His Leu Asp Ile Thr Asp Asp Tyr<br>            1130           1135           1140 | 3429 |

-continued

```
ccc aac agc aga aac aag gtc gtg aag ctg tcc ctg aag ccc tac      3474
Pro Asn Ser Arg Asn Lys Val Val Lys Leu Ser Leu Lys Pro Tyr
        1145                1150                1155 aga ttc gac gtg tac ctg gac aat ggc gtg tac aag ttc gtg acc      3519
Arg Phe Asp Val Tyr Leu Asp Asn Gly Val Tyr Lys Phe Val Thr
    1160                1165                1170 gtg aag aat ctg gat gtg atc aaa aaa gaa aac tac tac gaa gtg      3564
Val Lys Asn Leu Asp Val Ile Lys Lys Glu Asn Tyr Tyr Glu Val
    1175                1180                1185 aat agc aag tgc tat gag gaa gct aag aag ctg aag aag atc agc      3609
Asn Ser Lys Cys Tyr Glu Glu Ala Lys Lys Leu Lys Lys Ile Ser
    1190                1195                1200 aac cag gcc gag ttt atc gcc tcc ttc tac aac aac gat ctg atc      3654
Asn Gln Ala Glu Phe Ile Ala Ser Phe Tyr Asn Asn Asp Leu Ile
    1205                1210                1215 aag atc aac ggc gag ctg tat aga gtg atc ggc gtg aac aac gac      3699
Lys Ile Asn Gly Glu Leu Tyr Arg Val Ile Gly Val Asn Asn Asp
    1220                1225                1230 ctg ctg aac cgg atc gaa gtg aac atg atc gac atc acc tac cgc      3744
Leu Leu Asn Arg Ile Glu Val Asn Met Ile Asp Ile Thr Tyr Arg
    1235                1240                1245 gag tac ctg gaa aac atg aac gac aag agg ccc ccc agg atc att      3789
Glu Tyr Leu Glu Asn Met Asn Asp Lys Arg Pro Pro Arg Ile Ile
    1250                1255                1260 aag aca atc gcc tcc aag acc cag agc att aag aag tac agc aca      3834
Lys Thr Ile Ala Ser Lys Thr Gln Ser Ile Lys Lys Tyr Ser Thr
    1265                1270                1275 gac att ctg ggc aac ctg tat gaa gtg aaa tct aag aag cac cct      3879
Asp Ile Leu Gly Asn Leu Tyr Glu Val Lys Ser Lys Lys His Pro
    1280                1285                1290 cag atc atc aaa aag ggc aaa agg ccg gcg gcc acg aaa aag gcc      3924
Gln Ile Ile Lys Lys Gly Lys Arg Pro Ala Ala Thr Lys Lys Ala
    1295                1300                1305 ggc cag gca aaa aag aaa aag gga tcc tac cca tac gat gtt cca      3969
Gly Gln Ala Lys Lys Lys Lys Gly Ser Tyr Pro Tyr Asp Val Pro
    1310                1315                1320 gat tac gct tac cca tac gat gtt cca gat tac gct tac cca tac      4014
Asp Tyr Ala Tyr Pro Tyr Asp Val Pro Asp Tyr Ala Tyr Pro Tyr
    1325                1330                1335 gat gtt cca gat tac gct taa                                      4035
Asp Val Pro Asp Tyr Ala
    1340
```

```
<210> SEQ ID NO 40
<211> LENGTH: 1343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Tyr Lys Asp His Asp Gly Asp Tyr Lys Asp His Asp Ile Asp Tyr
1               5                   10                  15

Lys Asp Asp Asp Asp Lys Gly Ala Pro Lys Lys Arg Lys Val Gly
            20                  25                  30

Gly Gly Gly Ser Gly Glu Gln Arg Ile Thr Leu Lys Asp Tyr Ala Met
        35                  40                  45

Arg Phe Gly Gln Thr Lys Thr Ala Lys Asp Leu Gly Val Tyr Gln Ser
    50                  55                  60
```

```
Ala Ile Asn Lys Ala Ile His Ala Gly Arg Lys Ile Phe Leu Thr Ile
 65                  70                  75                  80

Asn Ala Asp Gly Ser Val Tyr Ala Glu Glu Val Lys Pro Phe Pro Ser
                 85                  90                  95

Asn Lys Lys Thr Thr Ala Ala Gly Thr Gly Ser Gly Gly Met Glu
                100                 105                 110

Gln Arg Ile Thr Leu Lys Asp Tyr Ala Met Arg Phe Gly Gln Thr Lys
                115                 120                 125

Thr Ala Lys Asp Leu Gly Val Tyr Gln Ser Ala Ile Asn Lys Ala Ile
    130                 135                 140

His Ala Gly Arg Lys Ile Phe Leu Thr Ile Asn Ala Asp Gly Ser Val
145                 150                 155                 160

Tyr Ala Glu Glu Val Lys Pro Phe Pro Ser Asn Lys Lys Thr Thr Ala
                165                 170                 175

Gly Gly Gly Gly Ser Gly Gly Gly Ser Gly Ala Glu Ala Ala Ala
                180                 185                 190

Lys Glu Ala Ala Ala Lys Glu Ala Ala Ala Lys Glu Ala Ala Ala Lys
                195                 200                 205

Ala Leu Glu Ala Glu Ala Ala Lys Glu Ala Ala Ala Lys Glu Ala
    210                 215                 220

Ala Ala Lys Glu Ala Ala Ala Lys Ala Gly Gly Gly Ser Gly Ile
225                 230                 235                 240

His Gly Val Pro Ala Ala Lys Arg Asn Tyr Ile Leu Gly Leu Ala Ile
                245                 250                 255

Gly Ile Thr Ser Val Gly Tyr Gly Ile Ile Asp Tyr Glu Thr Arg Asp
                260                 265                 270

Val Ile Asp Ala Gly Val Arg Leu Phe Lys Glu Ala Asn Val Glu Asn
                275                 280                 285

Asn Glu Gly Arg Arg Ser Lys Arg Gly Ala Arg Arg Leu Lys Arg Arg
                290                 295                 300

Arg Arg His Arg Ile Gln Arg Val Lys Lys Leu Leu Phe Asp Tyr Asn
305                 310                 315                 320

Leu Leu Thr Asp His Ser Glu Leu Ser Gly Ile Asn Pro Tyr Glu Ala
                325                 330                 335

Arg Val Lys Gly Leu Ser Gln Lys Leu Ser Glu Glu Glu Phe Ser Ala
                340                 345                 350

Ala Leu Leu His Leu Ala Lys Arg Arg Gly Val His Asn Val Asn Glu
                355                 360                 365

Val Glu Glu Asp Thr Gly Asn Glu Leu Ser Thr Lys Glu Gln Ile Ser
                370                 375                 380

Arg Asn Ser Lys Ala Leu Glu Glu Lys Tyr Val Ala Glu Leu Gln Leu
385                 390                 395                 400

Glu Arg Leu Lys Lys Asp Gly Glu Val Arg Gly Ser Ile Asn Arg Phe
                405                 410                 415

Lys Thr Ser Asp Tyr Val Lys Glu Ala Lys Gln Leu Leu Lys Val Gln
                420                 425                 430

Lys Ala Tyr His Gln Leu Asp Gln Ser Phe Ile Asp Thr Tyr Ile Asp
                435                 440                 445

Leu Leu Glu Thr Arg Arg Thr Tyr Tyr Glu Gly Pro Gly Glu Gly Ser
    450                 455                 460

Pro Phe Gly Trp Lys Asp Ile Lys Glu Trp Tyr Glu Met Leu Met Gly
465                 470                 475                 480
```

```
His Cys Thr Tyr Phe Pro Glu Glu Leu Arg Ser Val Lys Tyr Ala Tyr
                485                 490                 495

Asn Ala Asp Leu Tyr Asn Ala Leu Asn Asp Leu Asn Asn Leu Val Ile
            500                 505                 510

Thr Arg Asp Glu Asn Glu Lys Leu Glu Tyr Tyr Glu Lys Phe Gln Ile
        515                 520                 525

Ile Glu Asn Val Phe Lys Gln Lys Lys Pro Thr Leu Lys Gln Ile
530                 535                 540

Ala Lys Glu Ile Leu Val Asn Glu Glu Asp Ile Lys Gly Tyr Arg Val
545                 550                 555                 560

Thr Ser Thr Gly Lys Pro Glu Phe Thr Asn Leu Lys Val Tyr His Asp
                565                 570                 575

Ile Lys Asp Ile Thr Ala Arg Lys Glu Ile Ile Glu Asn Ala Glu Leu
            580                 585                 590

Leu Asp Gln Ile Ala Lys Ile Leu Thr Ile Tyr Gln Ser Ser Glu Asp
        595                 600                 605

Ile Gln Glu Glu Leu Thr Asn Leu Asn Ser Glu Leu Thr Gln Glu Glu
610                 615                 620

Ile Glu Gln Ile Ser Asn Leu Lys Gly Tyr Thr Gly Thr His Asn Leu
625                 630                 635                 640

Ser Leu Lys Ala Ile Asn Leu Ile Leu Asp Glu Leu Trp His Thr Asn
                645                 650                 655

Asp Asn Gln Ile Ala Ile Phe Asn Arg Leu Lys Leu Val Pro Lys Lys
            660                 665                 670

Val Asp Leu Ser Gln Gln Lys Glu Ile Pro Thr Thr Leu Val Asp Asp
        675                 680                 685

Phe Ile Leu Ser Pro Val Val Lys Arg Ser Phe Ile Gln Ser Ile Lys
690                 695                 700

Val Ile Asn Ala Ile Ile Lys Lys Tyr Gly Leu Pro Asn Asp Ile Ile
705                 710                 715                 720

Ile Glu Leu Ala Arg Glu Lys Asn Ser Lys Asp Ala Gln Lys Met Ile
                725                 730                 735

Asn Glu Met Gln Lys Arg Asn Arg Gln Thr Asn Glu Arg Ile Glu Glu
            740                 745                 750

Ile Ile Arg Thr Thr Gly Lys Glu Asn Ala Lys Tyr Leu Ile Glu Lys
        755                 760                 765

Ile Lys Leu His Asp Met Gln Glu Gly Lys Cys Leu Tyr Ser Leu Glu
770                 775                 780

Ala Ile Pro Leu Glu Asp Leu Leu Asn Asn Pro Phe Asn Tyr Glu Val
785                 790                 795                 800

Asp His Ile Ile Pro Arg Ser Val Ser Phe Asp Asn Ser Phe Asn Asn
                805                 810                 815

Lys Val Leu Val Lys Gln Glu Glu Ala Ser Lys Lys Gly Asn Arg Thr
            820                 825                 830

Pro Phe Gln Tyr Leu Ser Ser Ser Asp Ser Lys Ile Ser Tyr Glu Thr
        835                 840                 845

Phe Lys Lys His Ile Leu Asn Leu Ala Lys Gly Lys Gly Arg Ile Ser
850                 855                 860

Lys Thr Lys Lys Glu Tyr Leu Leu Glu Glu Arg Asp Ile Asn Arg Phe
865                 870                 875                 880

Ser Val Gln Lys Asp Phe Ile Asn Arg Asn Leu Val Asp Thr Arg Tyr
                885                 890                 895

Ala Thr Arg Gly Leu Met Asn Leu Leu Arg Ser Tyr Phe Arg Val Asn
```

```
                    900             905             910
Asn Leu Asp Val Lys Val Lys Ser Ile Asn Gly Gly Phe Thr Ser Phe
            915             920             925
Leu Arg Arg Lys Trp Lys Phe Lys Lys Glu Arg Asn Lys Gly Tyr Lys
            930             935             940
His His Ala Glu Asp Ala Leu Ile Ile Ala Asn Ala Asp Phe Ile Phe
945             950             955             960
Lys Glu Trp Lys Lys Leu Asp Lys Ala Lys Lys Val Met Glu Asn Gln
            965             970             975
Met Phe Glu Glu Lys Gln Ala Glu Ser Met Pro Glu Ile Glu Thr Glu
            980             985             990
Gln Glu Tyr Lys Glu Ile Phe Ile Thr Pro His Gln Ile Lys His Ile
            995             1000            1005
Lys Asp Phe Lys Asp Tyr Lys Tyr Ser His Arg Val Asp Lys Lys
        1010            1015            1020
Pro Asn Arg Glu Leu Ile Asn Asp Thr Leu Tyr Ser Thr Arg Lys
        1025            1030            1035
Asp Asp Lys Gly Asn Thr Leu Ile Val Asn Asn Leu Asn Gly Leu
        1040            1045            1050
Tyr Asp Lys Asp Asn Asp Lys Leu Lys Lys Leu Ile Asn Lys Ser
        1055            1060            1065
Pro Glu Lys Leu Leu Met Tyr His His Asp Pro Gln Thr Tyr Gln
        1070            1075            1080
Lys Leu Lys Leu Ile Met Glu Gln Tyr Gly Asp Glu Lys Asn Pro
        1085            1090            1095
Leu Tyr Lys Tyr Tyr Glu Glu Thr Gly Asn Tyr Leu Thr Lys Tyr
        1100            1105            1110
Ser Lys Lys Asp Asn Gly Pro Val Ile Lys Lys Ile Lys Tyr Tyr
        1115            1120            1125
Gly Asn Lys Leu Asn Ala His Leu Asp Ile Thr Asp Asp Tyr Pro
        1130            1135            1140
Asn Ser Arg Asn Lys Val Val Lys Leu Ser Leu Lys Pro Tyr Arg
        1145            1150            1155
Phe Asp Val Tyr Leu Asp Asn Gly Val Tyr Lys Phe Val Thr Val
        1160            1165            1170
Lys Asn Leu Asp Val Ile Lys Lys Glu Asn Tyr Tyr Glu Val Asn
        1175            1180            1185
Ser Lys Cys Tyr Glu Glu Ala Lys Lys Leu Lys Lys Ile Ser Asn
        1190            1195            1200
Gln Ala Glu Phe Ile Ala Ser Phe Tyr Asn Asn Asp Leu Ile Lys
        1205            1210            1215
Ile Asn Gly Glu Leu Tyr Arg Val Ile Gly Val Asn Asn Asp Leu
        1220            1225            1230
Leu Asn Arg Ile Glu Val Asn Met Ile Asp Ile Thr Tyr Arg Glu
        1235            1240            1245
Tyr Leu Glu Asn Met Asn Asp Lys Arg Pro Pro Arg Ile Ile Lys
        1250            1255            1260
Thr Ile Ala Ser Lys Thr Gln Ser Ile Lys Lys Tyr Ser Thr Asp
        1265            1270            1275
Ile Leu Gly Asn Leu Tyr Glu Val Lys Ser Lys Lys His Pro Gln
        1280            1285            1290
Ile Ile Lys Lys Gly Lys Arg Pro Ala Ala Thr Lys Lys Ala Gly
        1295            1300            1305
```

```
Gln Ala Lys Lys Lys Lys Gly Ser Tyr Pro Tyr Asp Val Pro Asp
    1310            1315                1320

Tyr Ala Tyr Pro Tyr Asp Val Pro Asp Tyr Ala Tyr Pro Tyr Asp
    1325            1330                1335

Val Pro Asp Tyr Ala
    1340
```

The invention claimed is:

1. A cellular composition for administration to a subject in need thereof, the cellular composition comprising;
   a plurality of genetically modified immune cells, the plurality of genetically modified immune cells genetically modified to express an engineered polypeptide, wherein the genetic modification comprises:
   (a) transfecting a plurality of immune cells with a first plasmid, the first plasmid encoding;
      (i) a first guide ribonucleic acid targeting a first target genomic sequence in the plurality of immune cells, wherein the first target genomic sequence encodes a polypeptide of a first regulatory pathway and the polypeptide comprises argininosuccinate synthase 1;
      (ii) a second guide ribonucleic acid targeting a second target genomic sequence in the plurality of immune cells;
      (iii) an effector cassette encoding the engineered polypeptide;
      (iv) a first flanking genomic sequence, and;
      (v) a second flanking genomic sequence, wherein the first flanking genomic sequence and the second flanking genomic sequence flank a target genomic sequence in the plurality of immune cells; and
   (b) transfecting the plurality of immune cells with a second plasmid, the second plasmid encoding a TAT-tagged Cas9 protein, wherein the first guide ribonucleic acid directs the TAT-tagged Cas9 protein to cleave the target genomic sequence in the plurality of immune cells.

2. The cellular composition of claim 1, wherein the first and the second plasmids are co-transfected into the plurality of immune cells.

3. The cellular composition of claim 1, wherein the genetic modification further comprises;
   (c) forming an endonuclease complex in the plurality of immune cells, wherein the endonuclease complex comprises the TAT-tagged Cas9 and the first guide ribonucleic acid;
   (d) cleaving a first allele of the first target genomic sequence in the plurality of immune cells by the endonuclease complex;
   (e) inserting the first guide ribonucleic acid, the second guide ribonucleic acid, and the effector cassette encoding the engineered polypeptide into the cleaved portion of the first allele of the first target genomic sequence;
   (f) cleaving a second allele of the first target genomic sequence in the plurality of immune cells by the endonuclease complex; and
   (g) inserting the first guide ribonucleic acid, the second guide ribonucleic acid, and the effector cassette encoding the engineered polypeptide into the cleaved portion of the second allele of the first target genomic sequence.

4. The cellular composition of claim 3, wherein the inserting of step (e) and step (g) further comprises homology directed repair.

5. The cellular composition of claim 3, wherein steps (e) (g) cause a biallelic insertional mutation into the first target genomic sequence.

6. The cellular composition of claim 3, wherein the genetic modification further comprises;
   (h) cleaving the second target genomic sequence in the plurality of immune cells, wherein the second guide ribonuclease directs the TAT-tagged Cas9 to cleave the second target genomic sequence at a catalytic residue.

7. The cellular composition of claim 6, wherein the cleaving of step (h) further comprises non-homologous end-joining.

8. The cellular composition of claim 6, wherein the cleaving of step (h) results in a biallelic mutation of the second target genomic sequence.

9. The cellular composition of claim 1, wherein the plurality of immune cells is selected from a group consisting of T cells, natural killer cells, B cells, macrophages, monocytes, neutrophils and antigen presenting cells.

10. The cellular composition of claim 1, wherein the first target genomic sequence or the second target genomic sequence is naturally occurring in the plurality of immune cells.

11. The cellular composition of claim 1, wherein the second target genomic sequence encodes a polypeptide of a second regulatory pathway in the plurality of immune cells.

12. The cellular composition of claim 1, wherein the second target genomic sequence is a non-naturally occurring sequence inserted into the genomic DNA of the plurality of immune cells, and wherein the non-naturally occurring sequence is a binding site for a polypeptide.

13. The cellular composition of claim 12, wherein the polypeptide binds to a molecule, wherein the molecule is a drug, an amino acid or a hairpin RNA.

14. The cellular composition of claim 1, wherein the second target genomic sequence encodes a suicide gene.

15. A cellular composition for administration to a subject in need thereof, the cellular composition comprising;
    a plurality of genetically modified immune cells, the plurality of genetically modified immune cells genetically modified to express an engineered polypeptide, wherein the genetic modification comprises:
    (a) transducing a plurality of immune cells with a first vector, the first vector encoding;
       (i) a first guide ribonucleic acid targeting a first target genomic sequence in the plurality of immune cells, wherein the first target genomic sequence encodes a polypeptide of a first regulatory pathway and the polypeptide comprises argininosuccinate synthase 1;
       (ii) a second guide ribonucleic acid targeting a second target genomic sequence in the plurality of immune cells;

(iii) an effector cassette encoding the engineered polypeptide;
(iv) a first flanking genomic sequence, and;
(v) a second flanking genomic sequence, wherein the first flanking genomic sequence and the second flanking genomic sequence flank a first target genomic sequence in the plurality of immune cells; and
(b) transducing the plurality of immune cells with a second vector, the second vector encoding a TAT-tagged Cas9 protein, wherein the first guide ribonucleic acid directs the TAT-tagged Cas9 protein to cleave the first target genomic sequence in the plurality of immune cells.

16. The cellular composition of claim 15, wherein the genetic modification further comprises;
(c) forming an endonuclease complex in the plurality of immune cells, wherein the endonuclease complex comprises the TAT-tagged Cas9 and the first guide ribonucleic acid;
(d) cleaving a first allele of the first target genomic sequence in the plurality of immune cells by the endonuclease complex;
(e) inserting the first guide ribonucleic acid, the second guide ribonucleic acid, and the effector cassette encoding the engineered polypeptide into the cleaved portion of the first allele of the first target genomic sequence;
(f) cleaving a second allele of the first target genomic sequence in the plurality of immune cells by the endonuclease complex; and
(g) inserting the first guide ribonucleic acid, the second guide ribonucleic acid, and the effector cassette encoding the engineered polypeptide into the cleaved portion of the second allele of the first target genomic sequence.

17. The cellular composition of claim 16, wherein the inserting of step (e) and step (g) further comprises homology directed repair.

18. The cellular composition of claim 16, wherein steps (e) (g) cause a biallelic insertional mutation into the first target genomic sequence.

19. The cellular composition of claim 16, wherein the genetic modification further comprises;
(h) cleaving the second target genomic sequence in the plurality of immune cells, wherein the second guide ribonuclease directs the TAT-tagged Cas9 to cleave the second target genomic sequence at a catalytic residue.

* * * * *